(12) United States Patent
Christensen et al.

(10) Patent No.: US 12,336,995 B2
(45) Date of Patent: Jun. 24, 2025

(54) COMBINATION THERAPIES

(71) Applicant: Mirati Therapeutics, Inc., San Diego, CA (US)

(72) Inventors: James Gail Christensen, Carlsbad, CA (US); Lars Daniel Engstrom, Carlsbad, CA (US); Ruth Wei Aranda, San Diego, CA (US); Jill Hallin, San Diego, CA (US); Peter Olson, San Diego, CA (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 515 days.

(21) Appl. No.: 17/275,176

(22) PCT Filed: Sep. 9, 2019

(86) PCT No.: PCT/US2019/050227
§ 371 (c)(1),
(2) Date: Mar. 10, 2021

(87) PCT Pub. No.: WO2020/055756
PCT Pub. Date: Mar. 19, 2020

(65) Prior Publication Data
US 2022/0054491 A1   Feb. 24, 2022

Related U.S. Application Data

(60) Provisional application No. 62/729,189, filed on Sep. 10, 2018.

(51) Int. Cl.
| | | |
|---|---|---|
| A61K 31/519 | (2006.01) |
| A61K 31/517 | (2006.01) |
| A61K 31/5377 | (2006.01) |
| A61K 31/5386 | (2006.01) |
| A61K 31/541 | (2006.01) |
| A61K 45/06 | (2006.01) |
| C07K 16/28 | (2006.01) |

(52) U.S. Cl.
CPC .......... *A61K 31/519* (2013.01); *A61K 31/517* (2013.01); *A61K 31/5377* (2013.01); *A61K 31/5386* (2013.01); *A61K 31/541* (2013.01); *A61K 45/06* (2013.01); *C07K 16/2863* (2013.01)

(58) Field of Classification Search
CPC .............. A61K 31/519; A61K 31/5377; A61K 31/5386; A61K 31/541; C07K 16/2863
See application file for complete search history.

(56) References Cited

U.S. PATENT DOCUMENTS

| | | | |
|---|---|---|---|
| 8,163,763 B2 | 4/2012 | Bergeron et al. | |
| 8,426,401 B2 | 4/2013 | Bian et al. | |
| 9,562,019 B2 | 2/2017 | Djaballah et al. | |
| 9,840,516 B2 | 12/2017 | Li et al. | |
| 10,125,134 B2 * | 11/2018 | Blake | A61P 35/02 |
| 10,647,715 B2 * | 5/2020 | Marx | A61P 35/00 |
| 10,689,377 B2 * | 6/2020 | Blake | A61P 35/00 |
| 11,267,812 B2 * | 3/2022 | Fischer | A61P 43/00 |
| 11,890,285 B2 * | 2/2024 | Briere | C07K 16/2827 |
| 2003/0191143 A1 | 10/2003 | Pitts et al. | |
| 2003/0228663 A1 | 12/2003 | Lowman et al. | |
| 2004/0023957 A1 | 2/2004 | Wang et al. | |
| 2006/0018899 A1 | 1/2006 | Kao et al. | |
| 2006/0235046 A1 | 10/2006 | Zacharchuk et al. | |
| 2007/0232607 A1 | 10/2007 | Bradbury et al. | |
| 2008/0051395 A1 | 2/2008 | Uehling et al. | |
| 2008/0125448 A1 | 5/2008 | Qian et al. | |
| 2008/0139590 A1 | 6/2008 | Qian et al. | |
| 2008/0194578 A1 | 8/2008 | Qian et al. | |
| 2008/0274114 A1 | 11/2008 | Beidler et al. | |
| 2009/0029968 A1 | 1/2009 | Barlaam et al. | |
| 2009/0111772 A1 | 4/2009 | Cai et al. | |
| 2009/0187007 A1 | 7/2009 | Lowman et al. | |
| 2009/0209758 A1 | 8/2009 | Qian et al. | |
| 2009/0285837 A1 | 11/2009 | Kao et al. | |
| 2010/0034689 A1 | 2/2010 | Hirata et al. | |
| 2010/0081654 A1 | 4/2010 | Stockwell et al. | |
| 2010/0117110 A1 | 5/2010 | Park et al. | |

(Continued)

FOREIGN PATENT DOCUMENTS

| | | |
|---|---|---|
| WO | 02/053558 A1 | 7/2002 |
| WO | 02/087513 A2 | 11/2002 |

(Continued)

OTHER PUBLICATIONS

Herwig P. Moll et al. Afatinib restrains K-RAS-driven lung tumorigenesis.Sci. Transl. Med. 10, eaao2301 (2018). DOI:10.1126/scitranslmed.aao2301. (Year: 2018).*
Of G. Patani et al. Bioisosterism: A Rational Approach in Drug Design. Chem. Rev. 1996, 96, 8, 3147-3176. https://doi.org/10.1021/cr950066q. (Year: 1996).*
M. Janes, et al. (Targeting KRAS Mutant Cancers with a Covalent G12C-Specific Inhibitor. Cell. Jan. 25, 2018;172(3):578-589.e17. doi: 10.1016/j.cell.2018.01.006. (Year: 2018).*
G. Patani et al. Bioisosterism: A Rational Approach in Drug Design. Chem. Rev. 1996, 96, 8, 3147-3176. https://doi.org/10.1021/cr950066q. (Year: 1996).*
E. V. Cutsem et al. (Cetuximab and Chemotherapy as Initial Treatment for Metastatic Colorectal Cancer, N Engl J Med 2009;360: 1408-1417, DOI: 10.1056/NEJMoa0805019. (Year: 2009).*

(Continued)

*Primary Examiner* — Medhanit W Bahta
*Assistant Examiner* — Manahil Mirghani Ali Abdalhameed
(74) *Attorney, Agent, or Firm* — Roy Issac

(57) ABSTRACT

The present invention relates to combination therapies for treating KRas G12C cancers. In particular, the present invention relates to methods of treating cancer in a subject in need thereof, comprising administering to the subject a therapeutically effective amount of a combination of a pan ErbB family inhibitor and a KRAS G12C inhibitor of Formula (I), Formula (I-A) or Formula (I-B), pharmaceutical compositions comprising a therapeutically effective amounts of the inhibitors, kits comprising the compositions and methods of use therefor.

36 Claims, No Drawings

(56) References Cited

U.S. PATENT DOCUMENTS

| | | |
|---|---|---|
| 2010/0120678 A1 | 5/2010 | Kuriyan et al. |
| 2010/0143295 A1 | 6/2010 | Gant et al. |
| 2010/0166755 A1 | 7/2010 | Beidler et al. |
| 2010/0196365 A1 | 8/2010 | Garcia-echeverria et al. |
| 2011/0033453 A1 | 2/2011 | Garcia-echeverria et al. |
| 2011/0159014 A1 | 6/2011 | Lowman et al. |
| 2011/0177095 A1 | 7/2011 | Harding et al. |
| 2011/0269244 A1 | 11/2011 | Petter et al. |
| 2011/0295004 A1 | 12/2011 | Qian et al. |
| 2011/0313137 A1 | 12/2011 | Zha |
| 2012/0034211 A1 | 2/2012 | Barbas, III |
| 2012/0094999 A1 | 4/2012 | Gray et al. |
| 2012/0308576 A1 | 12/2012 | Bukhalid et al. |
| 2012/0309942 A1 | 12/2012 | Li et al. |
| 2012/0316135 A1 | 12/2012 | Dalgarno et al. |
| 2013/0029978 A1 | 1/2013 | Kamino et al. |
| 2013/0137709 A1 | 5/2013 | Gray et al. |
| 2013/0189274 A1 | 7/2013 | Berkenblit et al. |
| 2013/0209461 A1 | 8/2013 | Brachmann et al. |
| 2013/0273033 A1 | 10/2013 | Goletz et al. |
| 2013/0289014 A1 | 10/2013 | Solca et al. |
| 2013/0296348 A1 | 11/2013 | Wu et al. |
| 2013/0344093 A1 | 12/2013 | Daly et al. |
| 2014/0005391 A1 | 1/2014 | Qian et al. |
| 2014/0038940 A1 | 2/2014 | Xu et al. |
| 2014/0038981 A1 | 2/2014 | Xu et al. |
| 2014/0141000 A1 | 5/2014 | Chiu et al. |
| 2014/0155606 A1 | 6/2014 | Qian et al. |
| 2014/0161722 A1 | 6/2014 | Garcia-echeverria et al. |
| 2014/0178412 A1 | 6/2014 | Qin et al. |
| 2014/0221403 A1 | 8/2014 | Qian et al. |
| 2014/0286969 A1 | 9/2014 | Tschoepe et al. |
| 2014/0288045 A1 | 9/2014 | Ren et al. |
| 2015/0025055 A1 | 1/2015 | Lee et al. |
| 2015/0126508 A1 | 5/2015 | Li et al. |
| 2015/0166664 A1 | 6/2015 | Goletz et al. |
| 2015/0175558 A1 | 6/2015 | Stockwell et al. |
| 2015/0239900 A1 | 8/2015 | Li et al. |
| 2015/0246047 A1 | 9/2015 | Xu et al. |
| 2015/0250778 A1 | 9/2015 | Brachmann et al. |
| 2015/0274678 A1 | 10/2015 | Qian et al. |
| 2015/0284340 A1 | 10/2015 | Qian et al. |
| 2015/0337042 A1 | 11/2015 | Reilly et al. |
| 2015/0352225 A1 | 12/2015 | Rabuka et al. |
| 2016/0016948 A1 | 1/2016 | Bryan et al. |
| 2016/0031898 A1 | 2/2016 | Ren et al. |
| 2016/0051695 A1 | 2/2016 | Lin et al. |
| 2016/0096893 A1 | 4/2016 | Chen et al. |
| 2016/0102076 A1 | 4/2016 | Suh et al. |
| 2016/0108019 A1 | 4/2016 | Li et al. |
| 2016/0137610 A1 | 5/2016 | Gray et al. |
| 2016/0166571 A1 | 6/2016 | Janes et al. |
| 2016/0229836 A1 | 8/2016 | Stockwell et al. |
| 2016/0244469 A1 | 8/2016 | Zhu et al. |
| 2016/0257682 A1 | 9/2016 | Bryan et al. |
| 2016/0264627 A1 | 9/2016 | Henning et al. |
| 2016/0297774 A1 | 10/2016 | Li et al. |
| 2016/0332994 A1 | 11/2016 | Lee et al. |
| 2016/0375148 A1 | 12/2016 | Li |
| 2017/0008856 A1 | 1/2017 | Zhang |
| 2017/0022184 A1 | 1/2017 | Li et al. |
| 2017/0115303 A1 | 4/2017 | Cravatt et al. |
| 2017/0174697 A1 | 6/2017 | Long |
| 2017/0183330 A1 | 6/2017 | Long |
| 2017/0190672 A1 | 7/2017 | Mani et al. |
| 2017/0197945 A1 | 7/2017 | Li et al. |
| 2017/0218073 A1 | 8/2017 | Jiang et al. |
| 2017/0267671 A1 | 9/2017 | Kumar et al. |
| 2017/0267765 A1 | 9/2017 | Tsao |
| 2017/0342055 A1 | 11/2017 | Bunker et al. |
| 2017/0355683 A1 | 12/2017 | Sheng et al. |
| 2017/0362203 A1 | 12/2017 | Peng et al. |
| 2017/0362204 A1 | 12/2017 | Gray et al. |
| 2018/0008607 A1 | 1/2018 | Xu et al. |
| 2018/0015087 A1 | 1/2018 | Liu et al. |
| 2018/0016268 A1 | 1/2018 | Kumar et al. |
| 2018/0022816 A1 | 1/2018 | De Goeij et al. |
| 2018/0022820 A1 | 1/2018 | Li et al. |
| 2018/0036405 A1 | 2/2018 | Daly et al. |
| 2018/0050993 A1 | 2/2018 | Slassi et al. |
| 2018/0057608 A1 | 3/2018 | Jung et al. |
| 2018/0066066 A1 | 3/2018 | Zhang et al. |
| 2018/0072723 A1* | 3/2018 | Blake .................... A61P 35/00 |
| 2018/0094062 A1 | 4/2018 | Bossenmaier et al. |
| 2018/0118757 A1 | 5/2018 | Li et al. |
| 2018/0118761 A1 | 5/2018 | Sebti et al. |
| 2018/0118837 A1 | 5/2018 | Bossenmaier et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0155433 A1 | 6/2018 | Chardès et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0258173 A1 | 9/2018 | Chiu et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2018/0306049 A1 | 10/2018 | Romanov |
| 2018/0362443 A1 | 12/2018 | Lavallee et al. |
| 2019/0040143 A1 | 2/2019 | Chowdhury et al. |
| 2019/0151328 A1 | 5/2019 | Hettmann et al. |
| 2019/0177428 A1 | 6/2019 | Fuh et al. |
| 2019/0194347 A1 | 6/2019 | Elis et al. |
| 2019/0194350 A1 | 6/2019 | Kontermann et al. |
| 2019/0209704 A1 | 7/2019 | Jackson et al. |
| 2019/0216924 A1 | 7/2019 | Elis et al. |
| 2019/0248918 A1 | 8/2019 | Chen et al. |
| 2019/0263930 A1 | 8/2019 | Rothe et al. |
| 2020/0262837 A1 | 8/2020 | Marx et al. |
| 2020/0399297 A1 | 12/2020 | Campbell et al. |
| 2022/0040181 A1* | 2/2022 | Engstrom ............... A61P 35/02 |
| 2022/0040182 A1* | 2/2022 | Olson .................. A61K 31/436 |
| 2022/0054492 A1* | 2/2022 | Aranda ............... A61K 31/4375 |
| 2022/0079947 A1* | 3/2022 | Christensen ....... A61K 31/5355 |
| 2022/0096482 A1* | 3/2022 | Christensen ............ A61P 35/00 |
| 2022/0331324 A1* | 10/2022 | Engstrom ............... A61P 35/00 |
| 2023/0357231 A1* | 11/2023 | Andres .................... A61P 35/00 |
| 2023/0383359 A1* | 11/2023 | Christensen ......... C12Q 1/6886 |
| 2024/0101553 A1* | 3/2024 | Marx ..................... A61P 35/00 |

FOREIGN PATENT DOCUMENTS

| | | |
|---|---|---|
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |

(56) References Cited

FOREIGN PATENT DOCUMENTS

| | | |
|---|---|---|
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 2019099524 A1 | 5/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |

(56) References Cited

FOREIGN PATENT DOCUMENTS

| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |

OTHER PUBLICATIONS

R. Adams et al. (Inhibition of EGFR, HER2, and HER3 signalling in patients with colorectal cancer wild-type for BRAF, PIK3CA, KRAS, and NRAS (FOCUS4-D): a phase 2-3 randomised trial. The Lancet Gastroenterology & Hepatology, Mar. 2018, V. 3, IS. 3, p. 162-171. (Year: 2018).*

Sung, Y. et al., "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436, Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

Singh et al., "A Gene Expression Signature Associated with K-Ras Addiction" Reveals Regulators of EMT and Tumor Cell Survival, Cancer Cell 15, p. 489-500, Jun. 2, 2009.

Stephen et al., "Dragging Ras Back in the Ring", Cancer Cell 25, p. 272, Mar. 17, 2014.

Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.

Simanshu et al., "RAS Proteins and Their Regulators in Human Disease", Cell 170, p. 17, Jun. 29, 2017.

Pacold et al., "Crystal Structure and Functional Analysis of Ras Binding to Its Effector Phosphoinositide 3-Kinase gamma", Cell, vol. 103, p. 931-943, Dec. 8, 2000.

Lech-Gustav et al., "The Renaissance of Ras", ACS Chem. Biol., 2014, 9, 2447-2458.

Karachaliou et al., "KRAS Mutations in Lung Cancer", Clinical Lung Cancer, vol. 14, No. 3, p. 2015-14, 2013.

Schwartz et al., "Covalent EGFR inhibitor analysis reveals importance of reversible interactions to potency and mechanisms of drug resistance", PNAS, vol. 111, No. 1, p. 173-178, Jan. 7, 2014.

Sun et al., "A method for the second-site screening of K-Ras in the presence of a covalently attached first-site ligand", J. Biomol. NMR (2014) vol. 60 p. 11-14.

Kyriakis, J., "Thinking Outside the Box about Ras", J. Biol. Chem. 2009, 284:10993-10994, published online Dec. 17, 2008.

Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.

Serafimova et al., "Reversible targeting of noncatalytic cysteines with chemically tuned electrophiles", Nat Chem Biol.; 8(5):471-476. doi:10.1038/nchembio.925.

Walker et al., "Structural insights into phosphoinositide 3-kinase catalysis and signalling", Nature vol. 402, p. 18 Nov. 1999; www.nature.com.

Barbie et al., "Systematic RNA interference reveals that oncogenic KRAS-driven cancers require TBK1", Nature, vol. 462, p. 108, Nov. 5, 2009; doi:10.1038/nature08460.

Zimmermann et al., "Small molecule inhibition of the KRAS-PDEdelta interaction impairs oncogenic KRAS signalling", Nature, vol. 497, p. 638, May 30, 2013.

Karnoub et al., "Ras oncogenes: split personalities", Nature Reviews, molecular Cell Biology, vol. 9, Jul. 2008 p. 517.

Nassar et al., "Ras/Rap effector specificity determined by charge reversal", Nature Structural Biology, vol. 3, No. 8, Aug. 1996.

De Rooij et al., "Minimal Ras-binding domain of Raf1 can be used as an activation-specific probe for Ras", Oncogene (1997) 14, 623-625, 1997 Stockton Press.

Cox et al., "The dark side of RAs: regulation of apoptosis", Oncogene (2003) 22, 8999-9006, 2003 Nature Publishing Group.

Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.

Grant et al., "Novel Allosteric Sites on Ras for Lead Generation", PLOS ONE, vol. 6, Issue 10, Oct. 2011.

Maegley et al., "Ras-catalyzed hydrolysis of GTP: A new perspective from model studies", Proc. Natl. Acad. Sci. USA, vol. 93, pp. 8160-8166, Aug. 1996.

Ahmadian et al., "Guanosine triphosphatase stimulation of oncogenic Ras mutants", Proc. Natl. Acad. Sci. USA, vol. 96, pp. 7065-7070, Jun. 1999.

Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.

Kotting et al., "The GAP arginine finger movement into the catalytic site of Ras increases the activation entropy", PNAS, vol. 105, No. 17, p. 6260-6265, Apr. 29, 2008.

Shaw et al., "Selective killing of K-ras mutant cancer cells by small molecule inducers of oxidative stress", PNAS, vol. 108, No. 21, p. 8773-8778, May 24, 2011.

Ischenko et al., "Direct reprogramming by oncogenic Ras and Myc", PNAS early edition 1, 2013.

Smith et al., "NMR-based functional profiling of RASopathies and oncogenic RAS mutations", PNAS, vol. 110, No. 12, p. 4574-4579, Mar. 19, 2013.

Shima, et al., "In silico discovery of small-molecule Ras inhibitors that display antitumor activity by blocking the Ras-effector interaction", PNAS, vol. 110, No. 20, p. 8182-8187, May 14, 2013.

Burns et al., "Approach for targeting Ras with small molecules that activate SOS-mediated nucleotide exchange", PNAS, vol. 111, No. 9, p. 3401-3406, Mar. 4, 2014.

Zeng et al., "Design of inhibitors of Ras-Raf interaction using a computational combinatorial algorithm", Protein Engineering, vol. 14, No. 1, p. 39-45, 2001.

(56) References Cited

OTHER PUBLICATIONS

Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi: 10.1016/j.tibs.2010.09.006.
Fell et al. 'Discovery of Tetrahydropyridopyrimidines as Irreversible Covalent Inhibitors of Kras-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 mailed Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
Nabet, B. et al., "It Takes Two to Target: A Study in KRAS Dimerization", pubs.acs.org/biochemistry, DOI: 10.1021.
O'Bryan, J., "Pharmacological Targeting of RAS: Recent Success with Direct Inhibitors", Pharmacological Research (2018), https://doi.org/10.1016/j.phrs.2018.10.021.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Ruess, D. et al., "Mutant KRAS-driven cancers depend on PTPN11/SHP2 phosphatase", Nature Medicine, Letters, https://doi.org/10.1038/s41591-018-0024-8.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancer-res.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer a Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.

Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Calles, et al., "Immunohistochemical Loss of LKB1 Is a Biomarker for More Aggressive Biology in KRAS-Mutant Lung Adenocarcinoma", Clin Cancer Res. 2015. 21(12).
Torralvo et al., "The Activity of Immune Checkpoint Inhibition in KRAS Mutated Non-small Cell Lung Cancer: A Single Centre Experience", Cancer Genomics & Proteomics, 2019. 16: 577-582.
International Search Report and Written Opinion for PCT Application No. PCT/US2019/0050227 mailed Jan. 30, 2020.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right column Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS ONE | DOI:10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.

(56) References Cited

OTHER PUBLICATIONS

Kaufman, J. et al., "Treatment of KRAS-Mutant Non-Small Cell Lung Cancer the End of the Beginning for Targeted Therapies", JAMA May 9, 2017 vol. 317, No. 18.
Kerr, E. et al., "Mutant KRAS copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: Kras G12C mutation is prognostic of poor outcome in resected lung adenocarcinomas and predictive of poor response to MEK inhibition in vitro", Mol Cancer Ther Nov. 12, 2013; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Rudoni, S. et al., "Role of guanine nucleotides in the regulation of the Ras/cAMP pathway in *Saccharomyces cerevisiae*", Biochimica et Biophysica Acta 1538 (2001) 181/\189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Alamgeer et al., (2013) "Novel Therapeutic Targets in Non-small Cell Lung Cancer", Current Opinion in Pharmacology, 13(3):394-401(8 Pages).
Bliss CI, (1939) "The Toxicity of Poisons Applied Jointly", Annals of Applied Biology, 26:585-615.
Chou et al., (1984) "Quantitative Analysis of Dose-Effect Relationships: The Combined Effects of Multiple Drugs or Enzyme Inhibitors", Advances in Enzyme Regulation, 22:27-55.
Dogan et al., (2012) "Molecular Epidemiology of EGFR and KRAS Mutations in 3,026 Lung Adenocarcinomas: Higher Susceptibility of Women to Smoking-related Kras-mutant Cancers", Clin Cancer Res., 18(22):6169-6177.
Ladanyi et al., (May 2008) "Lung adenocarcinoma: guiding EGFR-targeted therapy and beyond", Mod Pathol., 21 Suppl 2:S16-22.
McCormick, Frank, (2015) "KRAS as a Therapeutic Target", Clinical Cancer Research, 21(8):1797-1801.
Ostrem, J.M, (2013) "K-Ras (G12c) Inhibitors Allosterically Control GTP Affinity and Effector Interactions", Nature, 503(7477):548-551.
Rao et al., (Aug. 2018) "Dasatinib Sensitises KRAS-Mutant Cancer Cells to Mitogen-Activated Protein Kinase Kinase Inhibitor via Inhibition of TAZ Activity", European Journal of Cancer, 99:37-48.
Santos et al., (1984) "Malignant Activation of a K-Ras Oncogene in Lung Carcinoma but Not in Normal Tissue of the Same Patient", Science, 223(4637):661-664.
Sun et al., (2014) "Intrinsic resistance to MEK inhibition in KRAS mutant lung and colon cancer through transcriptional induction of ERBB3", Cell Reports, 7:86-93.
Yadav et al., (Sep. 25, 2015) "Searching for Drug Synergy in Complex Dose-Response Landscapes Using an Interaction Potency Model", Computational and Structural Biotechnology Journal, 13:504-513.

\* cited by examiner

COMBINATION THERAPIES

FIELD OF THE INVENTION

The present invention relates to combination therapies useful for treating cancer. In particular, the present invention relates to therapeutically effective combinations of a pan ErbB family inhibitor and a KRas G12C inhibitor, pharmaceutical compositions comprising the inhibitors, kits comprising the compositions and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors regulating a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRas in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well as those that target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

While the KRas G12C inhibitors disclosed herein are potent inhibitors of KRas G12C enzymatic activity and exhibit single agent activity inhibiting the in vitro proliferation of cell lines harboring a KRas G12C mutation, the relative potency and or observed maximal effect of any given KRas G12C inhibitor can vary between KRAS mutant cell lines. The reason or reasons for the range of potencies and observed maximal effect is not fully understood but certain cell lines appear to possess differing intrinsic resistance. Thus, there is a need to develop alternative approaches to maximize the potency, efficacy, therapeutic index and/or clinical benefit of KRas G12C inhibitors in vitro and in vivo.

The combination therapy of the present invention, in one aspect, synergistically increases the potency of KRas G12C inhibitors resulting in improved efficacy of KRas G12C inhibitors disclosed herein. The combination therapy of the present invention, in another aspect, provides improved clinical benefit to patients compared to treatment with KRas G12C inhibitors disclosed herein as a single agent.

SUMMARY OF THE INVENTION

In one aspect of the invention, provided herein are methods of treating cancer in a subject in need thereof, comprising administering to the subject a therapeutically effective amount of a combination of a pan ErbB family inhibitor and a KRAS G12C inhibitor of formula (I):

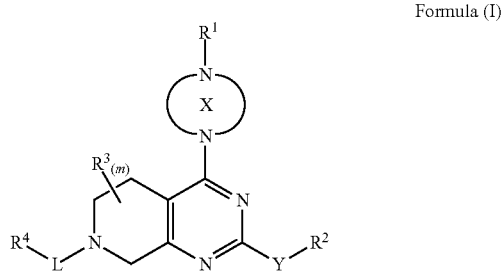

Formula (I)

or a pharmaceutically acceptable salt thereof, wherein:
X is a 4-12 membered saturated or partially saturated monocyclic, bridged or spirocyclic ring, wherein the saturated or partially saturated monocyclic ring is optionally substituted with one or more $R^8$.
Y is a bond, O, S or $NR^5$;
$R^1$ is —C(O)C($R^A$)=C($R^B$)$_p$ or —SO$_2$C($R^A$)=C($R^B$)$_p$;
$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;
Z is C1-C4 alkylene;
each $R^3$ is independently C1-C3 alkyl, oxo, or haloalkyl;
L is a bond, —C(O)—, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;
each $R^5$ is independently hydrogen or C1-C3 alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;
$R^8$ is oxo, C1-C3 alkyl, C2-C4 alkynyl, heteroalkyl, cyano, —C(O)O$R^5$, —C(O)N($R^5$)$_2$, —N($R^5$)$_2$, wherein the C1-C3 alkyl may be optionally substituted with cyano, halogen, —O$R^5$, —N($R^5$)$_2$, or heteroaryl
each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^{11}$ is haloalkyl;

$R^A$ is absent, hydrogen, deuterium, cyano, halogen, C1-C-3 alkyl, haloalkyl, heteroalkyl, —C(O)N($R^5$)$_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —ZN$R^5R^{11}$, —C(O)N($R^5$)$_2$, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

m is zero or an integer between 1 and 2;

p is one or two; and wherein, when ===== is a triple bond then $R^A$ is absent, $R^B$ is present and p equals one, or when ===== is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

Also included for use in the methods provided herein are KRas G12C inhibitor compounds of Formula I having the Formula I-A:

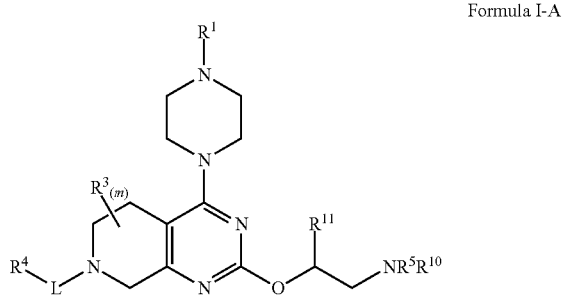

Formula I-A or a pharmaceutically acceptable salt thereof, wherein $R^1$, $R^3$, $R^4$, $R^5$, $R^{10}$, $R^{11}$, L and m are as defined for Formula I, and the piperazinyl ring is optionally substituted with $R^8$ wherein $R^8$ is as defined for Formula I.

Also included for use in the methods provided herein are KRas G12C inhibitor compounds of Formula I having the Formula I-B:

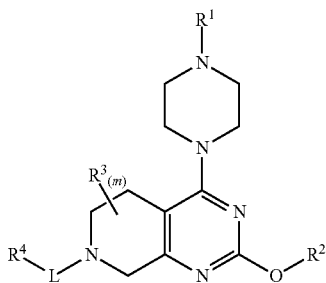

Formula I-B or a pharmaceutically acceptable salt thereof, wherein $R^1$, $R^3$, $R^4$, L and m are as defined for Formula I, $R^2$ is heterocyclylalkyl optionally substituted with one or more $R^9$ where $R^9$ is as defined for Formula I, and the piperazinyl ring is optionally substituted with $R^8$, where $R^8$ is as defined for Formula I.

In another aspect of the invention, pharmaceutical compositions are provided for use in the methods comprising a therapeutically effective amount of a combination of a pan ErbB family inhibitor and a KRas G12C inhibitor compound Formula I, Formula I-A, or Formula I-B, or a pharmaceutically acceptable salts thereof and a pharmaceutically acceptable excipient.

In one aspect of the invention, provided herein are methods of treating cancer in a subject in need thereof, comprising administering to the subject a therapeutically effective amount of a combination of a pan ErbB family inhibitor, or a pharmaceutically acceptable salt or a pharmaceutical composition thereof and a KRAS G12C inhibitor of Formula (I), Formula I-A or Formula I-B, or a pharmaceutically acceptable salt or a pharmaceutical composition thereof. In one embodiment, the cancer is a KRas G12C-associated cancer. In one embodiment, the KRas G12C-associated cancer is lung cancer.

In some aspects of the invention, KRas G12C inhibitor compounds and pan ErbB family inhibitors are the only active agents in the provided compositions and methods.

In one embodiment, the pan ErbB family inhibitor is an irreversible inhibitor. Examples of irreversible pan ErbB family inhibitors suitable for the provided compositions and methods include, but are not limited to, Afatinib; Dacomitinib; Canertinib; Poziotinib, AV 412; PF 6274484 and HKI 357.

In one embodiment, the pan ErbB family inhibitor is a reversible inhibitor. Examples of reversible pan ErbB family inhibitors suitable for the provided compositions and methods include, but are not limited to erlotinib, gefitinib, sapitinib; varlitinib; TAK-285 (N-[2-[4-[3-chloro-4-[(3-(trifluoromethyl)phenoxy]phenylamino]-5H-pyrrolo[3,2-d] pyrimidin-5-yl]ethyl]-3-hydroxy-3-methylbutyramide); AEE788 (6-[4-(4-Ethylpiperazin-1-ylmethyl)phenyl]-N-[1 (R)-phenylethyl]-7H-pyrrolo[2,3-d]pyrimidin-4-amine); tarloxotinib 3-[N-[4-(3-Bromo-4-chlorophenylamino) pyrido[3,4-d]pyrimidin-6-yl]carbamoyl]-N,N-dimethyl-N-(1-methyl-4-nitro-1H-imidazol-5-ylmethyl)-2(E)-propen-1-aminium bromide); BMS 599626/AC-480 (N-[4-[1-(3-Fluorobenzyl)-1H-indazol-5-ylamino]-5-methylpyrrolo[2, 1-f][1,2,4]triazin-6-yl]carbamic acid morpholin-3(S)-ylmethyl ester hydrochloride); and GW 583340 HCl (N-[3-chloro-4-(3-fluorobenzyloxy)phenyl]-6-[2-[2-(methylsulfonyl)ethylaminomethyl]thiazol-4-yl]quinazolin-4-amine).

In one embodiment, the pan ErbB family inhibitor is a combination of an EGFR inhibitor and a HER2 inhibitor, wherein the EGFR inhibitor and the HER2 inhibitor are a combination of two of: AG 1478 (N-(3-chlorophenyl)-6-methoxy-7-[11C]methoxyquinazolin-4-amine); AG 555 (2-cyano-3-(3,4-dihydroxyphenyl)-N-(3-phenylpropyl)-2 (E)-propenamide); AG 556 ((E)-2-cyano-3-(3,4-dihydroxyphenyl)-N-(4-phenylbutyl)acrylamide; AG 825 (3-[3-(benzothiazol-2-ylsulfanylmethyl)-4-hydroxy-5-methoxyphenyl]-2-cyano-2-propenamide); CP 724714 (2-methoxy-N-[3-[4-[3-methyl-4-(6-methylpyridin-3-yloxy)phenylamino]quinazolin-6-yl]-2(E)-propenyl]acetamide; BIBU 1361 (N-(3-chloro-4-fluorophenyl)-6-[4-(diethylaminomethyl)piperidin-1-yl]pyrimido[5,4-d]pyrimidin-4-amine); BIBU 1382; JNJ 28871063 ((E)-4-amino-6-[4-(benzyloxy)-3-chlorophenylamino]pyrimidine-5-carbaldehyde 0-[2-(4-morpholinyl)ethyl]oxime); PD 153035 (4-(3-bromophenylamino)-6,7-dimethoxyquinazoline); and PD 158780 ($N^4$-(3-bromophenyl)-$N^6$-methyl-pyrido[3,4-d]pyrimidine-4,6-diamine).

In one embodiment, the pan ErbB family inhibitor is an anti-EGFR antibody, a anti-HER2 antibody or combination of an anti-EGFR antibody and anti-HER2 antibody. Antibodies, including monoclonal antibodies, antibody conjugates and bispecific antibodies, targeting EGFR and/or HER2 are well known and a number of antibodies are commercially available for research and human clinical use.

Examples of anti-EGFR antibodies suitable for the provided compositions and methods include necitumumab, panitumumab and cetuximab. Examples of anti-HER2 antibodies suitable for the provided compositions and methods include, pertuzumab, trastuzumab, and trastuzumab emtansine.

In yet another aspect, the invention provides for methods for increasing the sensitivity of a cancer cell to a KRas G12C inhibitor, comprising contacting the cancer cell with a therapeutically effective amount of a combination of a KRas G12C inhibitor compound of Formula (I), Formula I-A, or Formula I-B, or a pharmaceutically acceptable salt or a pharmaceutical composition thereof and a pan ErbB family inhibitor or a pharmaceutically acceptable salt or a pharmaceutical composition thereof, wherein the pan ErbB family inhibitor synergistically increases the sensitivity of the cancer cell to the KRas G12C inhibitor. In one embodiment, the contacting is in vitro. In one embodiment, the contacting is in vivo.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a pan ErbB family inhibitor, or a pharmaceutically acceptable salt or a pharmaceutical composition thereof and a KRas G12C inhibitor compound of Formula I, Formula I-A, Formula I-B, or a pharmaceutically acceptable salt or a pharmaceutical composition thereof, wherein the pan ErbB family inhibitor synergistically increases the sensitivity of the KRas G12C-associated cancer to the KRas G12C inhibitor.

Also provided herein are kits comprising a pan ErbB inhibitor, or a pharmaceutically acceptable salt or a pharmaceutical composition thereof and a KRas G12C inhibitor compound of Formula (I), Formula I-A or Formula I-B, or a pharmaceutically acceptable salt or a pharmaceutical composition thereof. Also provided is a kit comprising a pan ErbB family inhibitor, or a pharmaceutically acceptable salt or a pharmaceutical composition thereof and a KRas G12C inhibitor compound of Formula (I), Formula I-A or Formula I-B, or a pharmaceutically acceptable salt or a pharmaceutical composition thereof, for use in treating a KRas G12C cancer.

In a related aspect, the invention provides a kit containing a dose of a pan ErbB inhibitor, or a pharmaceutically acceptable salt or a pharmaceutical composition thereof and a KRas G12C inhibitor compound of Formula (I), Formula I-A or Formula I-B, or a pharmaceutically acceptable salt or a pharmaceutical composition thereof in an amount effective to inhibit proliferation of cancer cells in a subject. The kit in some cases includes an insert with instructions for administration of the a pan ErbB family inhibitor, or a pharmaceutically acceptable salt or a pharmaceutical composition thereof and a KRas G12C inhibitor compound of Formula (I), Formula I-A or Formula I-B, or a pharmaceutically acceptable salt or a pharmaceutical composition thereof. The insert may provide a user with one set of instructions for using the a pan ErbB family inhibitor, or a pharmaceutically acceptable salt or a pharmaceutical composition thereof in combination with a KRas G12C inhibitor compound of Formula (I), Formula I-A or Formula I-B, or a pharmaceutically acceptable salt or a pharmaceutical composition thereof.

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

DETAILED DESCRIPTION OF THE INVENTION

The present invention relates to combination therapies for treating KRas G12C cancers. In particular, the present invention relates to methods of treating cancer in a subject in need thereof, comprising administering to the subject a therapeutically effective amount of a combination of a pan ErbB family inhibitor, or a pharmaceutically acceptable salt or a pharmaceutical composition thereof and a KRAS G12C inhibitor of Formula (I), Formula I-A or Formula I-B, or a pharmaceutically acceptable salt or a pharmaceutical composition thereof, pharmaceutical compositions each separately comprising a therapeutically effective amount of the inhibitors, kits comprising the compositions and methods of use therefor.

Combinations of a pan ErbB family inhibitor with a KRas G12C inhibitor compounds of Formula (I), Formula I-A or Formula I-B, or a pharmaceutically acceptable salt thereof synergistically increase the potency of the KRas G12C inhibitor compounds of Formula (I), Formula I-A or Formula I-B, or a pharmaceutically acceptable salt thereof against cancer cells that express KRas G12C thereby increasing the efficacy and therapeutic index of KRas G12C inhibitor compounds of Formula (I), Formula I-A or Formula I-B, and pharmaceutically acceptable salts thereof.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by Formula (I), Formula I-A and Formula I-B, and pharmaceutically acceptable salts thereof as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C. In one embodiment, the KRas G12C inhibitor is a compound selected from compound Nos 1-678 (as numbered in WO2019099524), or pharmaceutically acceptable salts thereof (e.g., Example Nos 234, 359, 478 or 507, or a pharmaceutically acceptable salt thereof).

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, an "ErbB family" or "ErbB family member" refers to a member of a mammalian transmembrane protein tyrosine kinase family including: EGFR, ErbB2 (HER2), ErbB3 (HER3), and ErbB4 (HER4).

As used herein, a "pan ErbB family inhibitor" refers to an agent, e.g., a compound or antibody, that is capable of negatively modulating or inhibiting all or a portion of the activity of at least one member of the ErbB family. The modulation or inhibition of one or more ErbB family members may occur through modulating or inhibiting kinase enzymatic activity of one or more ErbB family member or by blocking homodimerization or heterodimerization of ErbB family members. In some embodiments of the methods herein, the term "pan ErbB inhibitor" refers to the use of a single pan ErbB inhibitor. In some embodiments of the methods herein, the term "pan ErbB inhibitor" refers to the use of two pan ErbB inhibitors.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample (e.g., a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR, quantitative real-time RT-PCR, allele-specific genotyping or ddPCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to $-NH_2$;

The term "acyl" refers to $-C(O)CH_3$.

The term "alkyl" as employed herein refers to straight and branched chain aliphatic groups having from 1 to 12 carbon atoms, 1-8 carbon atoms 1-6 carbon atoms, or 1-3 carbon atoms which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain in which one or more hydrogen has been replaced by a halogen. Examples of haloalkyls are trifluoromethyl, difluoromethyl and fluoromethyl.

The term "haloalkyloxy" refers to $-O$-haloalkyl.

An "alkylene," group is an alkyl group, as defined hereinabove, that is positioned between and serves to connect two other chemical groups. Exemplary alkylene groups include, without limitation, methylene, ethylene, propylene, and butylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted.

Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

As used herein, the term "hydroxyalkyl" refers to -alkyl-OH.

The term "dihydroxyalkyl" refers to an alkyl group as defined herein wherein two carbon atoms are each substituted with a hydroxyl group.

The term "alkylaminyl" refers to —$NR^x$-alkyl, wherein $R^x$ is hydrogen. In one embodiment, $R^x$ is hydrogen.

The term "dialkylaminyl" refers to —$N(R^y)_2$, wherein each $R^y$ is C1-C3 alkyl.

The term "alkylaminylalkyl" refers to -alkyl-$NR^x$-alkyl, wherein $R^x$ is hydrogen. In one embodiment, $R^x$ is hydrogen.

The term "dialkylaminylalkyl" refers to -alkyl-$N(R^y)_2$, wherein each $R^y$ is C1-C4 alkyl, wherein the alkyl of the -alkyl-$N(R^y)_2$ may be optionally substituted with hydroxy or hydroxyalkyl.

An "aryl" group is a $C_6$-$C_{14}$ aromatic moiety comprising one to three aromatic rings, which is optionally substituted. As one embodiment, the aryl group is a $C_6$-$C_{10}$ aryl group. Examples of aryl groups include, without limitation, phenyl, naphthyl, anthracenyl, fluorenyl, and dihydrobenzofuranyl.

An "aralkyl" or "arylalkyl" group comprises an aryl group covalently linked to an alkyl group, either of which may independently be optionally substituted or unsubstituted. An example of an aralkyl group is ($C_1$-$C_6$)alkyl($C_6$-$C_{10}$)aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a ring structure having from about 3 to about 12 atoms, for example 4 to 8 atoms, wherein one or more atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with $R^7$ on carbon or nitrogen at one or more positions, wherein $R^7$ is as defined for Formula I. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, thiomorpholinyl, thiomorpholinyl 1,1 dioxide, morpholinyl, oxazepanyl, azabicyclohexanes, azabicycloheptanes and oxa azabicycloheptanes. Specifically excluded from the scope of this term are compounds having adjacent annular O and/or S atoms.

The term "heterocyclylalkyl" refers to a heterocyclyl group as defined herein linked to the remaining portion of the molecule via an alkyl linker, wherein the alkyl linker of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein, "an effective amount" of a compound is an amount that is sufficient to negatively modulate or inhibit the activity of the desired target, i.e., ErbB family member or KRas G12C. Such amount may be administered, for example, as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of ErbB family member(s) or KRas G12C. Such amount may be administered, for example, as a single dosage or may be administered according to a regimen, whereby it is effective.

As used herein, a "therapeutically effective amount of a combination" of two compounds is an amount that together synergistically increases the activity of the combination in comparison to the therapeutically effective amount of each compound in the combination, i.e., more than merely additive effect. Alternatively, in vivo, the therapeutically effective amount of the combination of a pan ErbB inhibitor, or a pharmaceutically acceptable salt or a pharmaceutical composition thereof and a KRas G12C inhibitor compound of Formula (I), Formula I-A, or Formula I-B, or a pharmaceutically acceptable salt or a pharmaceutical composition thereof, results in an increased duration of overall survival ("OS") in subjects relative to treatment with only the KRas G12C inhibitor. In one embodiment, the therapeutically effective amount of the combination of a pan ErbB inhibitor, or a pharmaceutically acceptable salt or a pharmaceutical composition thereof and a KRas G12C inhibitor compound of Formula (I), Formula I-A, or Formula I-B, or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a pan ErbB inhibitor, or a pharmaceutically acceptable salt or a pharmaceutical composition thereof and a KRas G12C inhibitor compound of Formula (I), Formula I-A, or Formula I-B, or a pharmaceutically acceptable salt or a pharmaceutical composition thereof, results in increased tumor regression in subjects relative to treatment with only the KRas G12C inhibitor. In one embodiment, the therapeutically effective amount of the combination of a pan ErbB inhibitor, or a pharmaceutically acceptable salt or a pharmaceutical composition thereof and a KRas G12C inhibitor compound of Formula (I), Formula I-A, or Formula I-B, or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a pan ErbB inhibitor, or a pharmaceutically acceptable salt or a pharmaceutical composition thereof and a KRas G12C inhibitor compound of Formula (I), Formula I-A, or Formula I-B, or a pharmaceutically acceptable salt or pharmaceutical composition thereof, results in an improvement in the duration of stable disease in subjects compared to treatment with only the KRas G12C inhibitor. Such amounts may be administered, for example, as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of a KRAS inhibitor or a pan ErbB family inhibitor or a pharmaceutically acceptable salt thereof, or the length of treatment time with a combination therapy described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

Inhibitor Compounds

In one aspect of the invention, provided herein are methods of treating cancer, for example a KRas G12C-associated cancer, in a subject in need thereof, comprising administering to the subject a therapeutically effective amount of a combination of a pan ErbB family inhibitor, or a pharmaceutically acceptable salt or a pharmaceutical composition thereof and a KRAS G12C inhibitor of Formula (I), Formula I-A or Formula I-B, or a pharmaceutically acceptable salt or a pharmaceutical composition thereof.

1. ErbB Family

Epidermal Growth Factor Receptor (EGFR) is a transmembrane protein tyrosine kinase of the ErbB receptor family. Upon binding epidermal growth factor (EGF), the EGFR receptor can homo-dimerize with another EGFR molecule or hetero-dimerize with another family member such as ErbB2 (HER2), ErbB3 (HER3), or ErbB4 (HER4). Homo- and/or hetero-dimerization of ErbB receptors results in the phosphorylation of key tyrosine residues in the intracellular domain and leads to the stimulation of numerous intracellular signal transduction pathways involved in cell proliferation and survival.

Overexpression of the EGFR gene has been identified in a variety of cancers including bladder, brain, head and neck, pancreas, lung, breast, ovary, colon, prostate, and kidney. In addition to overexpression, EGFR activating mutations have been detected in a subset of non-small cell lung cancers (NSCLCs) tumors. These mutations tend to occur within EGFR exons 18-21, which encodes a portion of the EGFR kinase domain. Approximately 90% of these mutations are exon 19 deletions or exon 21 L858R point mutations (Ladanyi and Pao (2008) Mod Path. May; 21 Suppl 2:S16-22. doi: 10.1038/modpathol.3801018). These mutations increase the kinase activity of EGFR, leading to hyperactivation of downstream pro-survival signaling pathways.

The frequency of overexpression and/or activating mutations of EGFR has made it a desired target for anticancer therapies and a number of EGFR inhibitors have been developed and are clinically available.

First generation erlotinib and gefitinib inhibit EGFR activity by competitively binding to the ATP binding site of the EGFR kinase domain; however additional mutations in the EGFR gene, e.g., the T790M mutation, produces mutant EGFR proteins to which drugs like erlotinib and gefitinib bind less well. Those mutations are associated with resistance to the drugs and to relapse in cancer patients bearing such mutation leading to the development of second generation EGFR inhibitors targeting the T790M mutant.

Furthermore, inhibition of the pathway-related enzyme MEK results in increased expression of ErbB family members, especially EGFR, that can lead to adaptive and acquired resistance to ErbB family inhibitors (Sun et al., (2014) Cell Reports 7:86-93).

2. Pan ErbB family Inhibitors

The pan ErbB family inhibitors used in the methods of the present invention may be reversible or irreversible ErbB family inhibitors. In one embodiment, the pan ErbB family inhibitor inhibits the activity of more than one ErbB family member.

In one embodiment, the pan ErbB family inhibitor is an irreversible inhibitor. Irreversible pan ErbB family inhibitors inhibit the activity of EGFR and HER2 by forming a covalent bond with the sulfhydryl group of cysteine 797 and cysteine 773, respectively, that blocks the binding of ATP to the intracellular catalytic domain. As such, these inhibitors are active against, for example, cell lines harboring EGFR exon 19 deletions/insertions, and L858R and T790M resistant mutations.

Exemplary irreversible pan ErbB family inhibitors for use in the methods include afatinib ((E)-N-(4-((3-chloro-4-fluorophenyl)amino)-7-((tetrahydrofuran-3-yl)oxy)quinazolin-6-yl)-4-(dimethylamino)but-2-enamide); dacomitinib ((2E)-N-{4-[(3-Chloro-4-fluorophenyl)amino]-7-methoxy-6-quinazolinyl}-4-(1-piperidinyl)-2-butenamide); canertinib (N-(4-((3-chloro-4-fluorophenyl)amino)-7-(3-morpholinopropoxy)quinazolin-6-yl)acrylamide); poziotinib (1-(4-((4-((3,4-dichloro-2-fluorophenyl)amino)-7-methoxyquinazolin-6-yl)oxy)piperidin-1-yl)prop-2-en-1-one); AV 412 (N-[4-[(3-Chloro-4-fluorophenyl)amino]-7-[3-methyl-3-(4-methyl-1-piperazinyl)-1-butyn-1-yl]-6-quinazolinyl]-2-propenamide); PF 6274484 (N-[4-[(3-Chloro-4-fluorophenyl)amino]-7-methoxy-6-quinazolinyl]-2-propenamide) and HKI 357 ((2E)-N-[[4-[[(3-Chloro-4-[(3-fluorophenyl)methoxy]phenyl]amino]-3-cyano-7-ethoxy-6-quinolinyl]-4-(dimethylamino)-2-butenamide), and pharmaceutically acceptable salts or pharmaceutical compositions thereof. In one embodiment, the irreversible pan ErbB family inhibitor is afatinib. In one embodiment, the irreversible pan ErbB family inhibitor is dacomitinib.

In one embodiment, the pan ErbB family inhibitor is a reversible inhibitor. Exemplary reversible pan EGFR family inhibitors include erlotinib ([6,7-Bis-(2-methoxy-ethoxy)-quinazolin-4-yl]-(3-ethynyl-phenyl)-amine)), gefitinib (4-(3'-chloro-4'-fluoroanilino)-7-methoxy-6-(3-morpholinopropoxy)quinazoline, sapitinib (2-(4-((4-((3-chloro-2-fluorophenyl)amino)-7-methoxyquinazolin-6-yl)oxy) piperidin-1-yl)-N-methylacetamide); varlitinib ((R)-N4-(3-chloro-4-(thiazol-2-ylmethoxy)phenyl)-N6-(4-methyl-4,5-dihydrooxazol-2-yl)quinazoline-4,6-diamine); TAK-285 (N-(2-(4-((3-chloro-4-(3-(trifluoromethyl)phenoxy)phenyl) amino)-5H-pyrrolo[3,2-d]pyrimidin-5-yl)ethyl)-3-hydroxy-3-methylbutanamide); AEE788 ((S)-6-(4-((4-ethylpiperazin-1-yl)methyl)phenyl)-N-(1-phenylethyl)-7H-pyrrolo[2,3-d]pyrimidin-4-amine); tarloxotinib 3-[N-[$^4$-(3-Bromo-4-chlorophenylamino)pyrido[3,4-d]pyrimidin-6-yl] carbamoyl]-N,N-dimethyl-N-(1-methyl-4-nitro-1H-imidazol-5-ylmethyl)-2(E)-propen-1-aminium bromide); BMS 599626 ((3S)-3-Morpholinylmethyl-[4-[[1-[(3-fluorophenyl)methyl]-1H-indazol-5-yl]amino]-5-methylpyrrolo [2,1-f][1,2,4]triazin-6-yl]-carbamate dihydrochloride); and GW 583340 HCl (N-[3-Chloro-4-[(3-fluorophenyl) methoxy]phenyl]-6-[2-[[[2-(methylsulfonyl)ethyl]amino] methyl]-4-thiazolyl]-4-quinazolinamine dihydrochloride), and pharmaceutically acceptable salts or pharmaceutical compositions thereof. In one embodiment, the reversible pan ErbB family inhibitor is sapitinib. In one embodiment, the reversible pan ErbB family inhibitor is tarloxotinib.

In one embodiment, the pan ErbB family inhibitor is a combination of an EGFR inhibitor and a HER2 inhibitor, wherein the EGFR inhibitor and the HER2 inhibitor are a combination of two of: AG 1478 HCl (N-(3-Chlorophenyl)-6,7-dimethoxy-4-quinazolinanine hydrochloride); AG 494 (E)-2-Cyano-3-(3,4-dihydroxyphenyl)-N-phenyl-2-propenamide; AG 555 (E)-2-Cyano-3-(3,4-dihydroxyphenyl)-N-(3-phenylpropyl)-2-propenamide; AG 556 (E)-2-Cyano-3-(3,4-dihydroxyphenyl)-N-(4-phenylbutyl)-2-propenamide; AG 825 (E)-3-[3-[2-Benzothiazolythio)methyl]-4-hydroxy-5-methoxyphenyl]-2-cyano-2-propenamide; CP 724714 (2-Methoxy-N-[(2E)-3-[4-[[3-methyl-4-[(6-methyl-3-pyridinyl)oxy]phenyl]amino]-6-quinazolinyl]-2-propen-1-yl]acetamide; BIBU 1361 diHCl (N-(3-Chloro-4-fluorophenyl)-6-[4-[(diethylamino)methyl]-1-piperidinyl]-pyrimido [5,4-d]pyrimidin-4-amine dihydrochloride); BIBU 1382 ($N^8$-(3-Chloro-4-fluorophenyl)-$N^2$-(1-methyl-4-piperidinyl)-pyrimido[5,4-d]pyrimidine-2,8-diamine dihydrochloride); JNJ 28871063 HCl (5E-4-Amino-6-(4-benzyloxy-3-chlorophenylamino)pyrimidine-5-carboxaldehyde N-(2-morpholin-4-ylethyl) oxime hydrochloride); PD 153035 (4-[(3-Bromophenyl)amino]-6,7-dimethoxyquinazoline hydrochloride); PD 158780 ($N^4$-(3-Bromophenyl)-$N^6$-methyl-pyrido[3,4-d]pyrimidine-4,6-diamine), and pharmaceutically acceptable salts or a pharmaceutical compositions thereof.

Methods for manufacturing reversible and irreversible pan ErbB family inhibitors that target wild type and mutant ErbB family members are well known to those skilled in the art and pan ErbB family inhibitors may be obtained from a wide-variety of commercial suppliers, in forms suitable for both research or human use. In addition, suitable reversible and irreversible pan ErbB family inhibitors for use in the compositions and methods disclosed herein, and methods for preparing such inhibitors are disclosed in US Patent Application Publication Nos: US20180050993; US20180016268; US20180008607; US20170362204; US 20170362203; US20170355683; US20170342055; US20170267671; US20170183330; US20170174697; 20170008856; US20160375148; US20160332994; US20160257682; US 20160244469; US 20160137610; US20160102076; US20160016948; US20150284340; US20150274678; US20150250778; US 20150246047; US20150126508; US20150025055; US 20140221403; US 20140178412; US20140161722; US20140155606; US20140038981; US20140038940; US20140005391; US 20130296348; US20130209461; US20130137709; US 20120316135L US 20120094999; US 20110295004; US 20110033453; US 20100196365; US20100143295; US 20100120678; US 20100034689; US 20090209758; US 20090111772; US20090029968; US20080194578; US 20080139590; US 2000125448; US 20080051395; US 20070232607; US 20060235046 and US20040023957.

In one embodiment, the pan ErbB family inhibitor is an anti-EGFR antibody, an anti-HER2 antibody or a combination of an anti-EGFR antibody and anti-HER2 antibody, or pharmaceutical compositions thereof. Antibodies, including monoclonal antibodies, antibody drug conjugates and bispecific antibodies, targeting EGFR and/or HER-2 are well known and a number of antibodies are commercially available for research and human clinical use.

Exemplary anti-EGFR monoclonal antibodies approved for human clinical use include, but are not limited to, necitumumab (Eli Lilly), panitumumab (Amgen) and cetuximab (ImClone). Other anti-EGFR antibodies suitable for use in the methods include EP384, H11, 11.6, 225 and 199.12 (Thermo Fisher), GT133 (GeneTex) and those disclosed in United States Patent Application Publication Nos: US 20080274114; US 20100166755; US 20100117110; US 20120034211; US 20120308576; US 20130273033; US 20130344093; US 20140286969; US 20150337042; US 20170218073; US 20170267765, US 20180036405, US 20180066066, US 20180094062, US 20180155433, US 20180306049, US 20180362443, US 20190040143, US 20190151328, US 20190194347, US 20190194350, US 20190209704, US 20190216924, and US 20190263930.

In one embodiment, the anti-EGFR monoclonal antibody is cetuximab.

Exemplary anti-HER-2 monoclonal antibodies approved for human clinical use include, but are not limited to, pertuzumab (Roche), trastuzumab (Roche) and trastuzumab emtansine (Roche). Other anti-Her2 antibodies, antibody drug conjugates and bispecific antibodies suitable for use in the methods include those disclosed in United States Patent Application Publication Nos: US 20030228663; US 20060018899; US 20090187007; US 20090285837; US 20110159014; US 20110177095; US 20110313137; US 20120309942; US 20150166664; US 20150352225; US 20160051695; US 20160096893, US 20180022816, US 20180022820, US 20180057608, US 20180118837, US 20180258173, US 20190177428, and US 20190248918.

2. KRas G12C Inhibitors

In one embodiment, the KRas G12C inhibitors used in the methods are compounds of Formula (I):

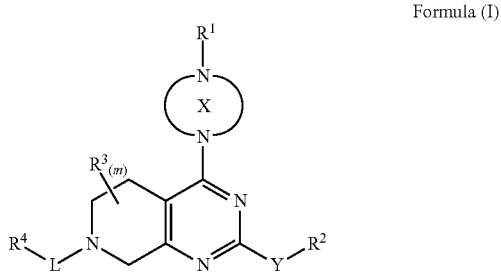

Formula (I)

or a pharmaceutically acceptable salt thereof, wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is —C(O)C($R^A$)═══C($R^B$)$_p$ or —SO$_2$C($R^A$)═══C($R^B$)$_p$;

$R^2$ is hydrogen, alkyl, hydroxyalkyl, dihydroxyalkyl, alkylaminylalkyl, dialkylaminylalkyl, —Z—$NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, oxo, or haloalkyl;

L is a bond, —C(O)—, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, —C(O)O$R^5$, —C(O)N($R^5$)$_2$, —N($R^5$)$_2$, wherein the C1-C3 alkyl may be optionally substituted with cyano, halogen, —$OR^5$, —N($R^5$)$_2$, or heteroaryl;

each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^{11}$ is haloalkyl;

$R^A$ is absent, hydrogen, deuterium, cyano, halogen, C1-C3 alkyl, haloalkyl, heteroalkyl, —C(O)N($R^5$)$_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —$ZNR^5R^{11}$, —C(O)N($R^5$)$_2$, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$;

m is zero or an integer between 1 and 2;

p is one or two; and wherein, when ═══ is a triple bond then $R^A$ is absent, $R^B$ is present and p equals one;

or when ═══ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

In one embodiment, KRas G12C inhibitors used in the methods herein include compounds having the Formula I-A:

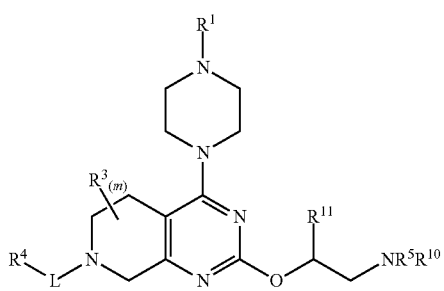

or a pharmaceutically acceptable salt thereof, wherein $R^1$, $R^3$, $R^4$, $R^5$, $R^{10}$, L and m are as defined for Formula I, $R^{11}$ is hydrogen, methyl or hydroxyalkyl, and the piperidinyl ring is optionally substituted with $R^8$ wherein $R^8$ is as defined for Formula I.

In one embodiment, KRas G12C inhibitors used in the methods herein include compounds having the Formula I-B:

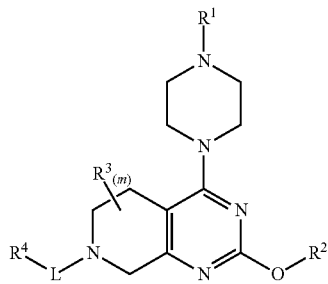

Formula I-B or a pharmaceutically acceptable salt thereof, wherein $R^1$, $R^3$, $R^4$, $R^9$, $R^{11}$, L and m are as defined for Formula I.

Nonlimiting examples of KRas G12C inhibitor compounds of Formula (I), Formula I-A and Formula I-B useful in the methods disclosed herein are selected from the group consisting of Example Nos 1-678 including the following structures:

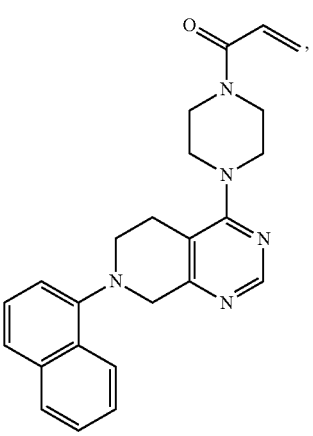

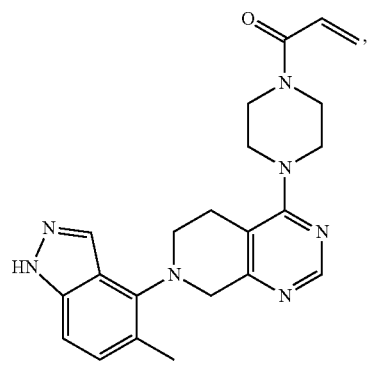

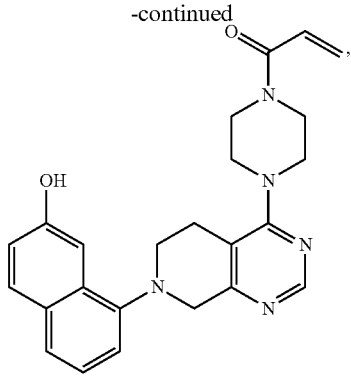

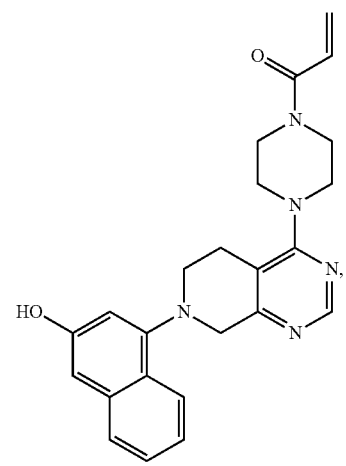

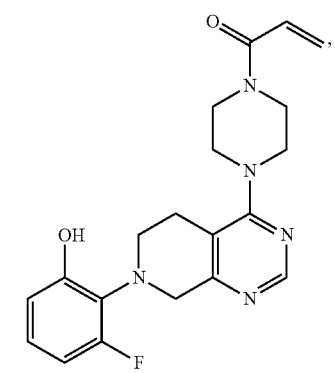

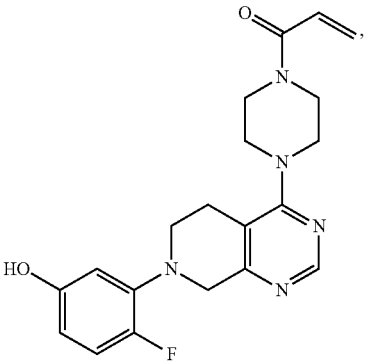

19
-continued
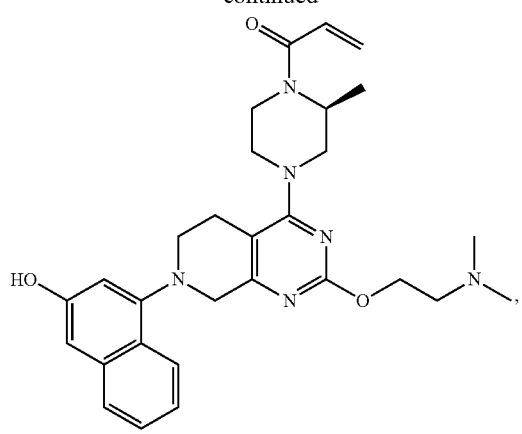
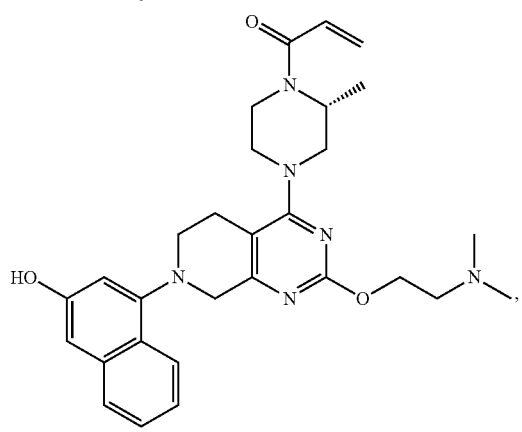
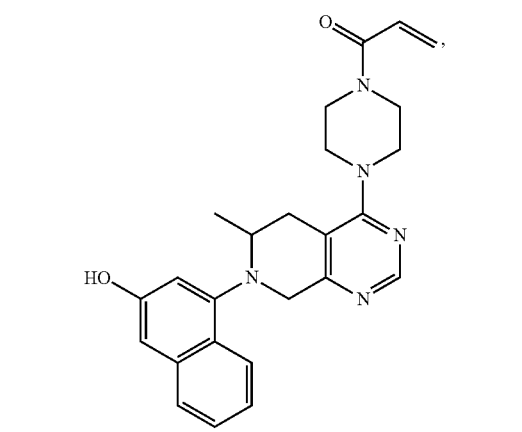
20
-continued
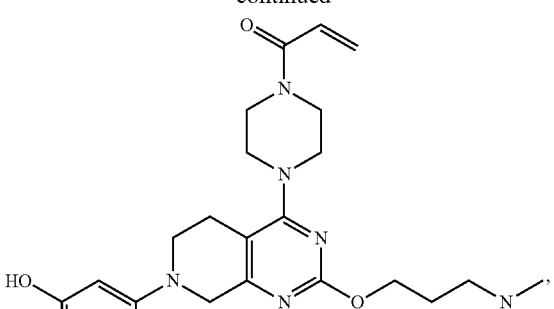
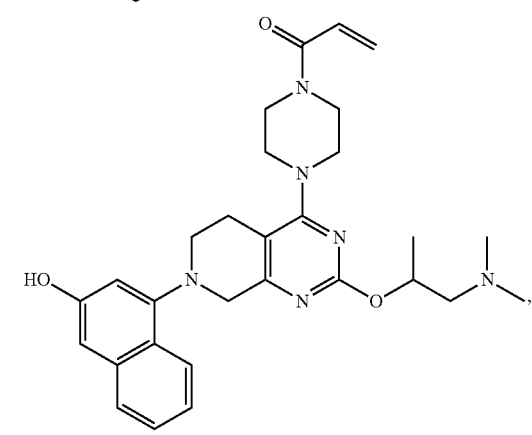
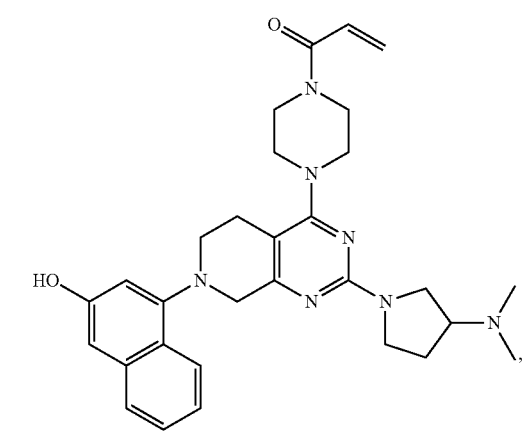
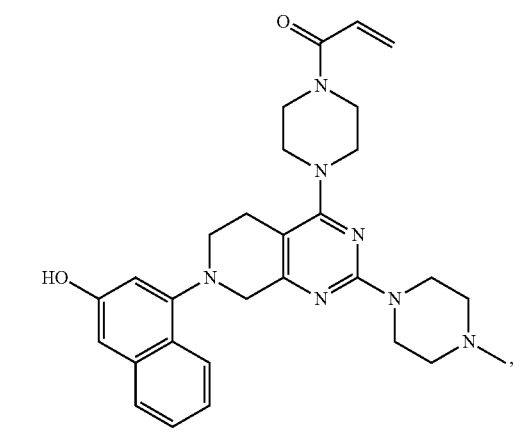

21
-continued
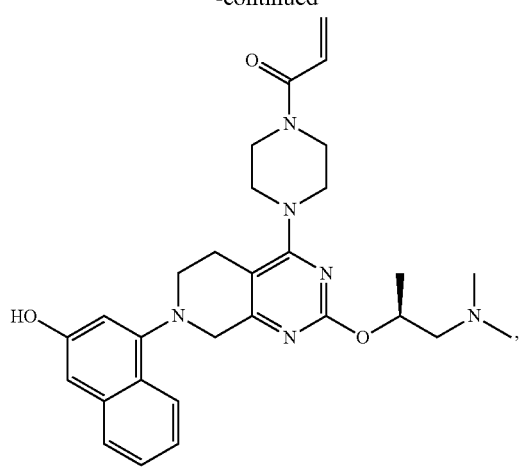
22
-continued
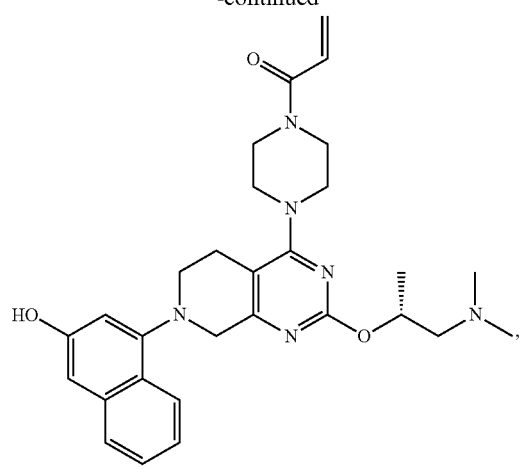
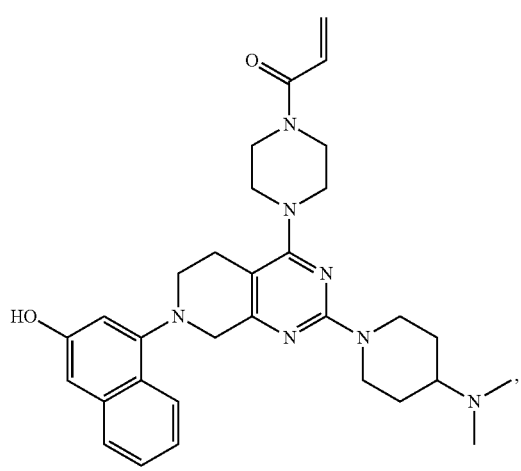
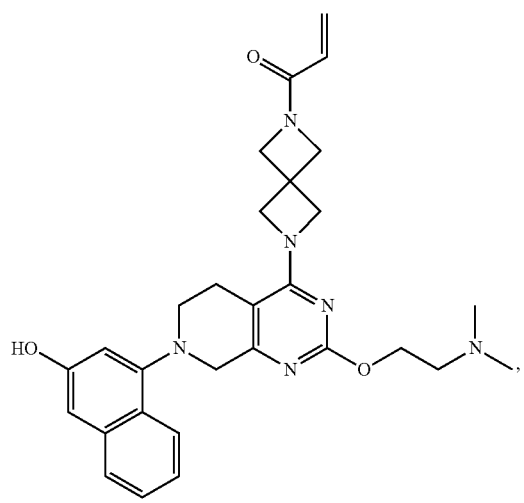
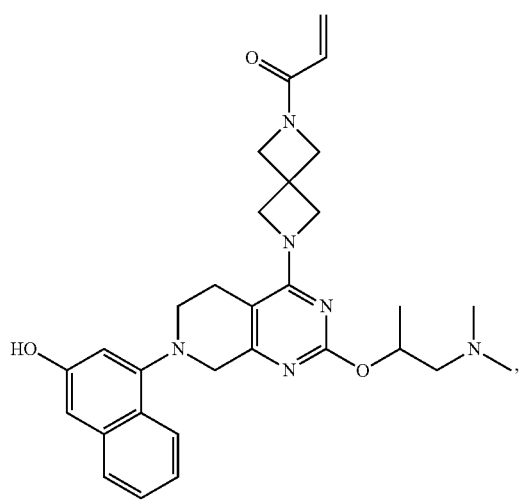
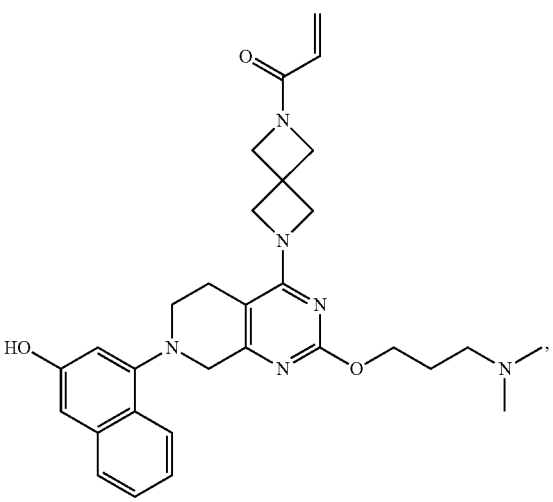

23
-continued
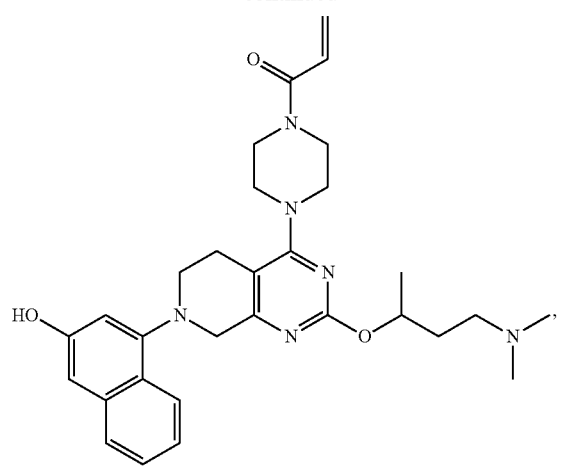
24
-continued
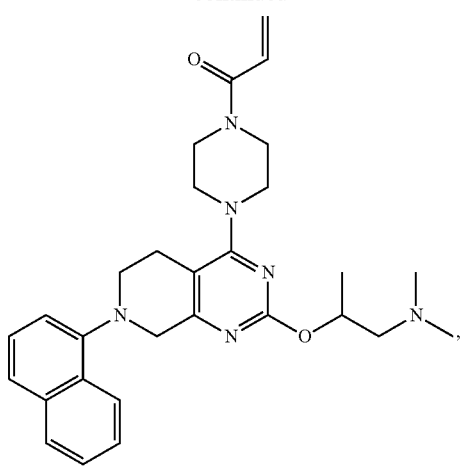
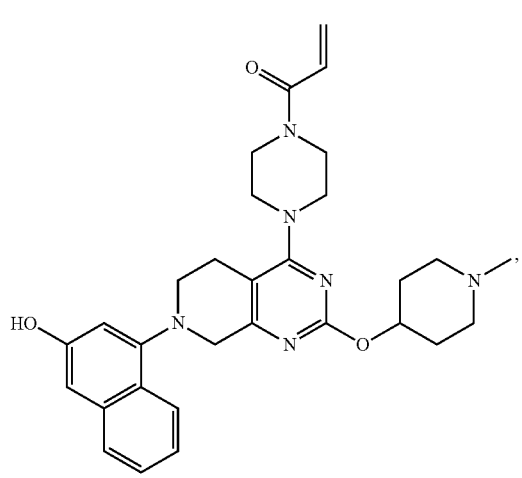
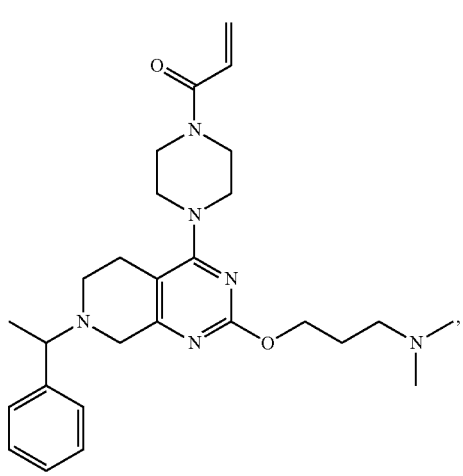
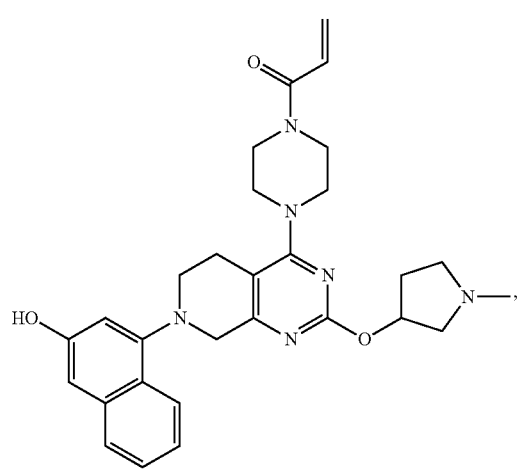
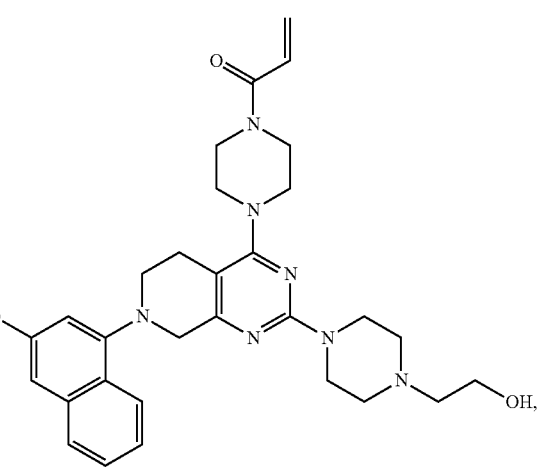

25
-continued
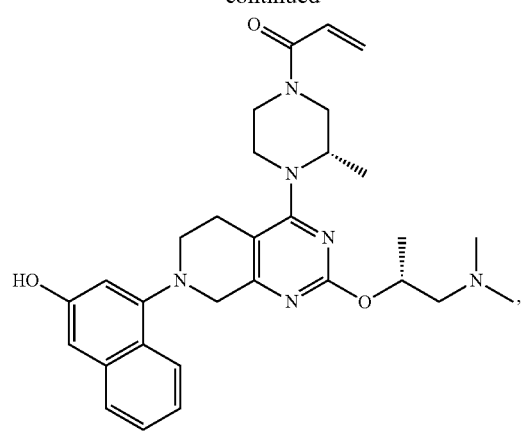
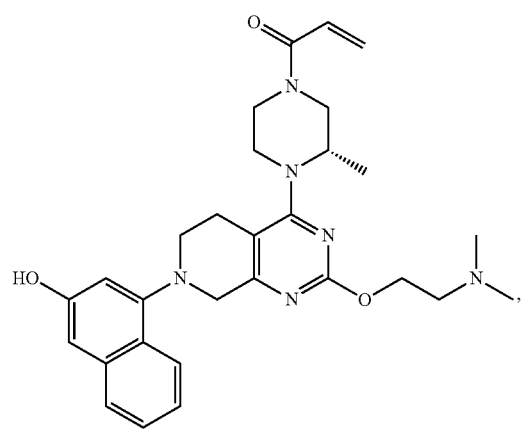
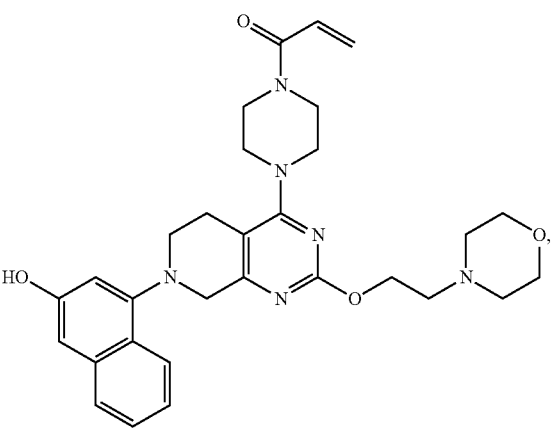
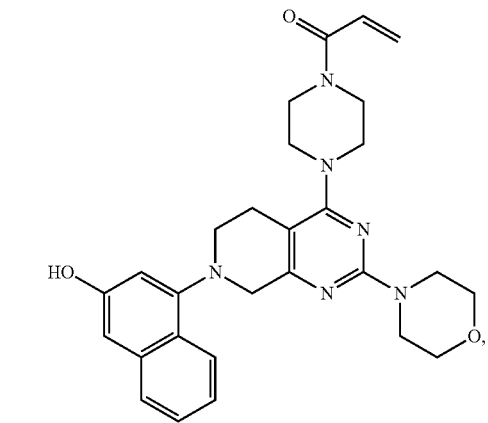
26
-continued
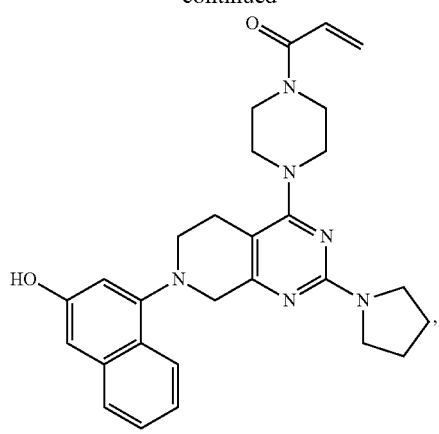
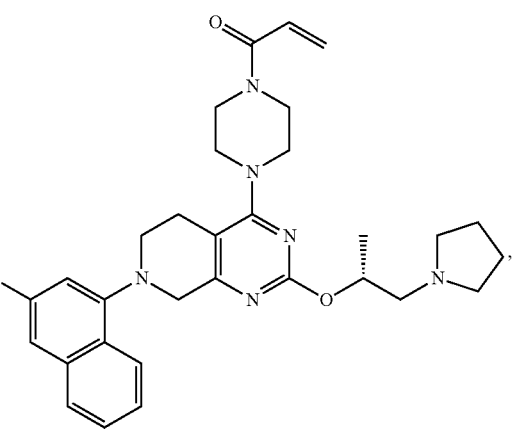
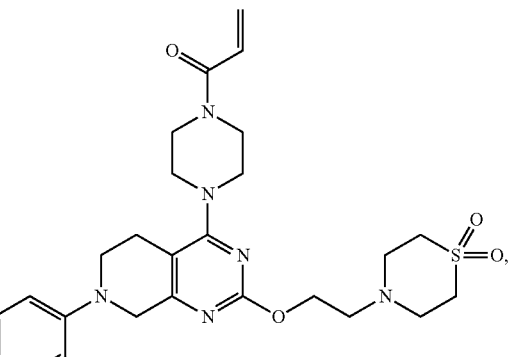
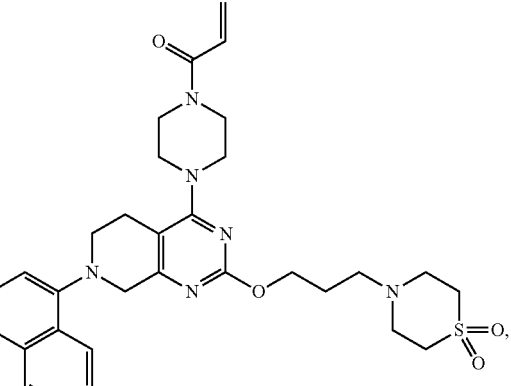

-continued
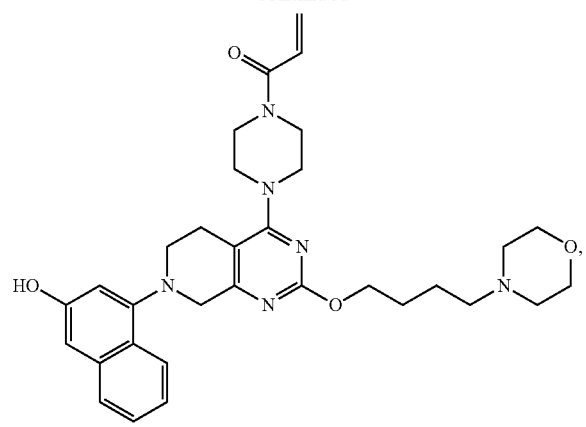
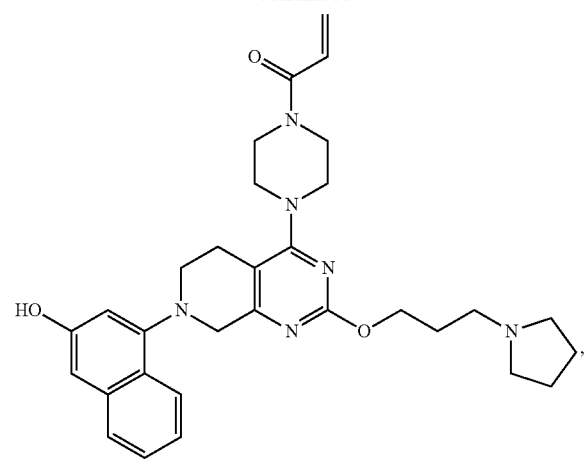
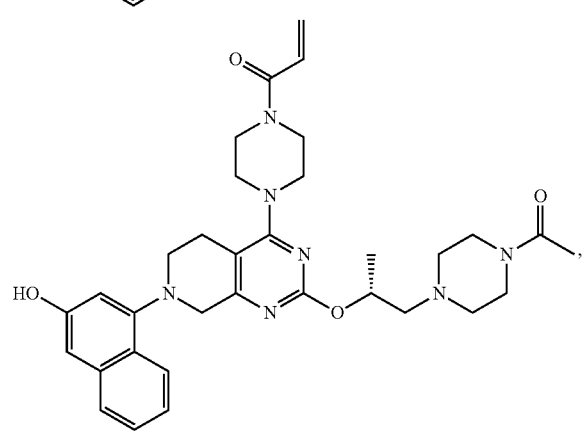
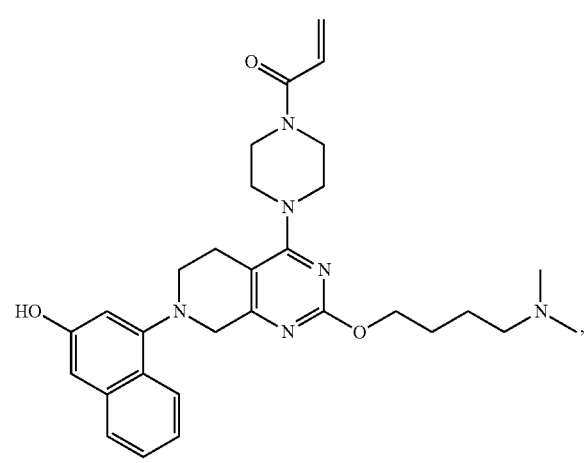
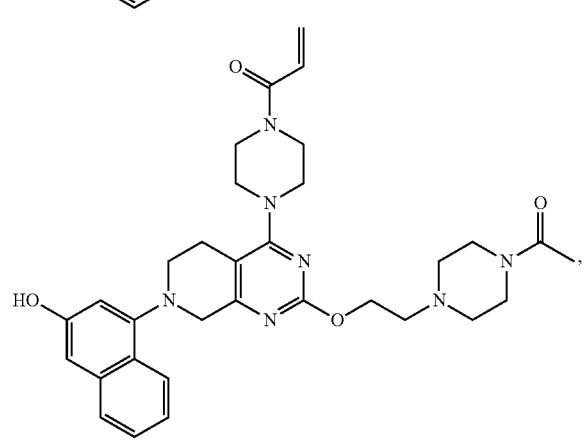
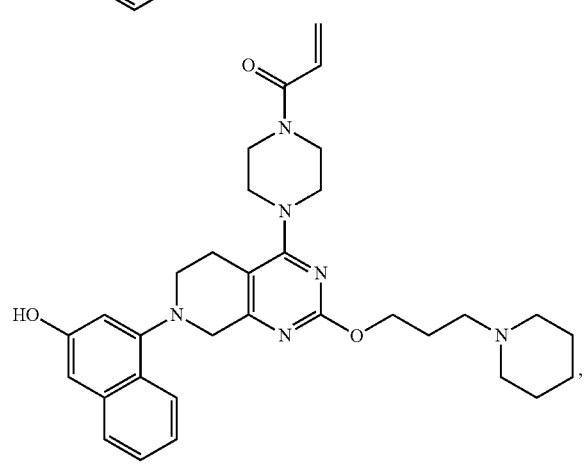
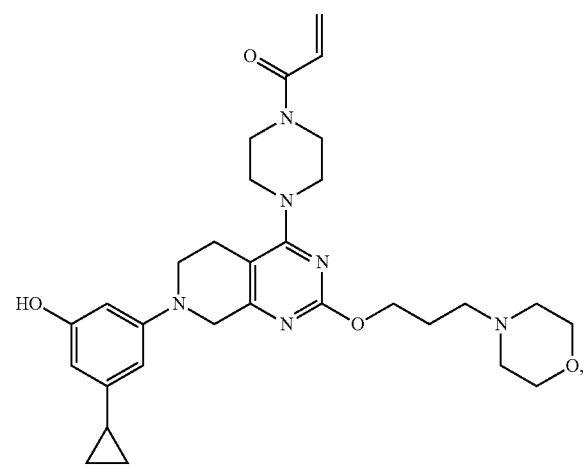

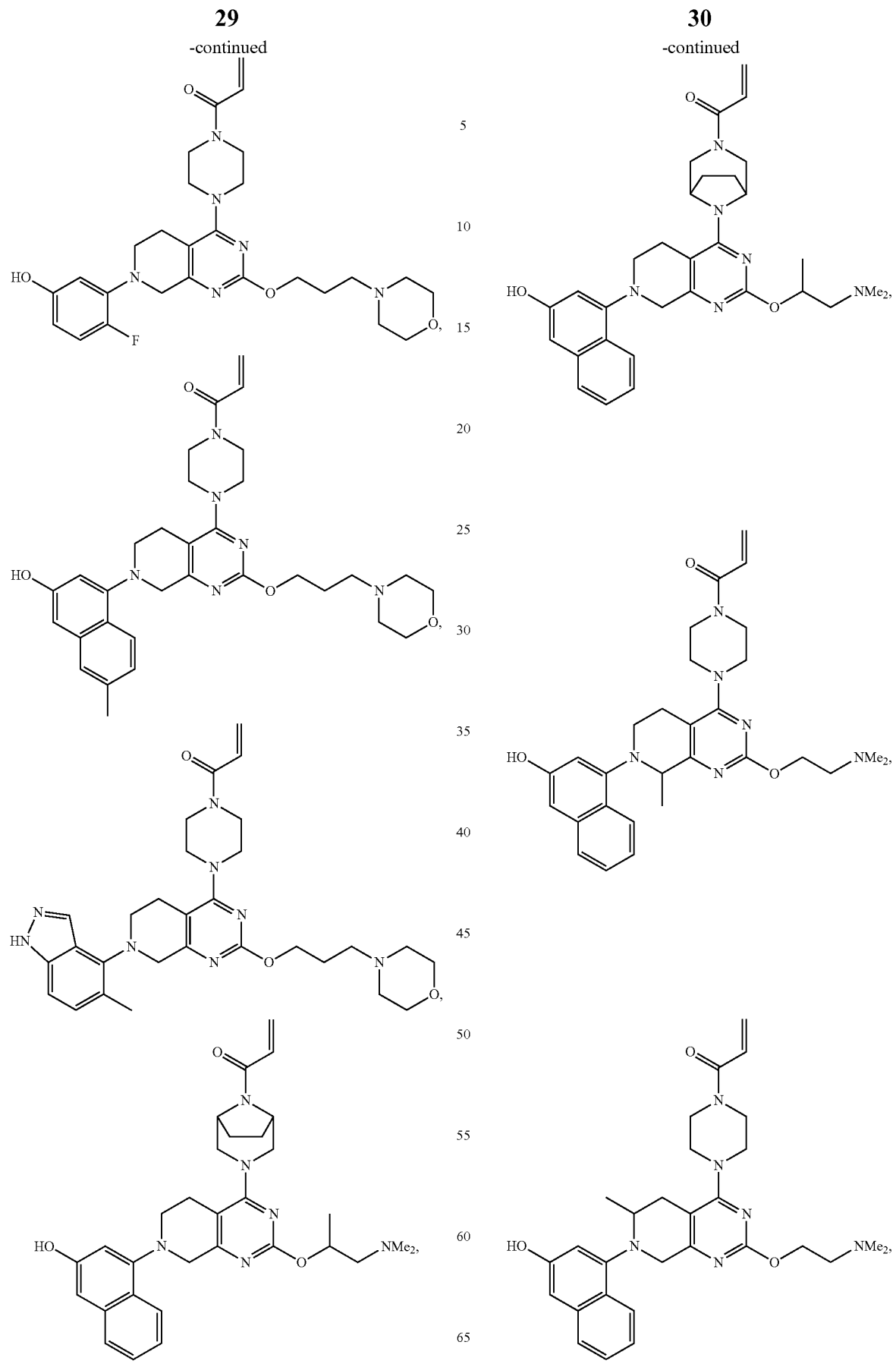

31
-continued
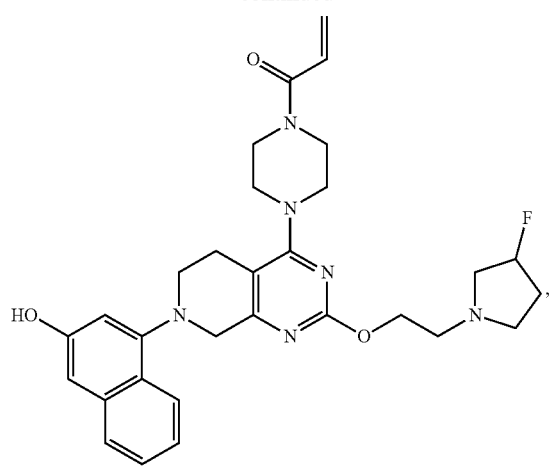
32
-continued
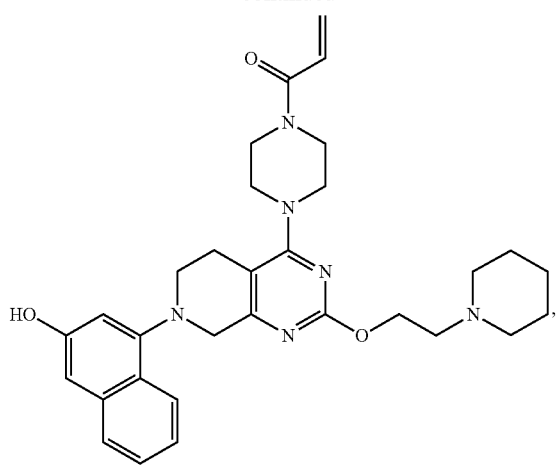
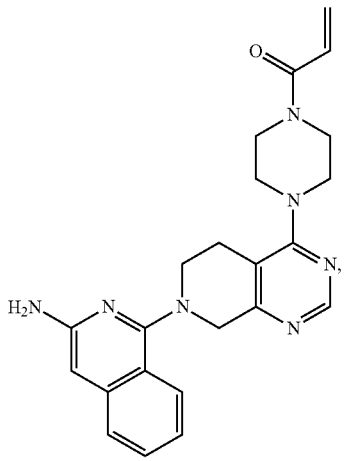

33
-continued
34
-continued
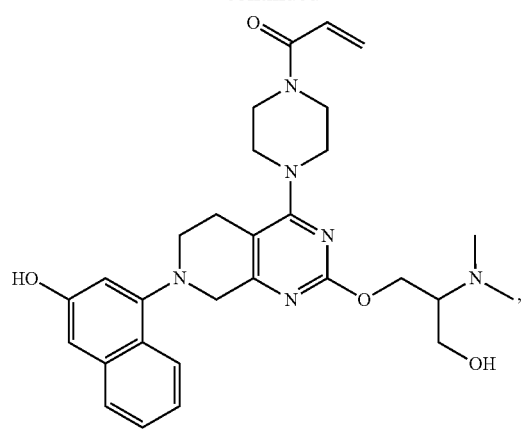
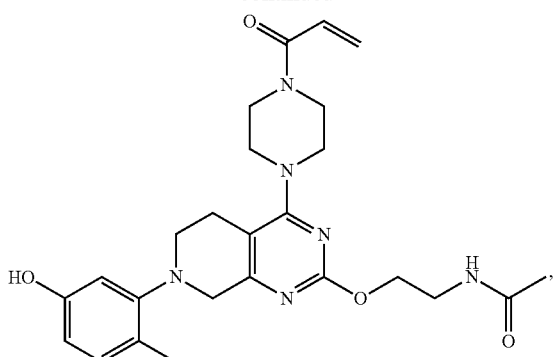

35
-continued
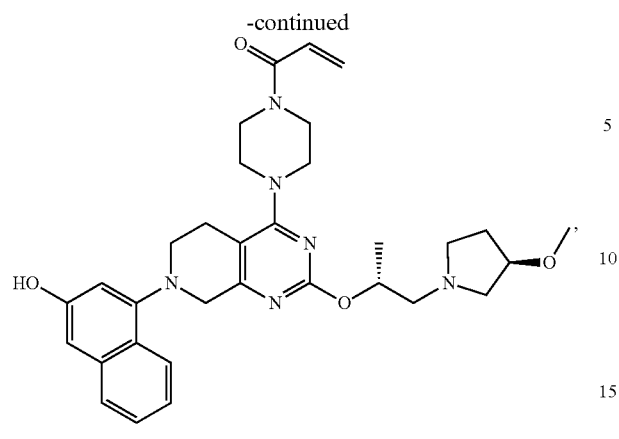
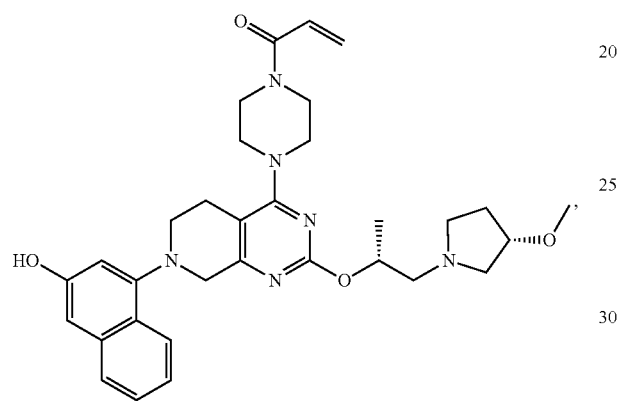
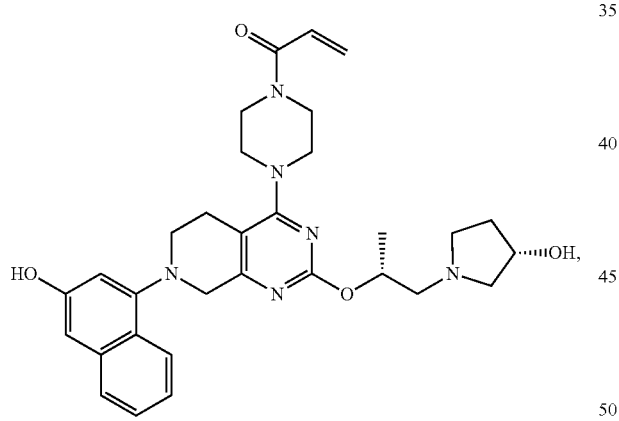
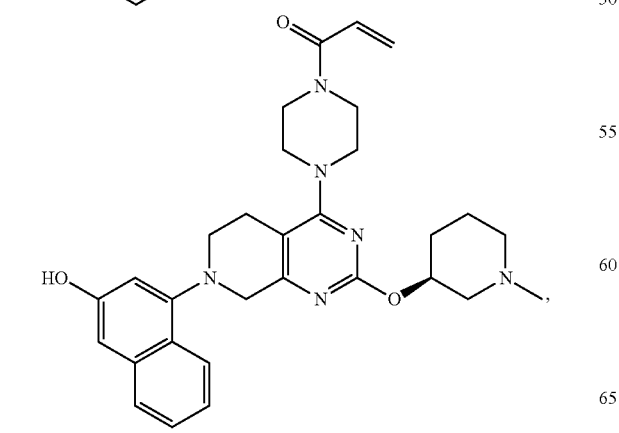
36
-continued
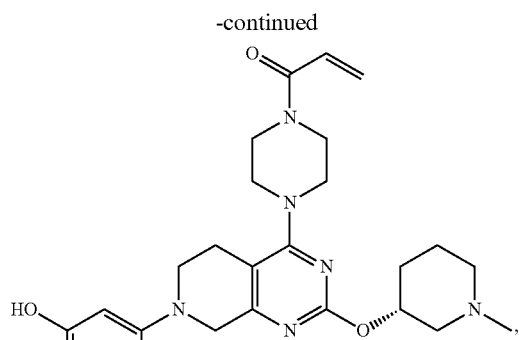
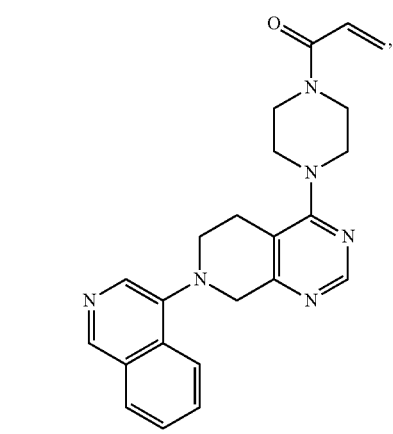
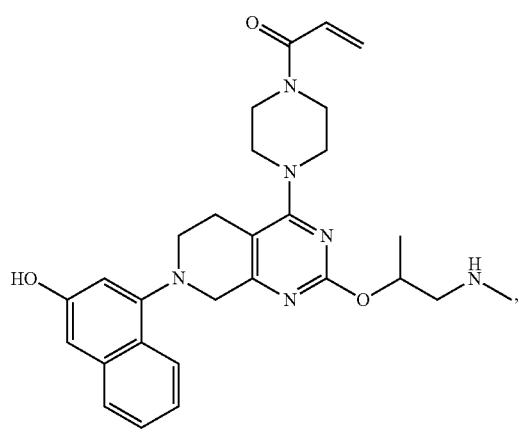

37
-continued
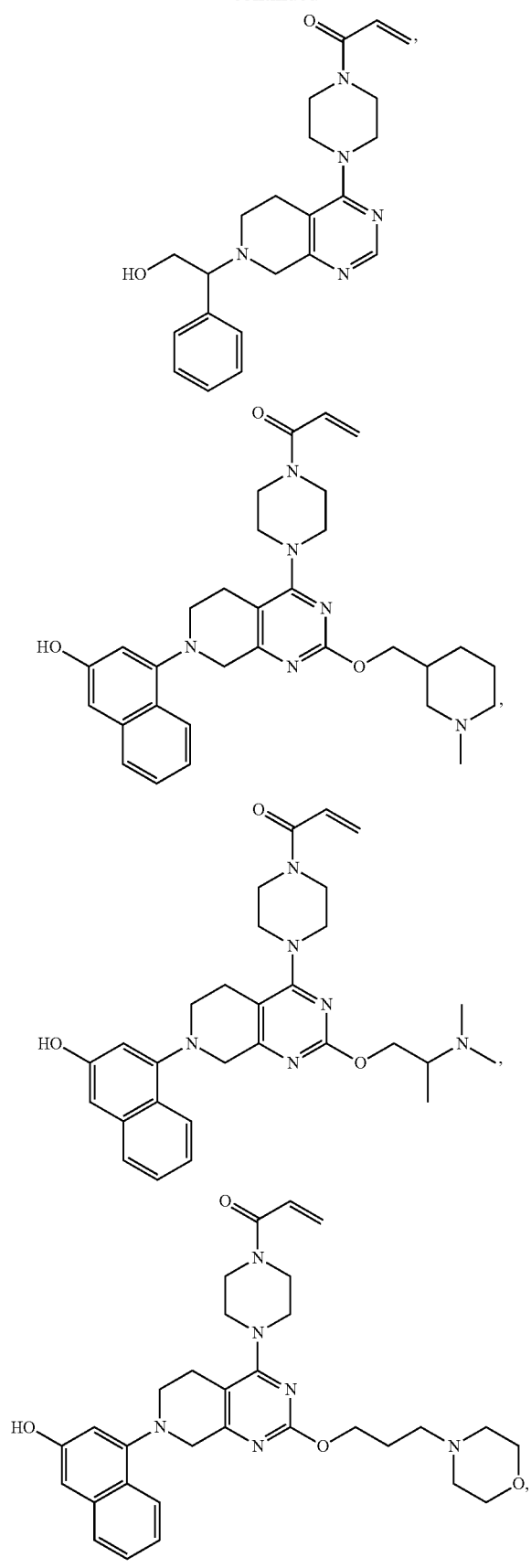
38
-continued
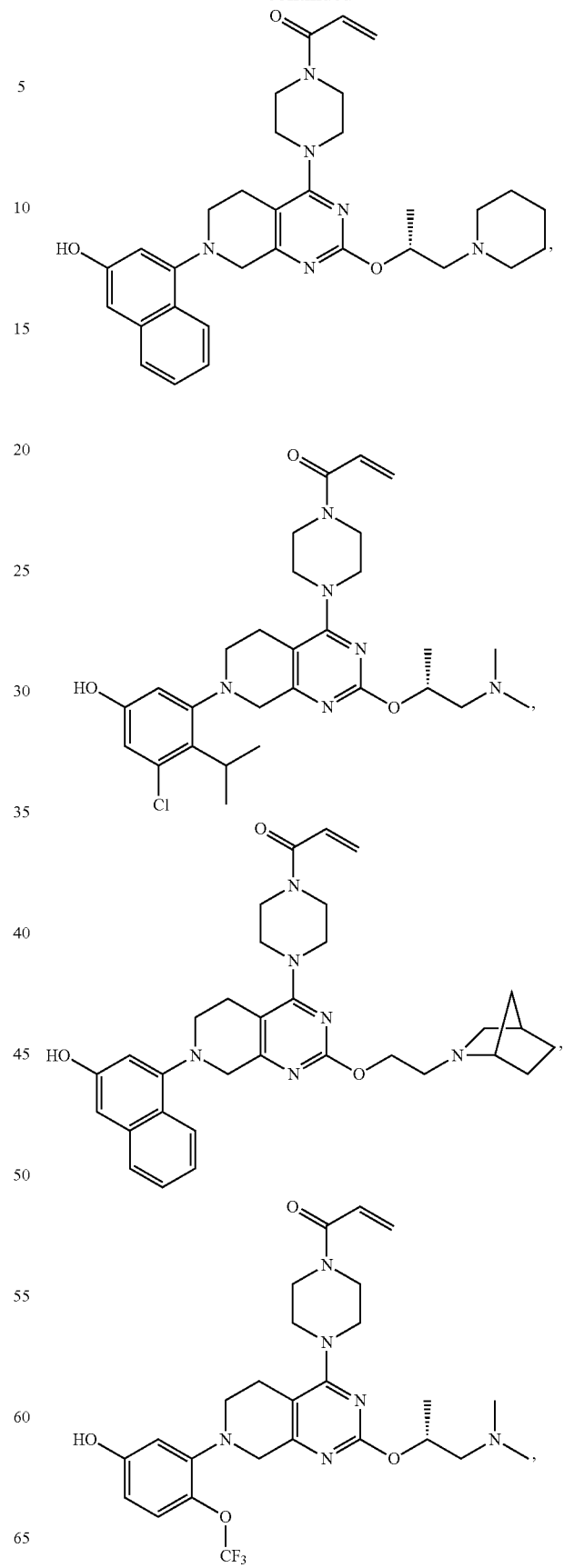

39
-continued
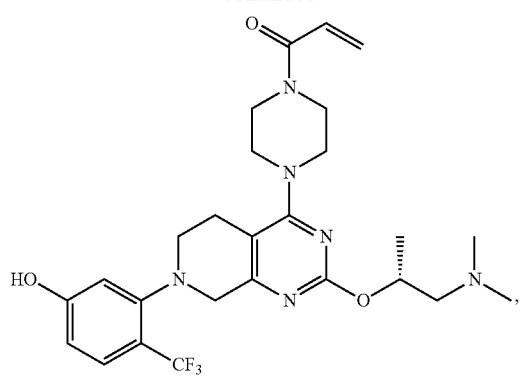
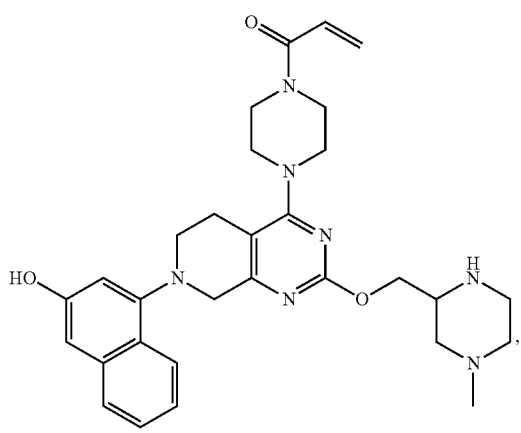
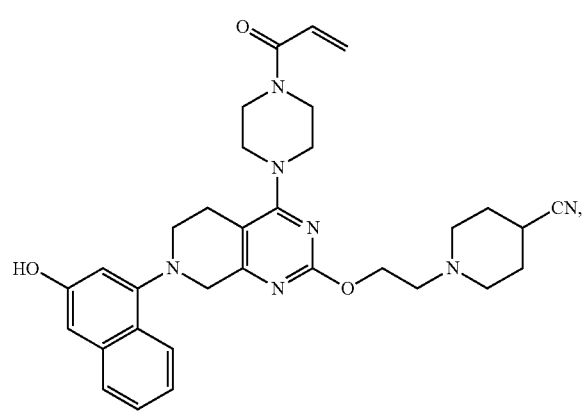
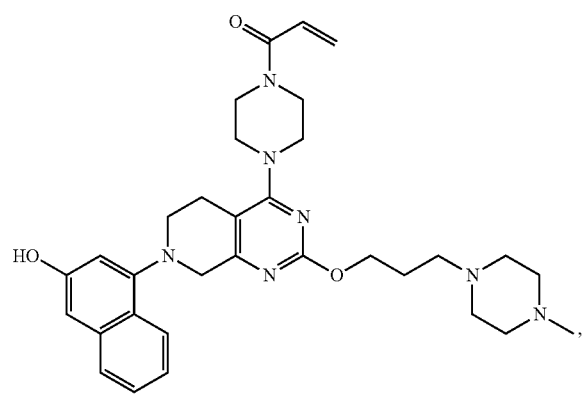
40
-continued
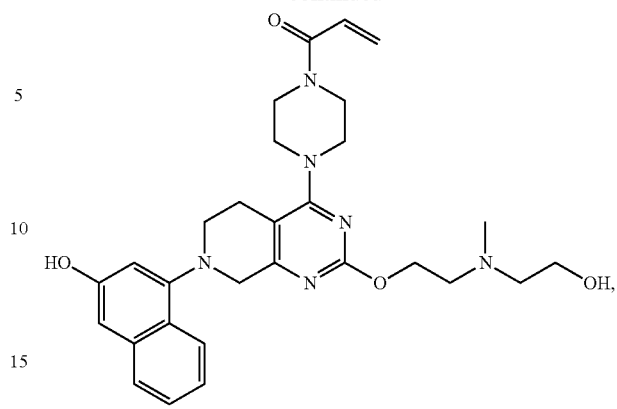
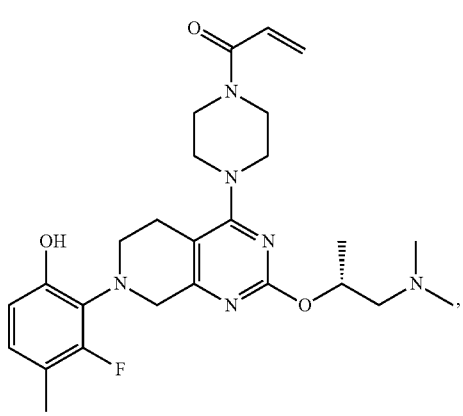
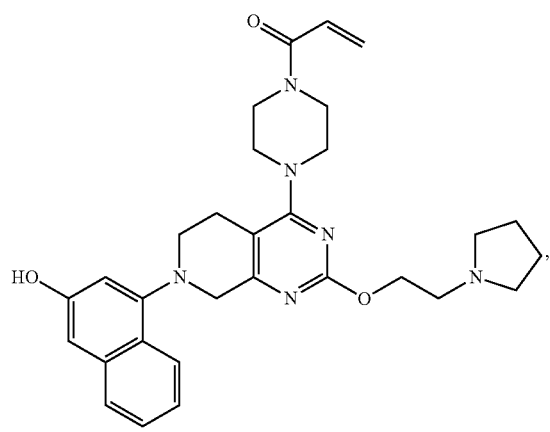
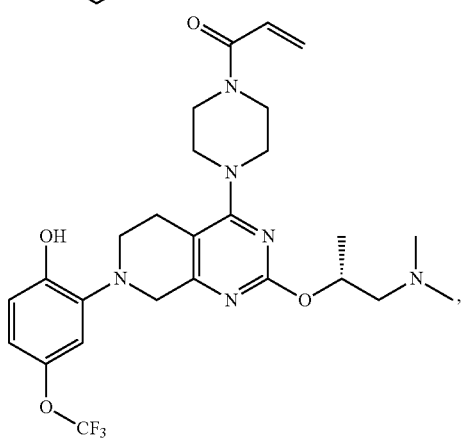

41
-continued
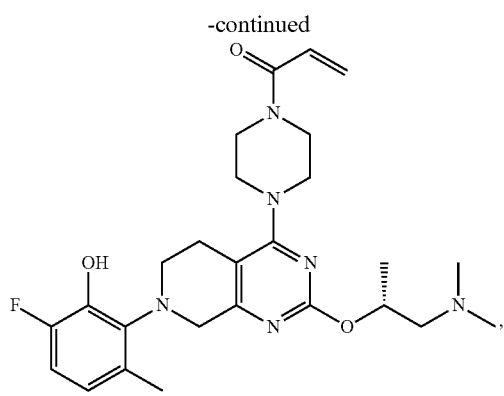
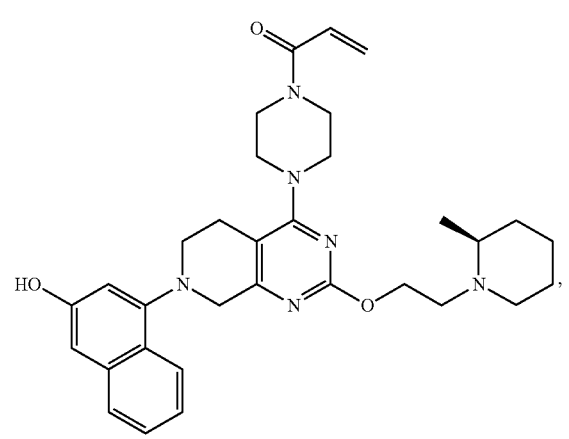
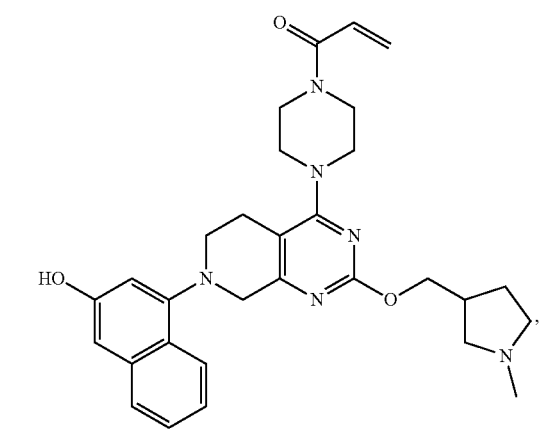
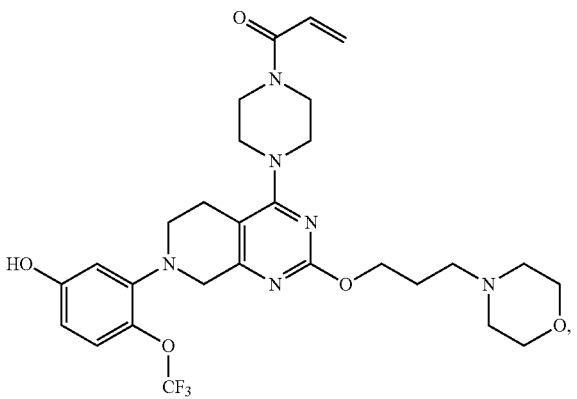
42
-continued
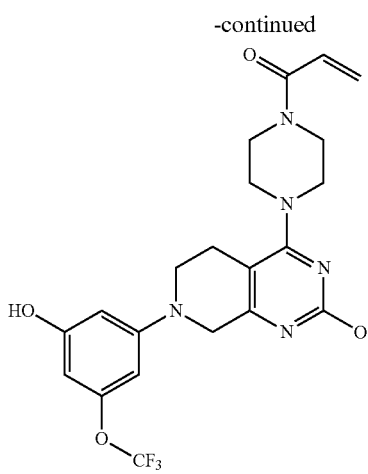
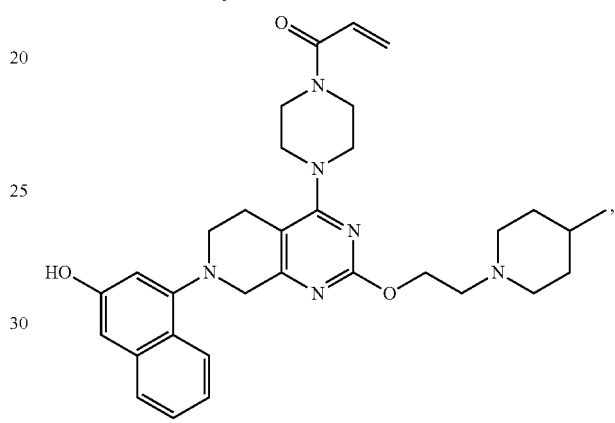
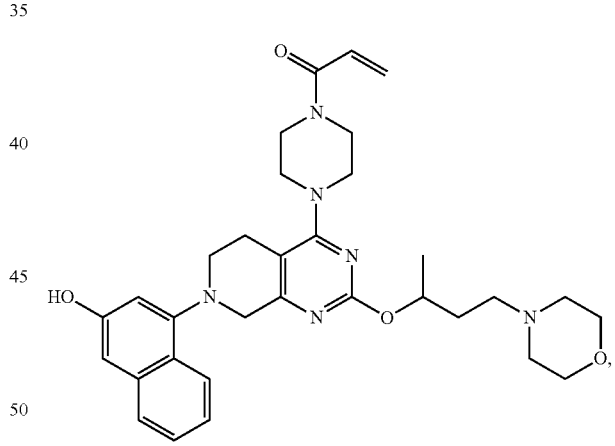
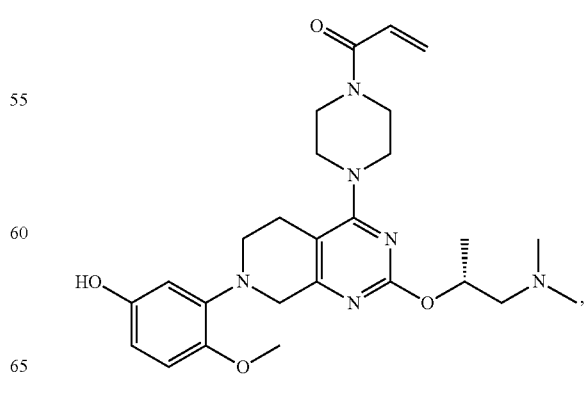

-continued
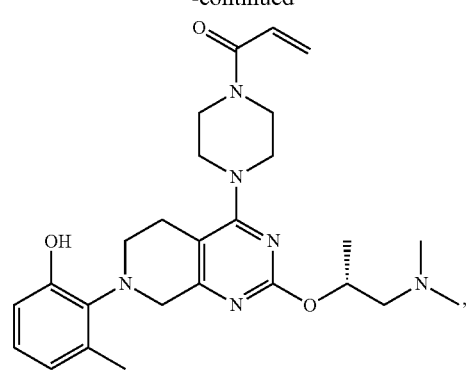
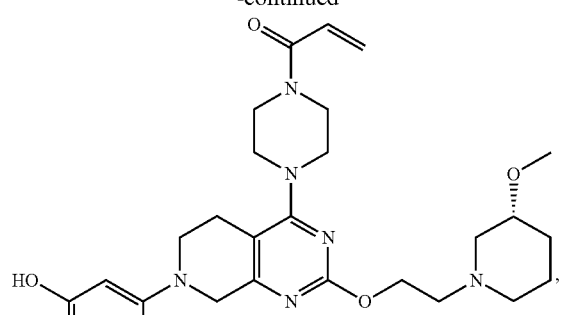
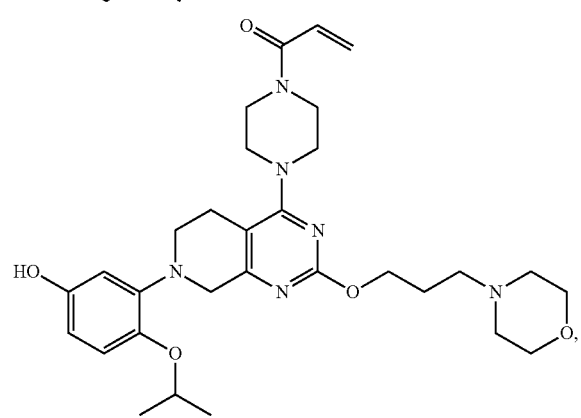
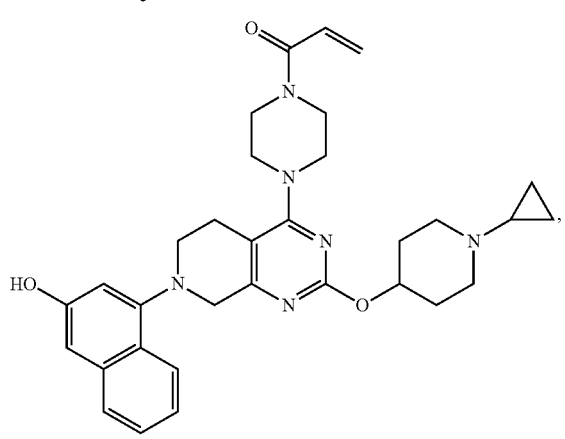
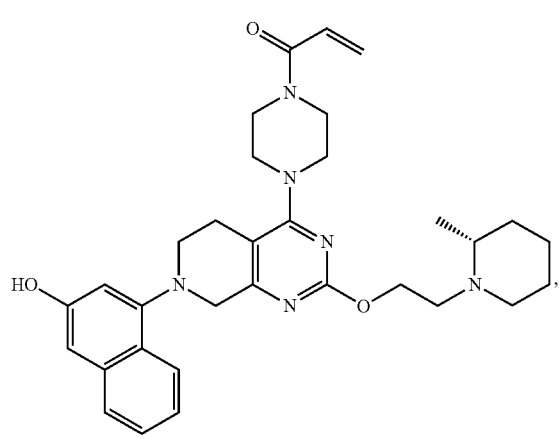
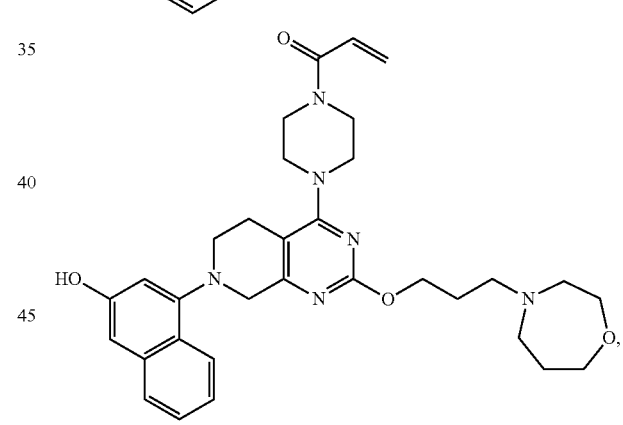
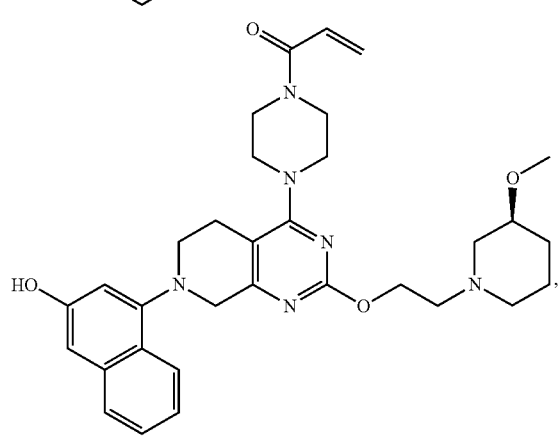
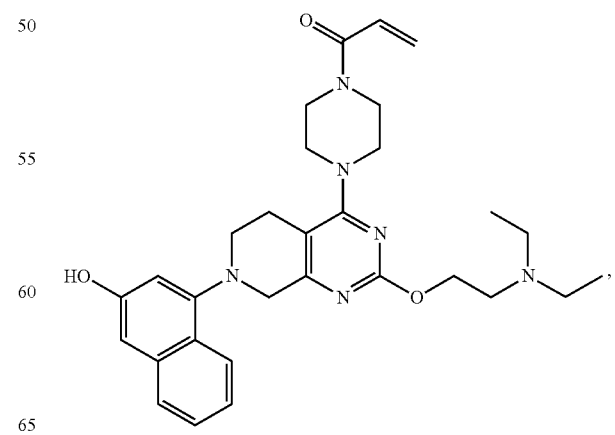

45
-continued
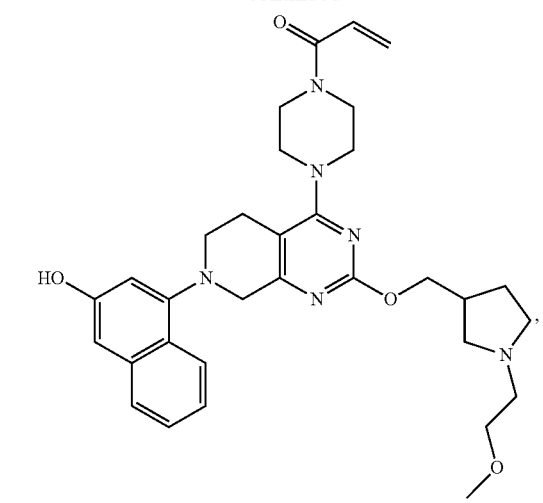
46
-continued
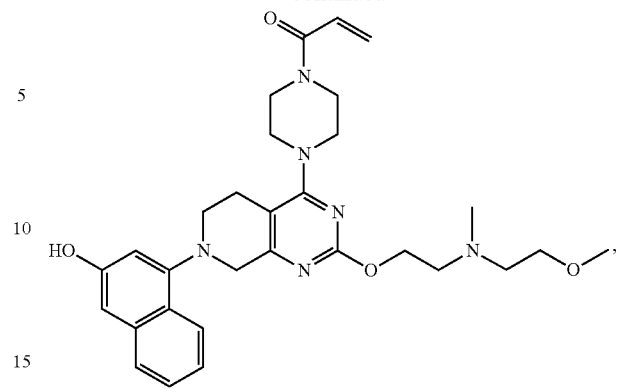
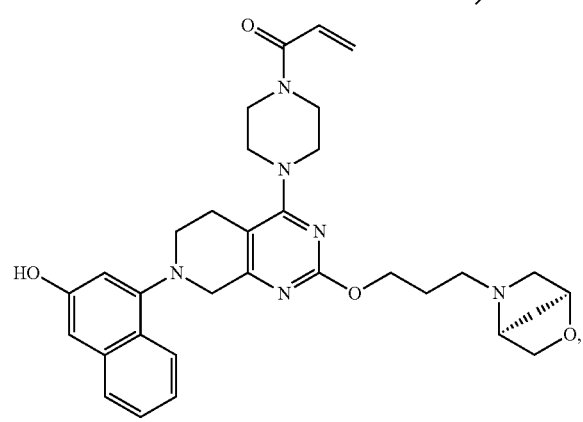
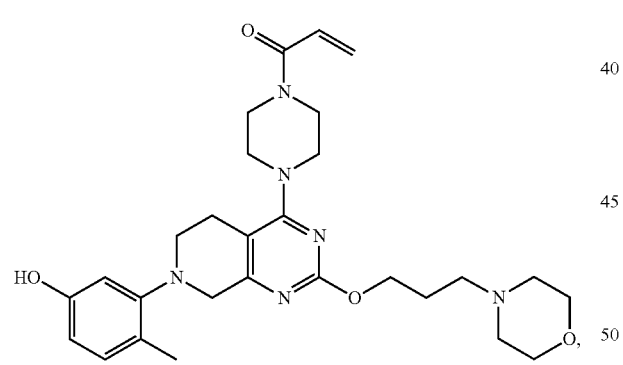
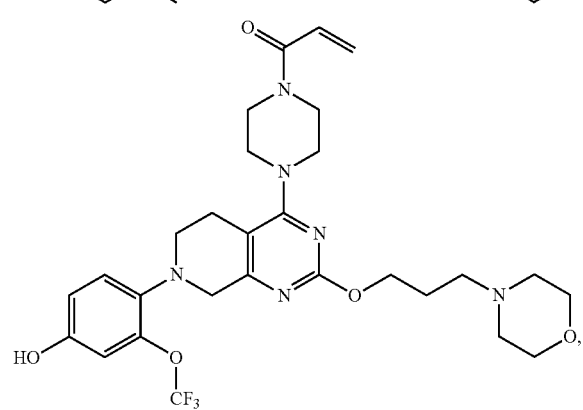
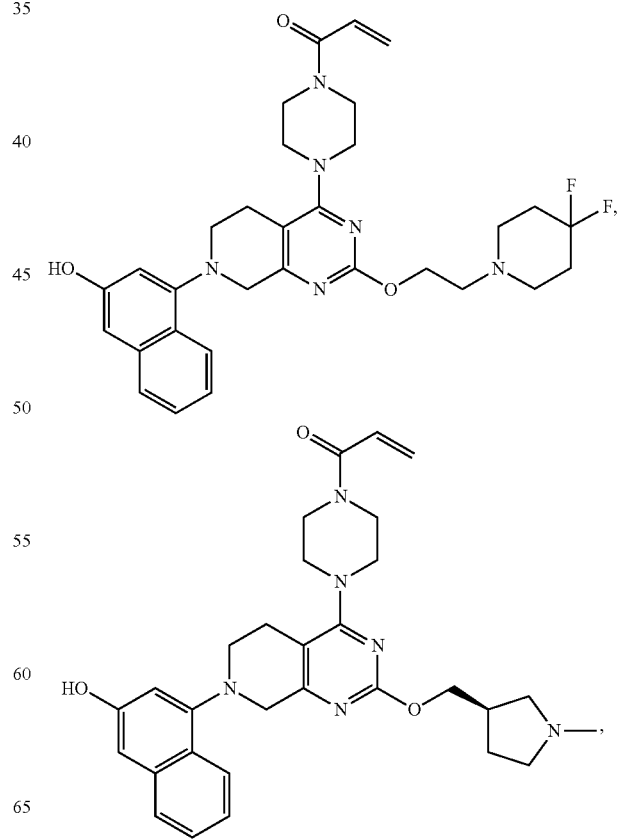

47
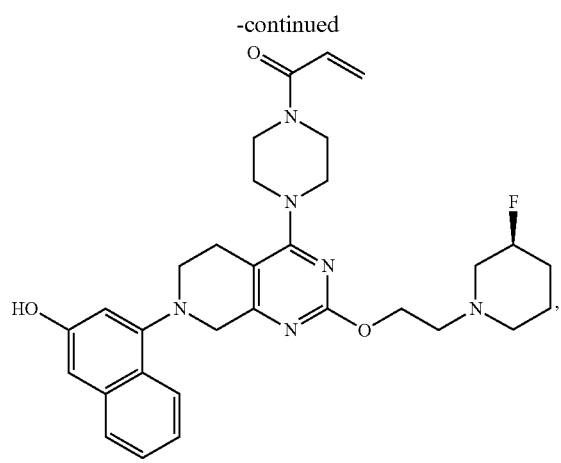
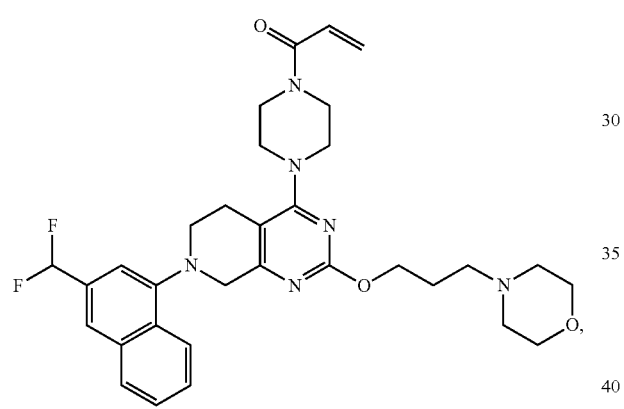
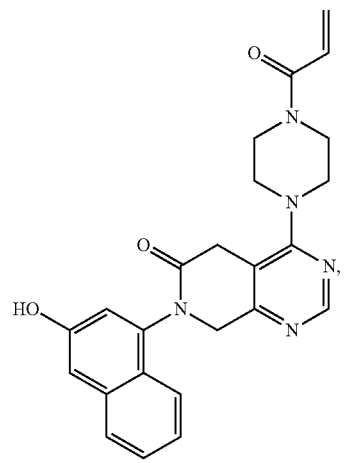
48
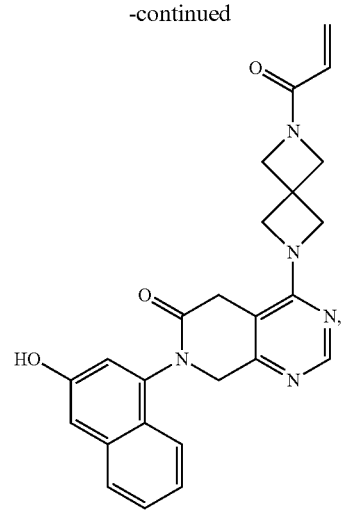
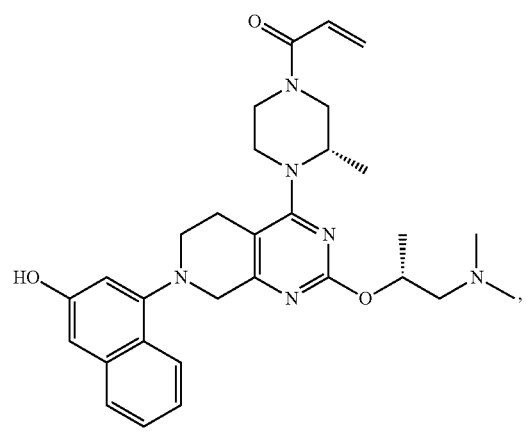
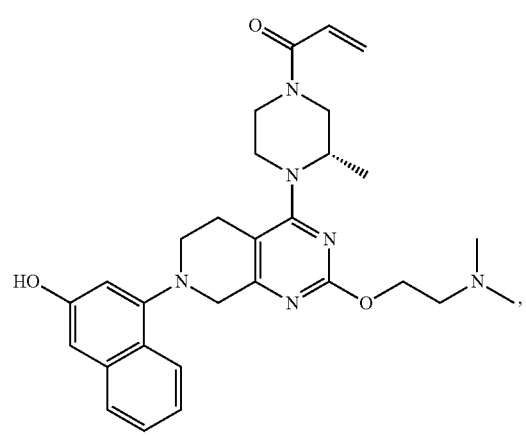

-continued

51
-continued
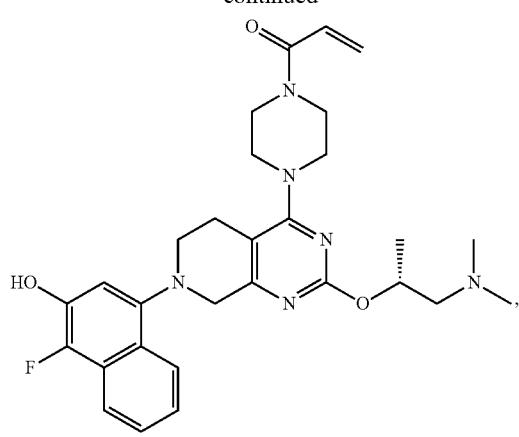
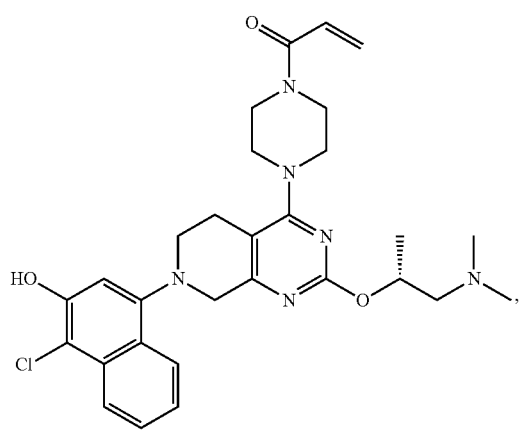
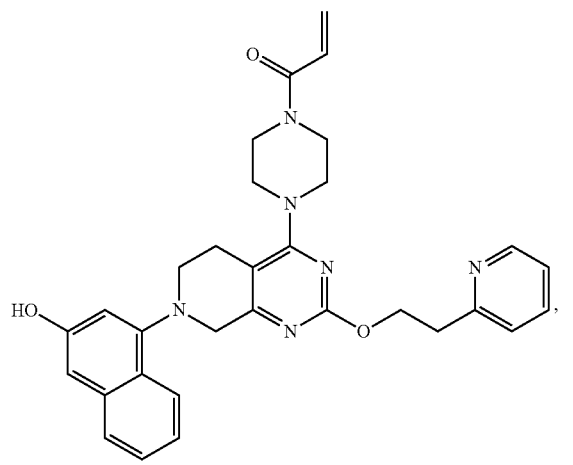
52
-continued
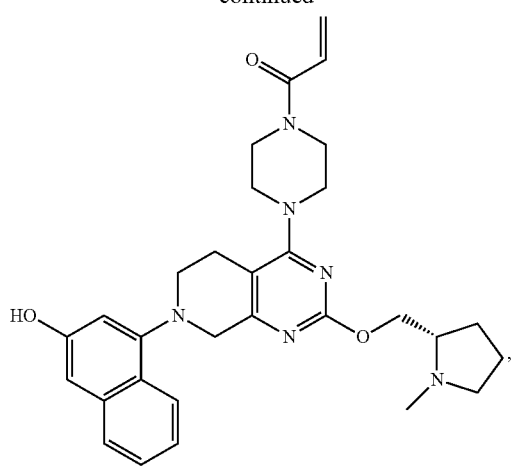
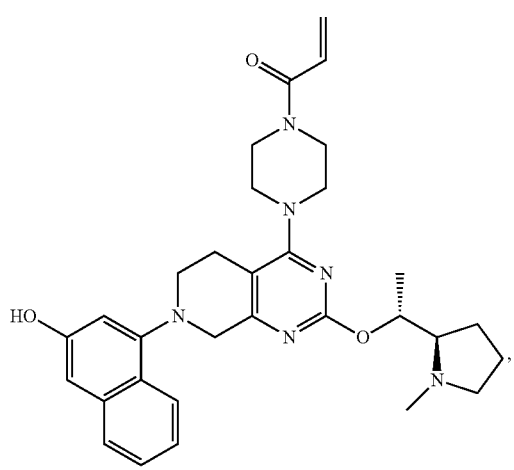

53
-continued
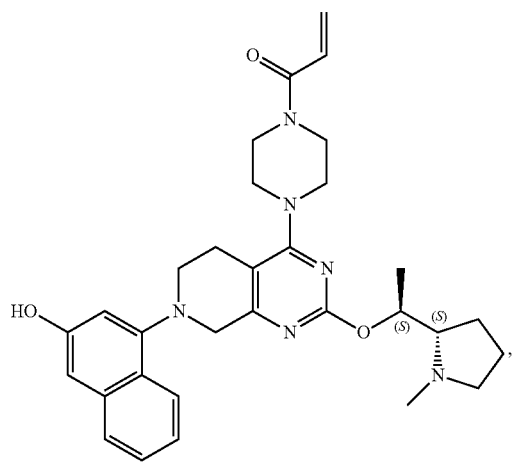
54
-continued
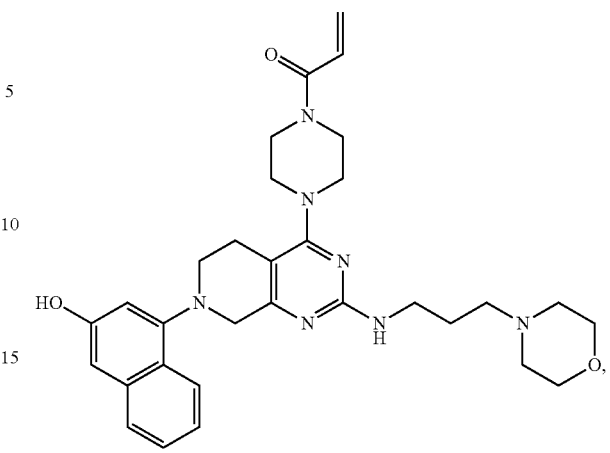
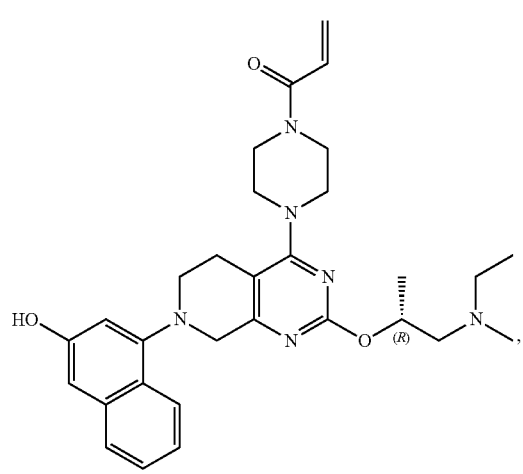
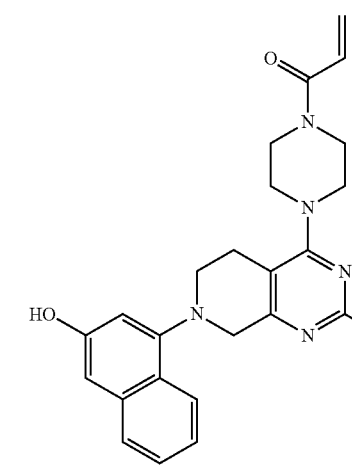
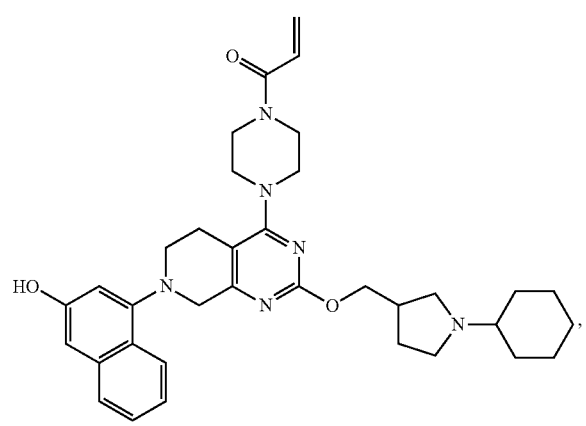
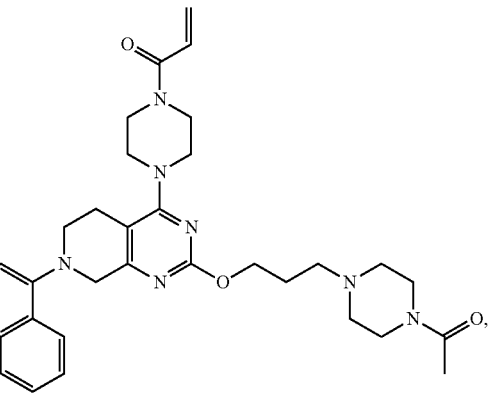

55
-continued
56
-continued
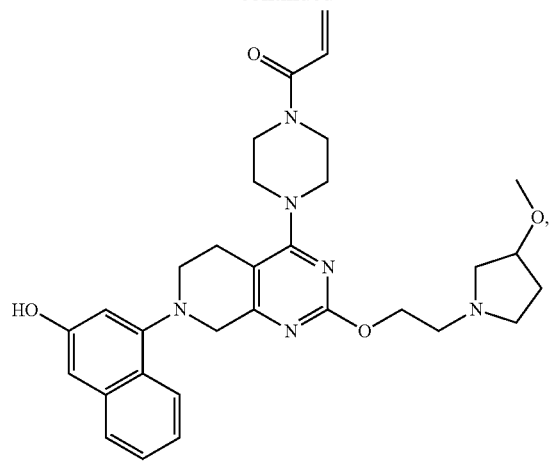
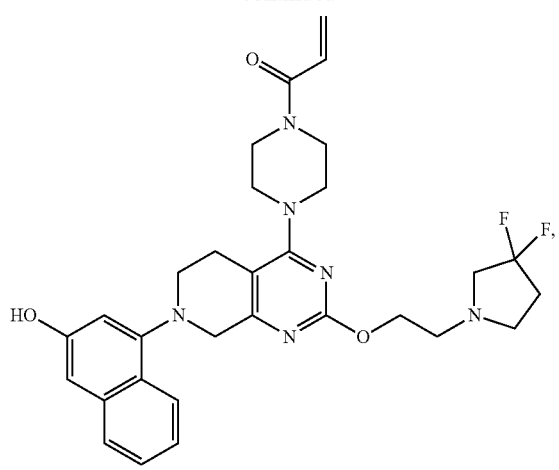
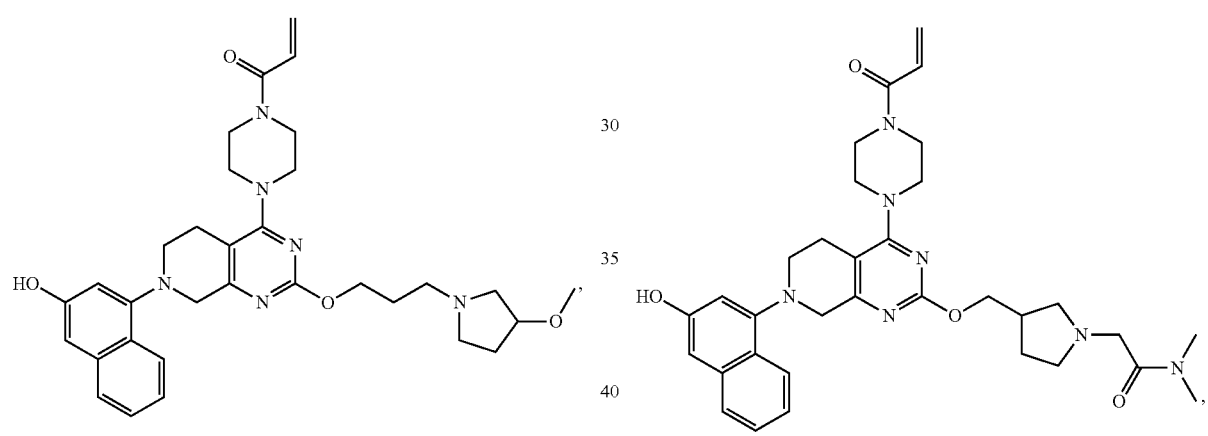
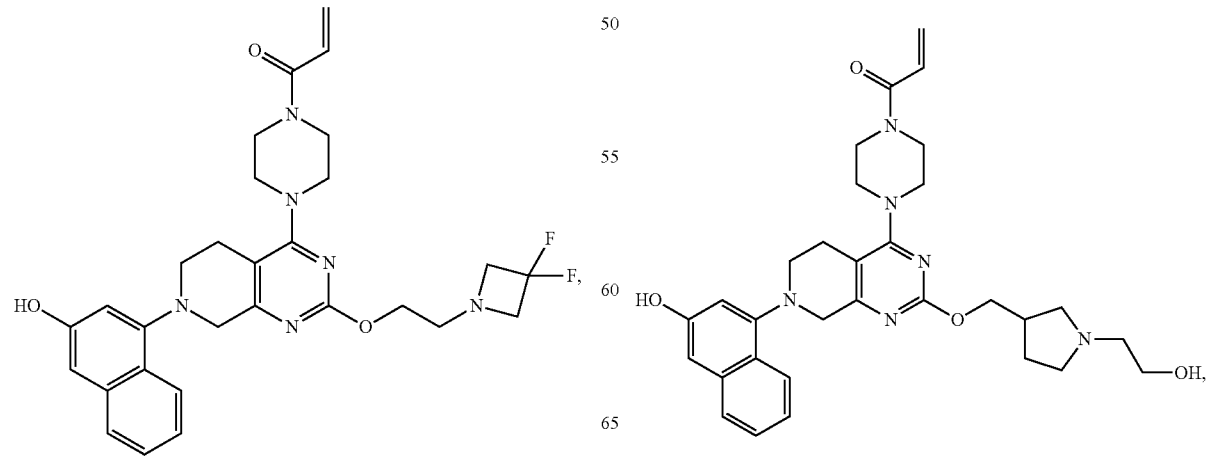

57
-continued
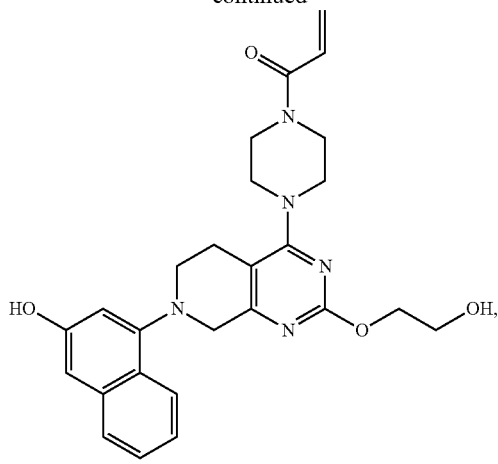
58
-continued
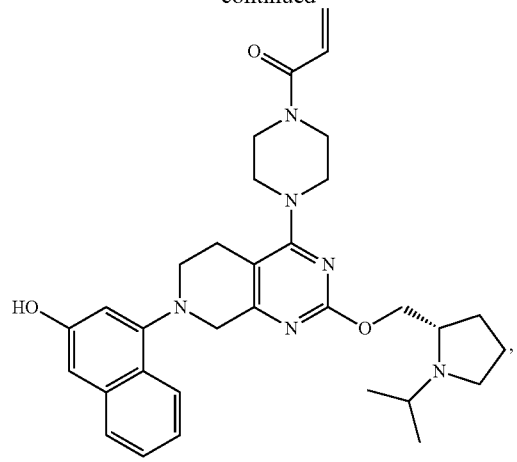
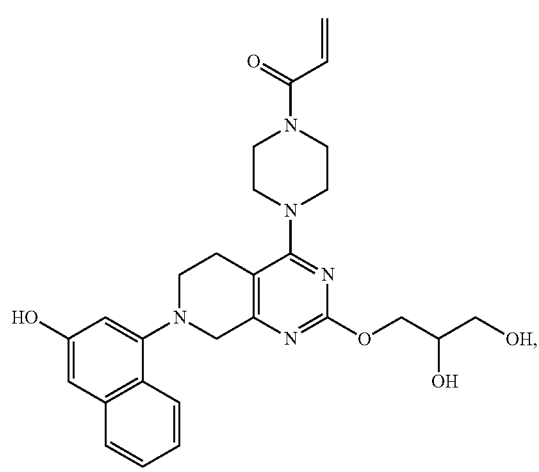
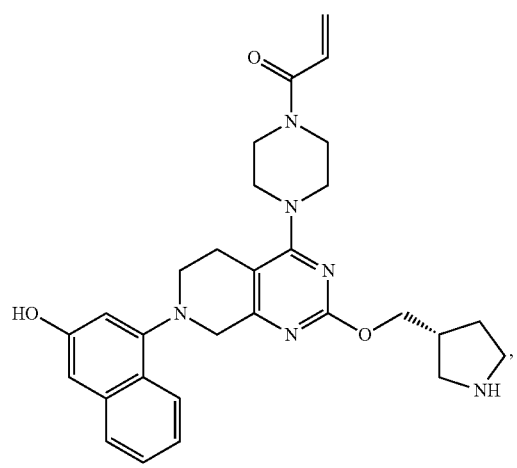
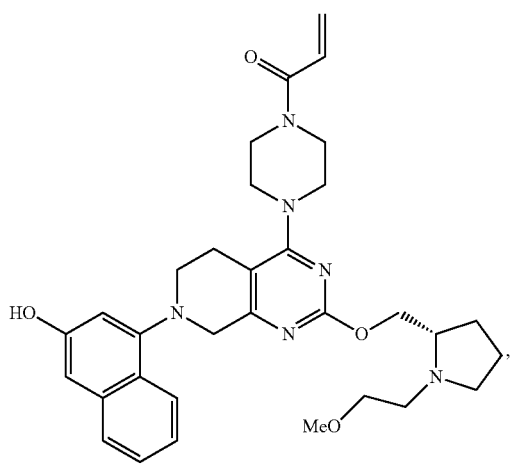
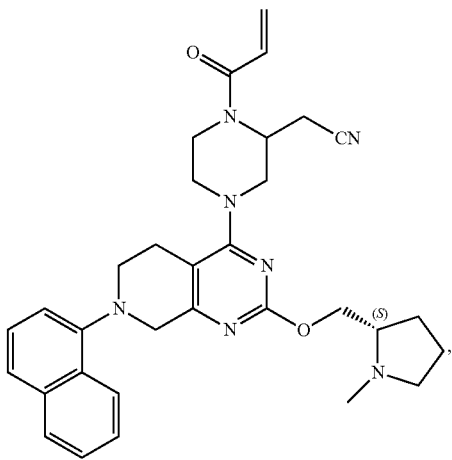

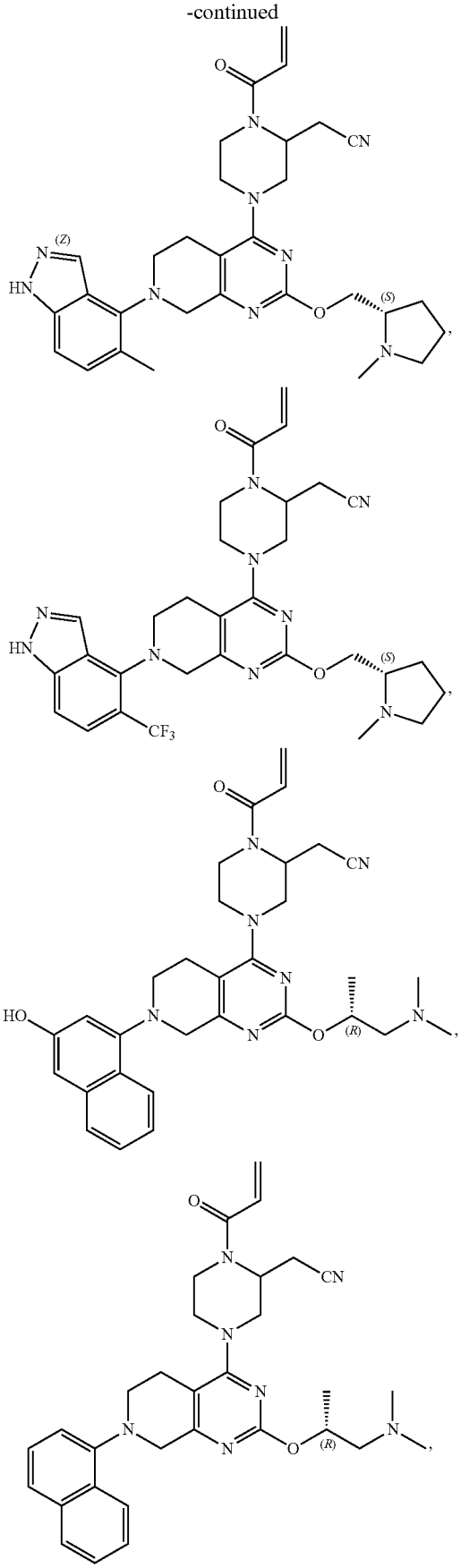
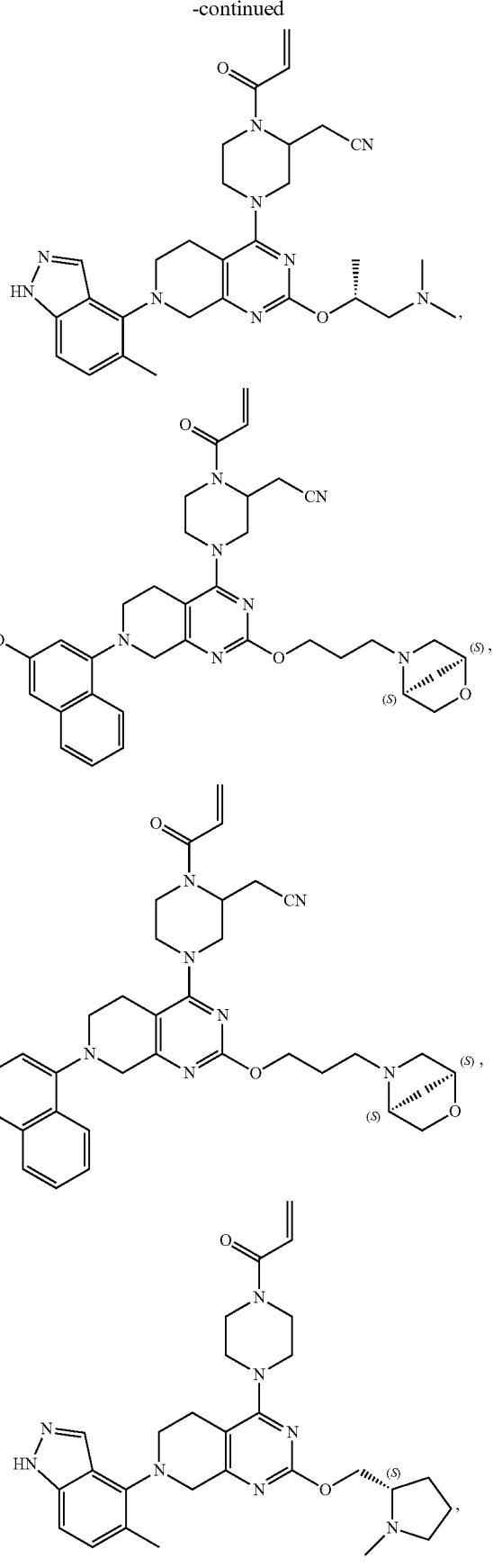

-continued
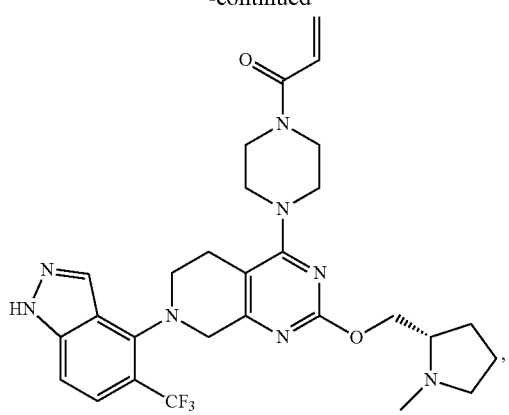
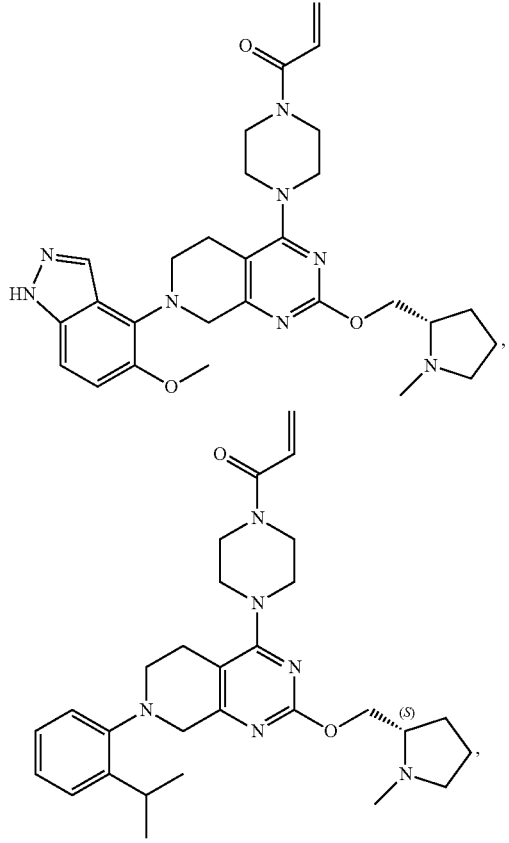
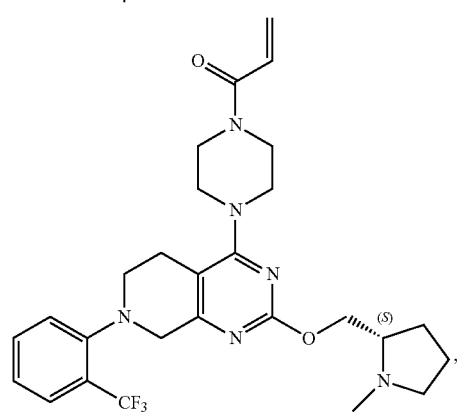
-continued
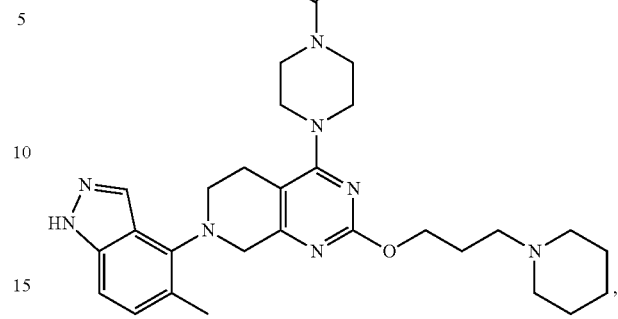
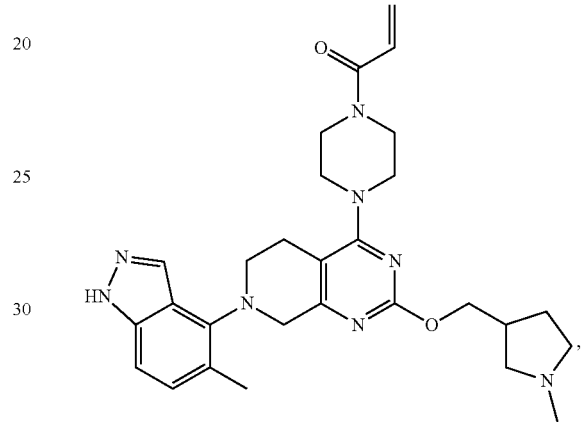
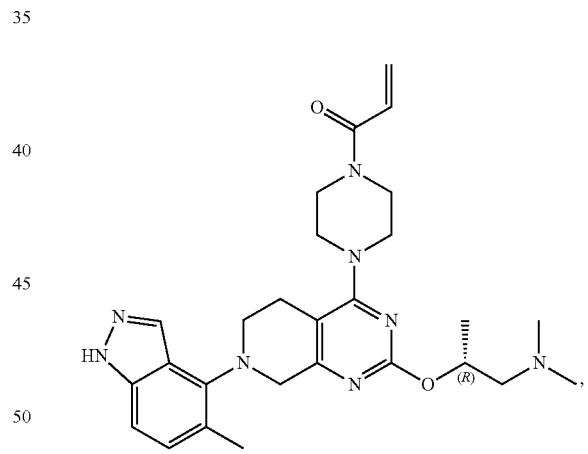
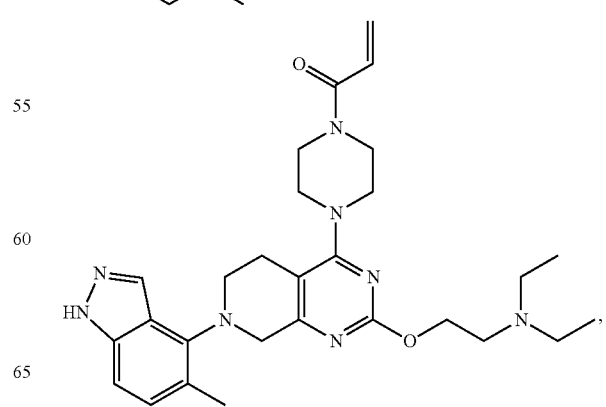

63
-continued
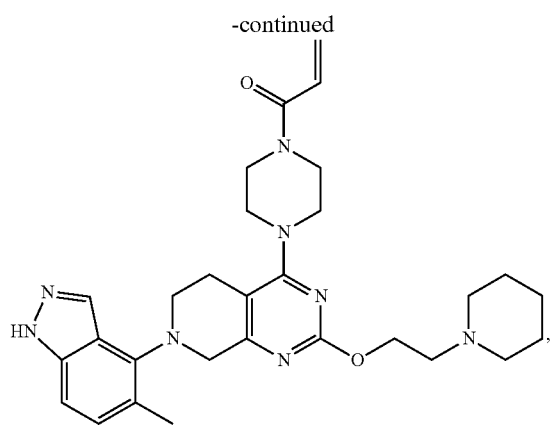
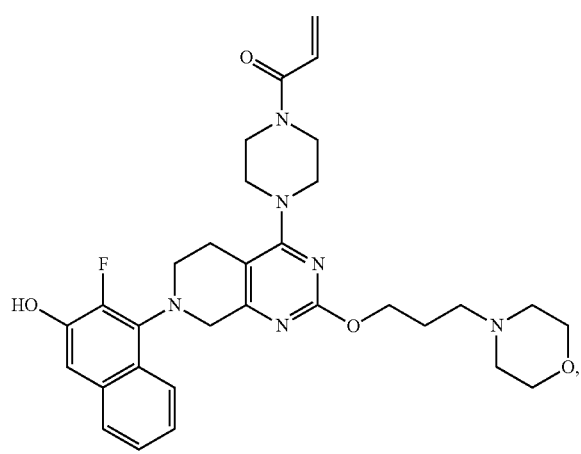
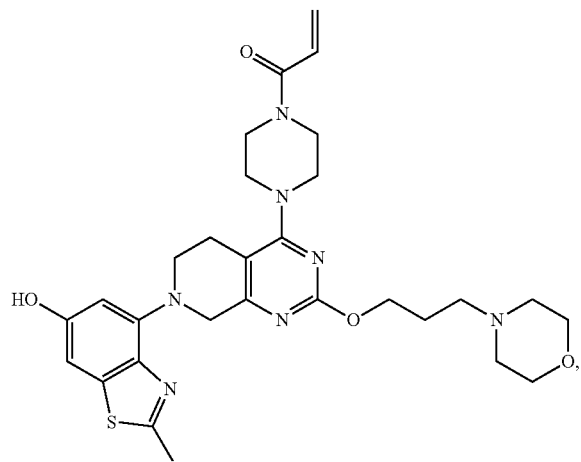
64
-continued
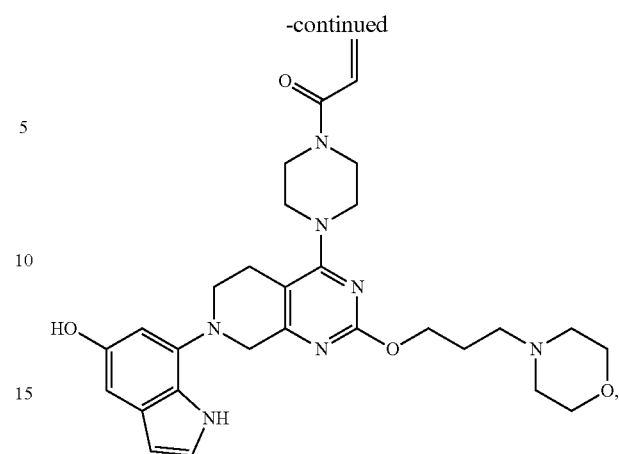
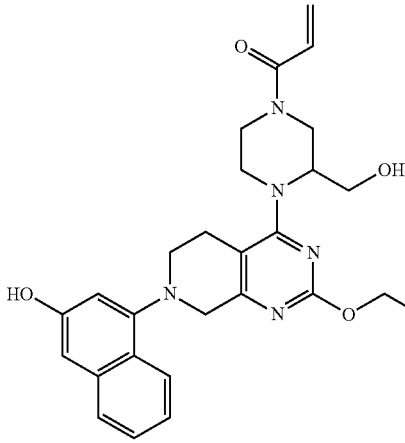
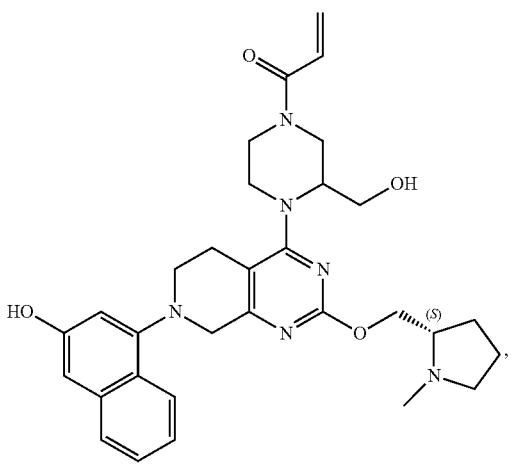

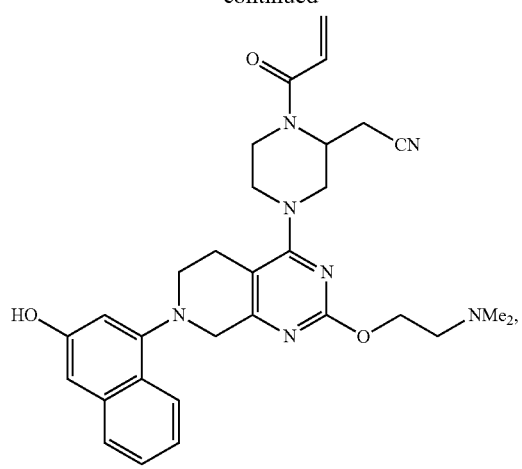
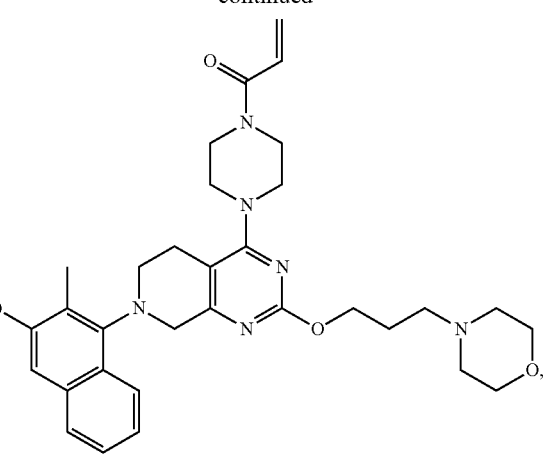
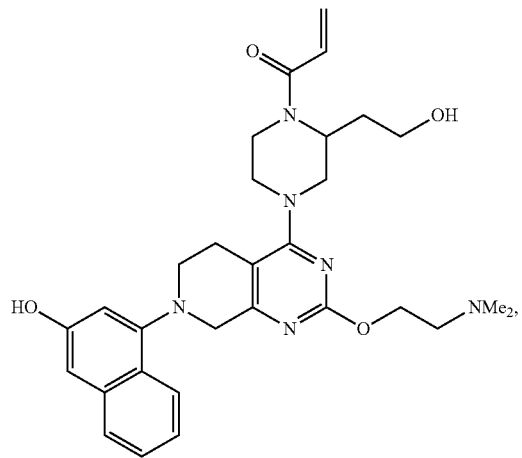
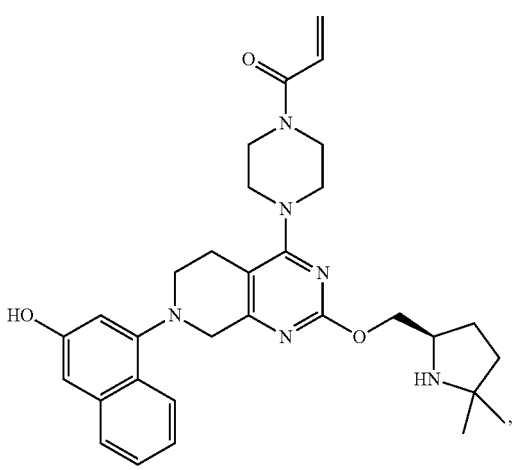
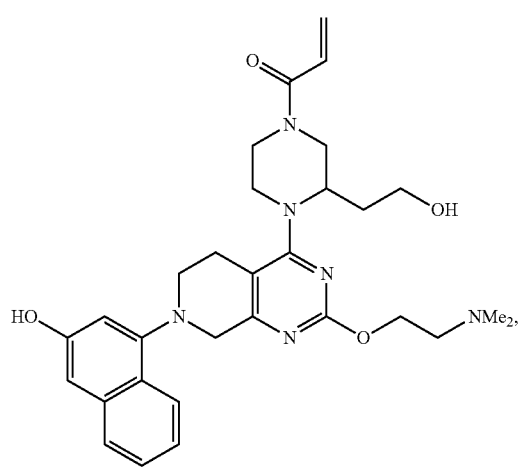
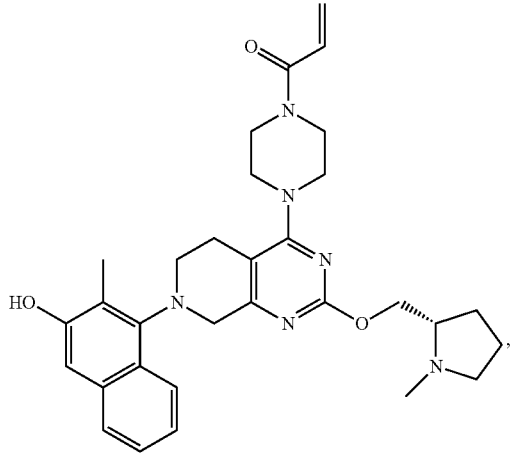

67
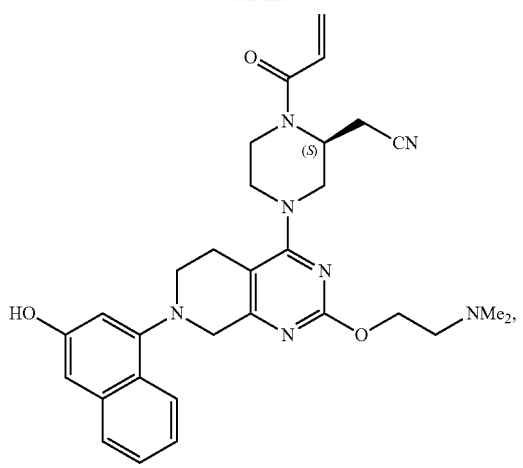
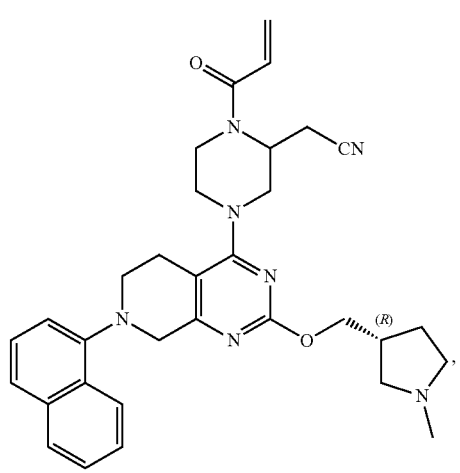
68
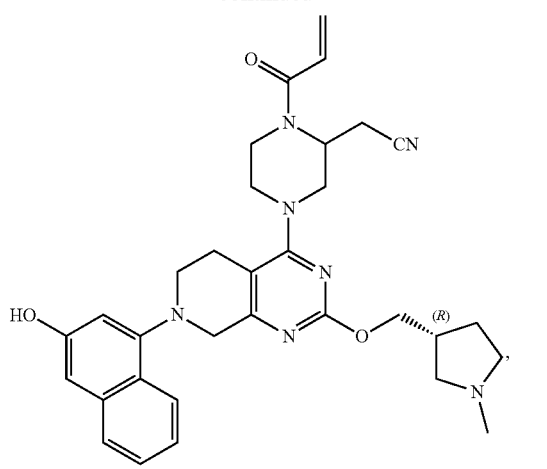
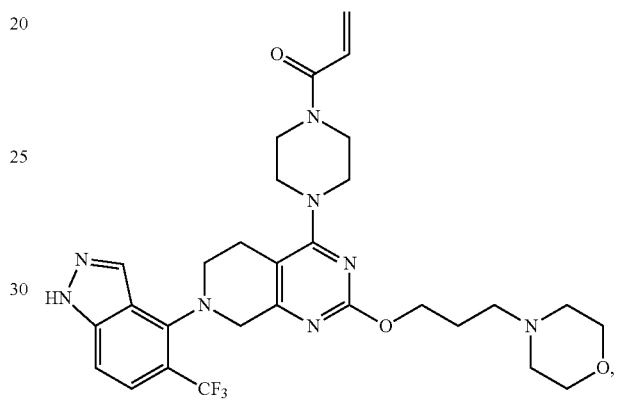
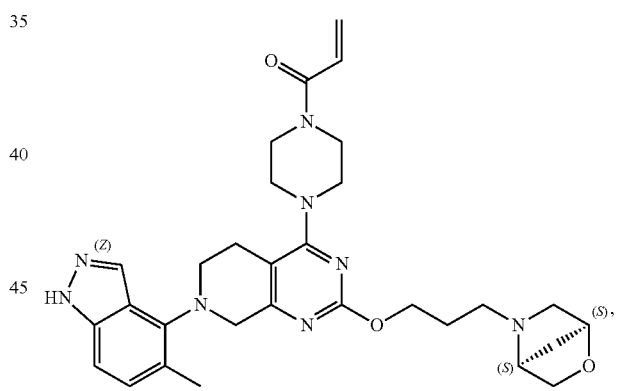
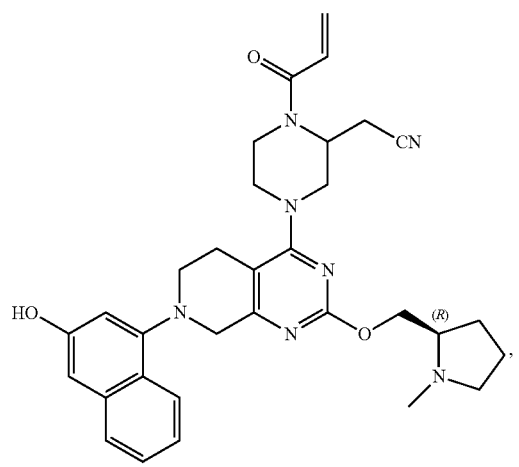
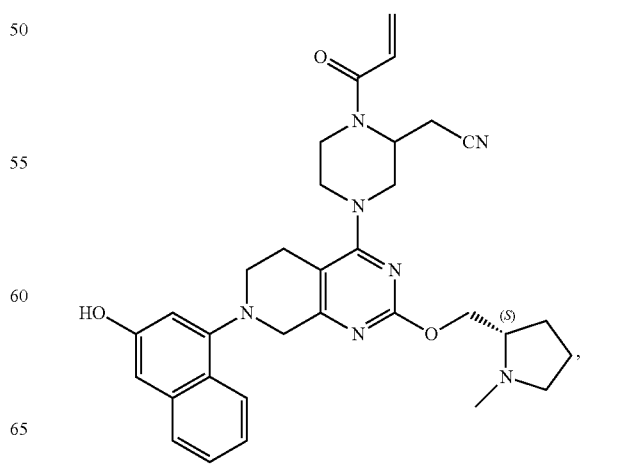

-continued
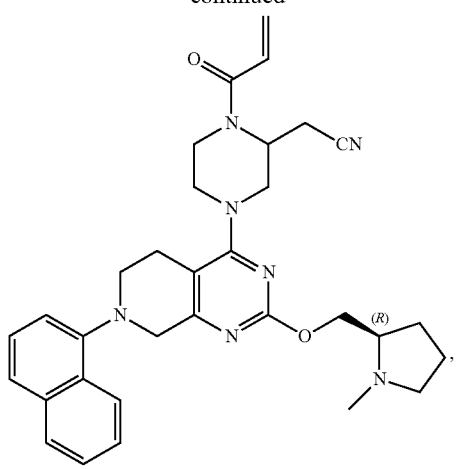
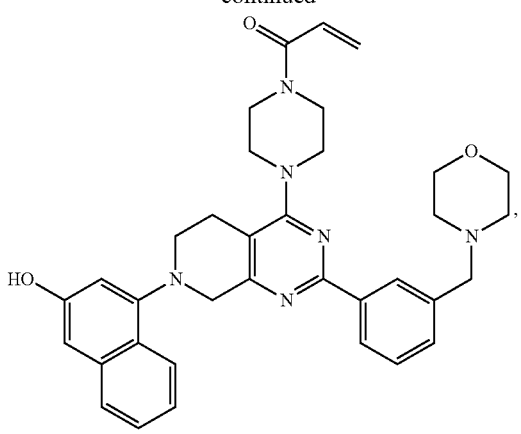
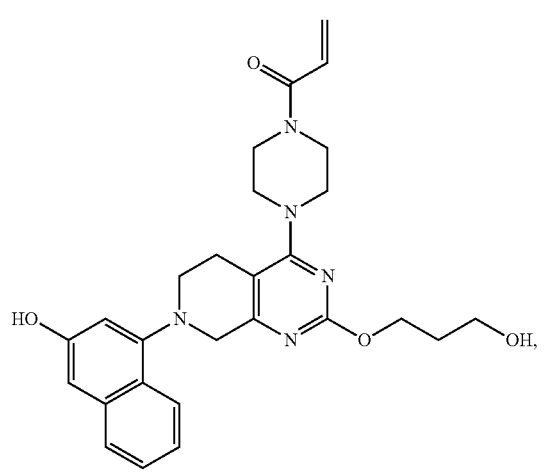
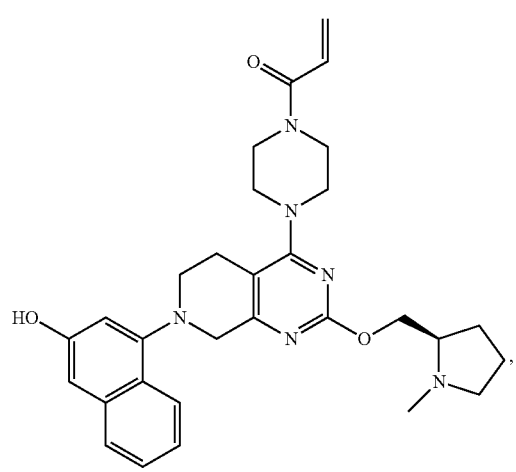
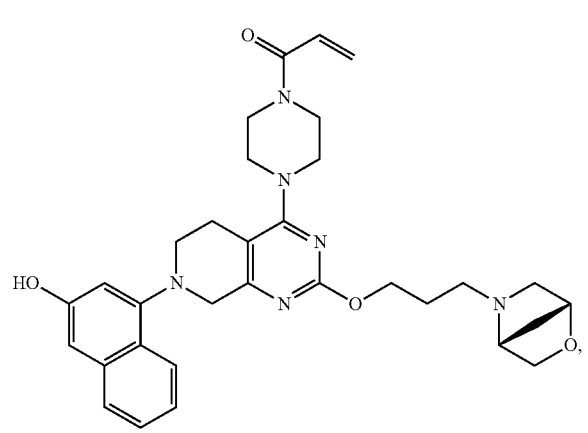
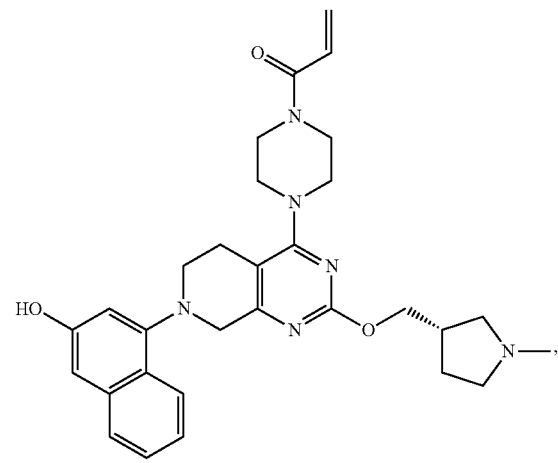

71
-continued
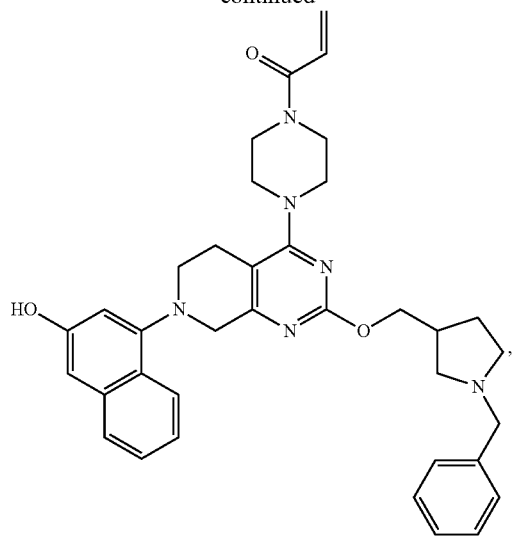
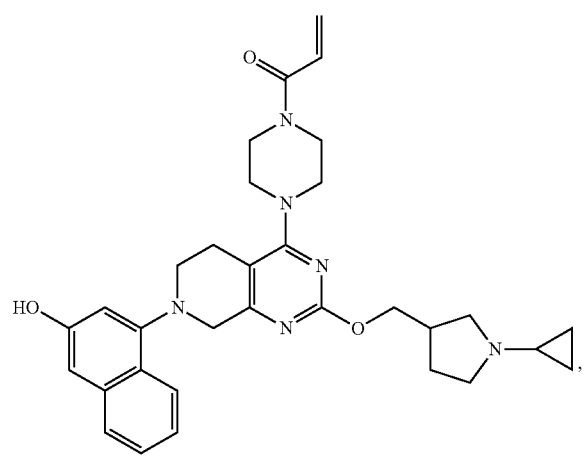
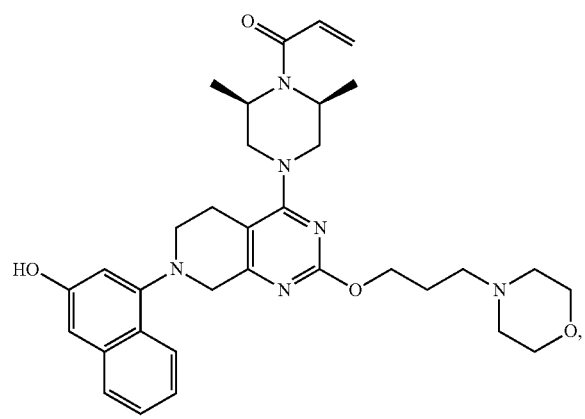
72
-continued
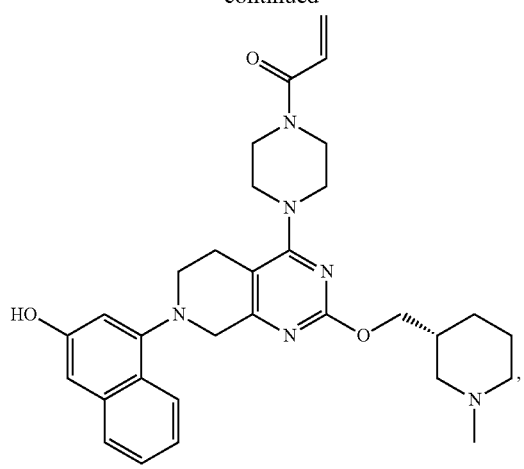
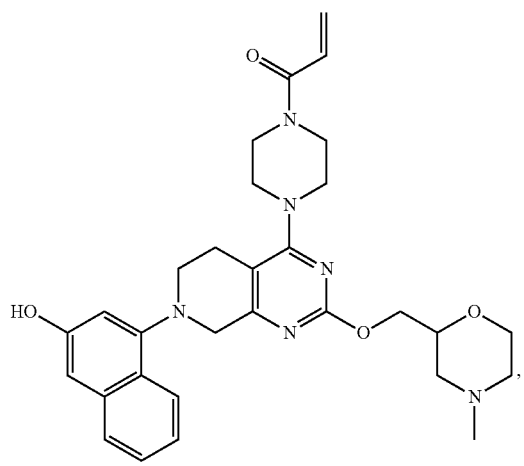
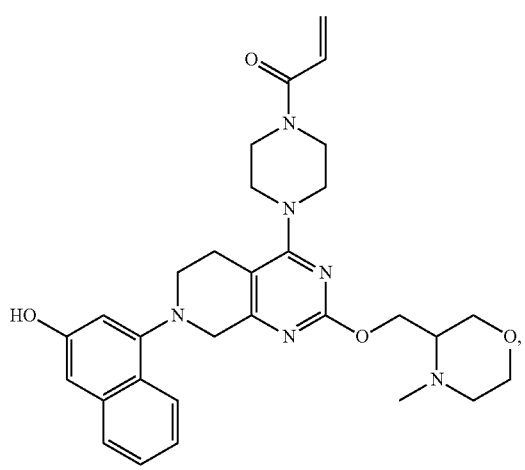

-continued
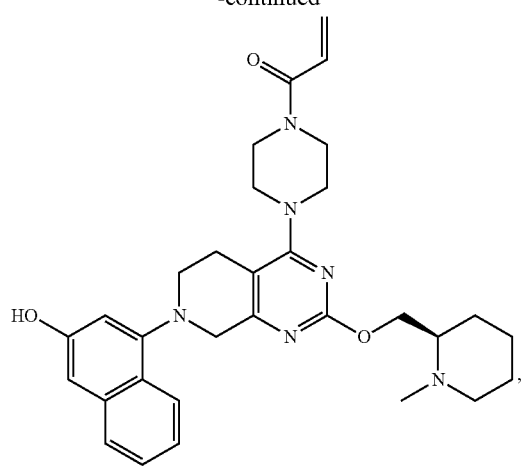
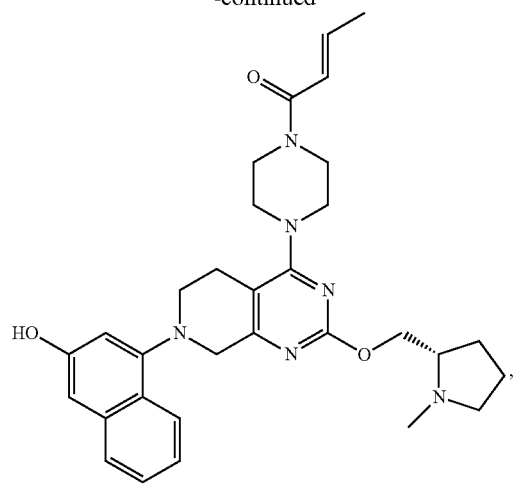
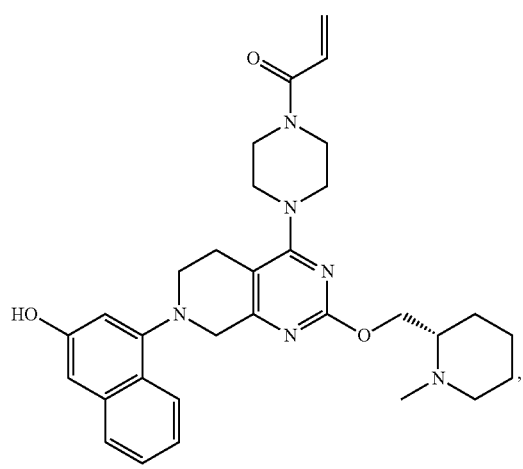
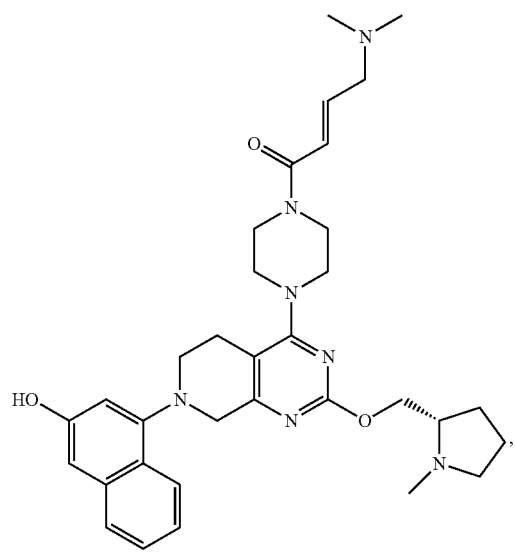
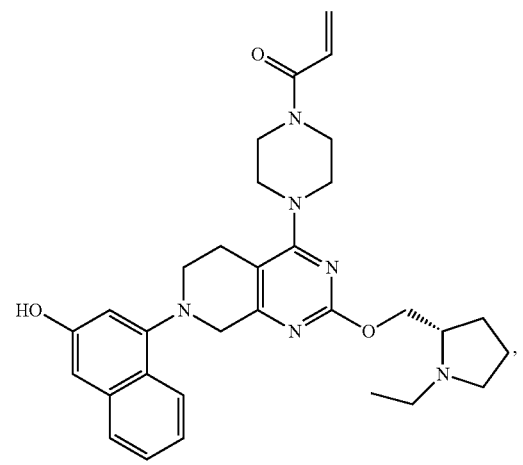
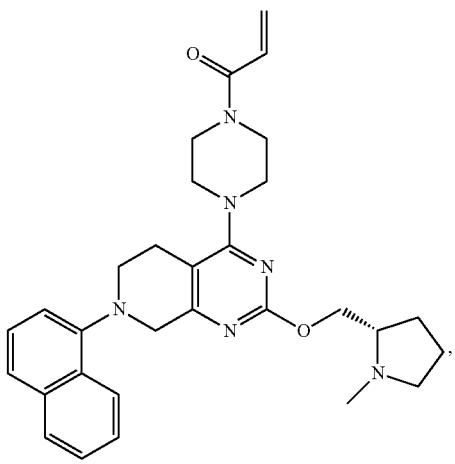

75
-continued
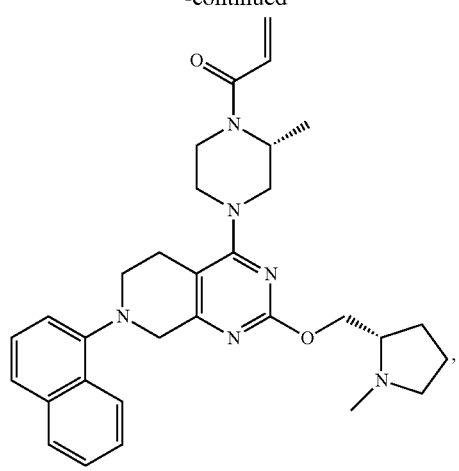
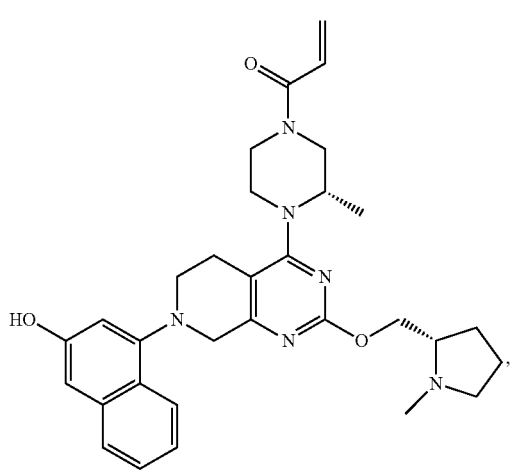
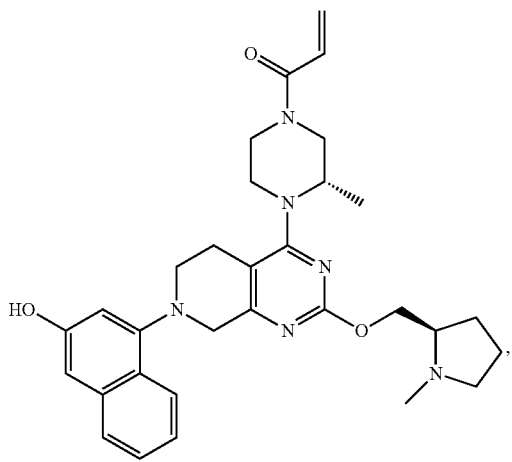
76
-continued
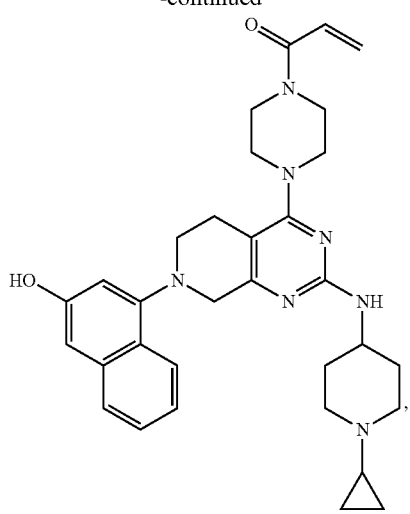
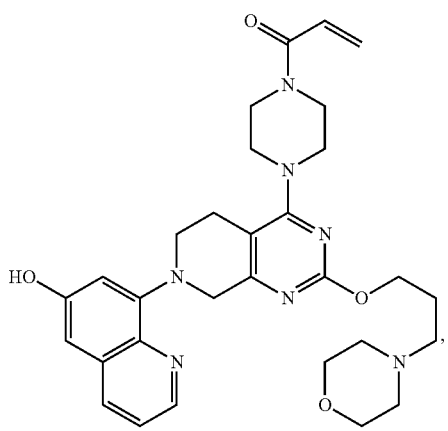
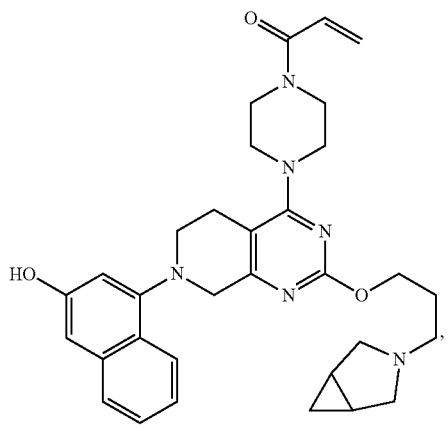

77
-continued
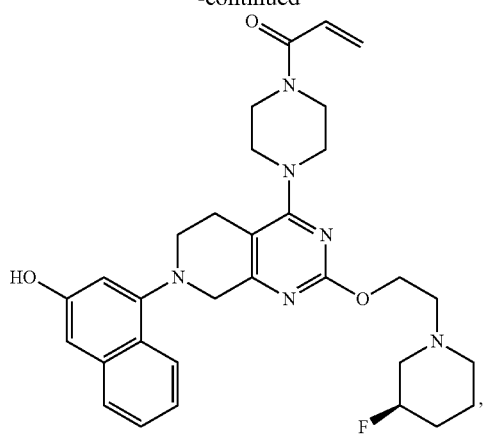
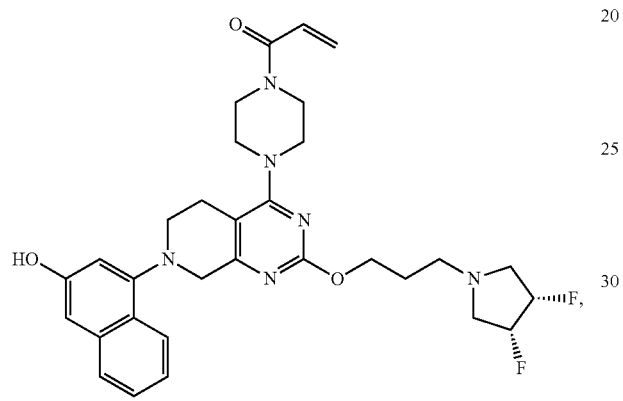
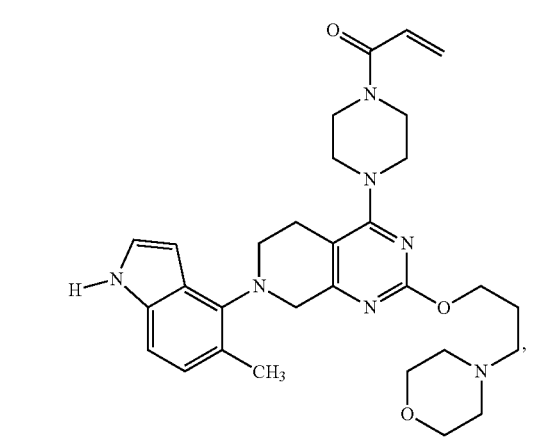
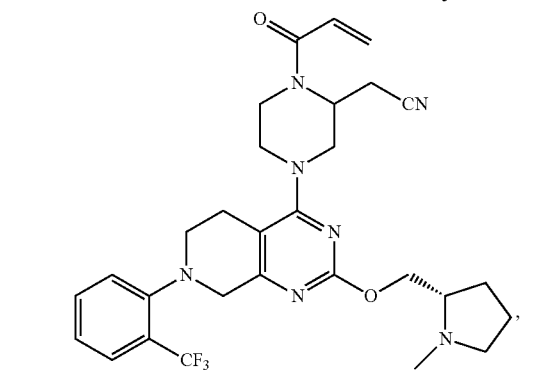
78
-continued
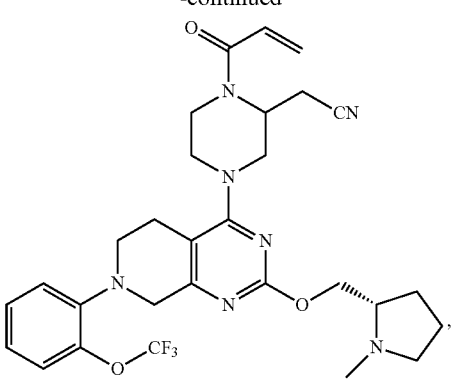
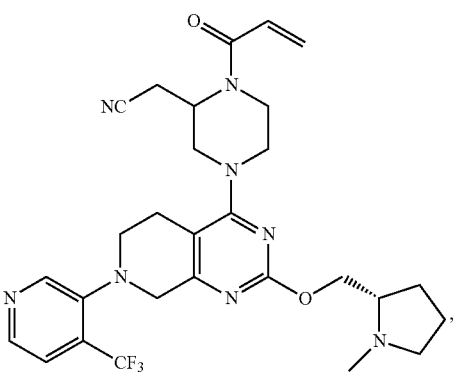
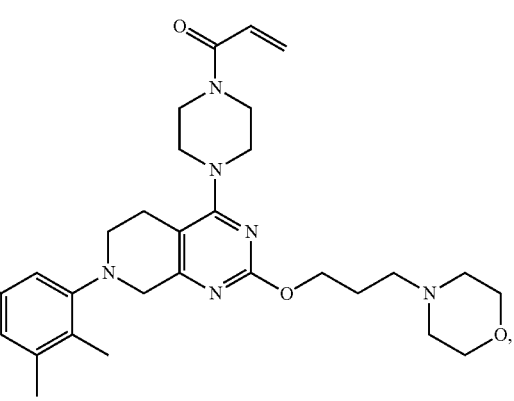
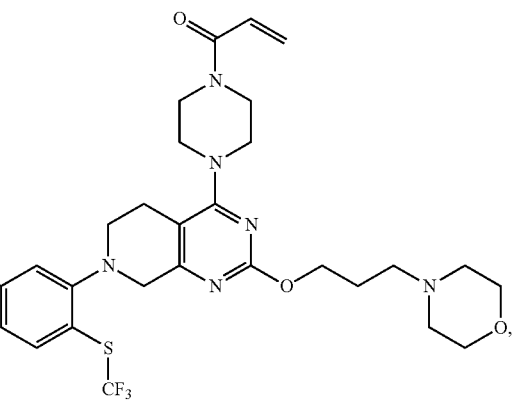

79
-continued
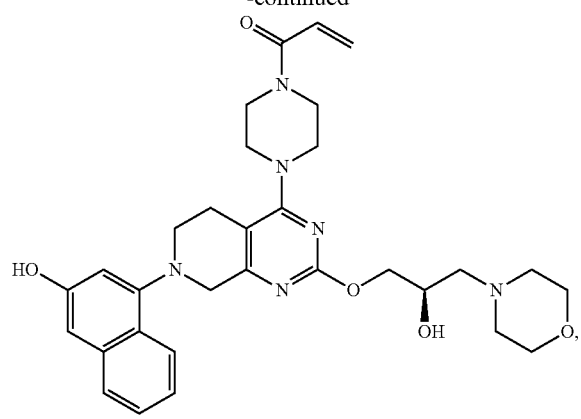
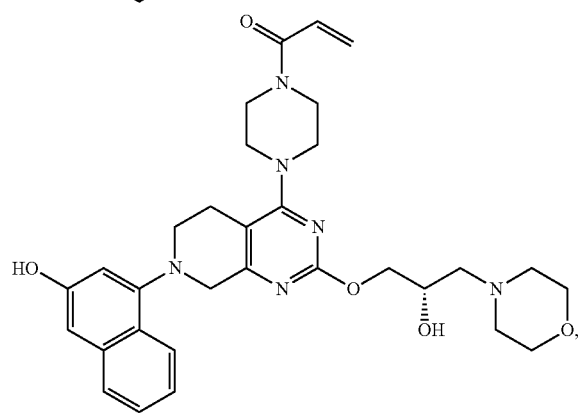
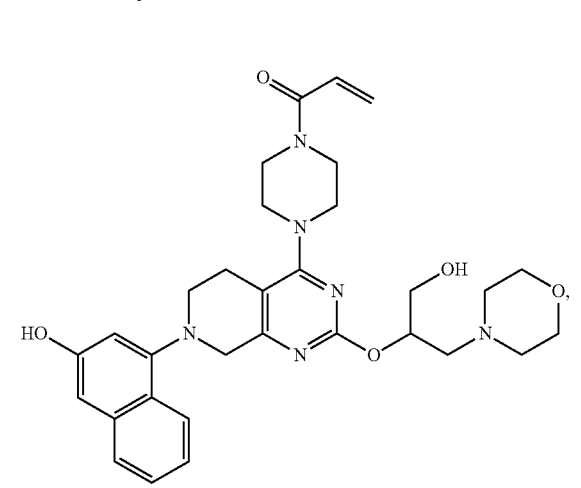
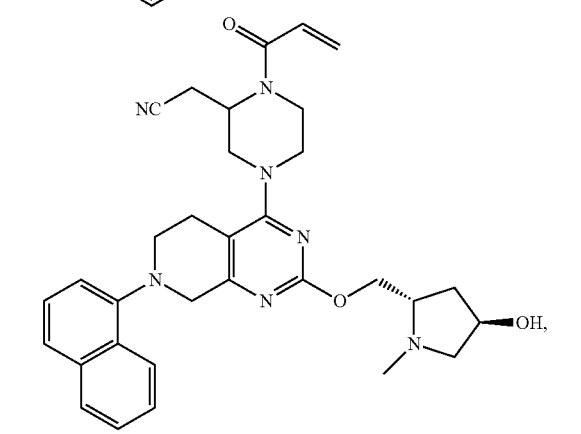
80
-continued
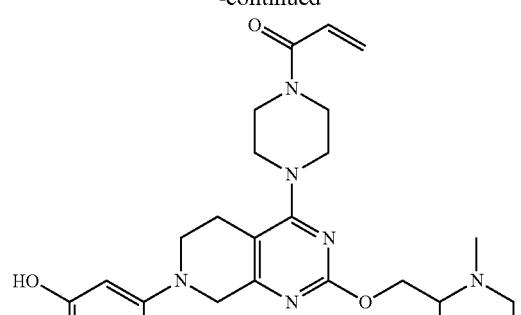
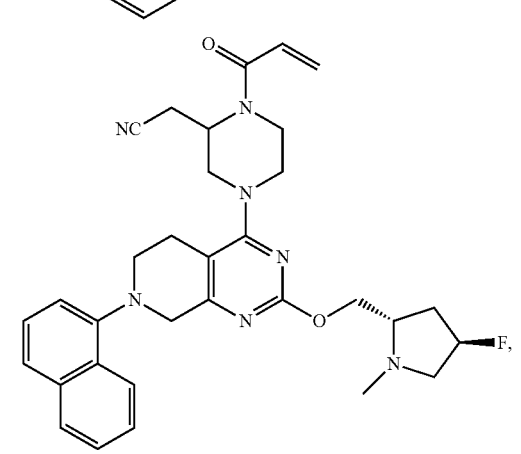
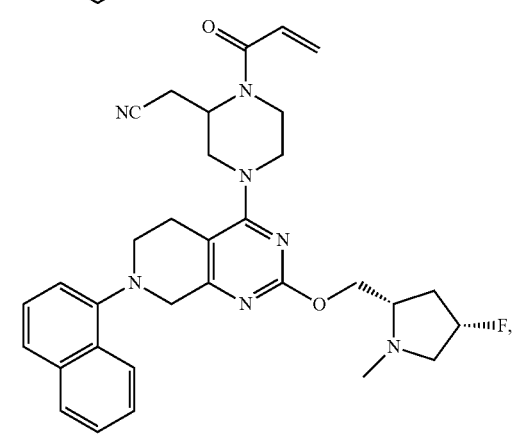
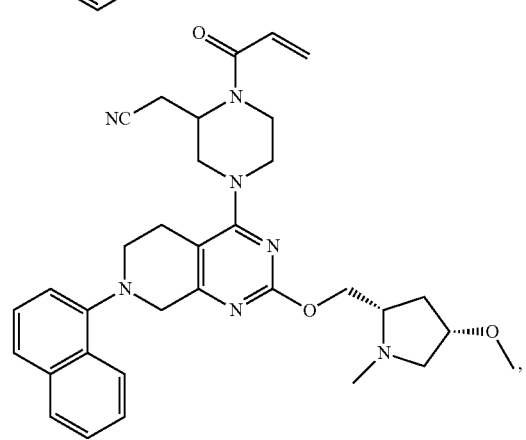

81
-continued
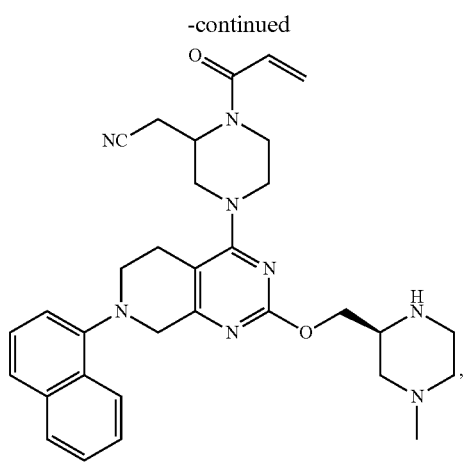
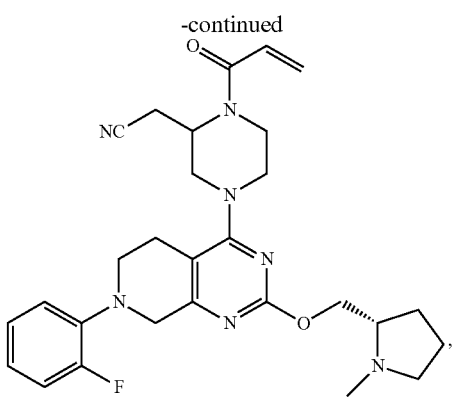
82
-continued
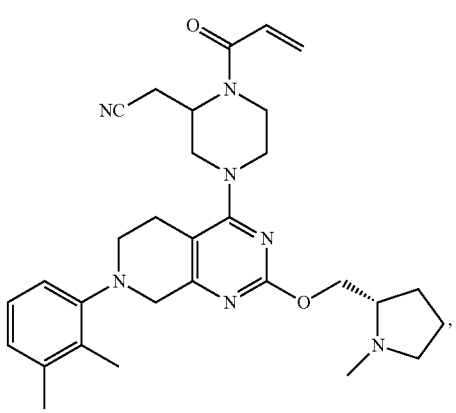
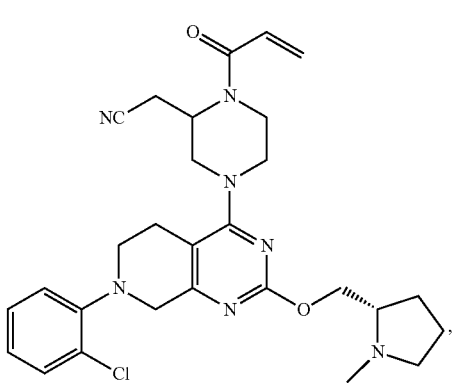
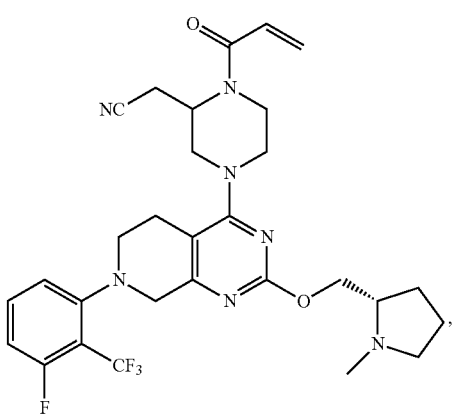

83
-continued
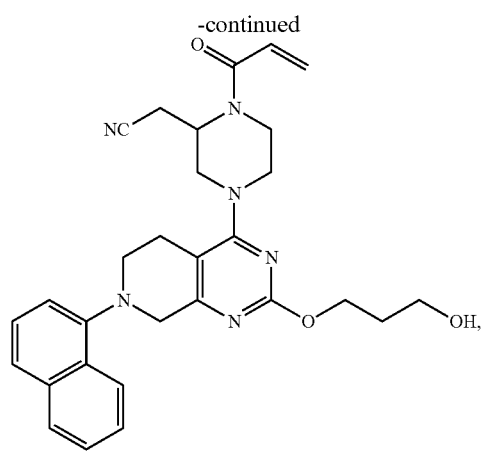
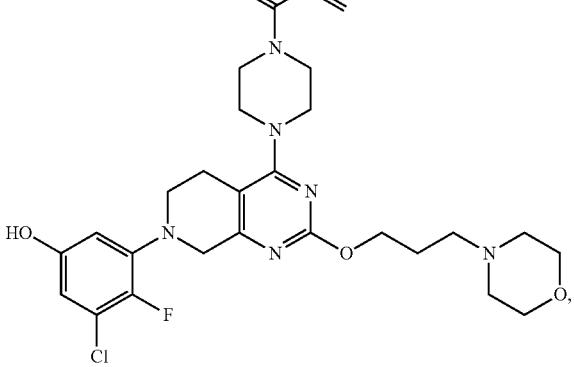
84
-continued
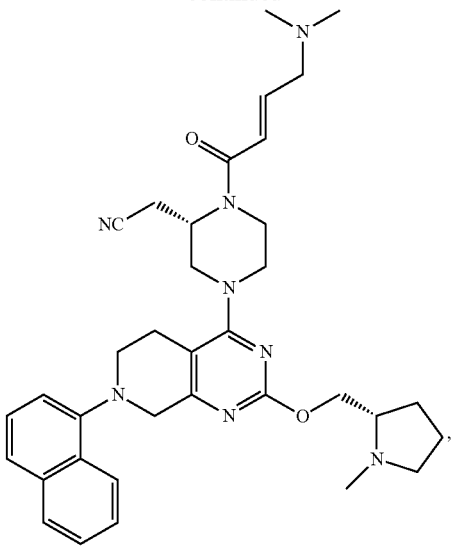
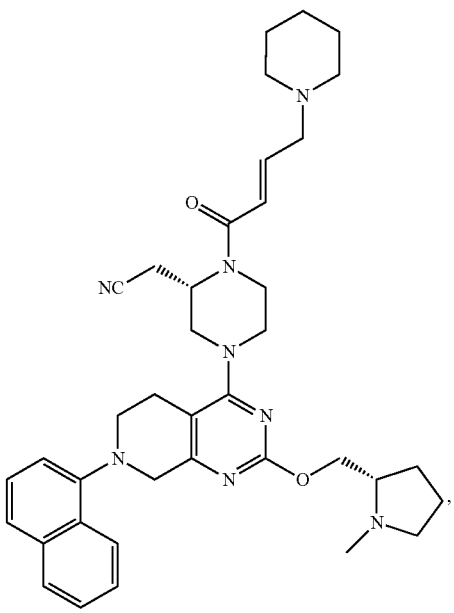
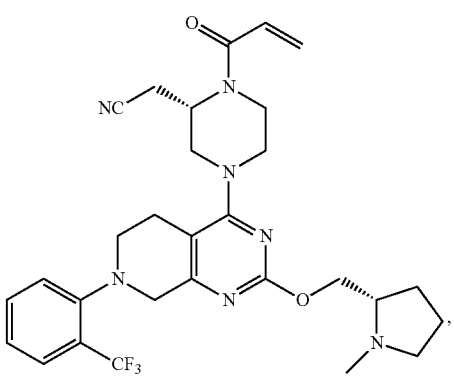

85
-continued
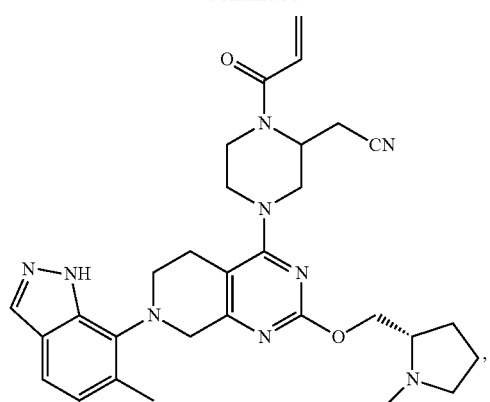
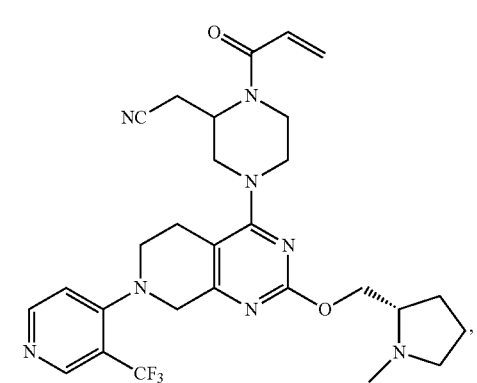
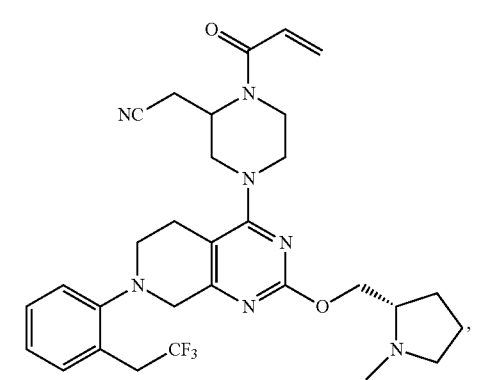
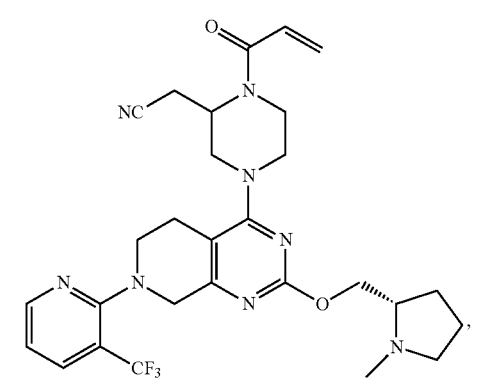
86
-continued
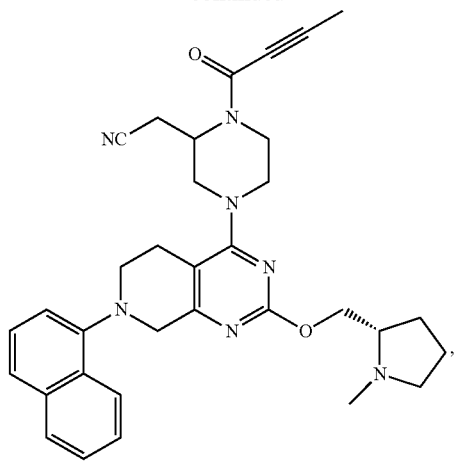
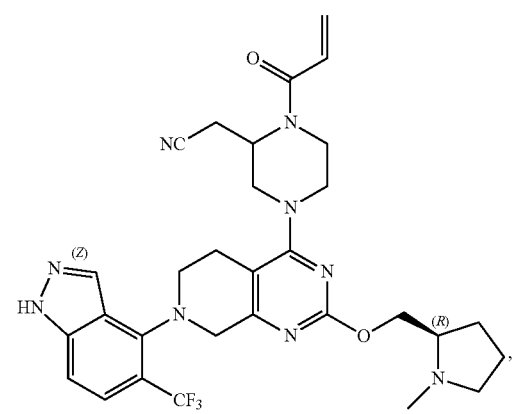
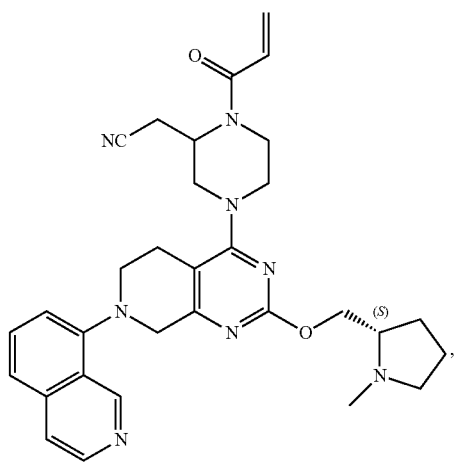

87
-continued
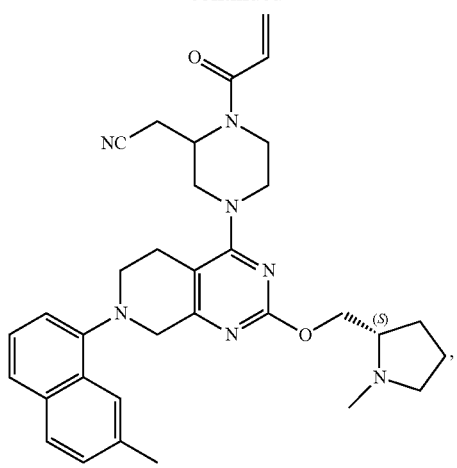
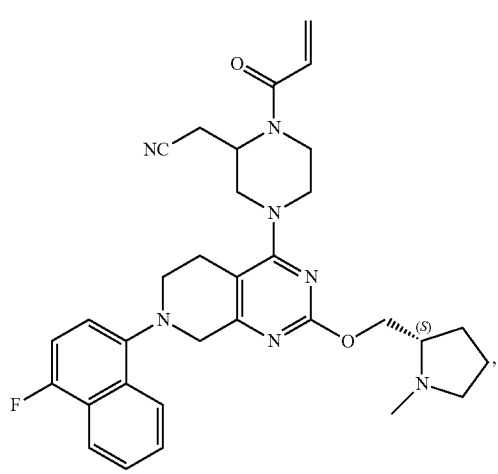
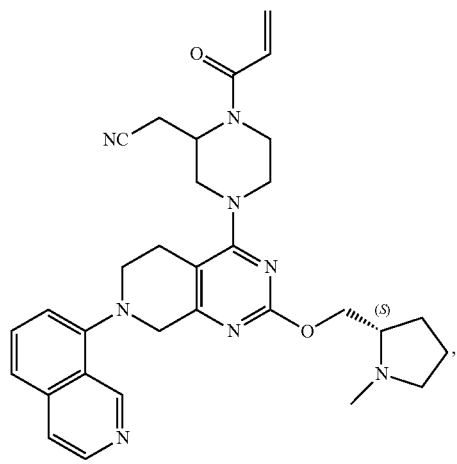
88
-continued
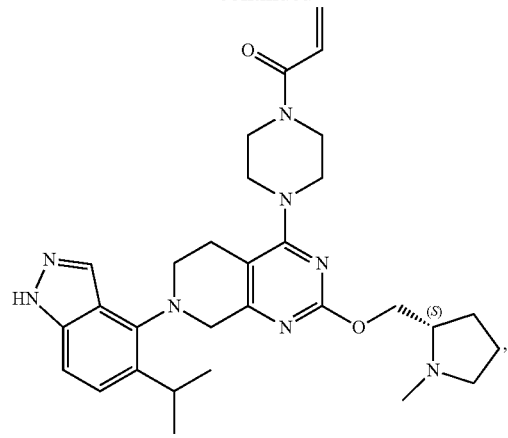
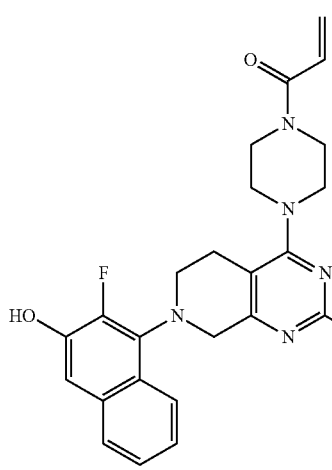
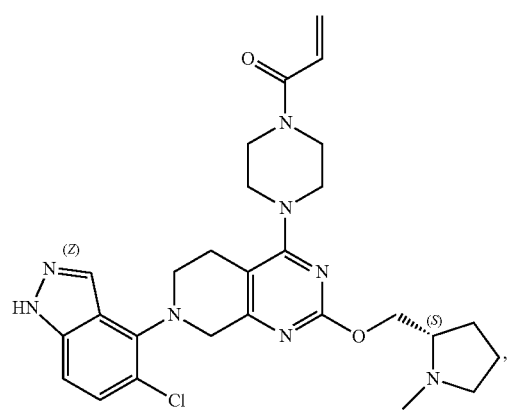

89
-continued
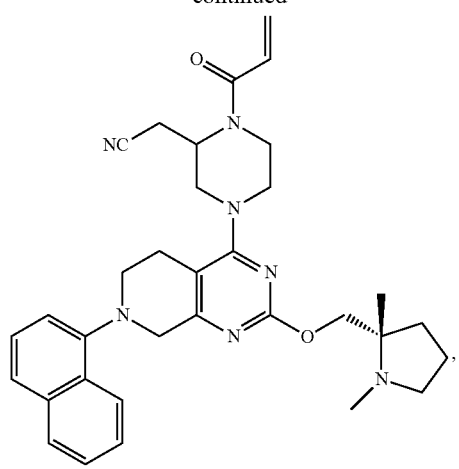
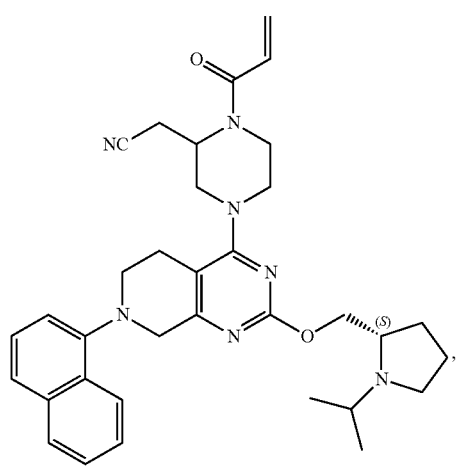
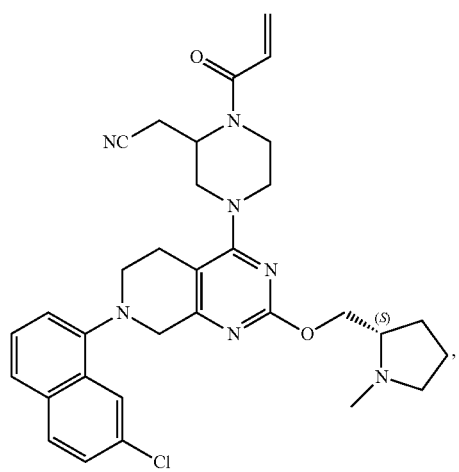
90
-continued
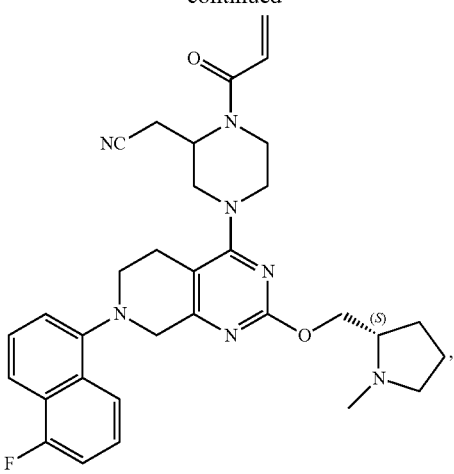
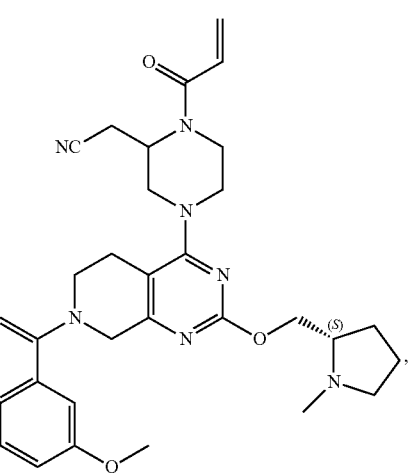
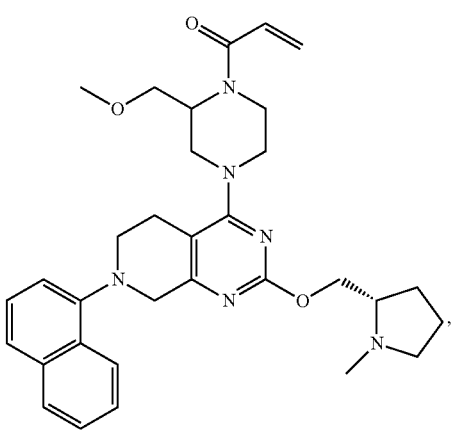

91
-continued
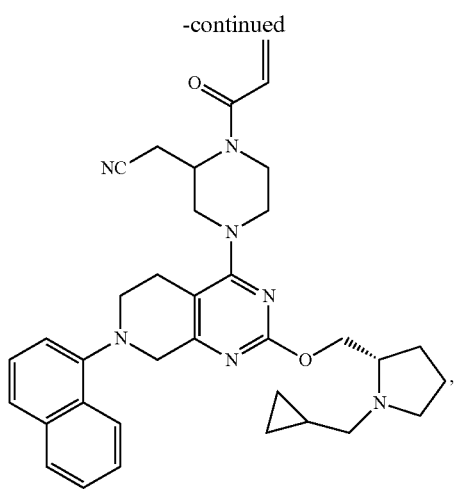
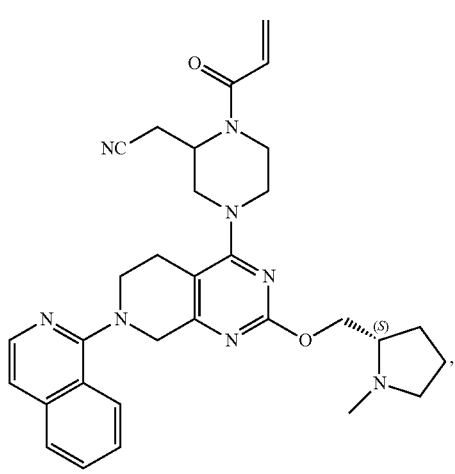
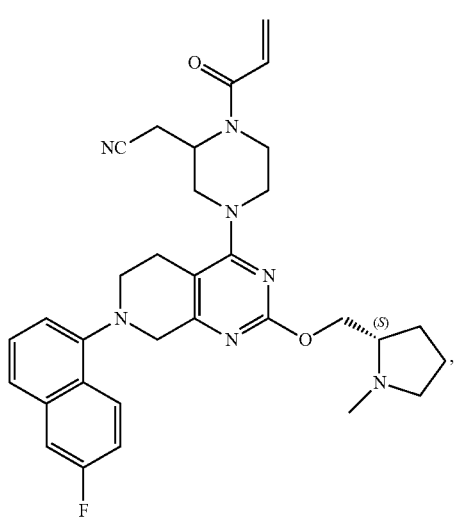
92
-continued
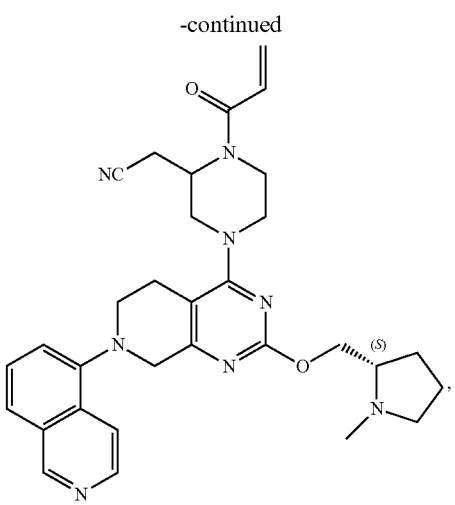
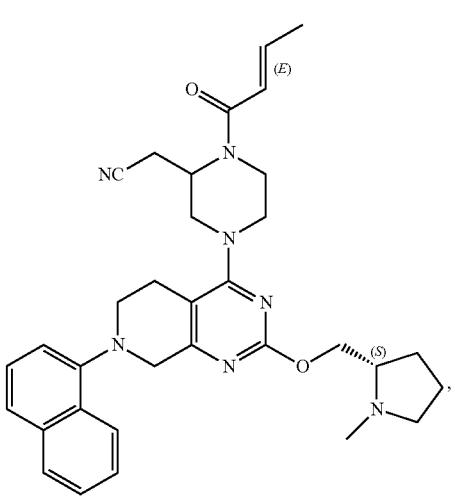
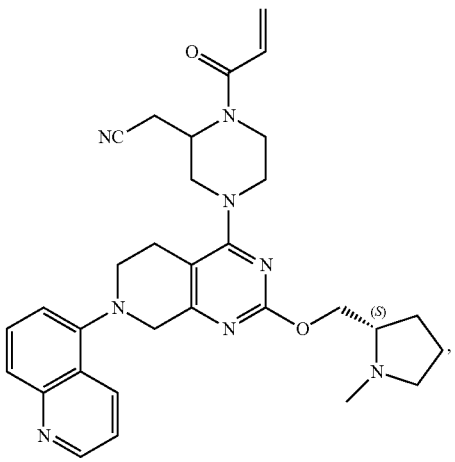

93
-continued
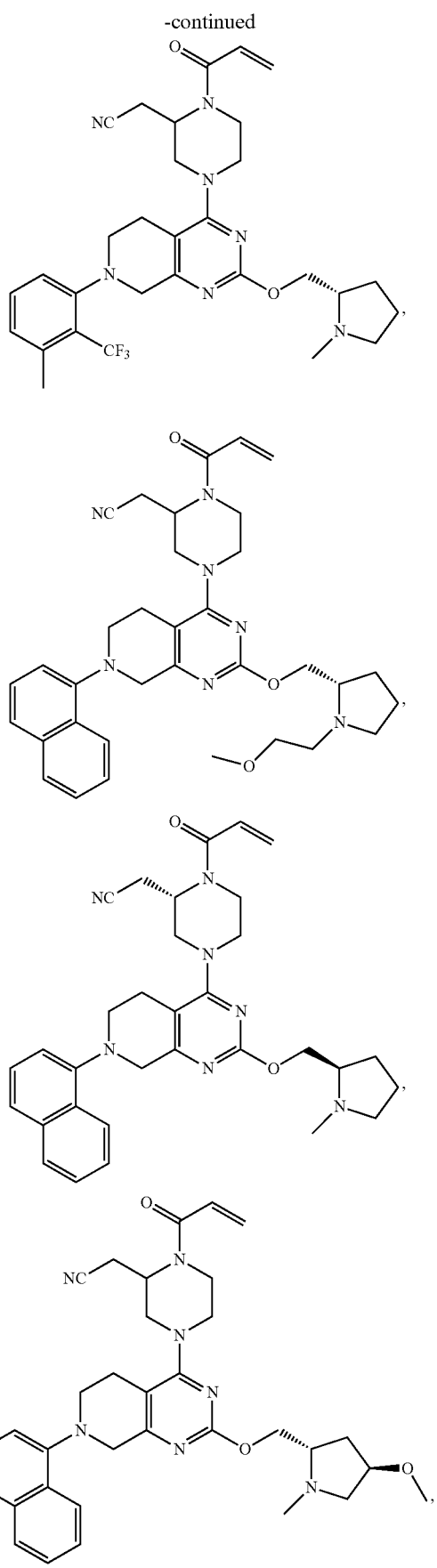
94
-continued
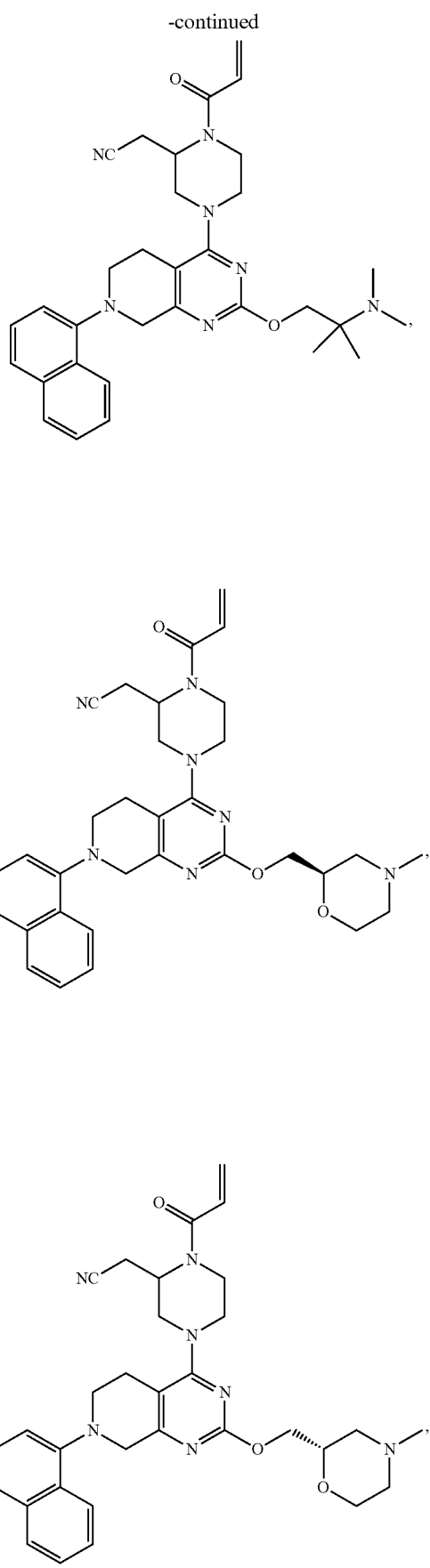

95
-continued
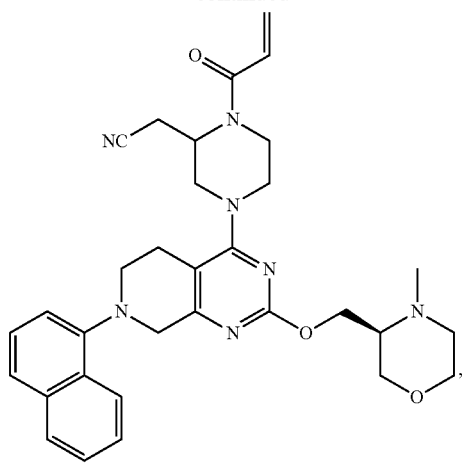
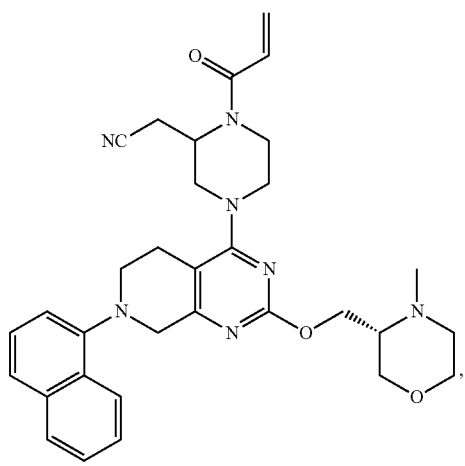
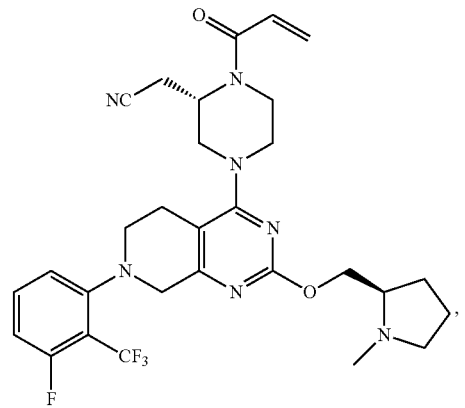
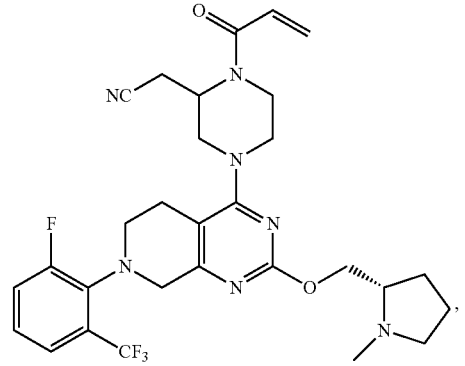
96
-continued
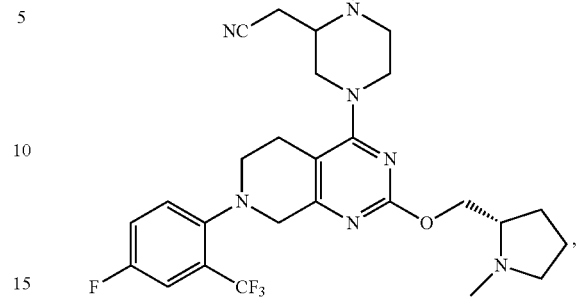
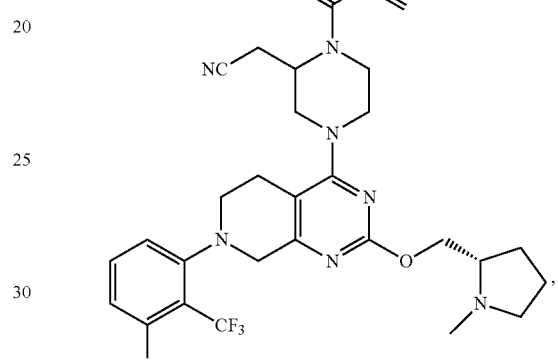
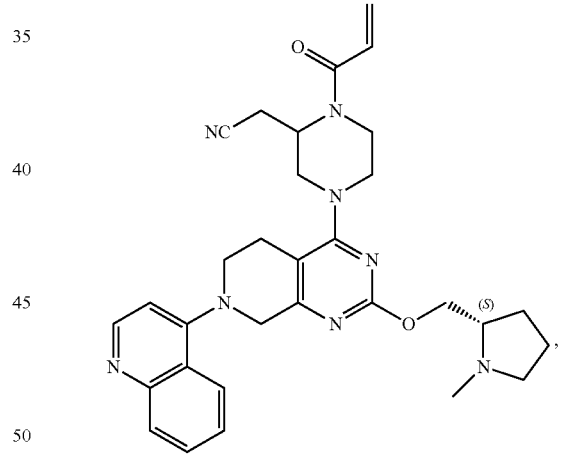
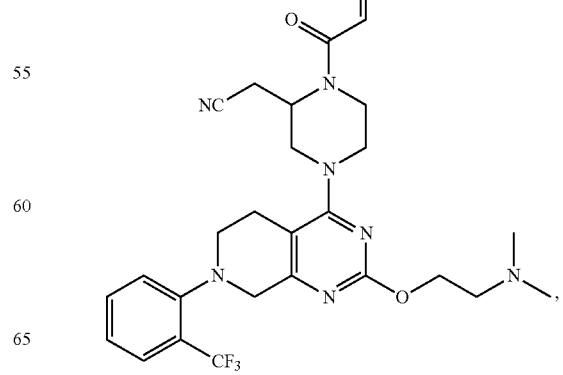

97
-continued
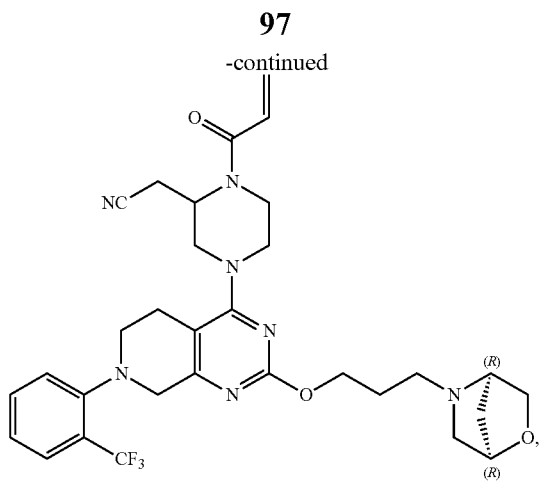
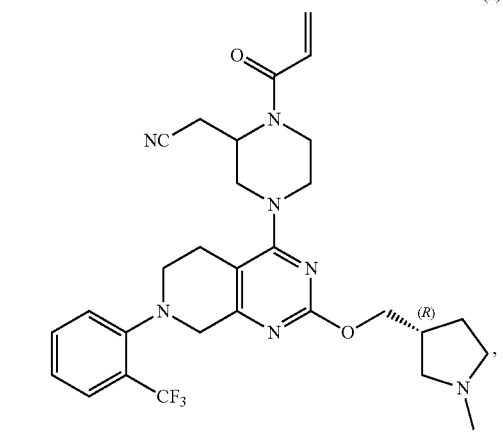
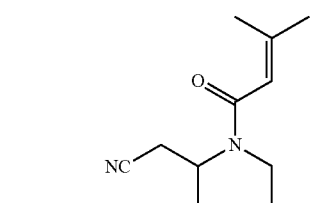
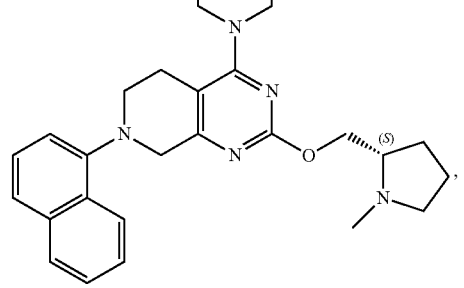
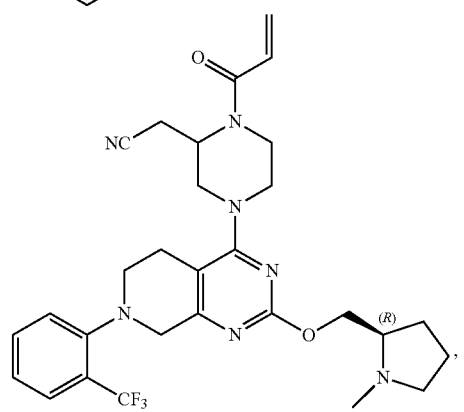
98
-continued
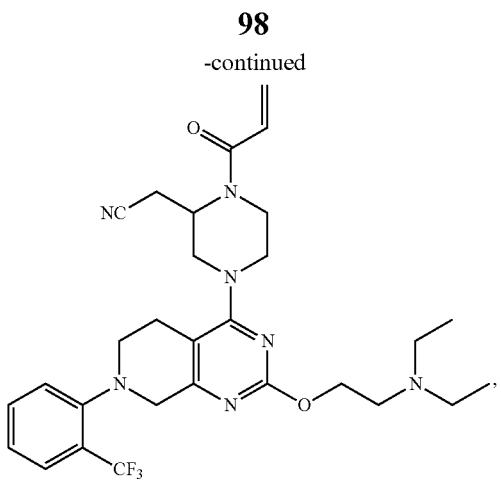
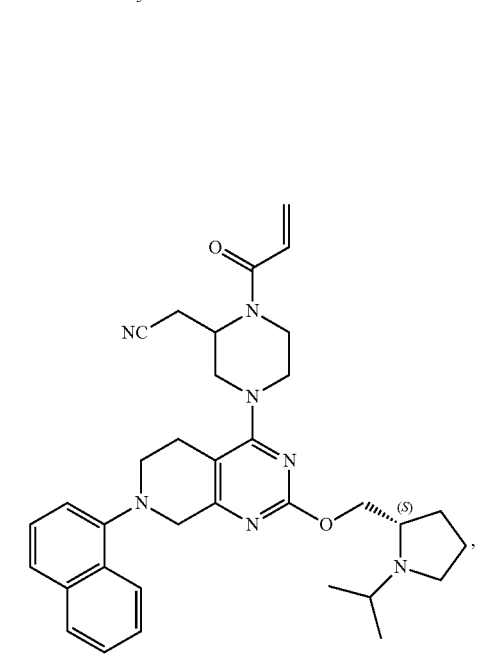
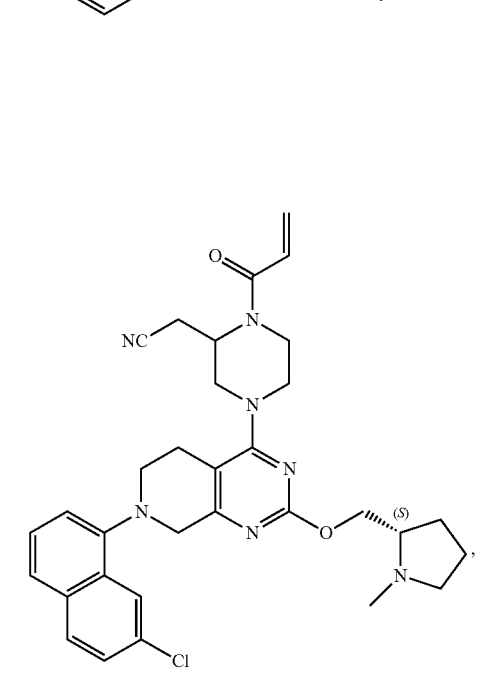

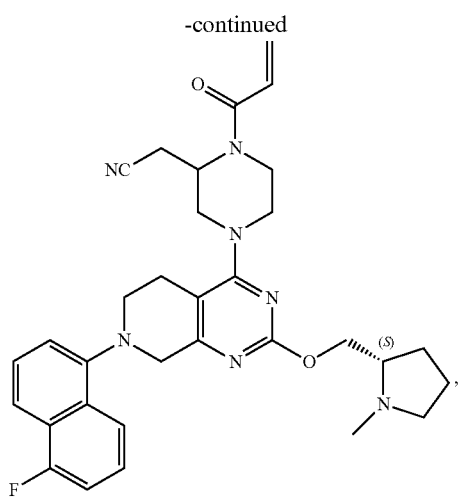
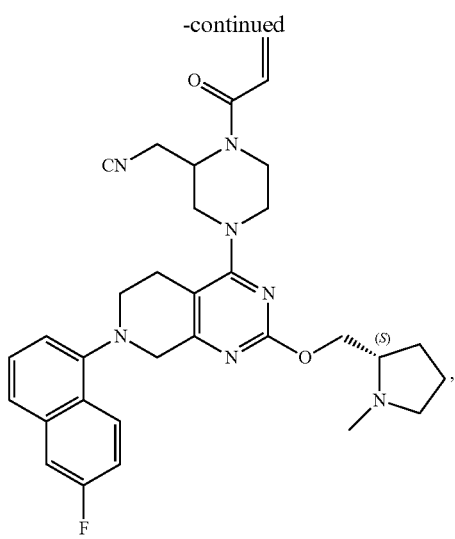
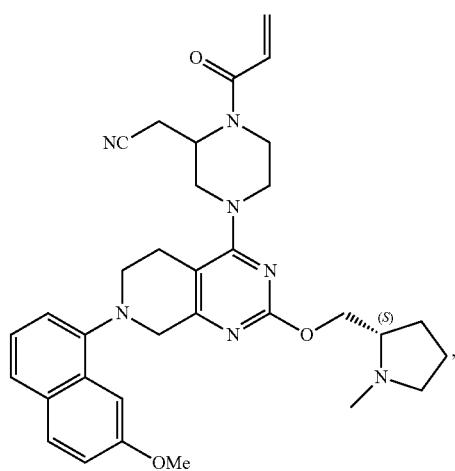
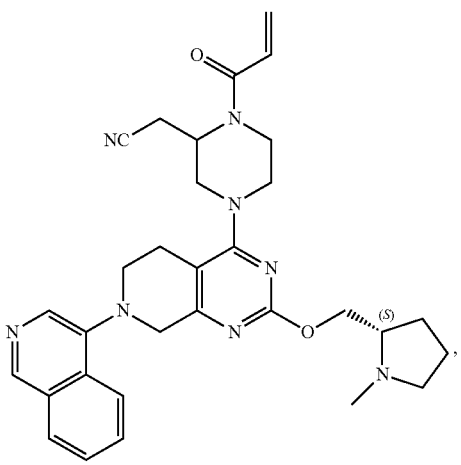
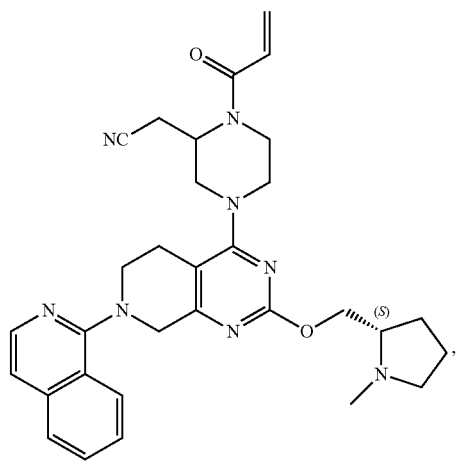
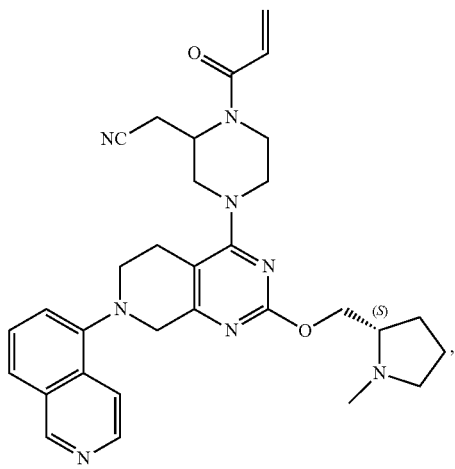

101
-continued
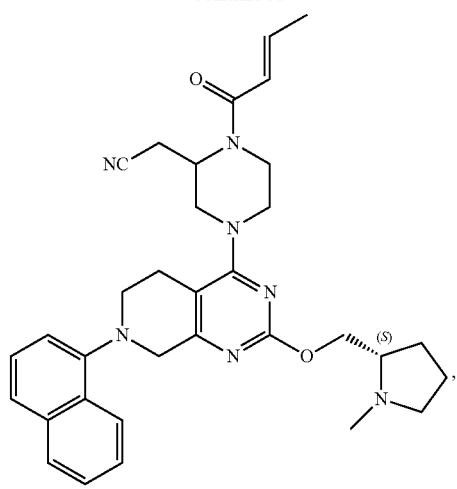
102
-continued
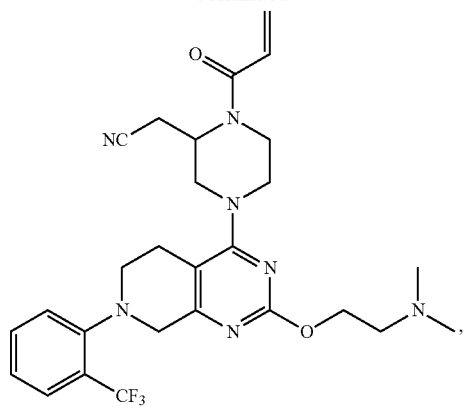
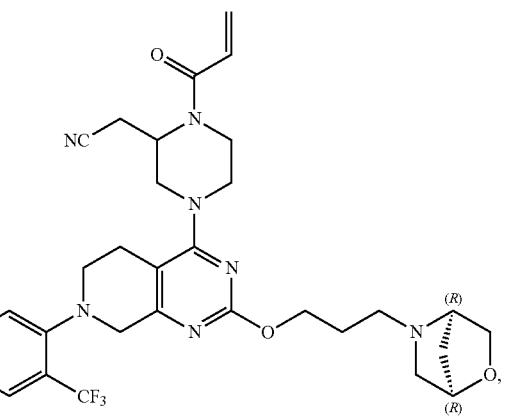
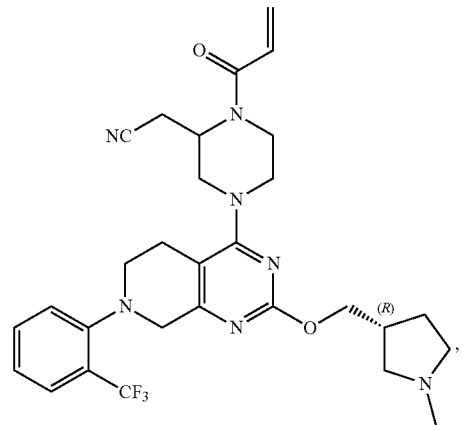
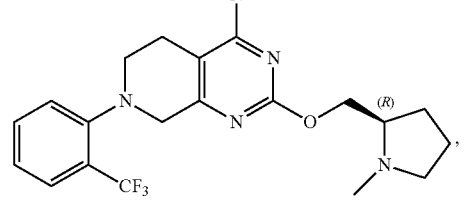

103
-continued
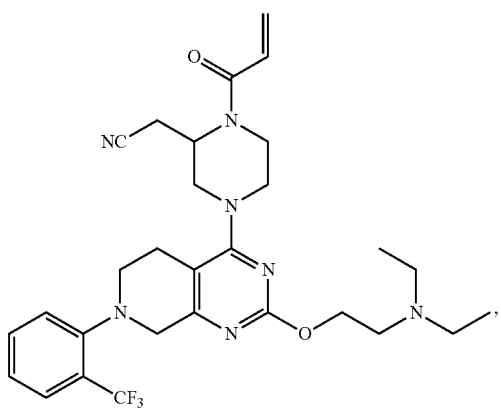
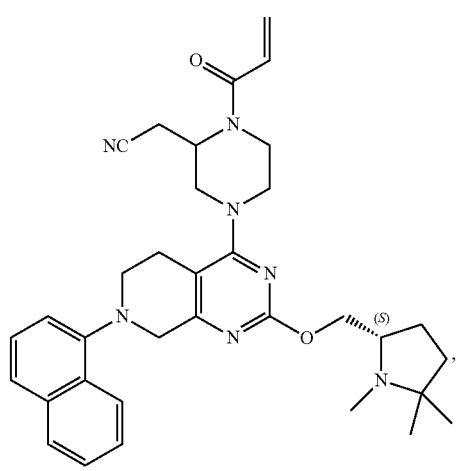
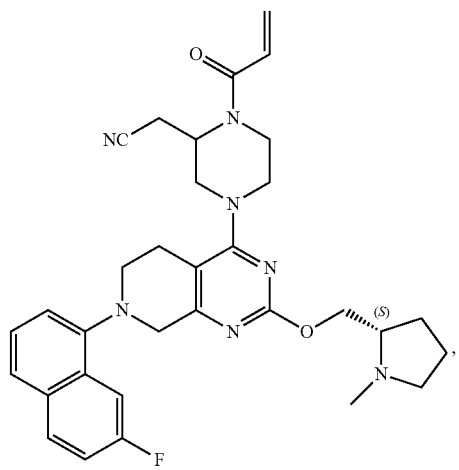
104
-continued
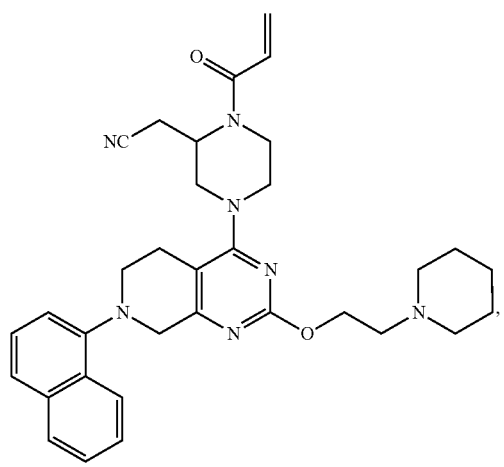
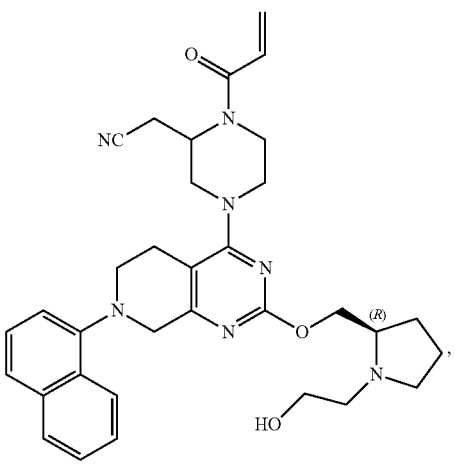
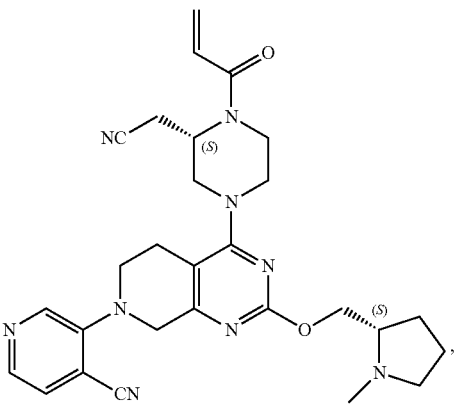

105
-continued
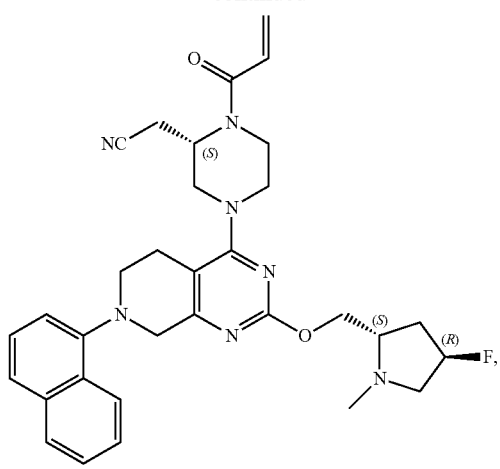
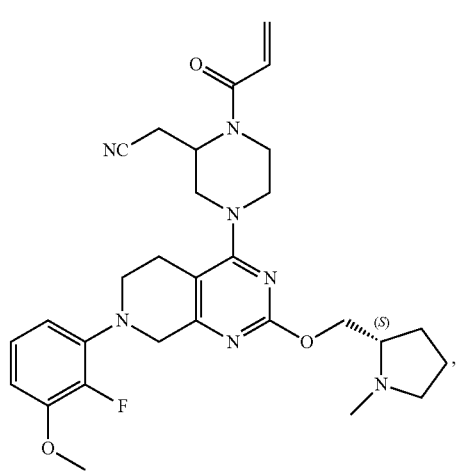
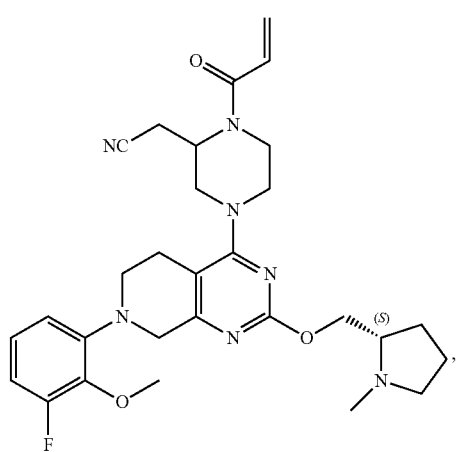
106
-continued
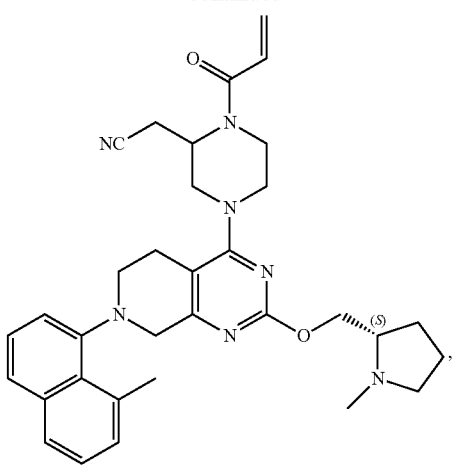
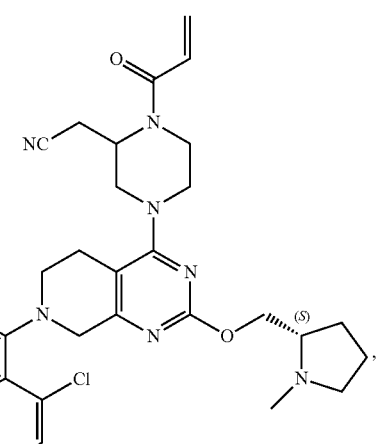
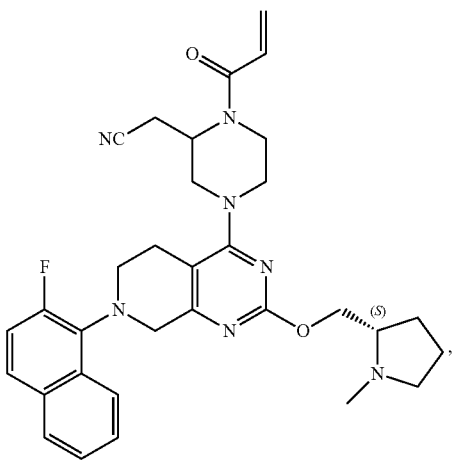

107
-continued
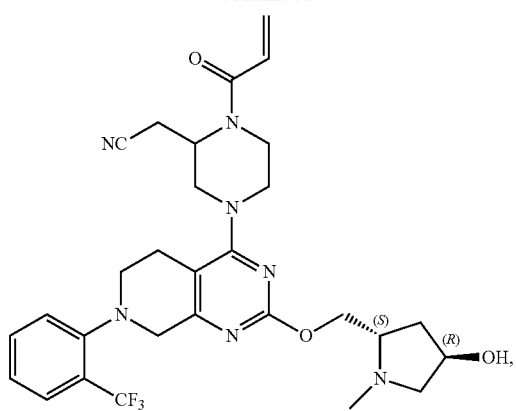
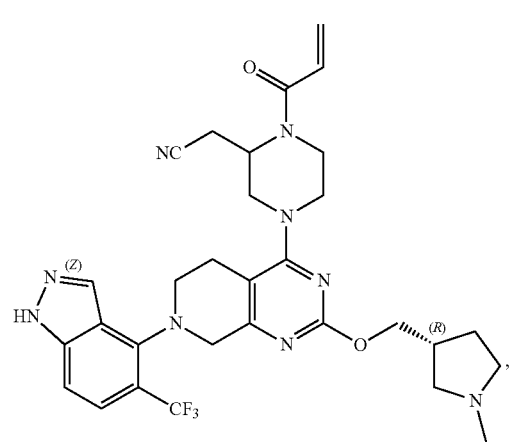
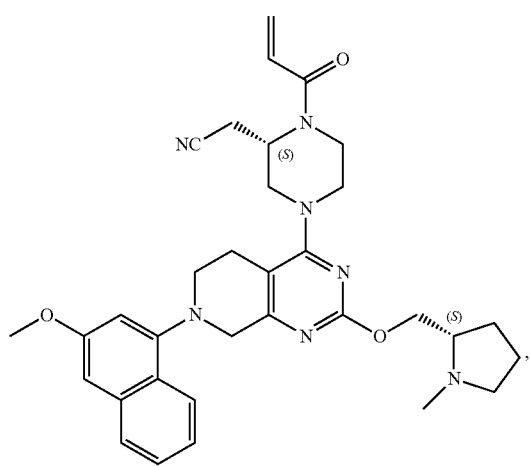
108
-continued
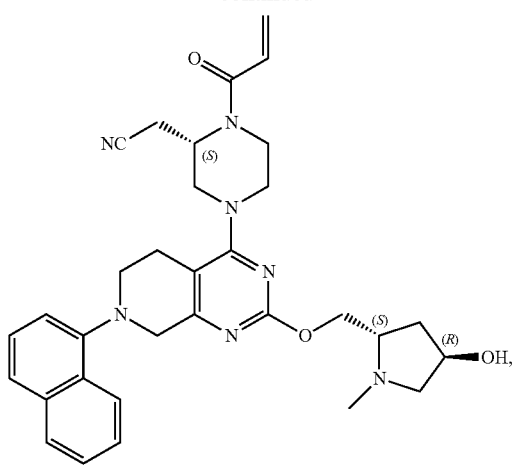
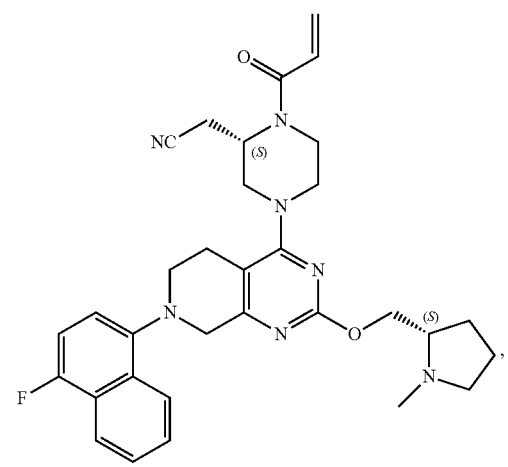
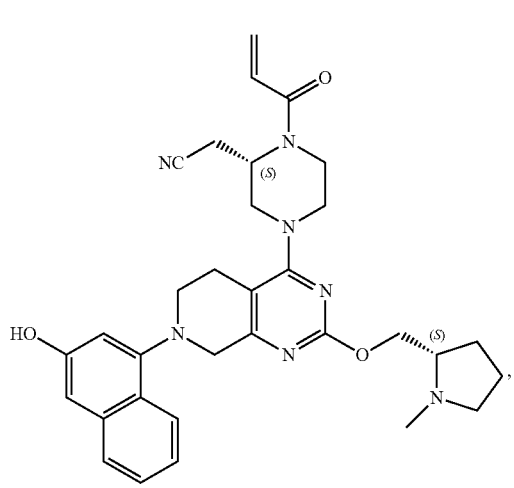

109
-continued
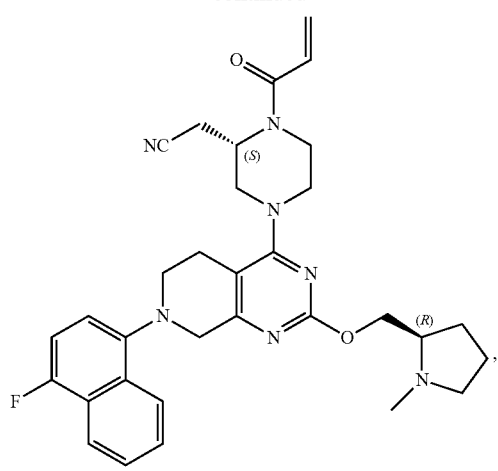
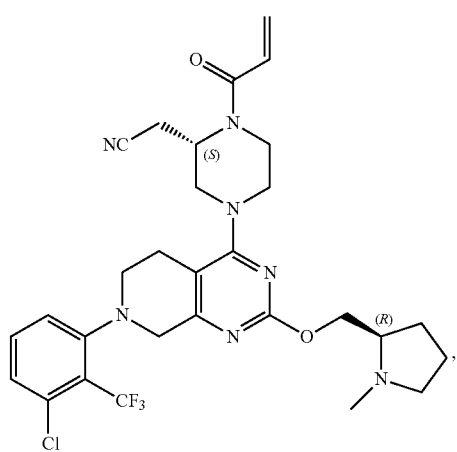
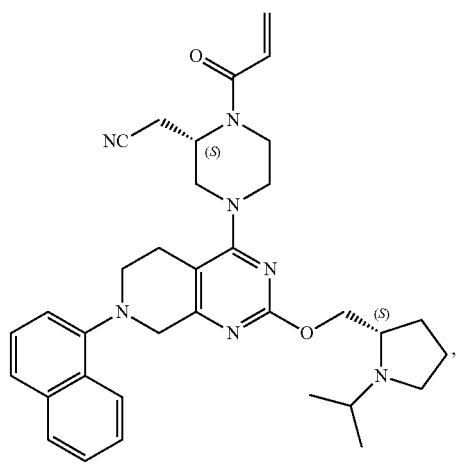
110
-continued
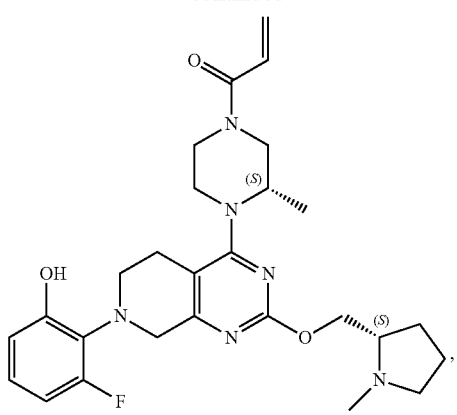
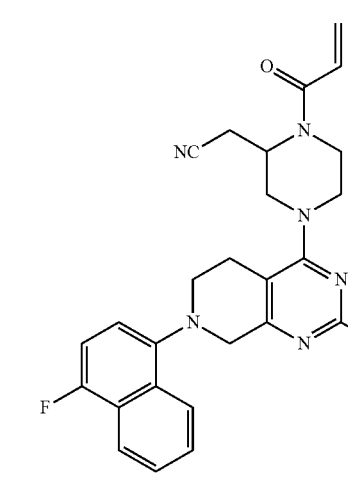
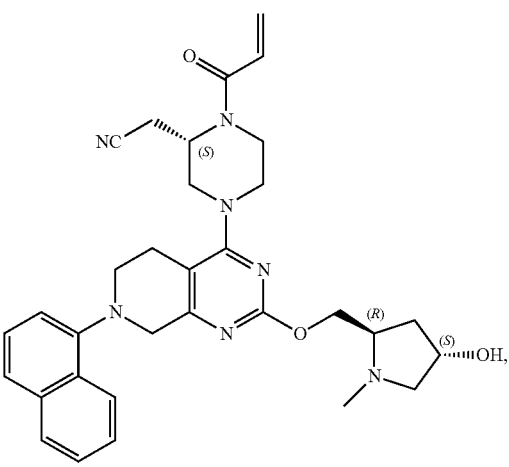

111
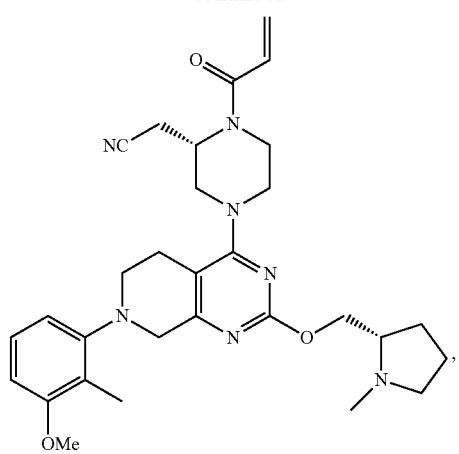
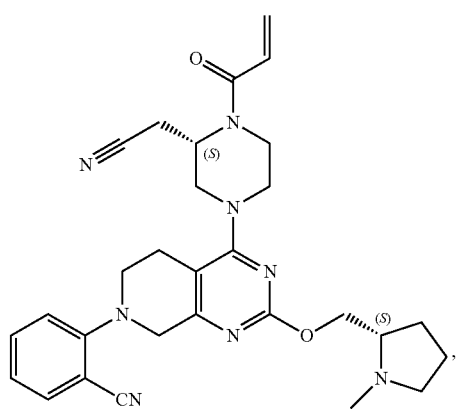
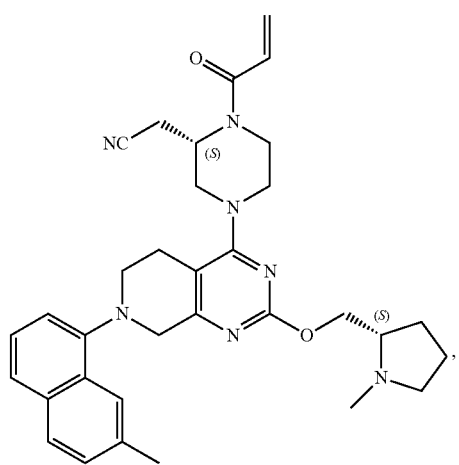
112
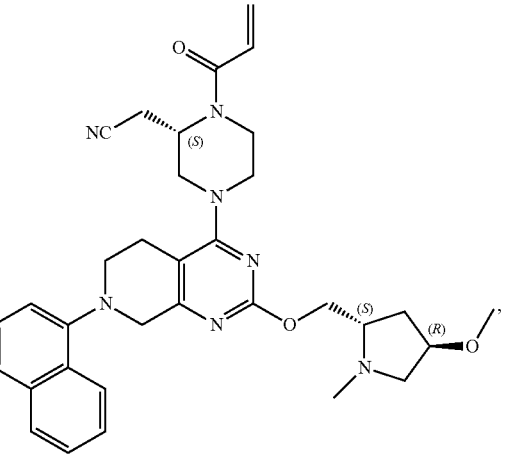
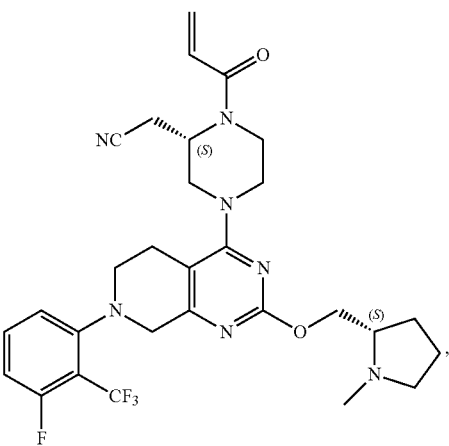
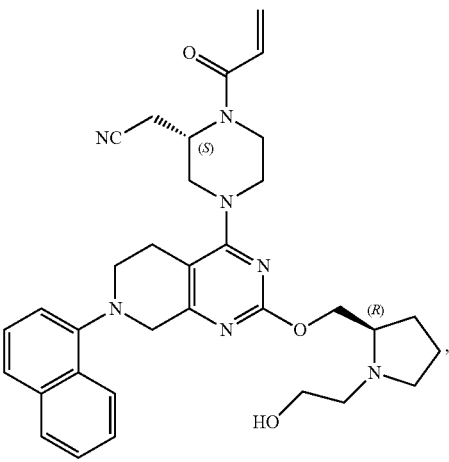

113
-continued
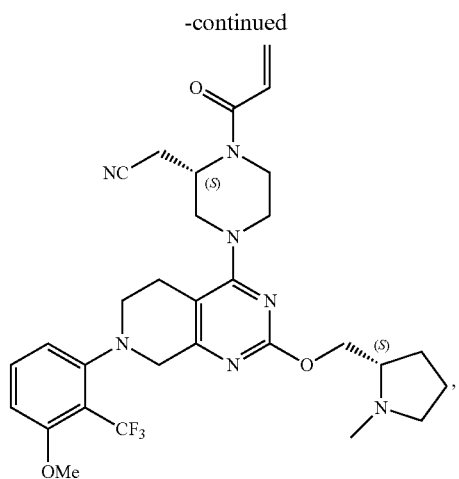
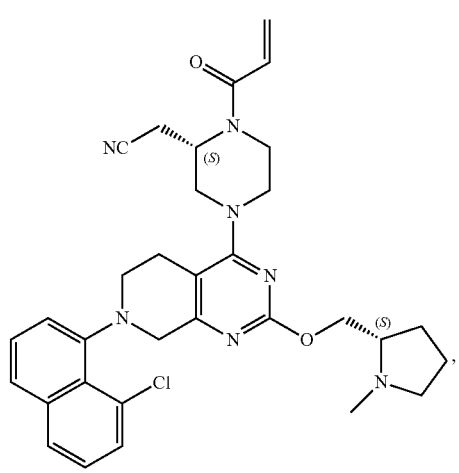
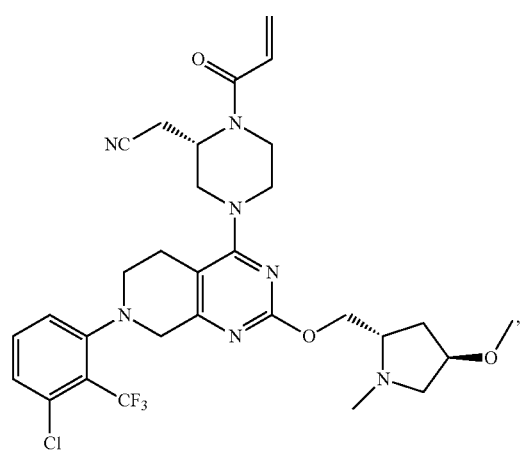
114
-continued
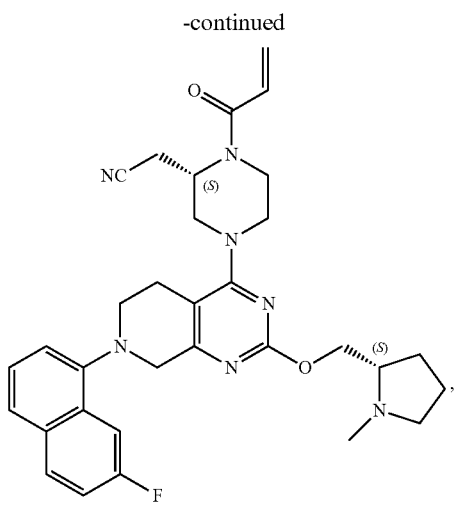
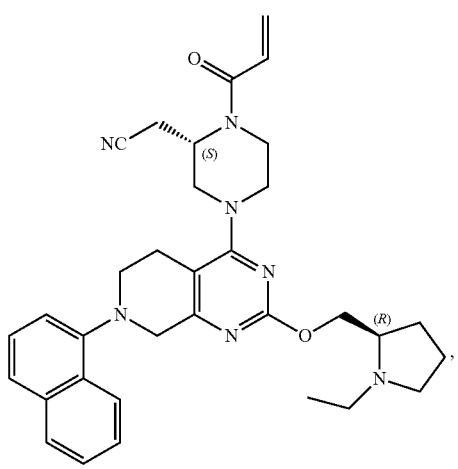
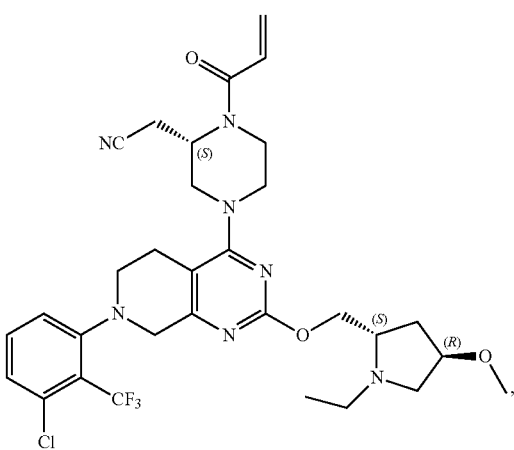

115
-continued
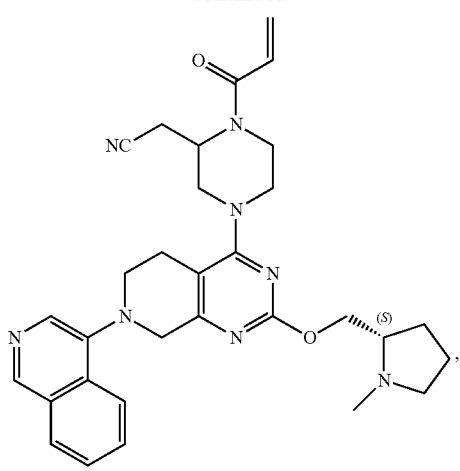
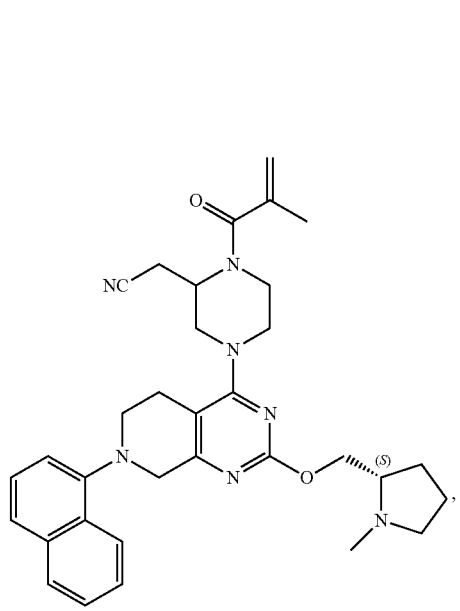
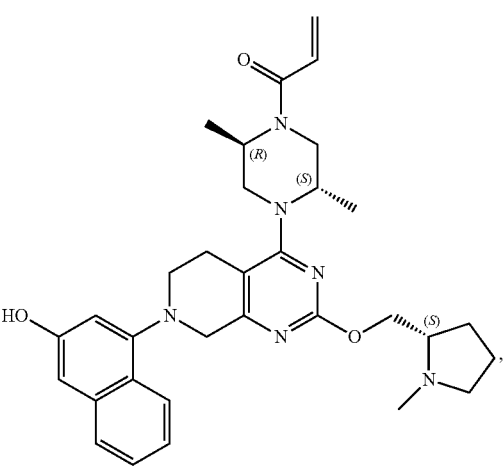
116
-continued
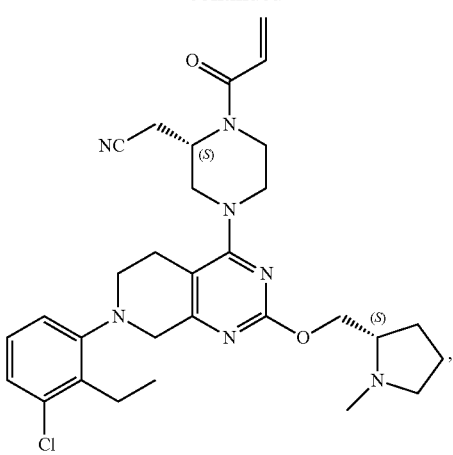
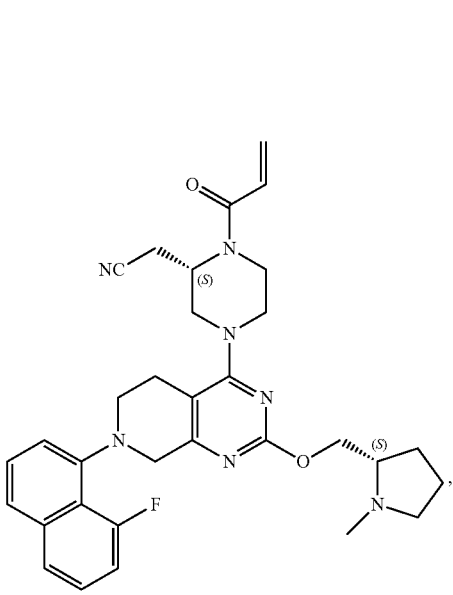
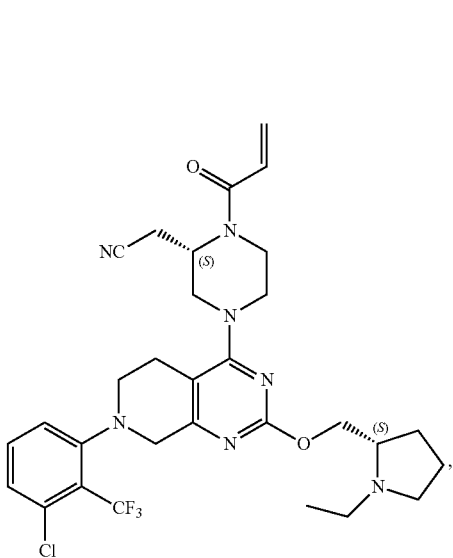

117
-continued
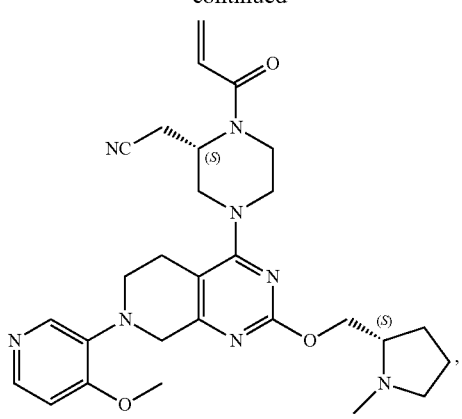
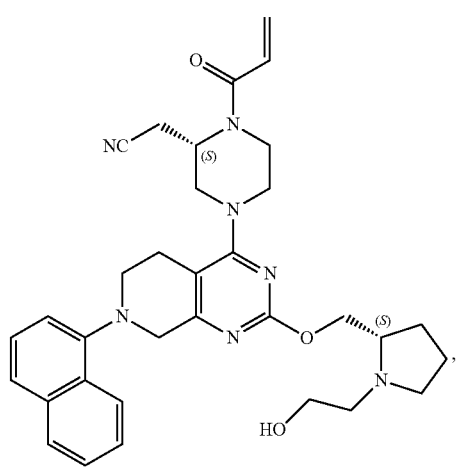
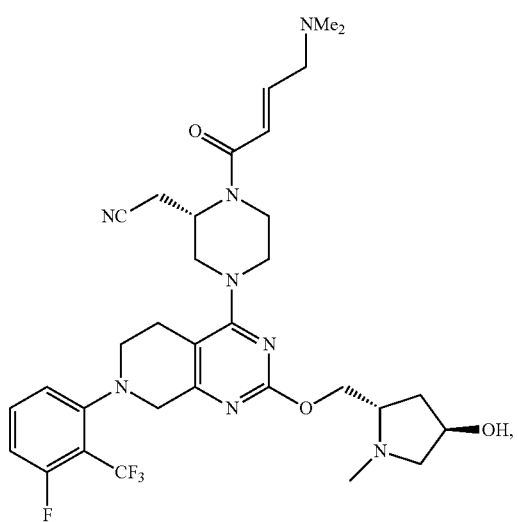
118
-continued
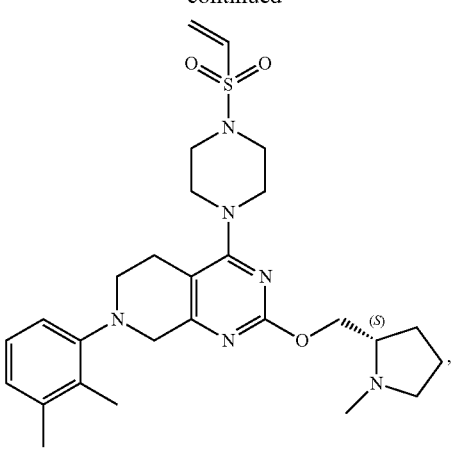
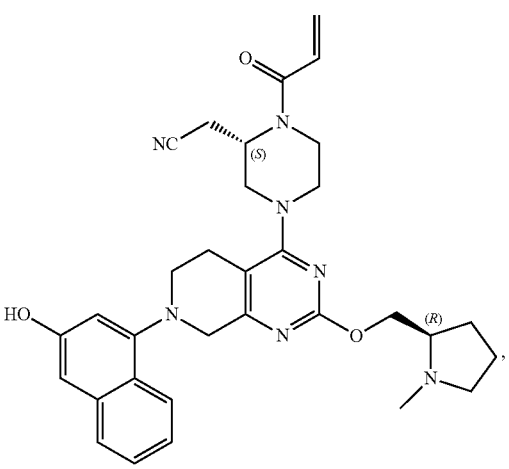
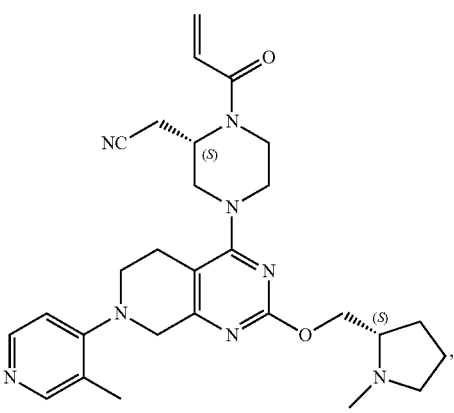

119
-continued
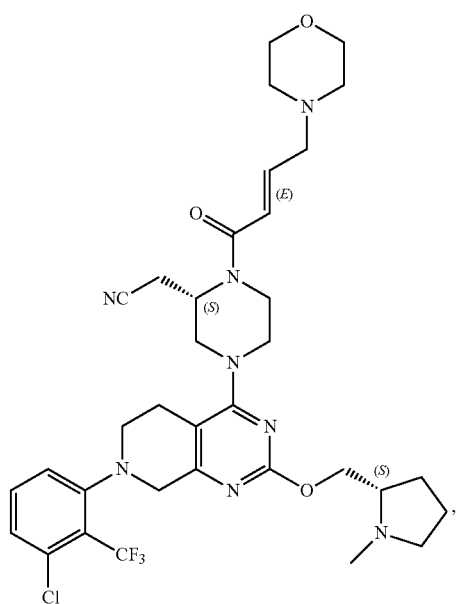
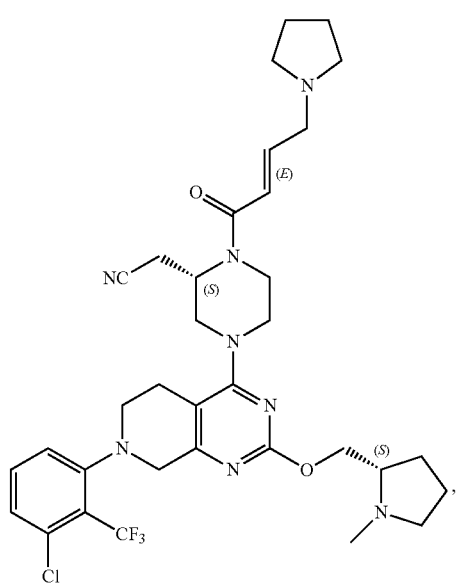
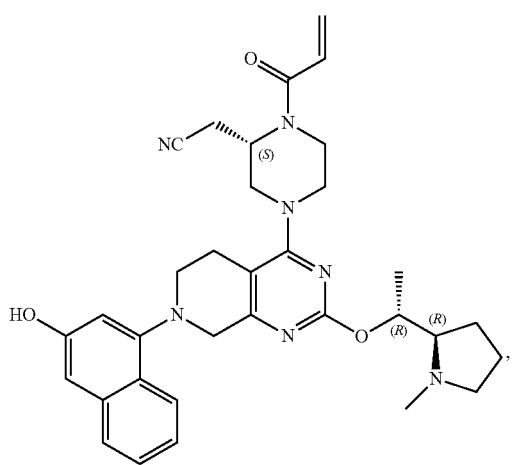
120
-continued
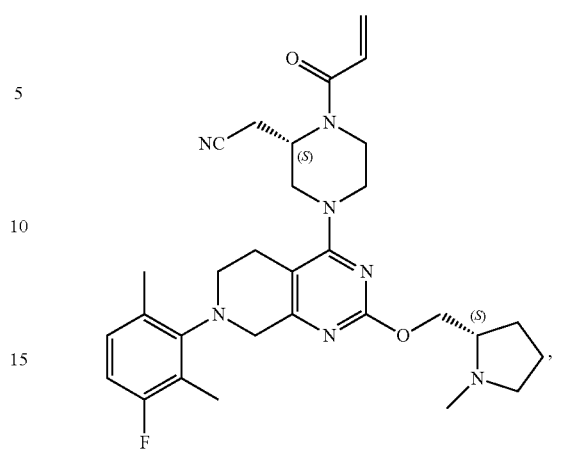
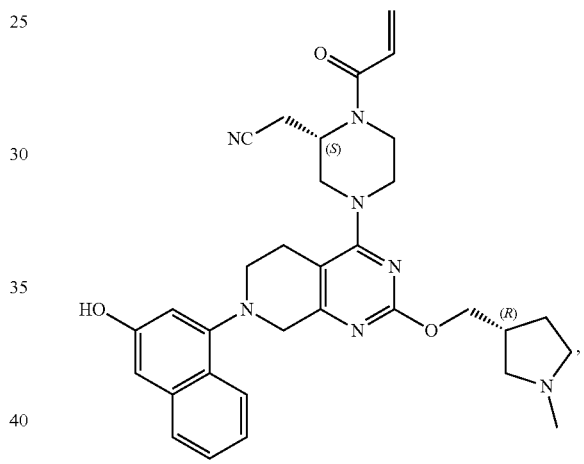
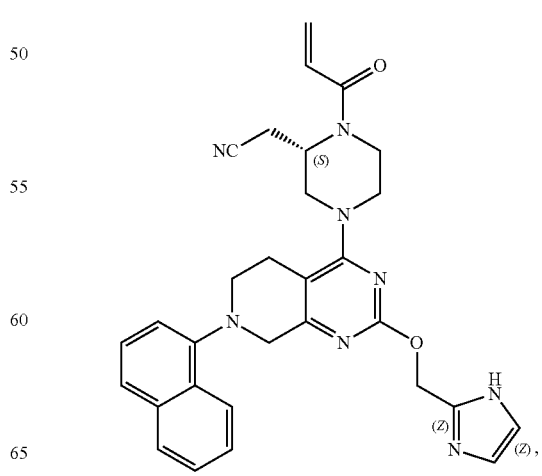

121
-continued
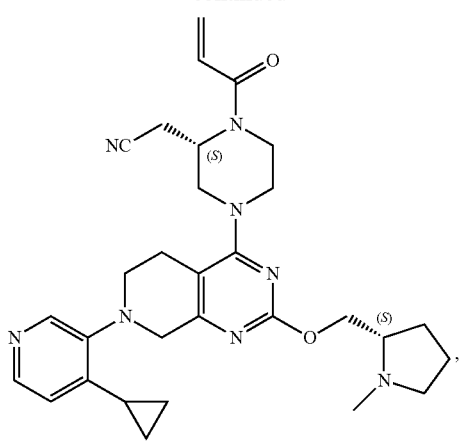
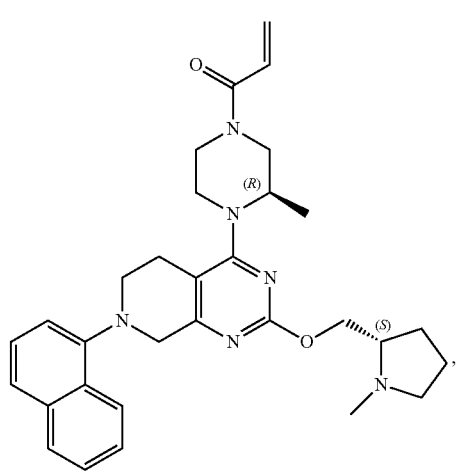
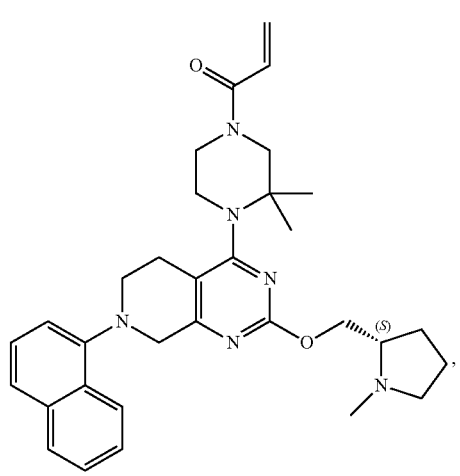
122
-continued
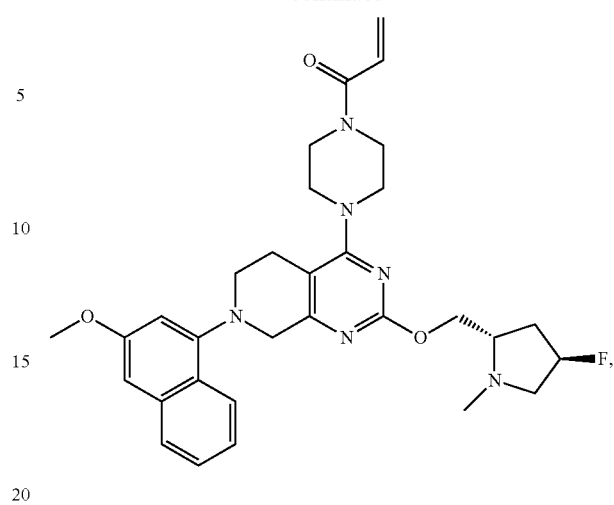
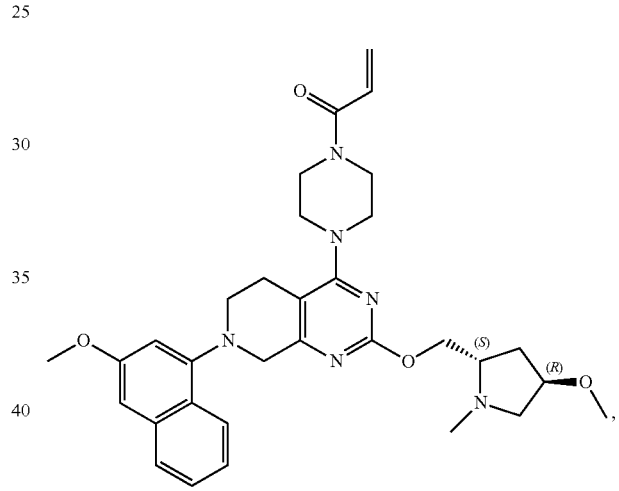
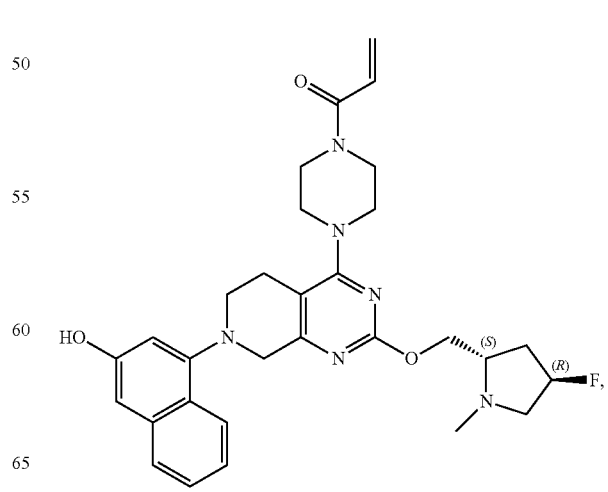

123
-continued
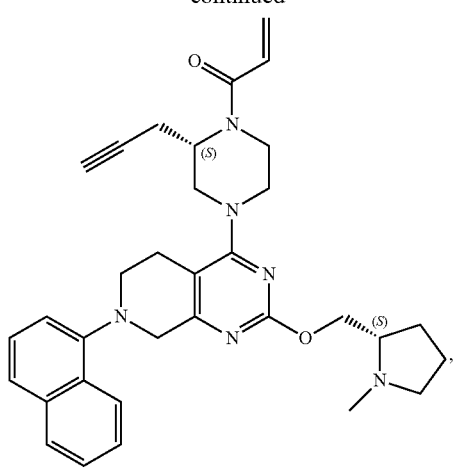
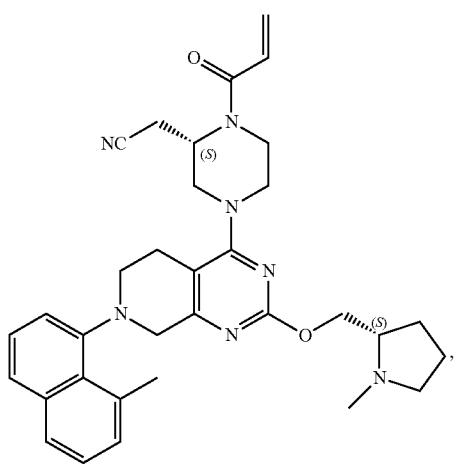
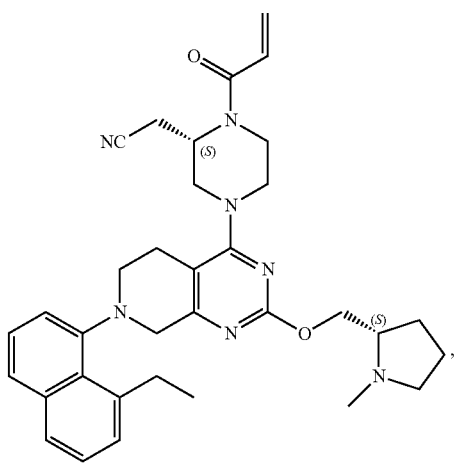
124
-continued
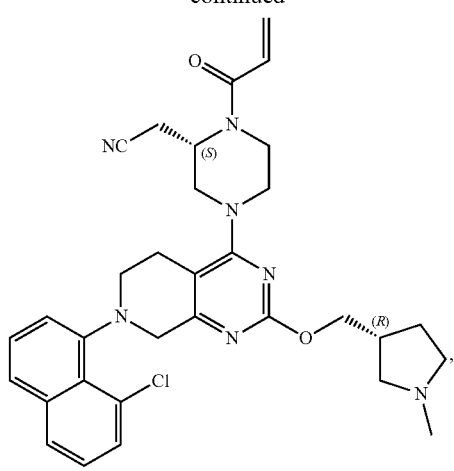
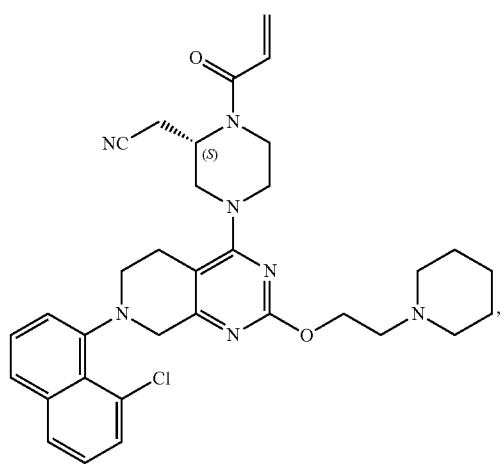
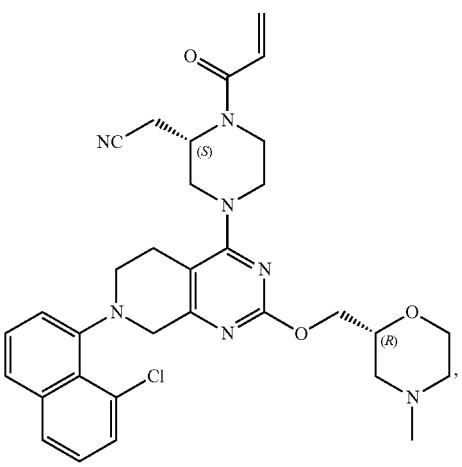

125
-continued
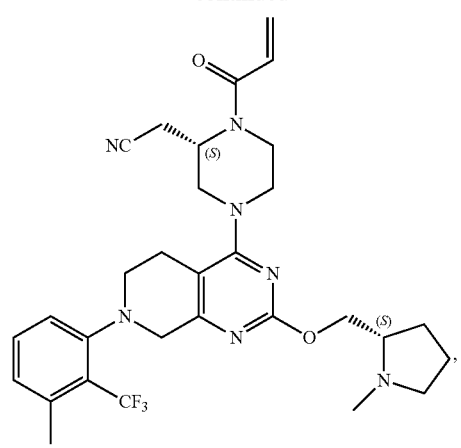
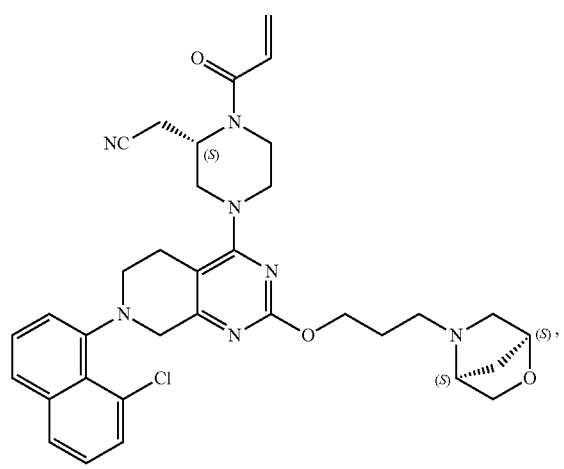
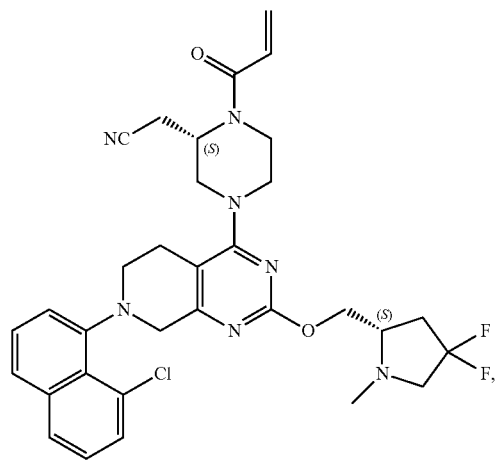
126
-continued
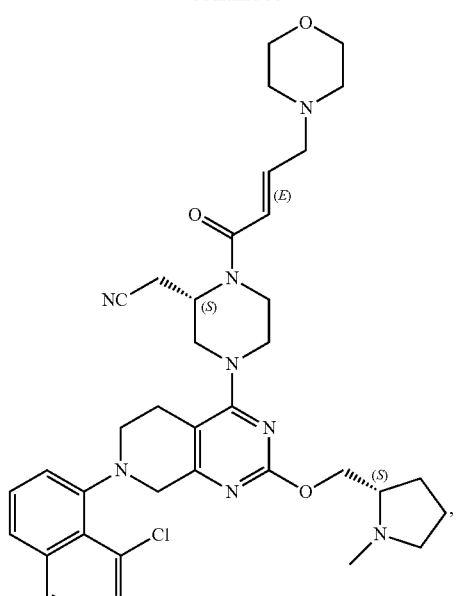
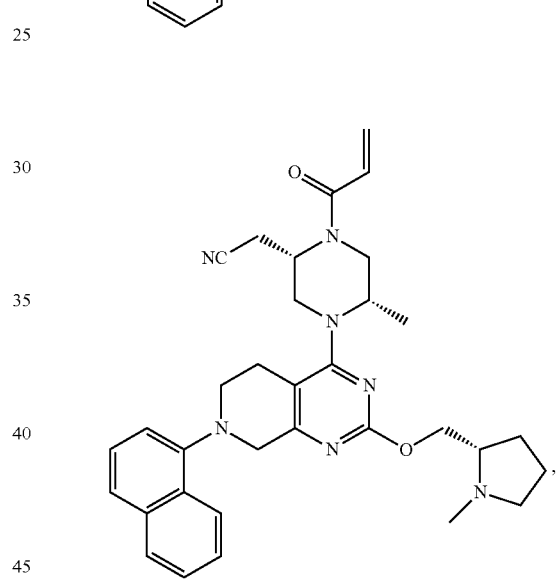
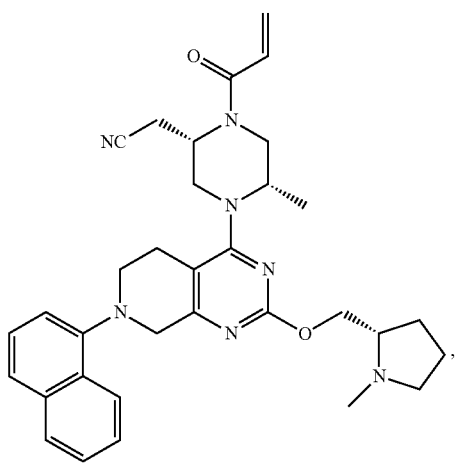
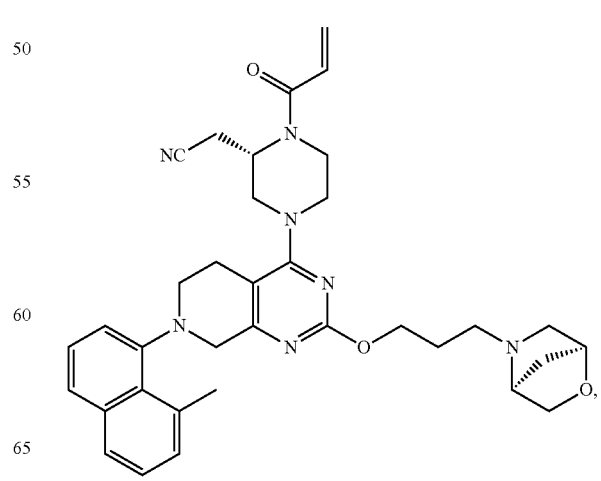
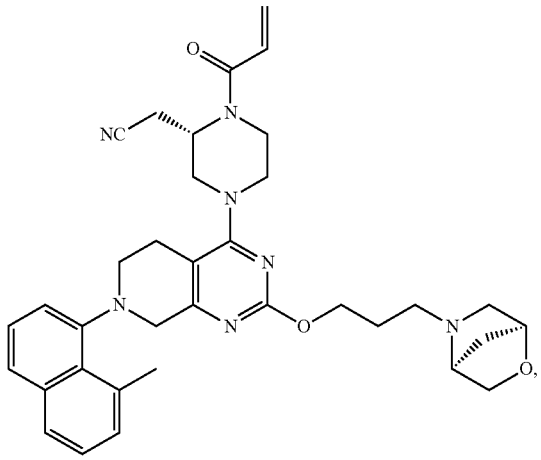

127
-continued
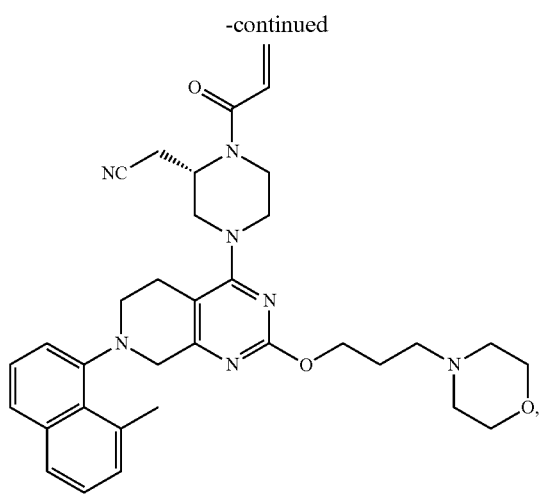
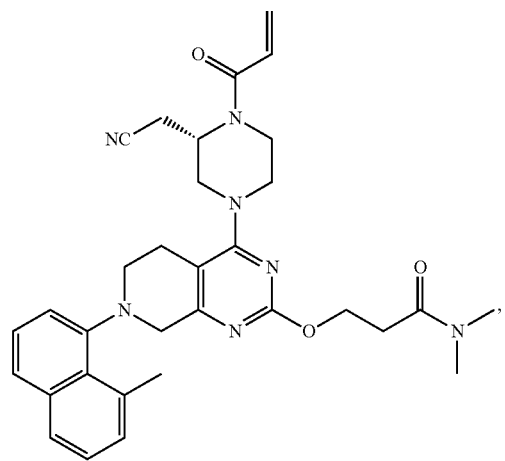
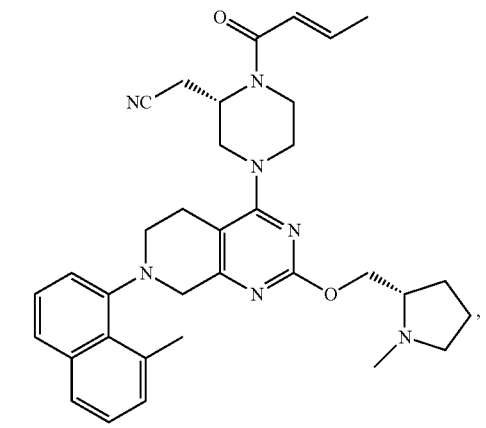
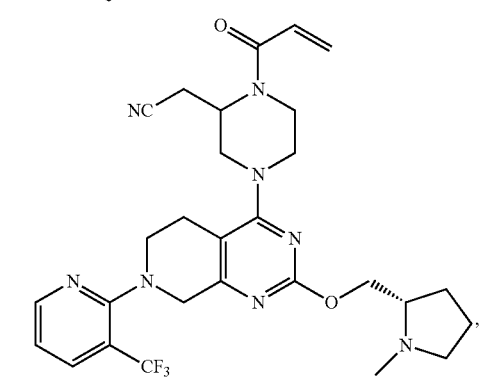
128
-continued
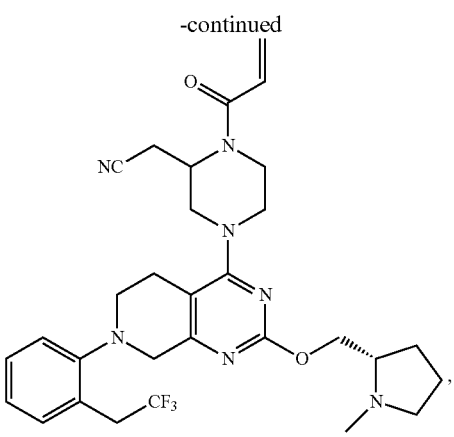
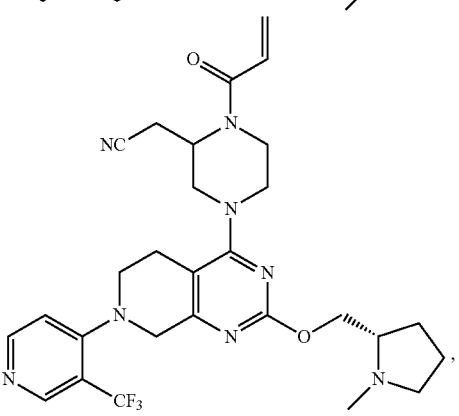
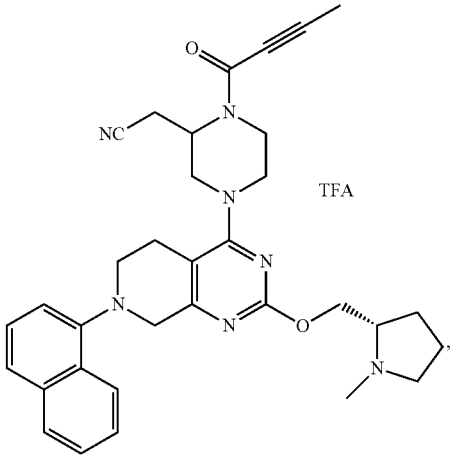
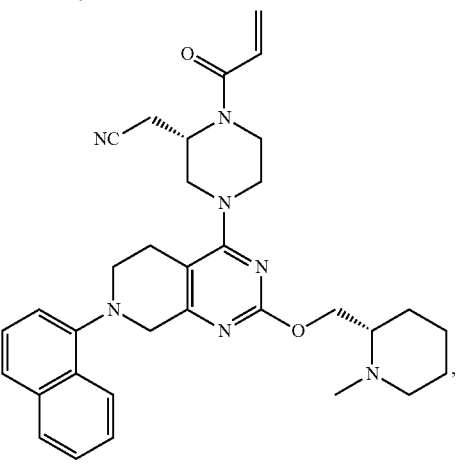

129
-continued
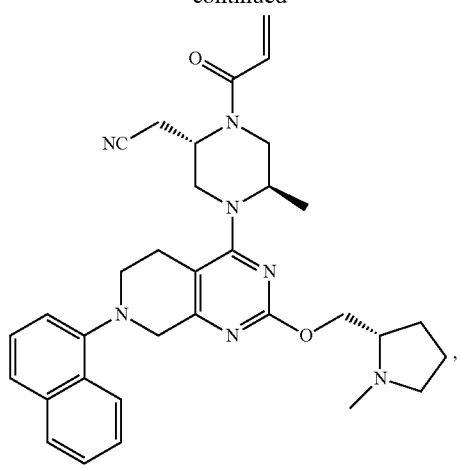
,
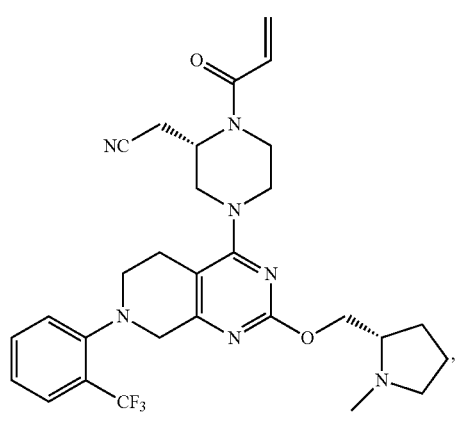
,
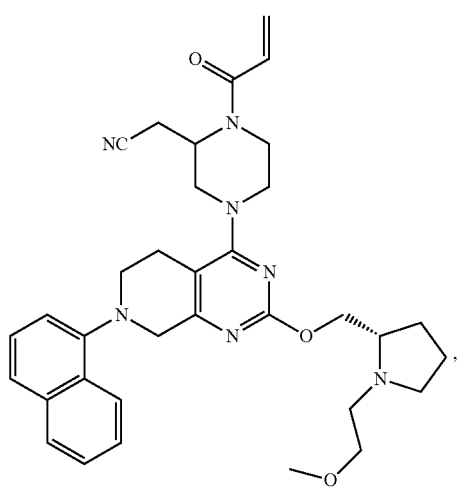
,
130
-continued
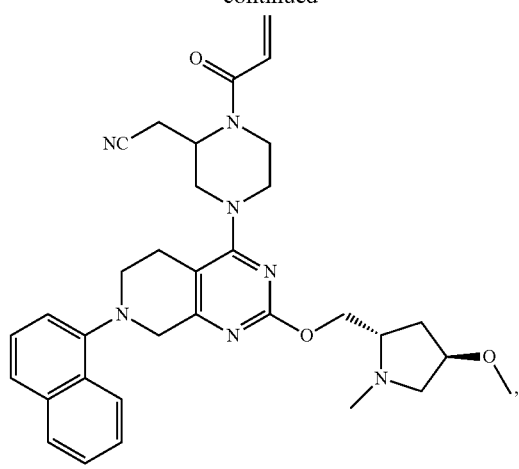
,
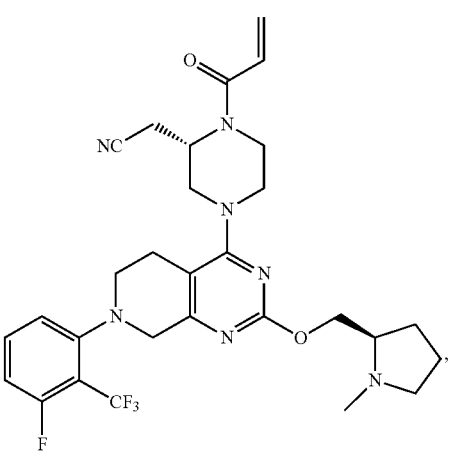
,
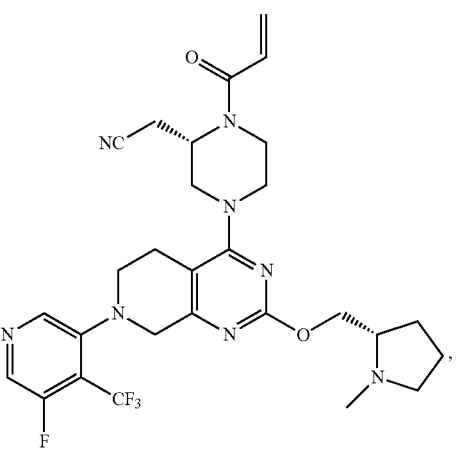

131
-continued
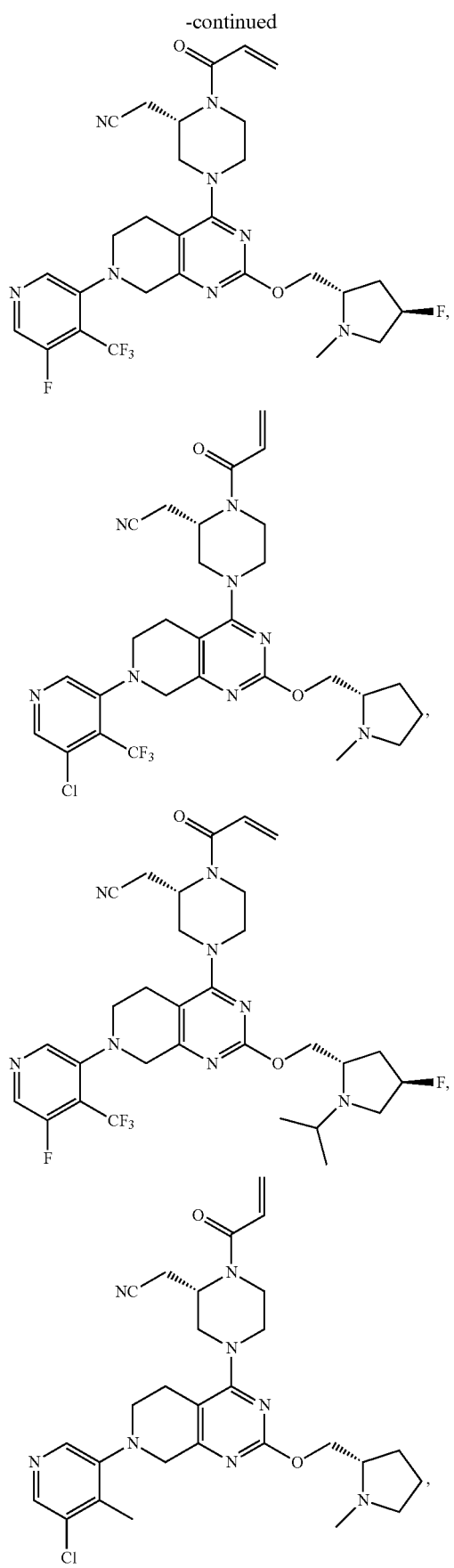
132
-continued
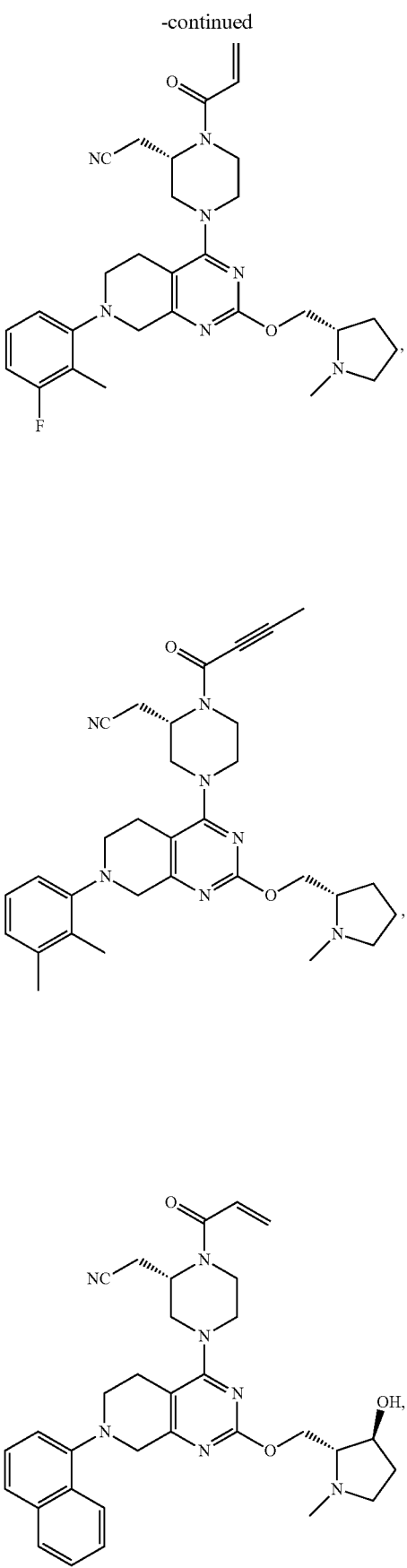

133
-continued
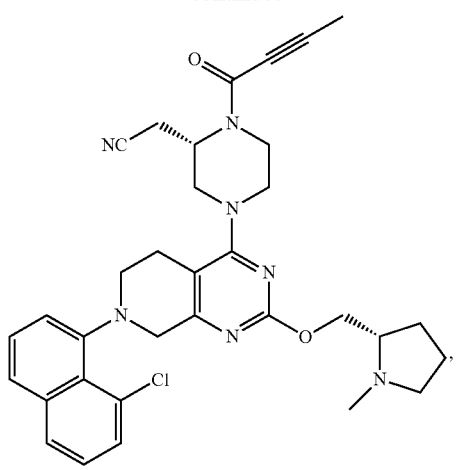
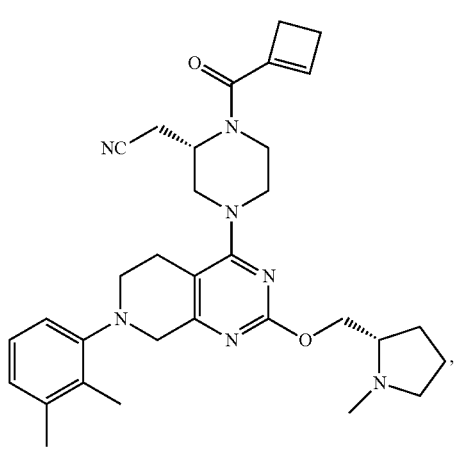
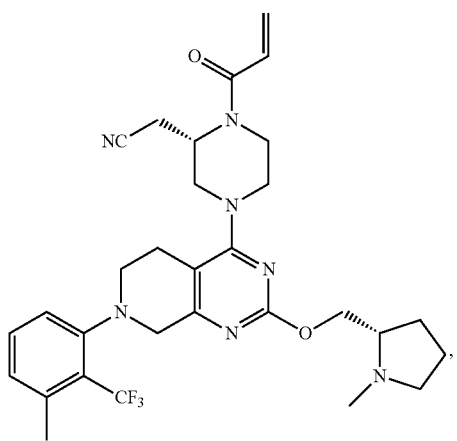
134
-continued
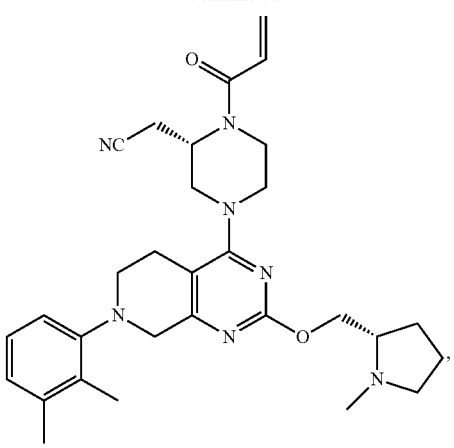
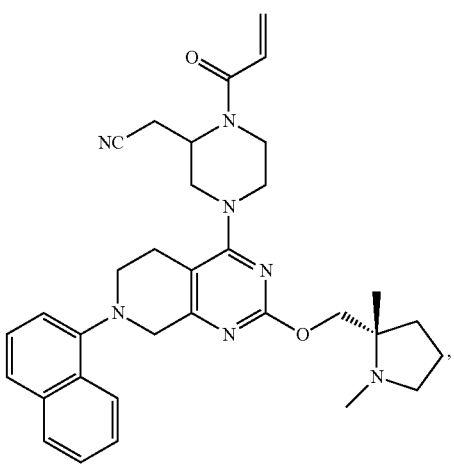
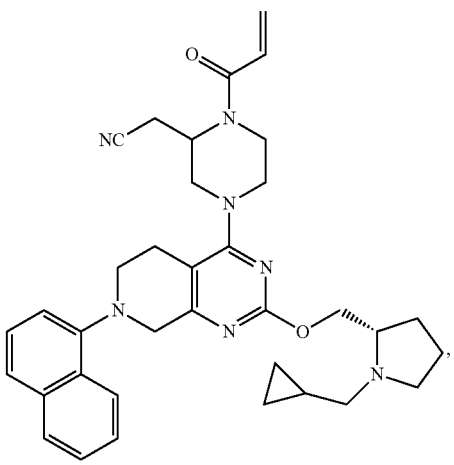

135
-continued
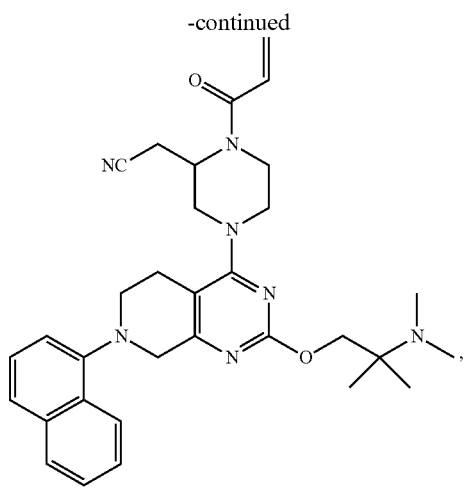
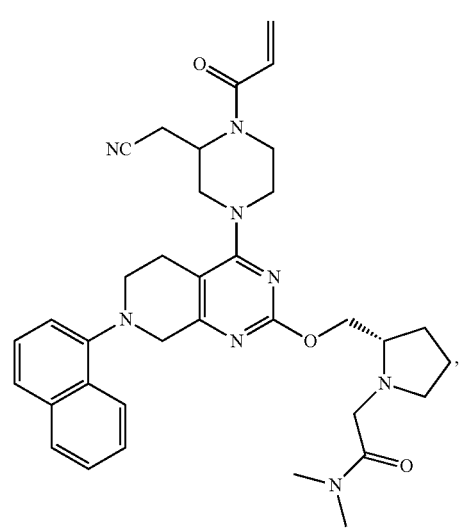
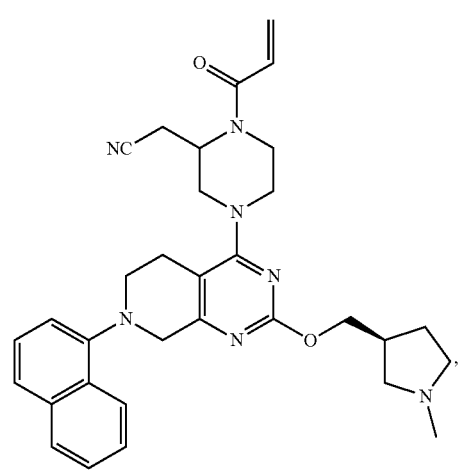
136
-continued
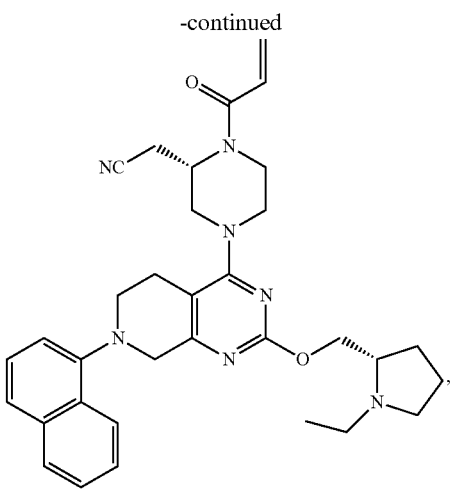
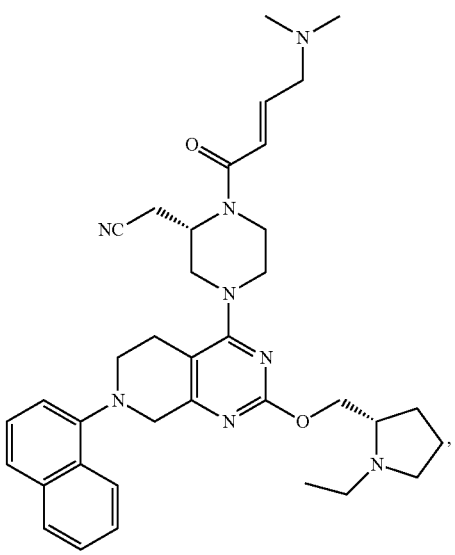
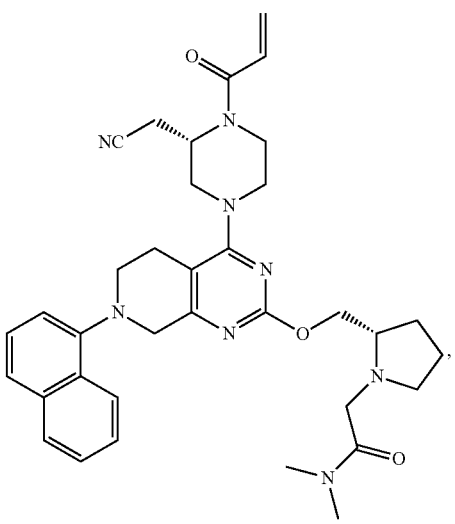

137
-continued
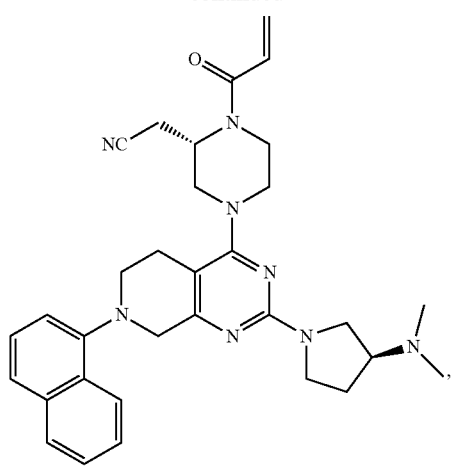
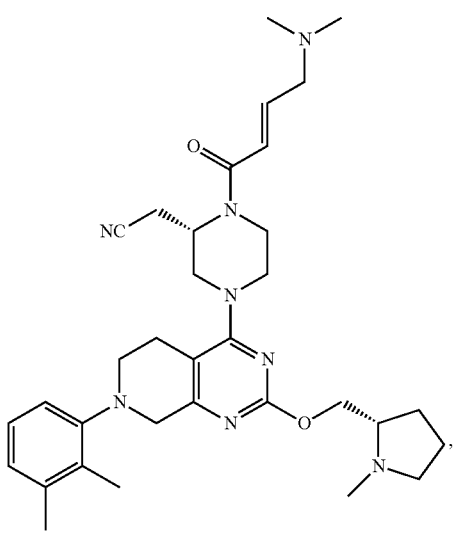
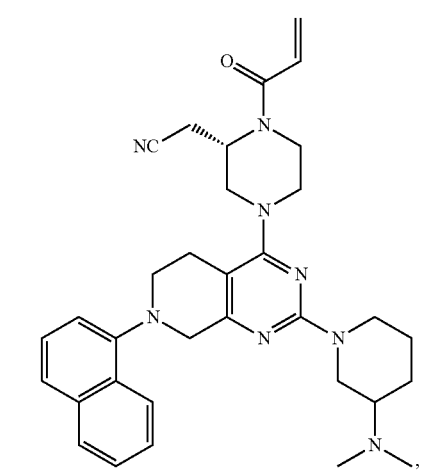
138
-continued
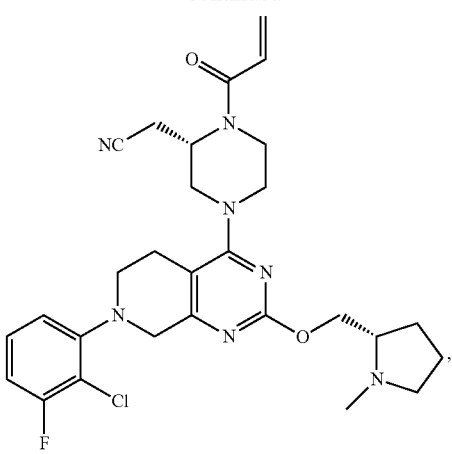
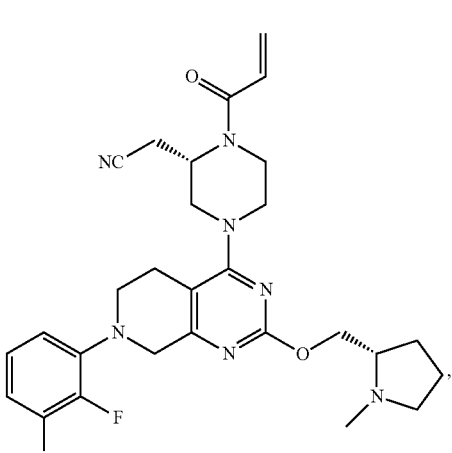
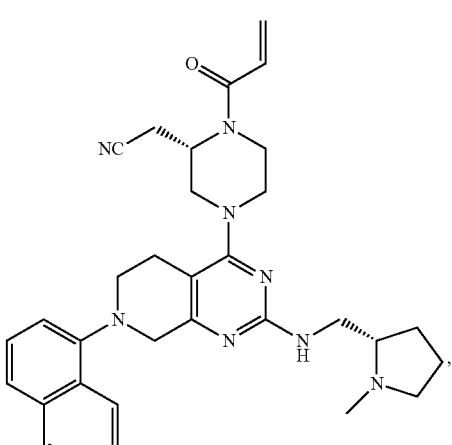

139
-continued
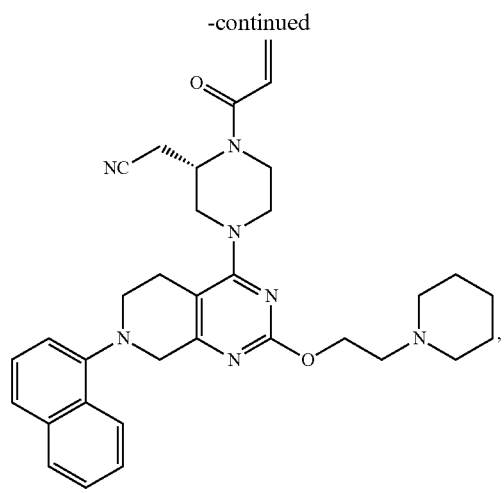
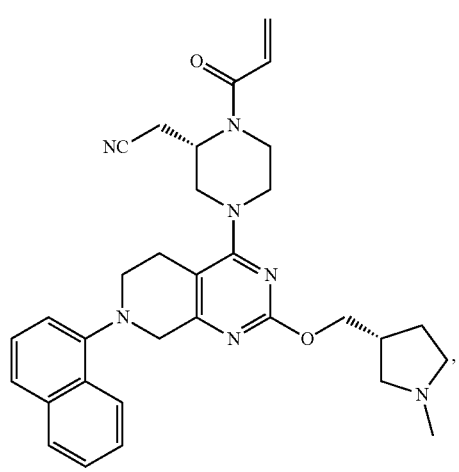
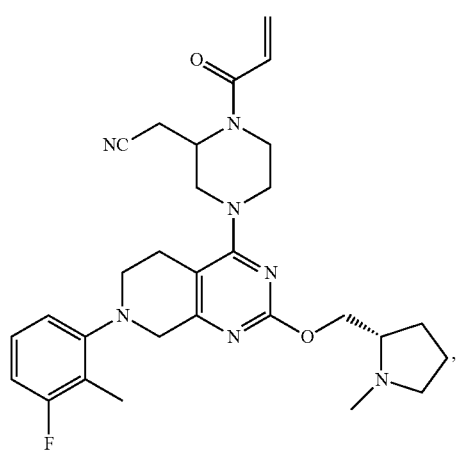
140
-continued
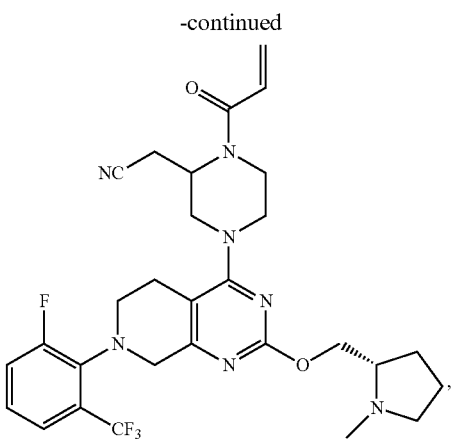
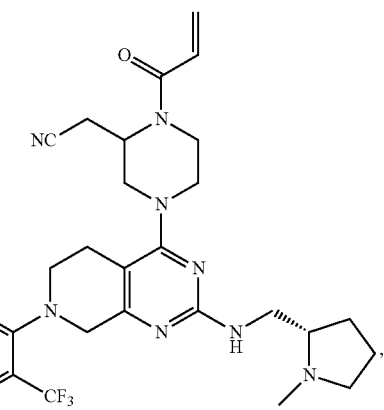
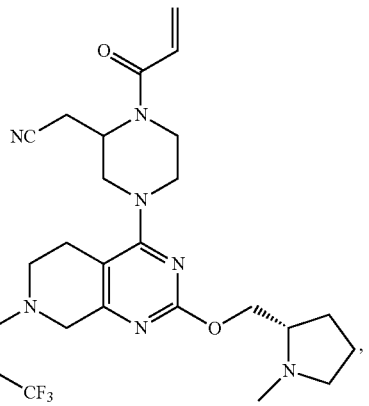
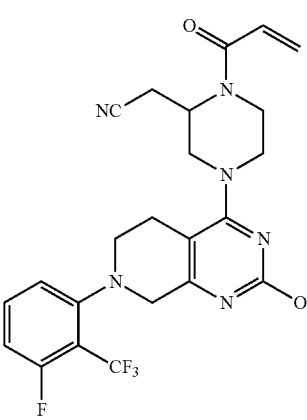

141
-continued
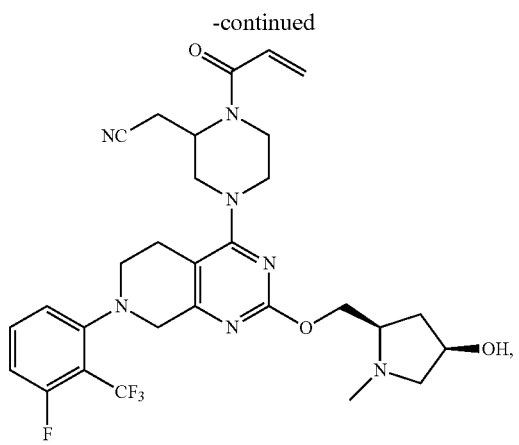
142
-continued
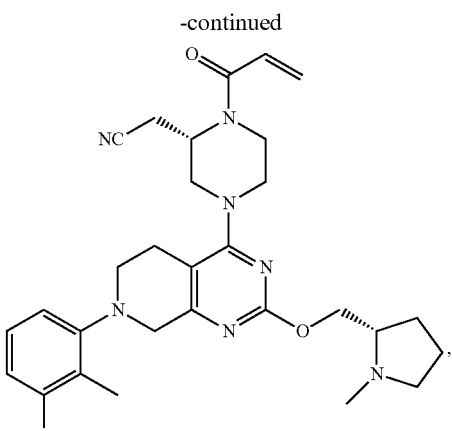
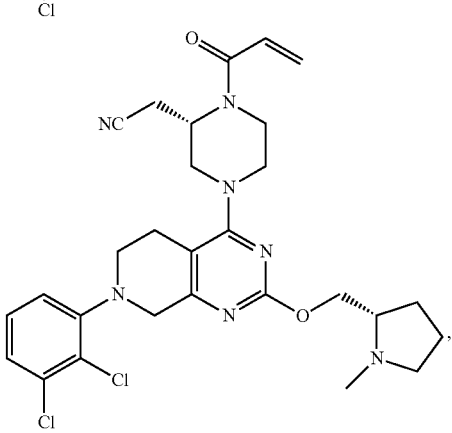
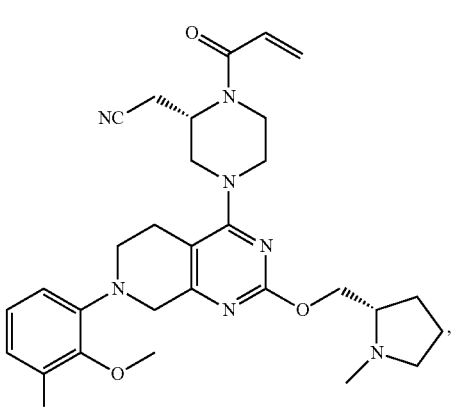
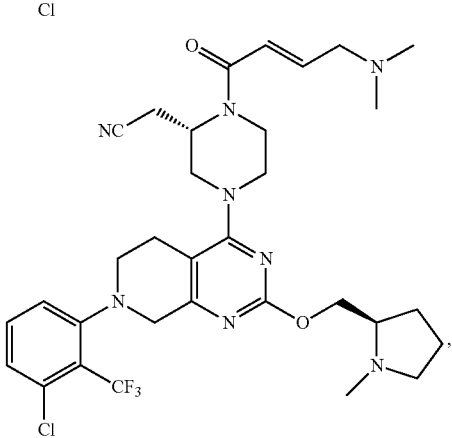

143
-continued
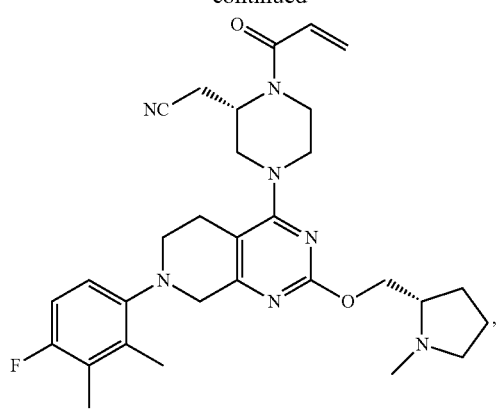
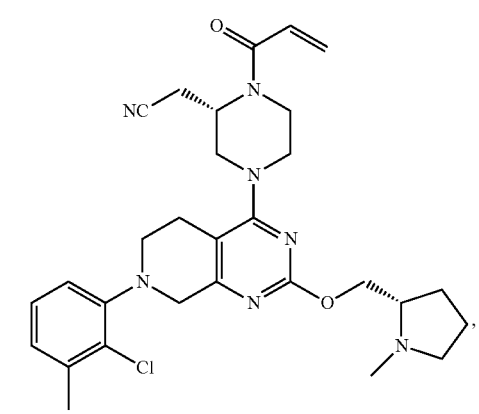
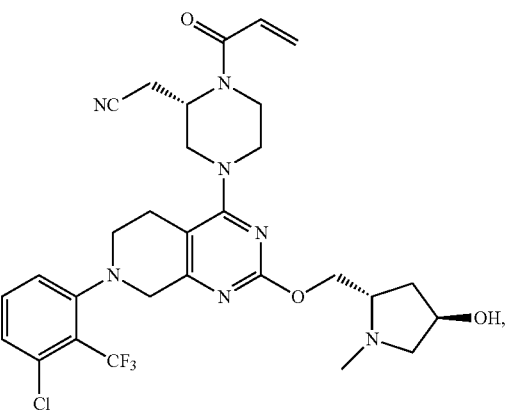
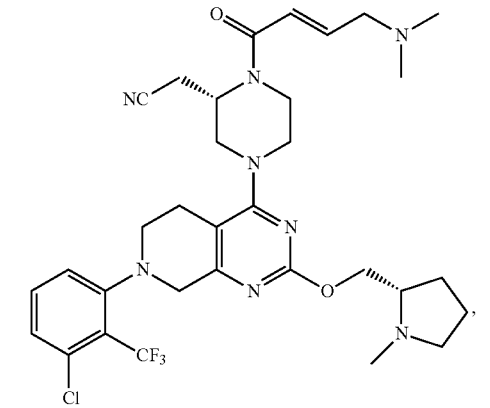
144
-continued
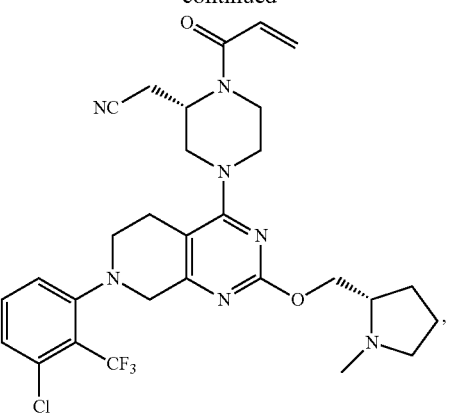
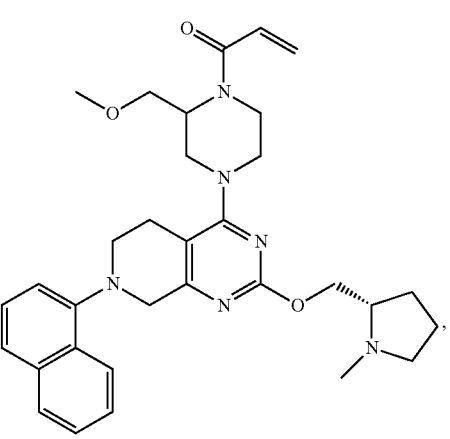
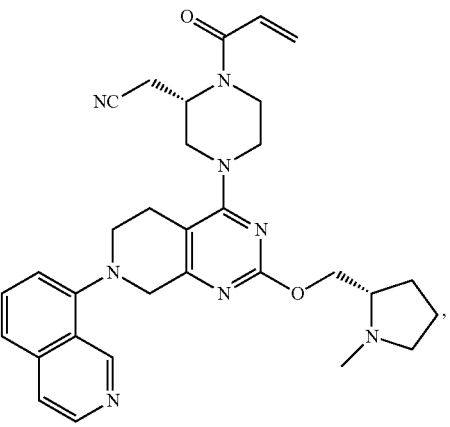
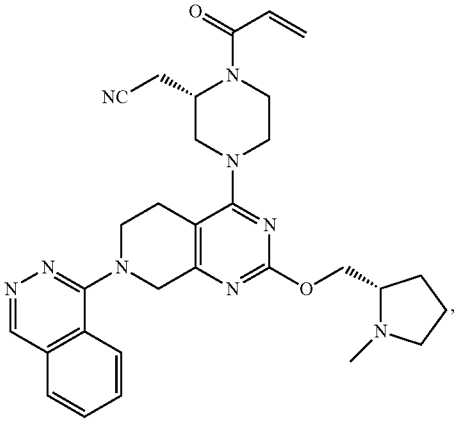

145 146
-continued -continued
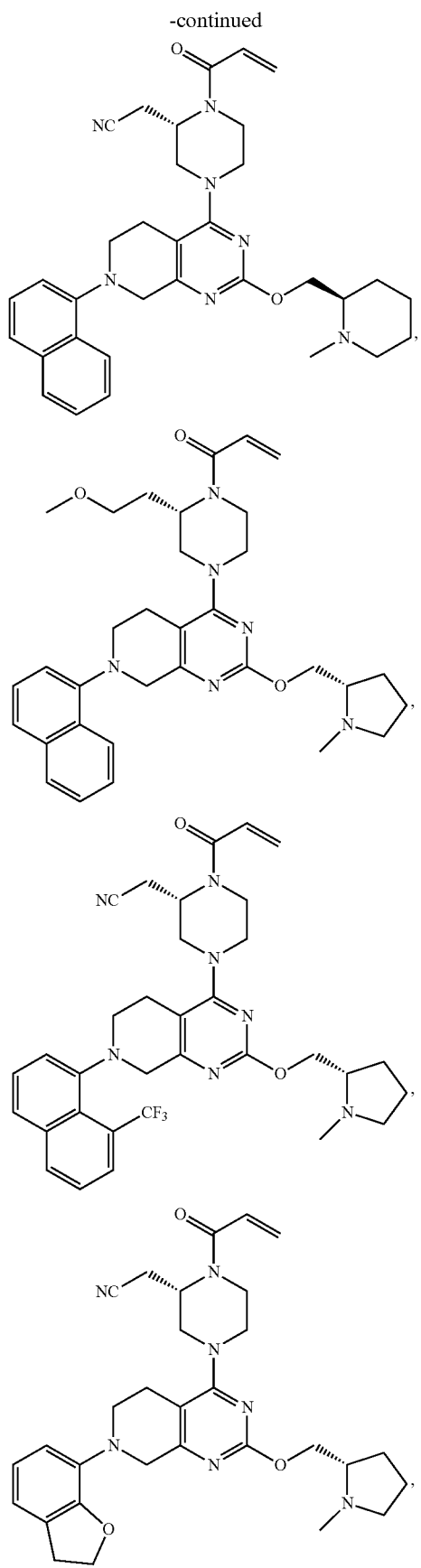
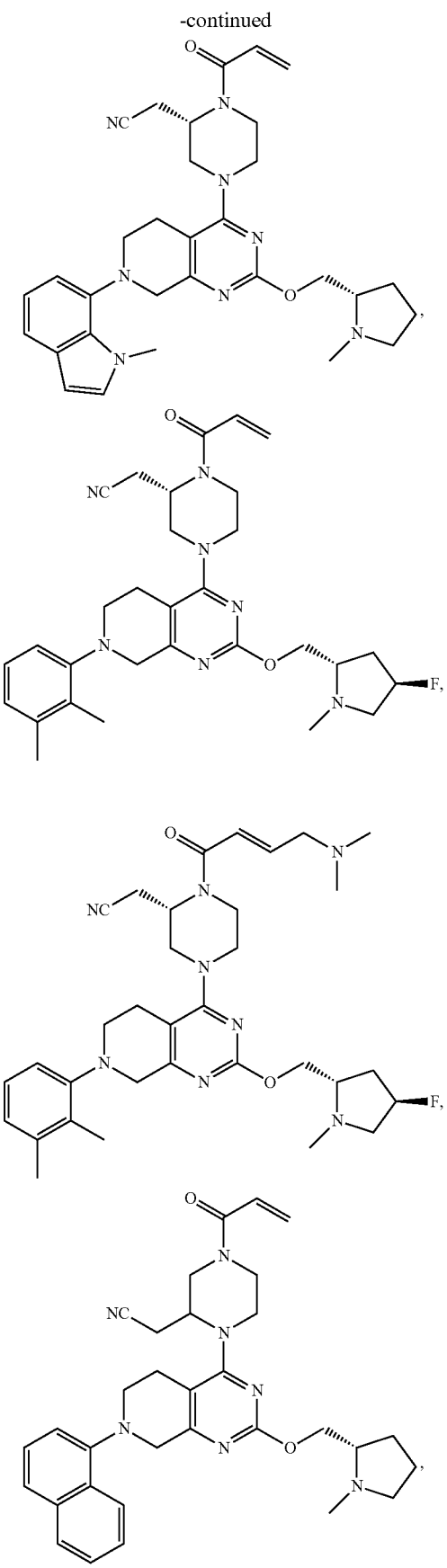

147
-continued
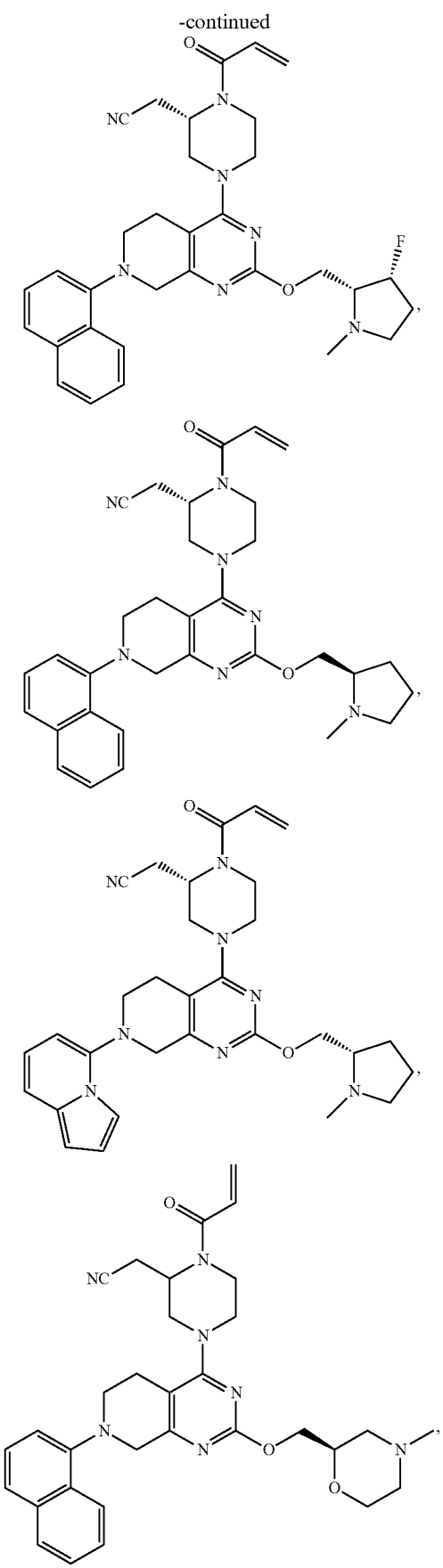
148
-continued
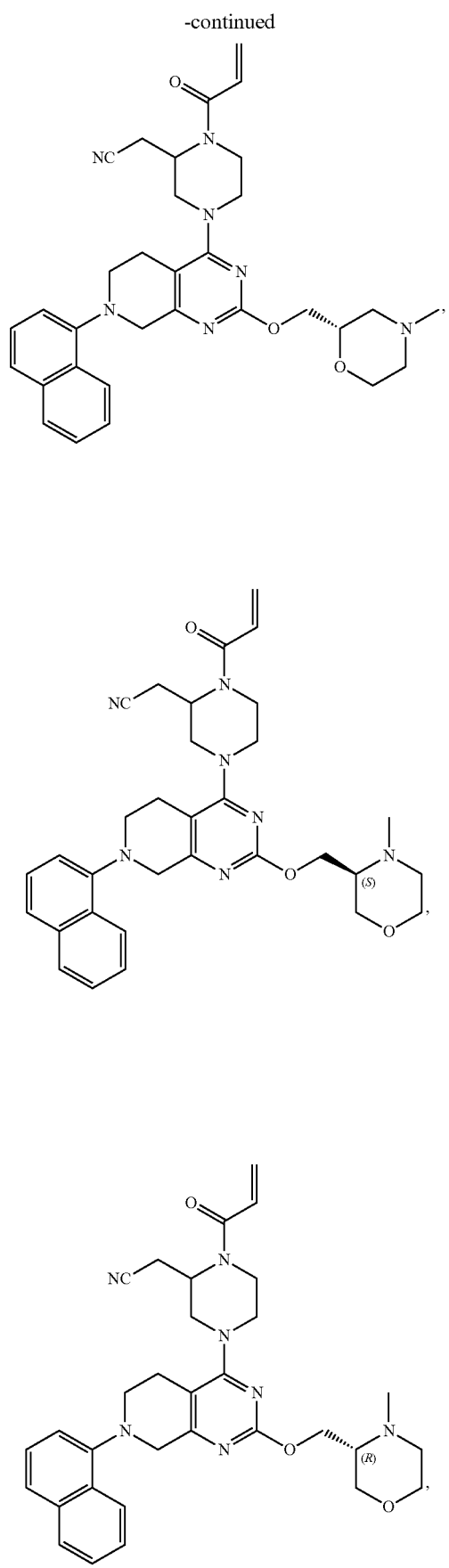

149
-continued
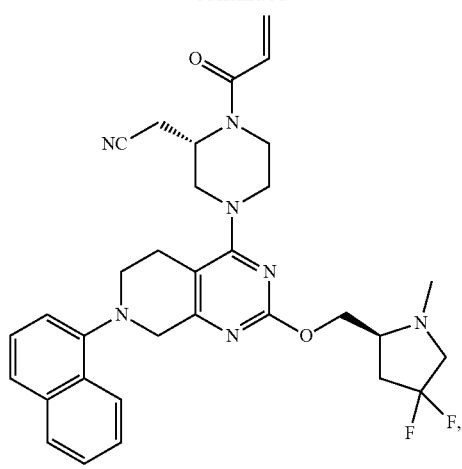
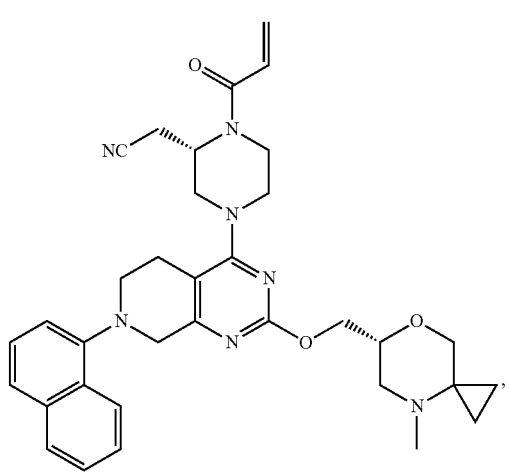
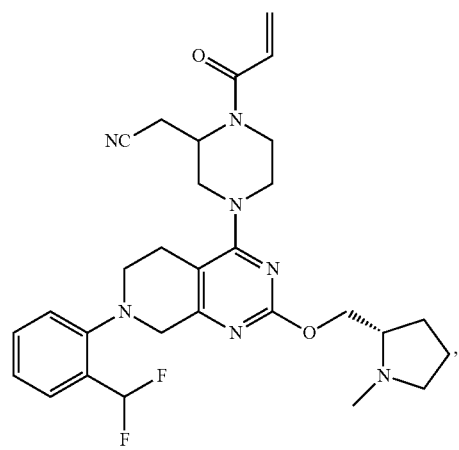
150
-continued
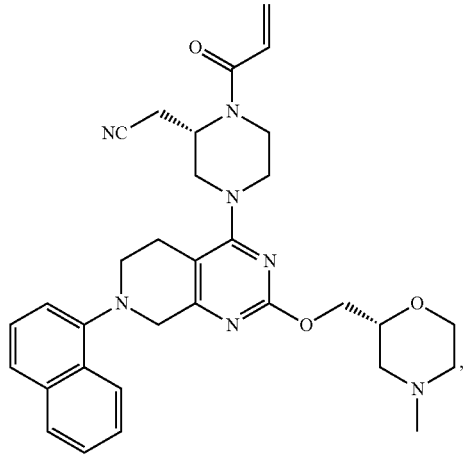
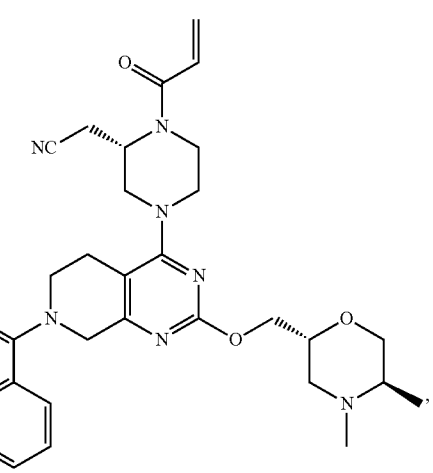
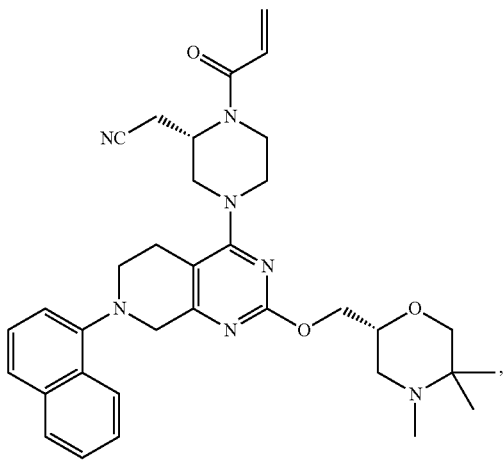

151
-continued
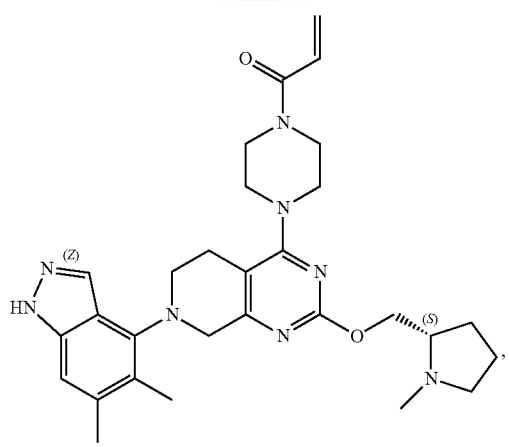
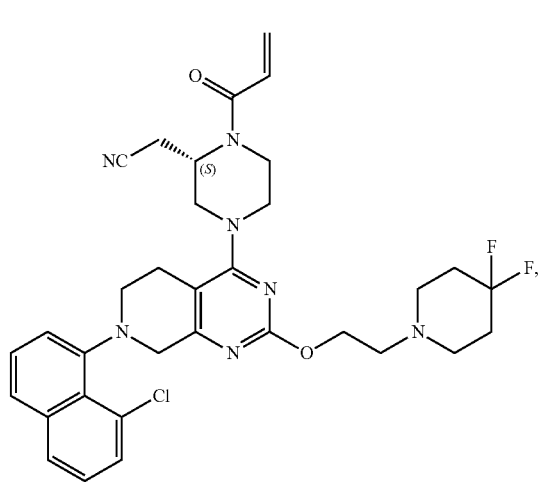
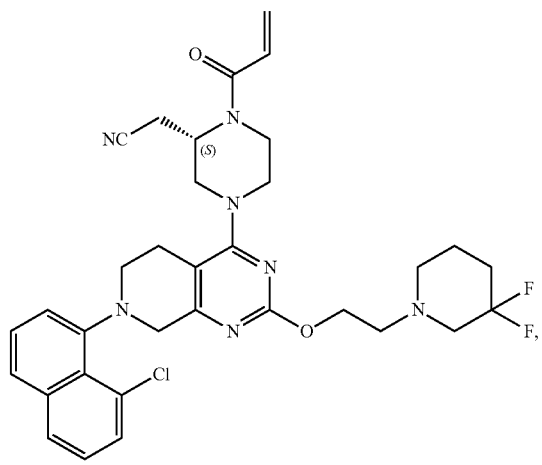
152
-continued
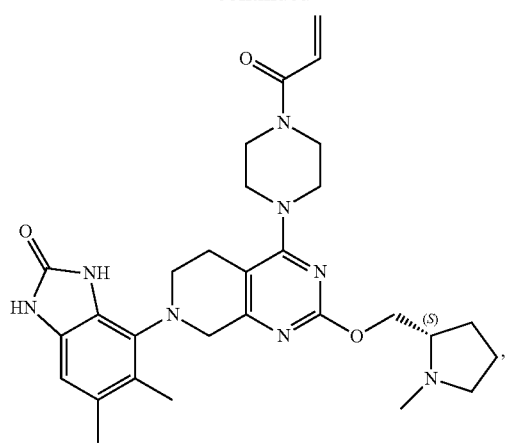
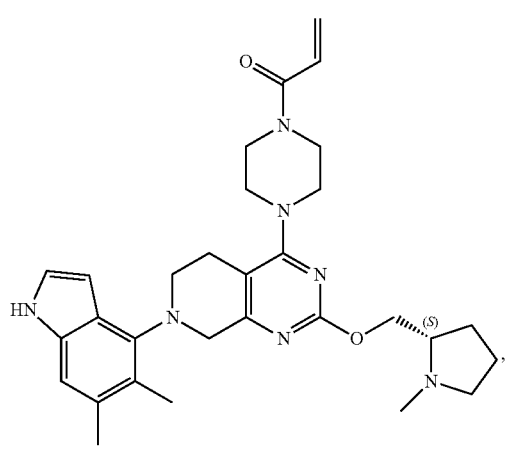
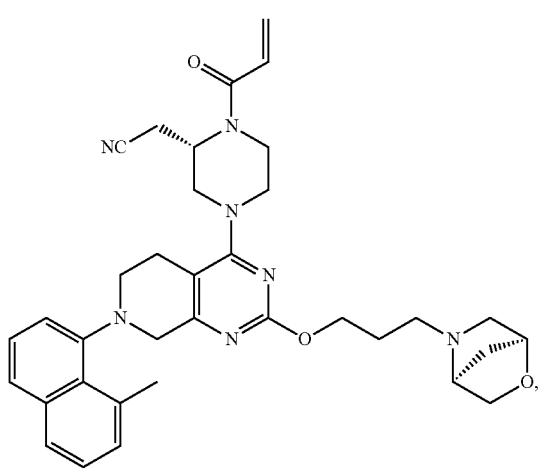

153
-continued
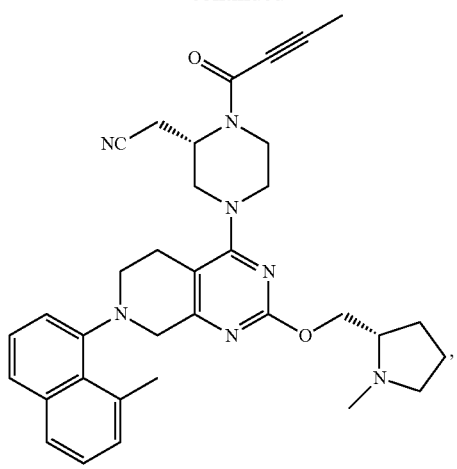
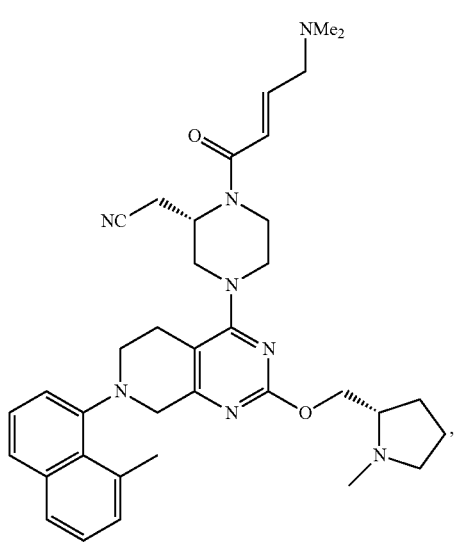
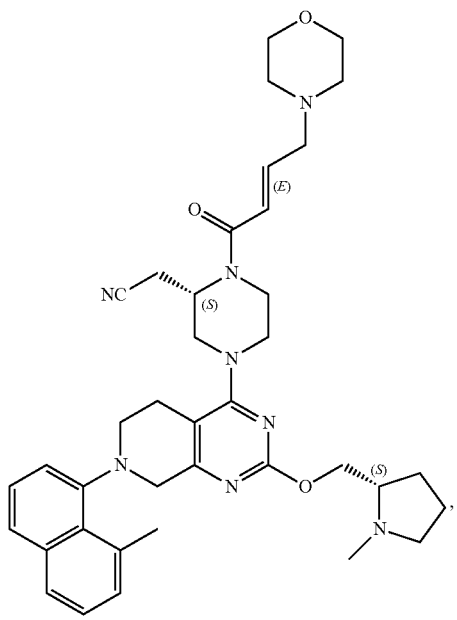
154
-continued
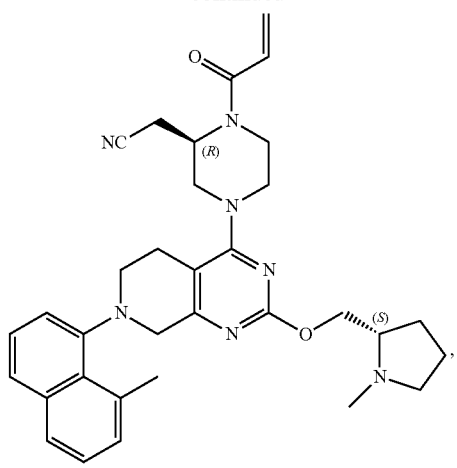
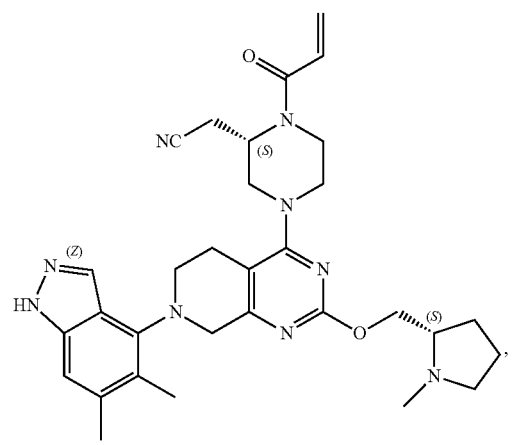
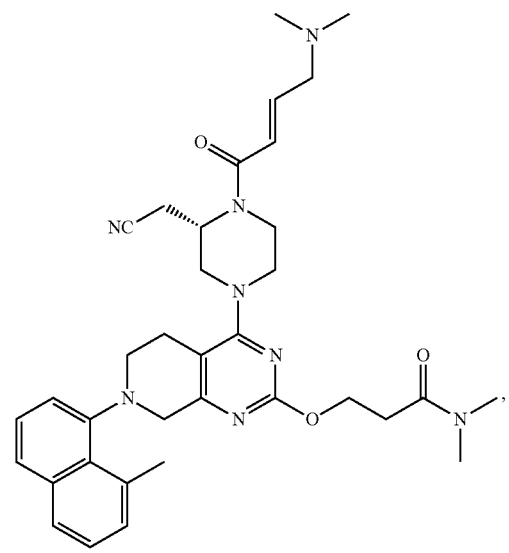

155
-continued
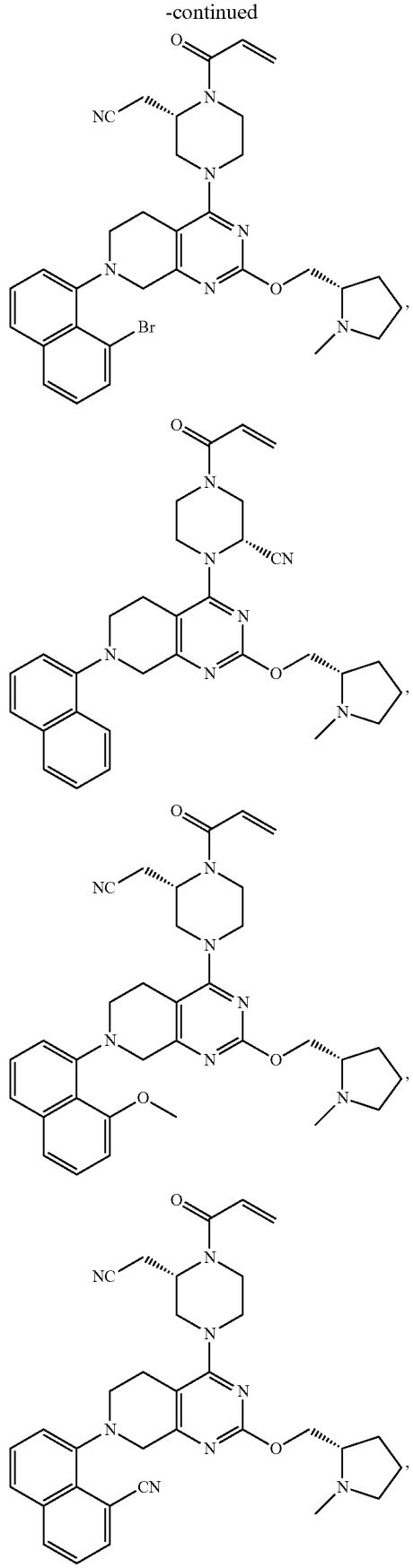
156
-continued
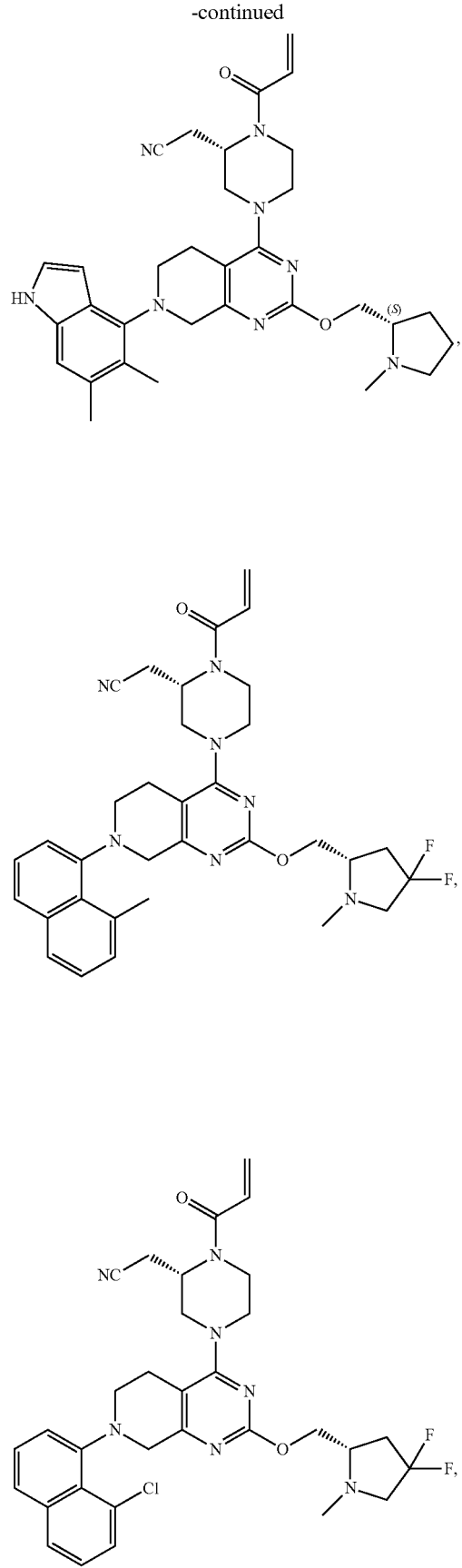

157
-continued
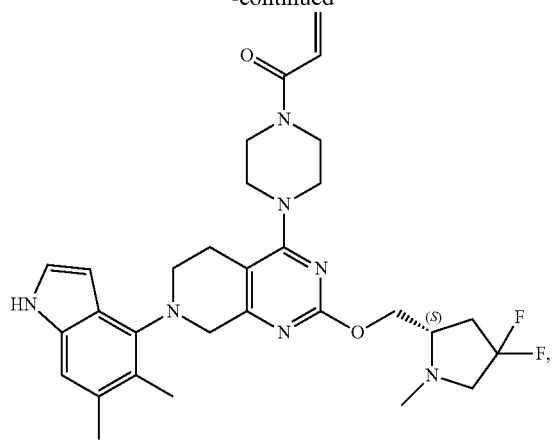
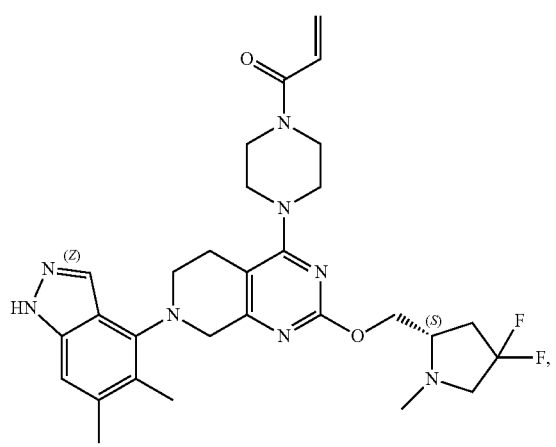
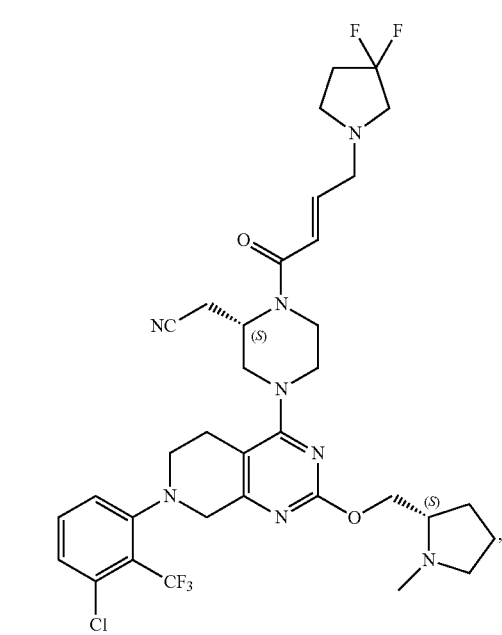
158
-continued
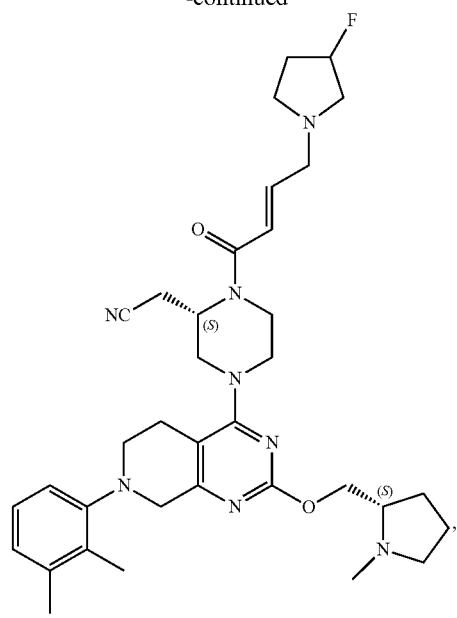
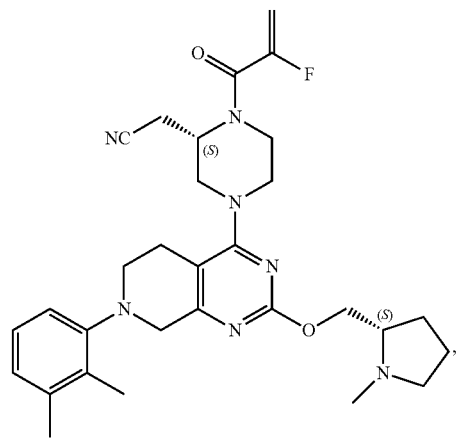

159
-continued
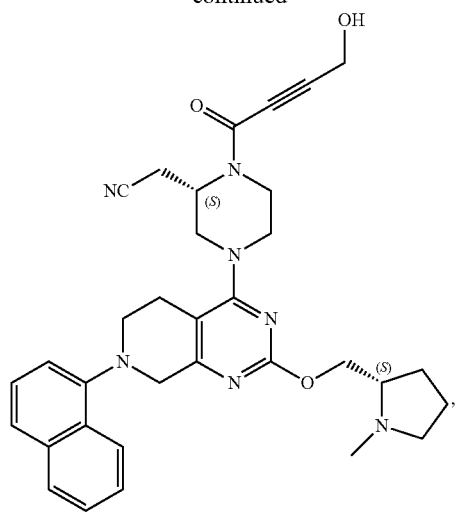
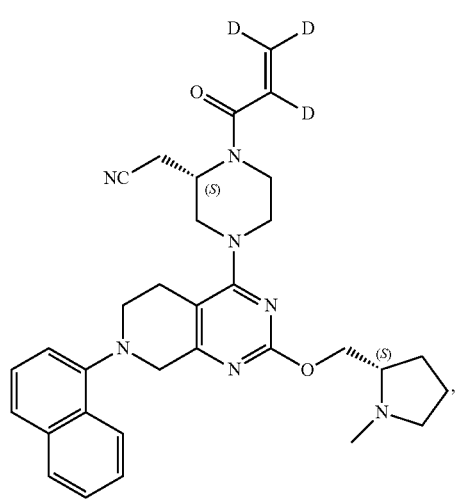
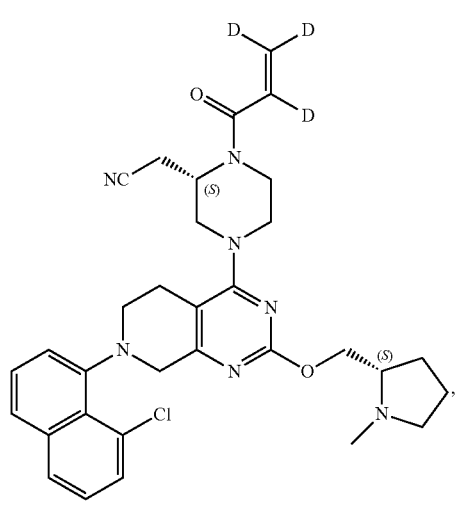
160
-continued
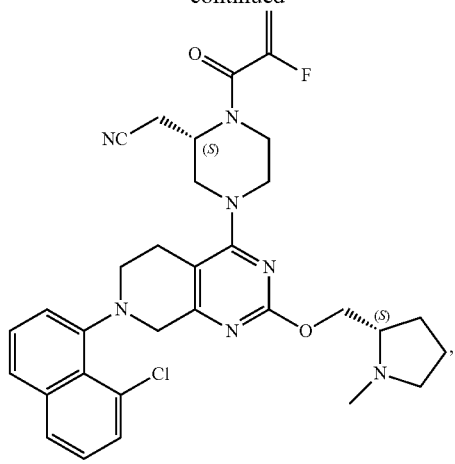
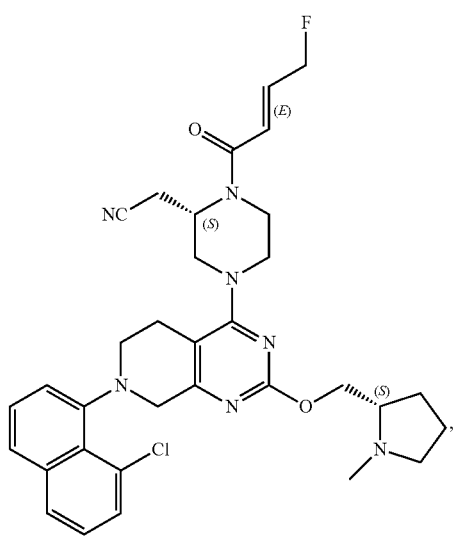
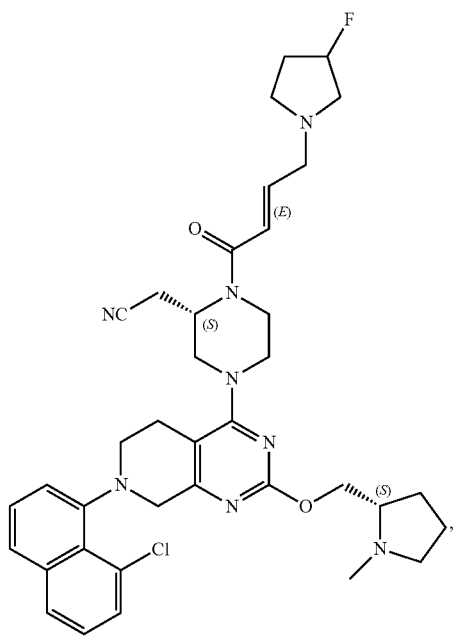

161
-continued
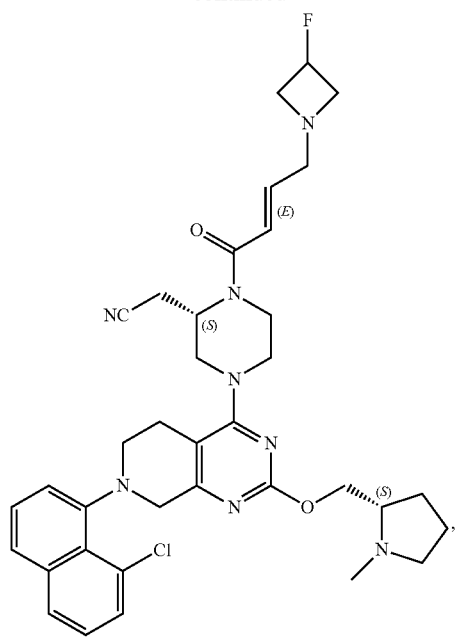
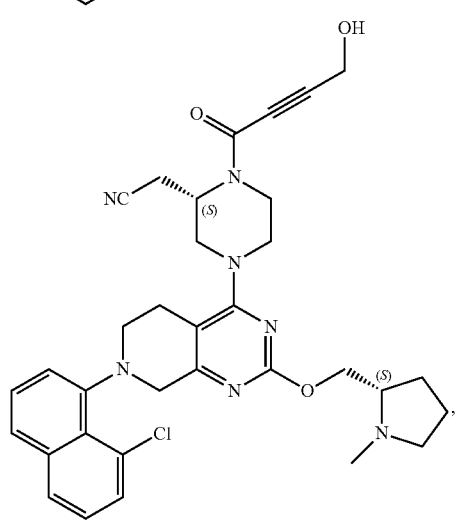
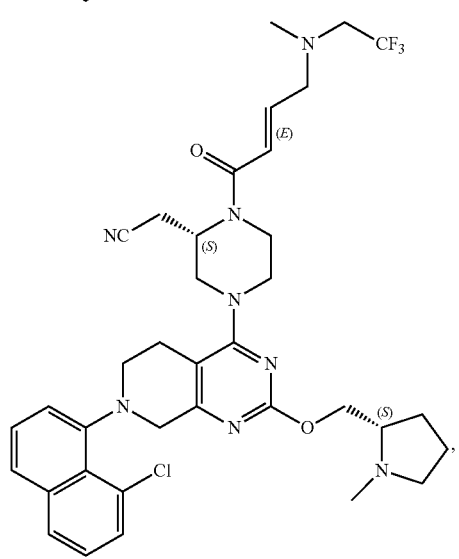
162
-continued
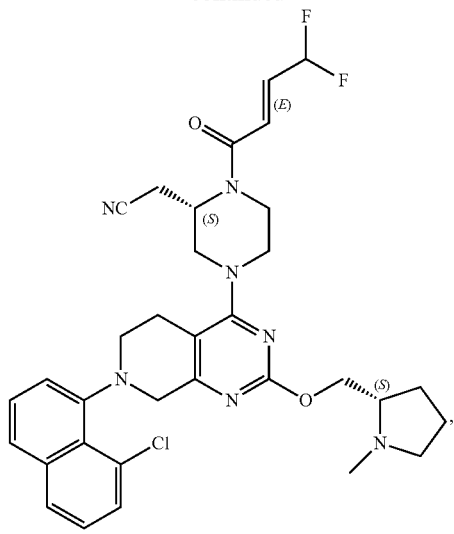
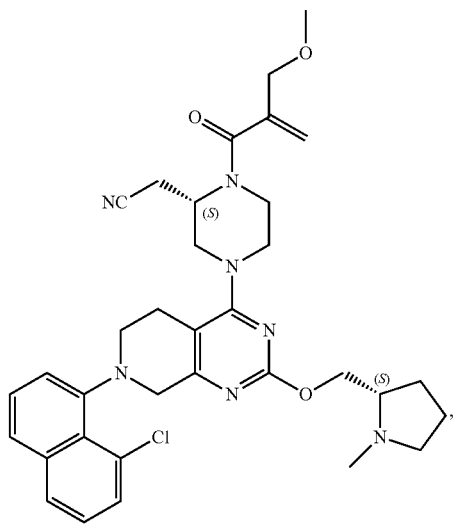
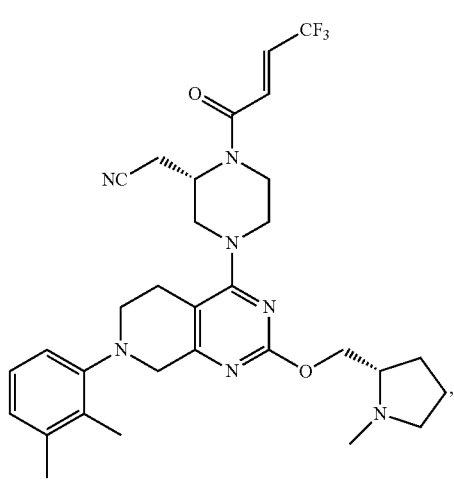

163
-continued
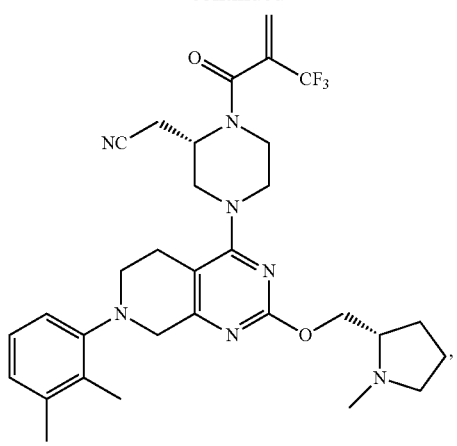
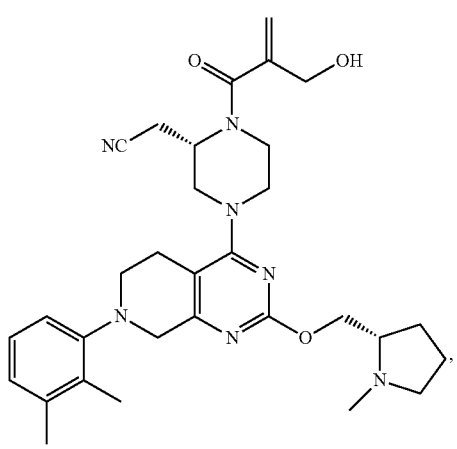
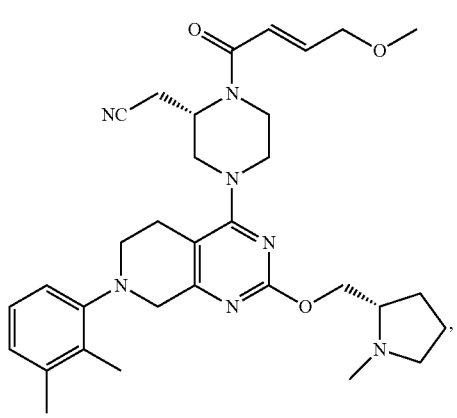
164
-continued
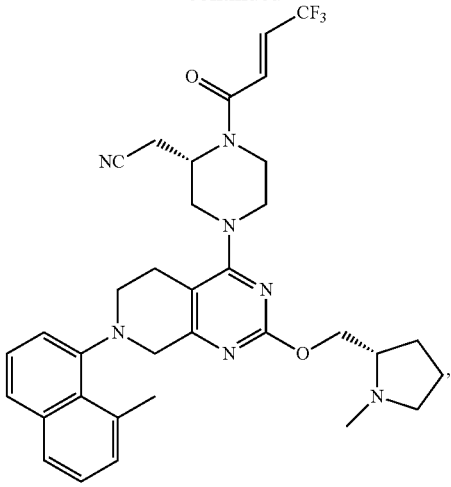
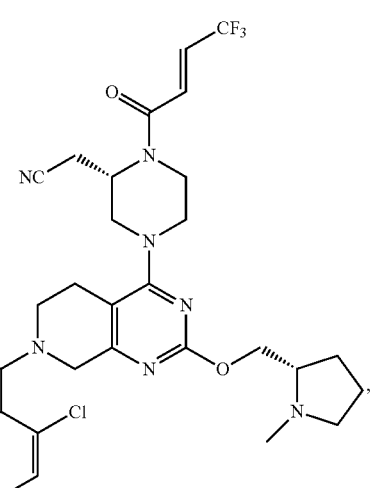
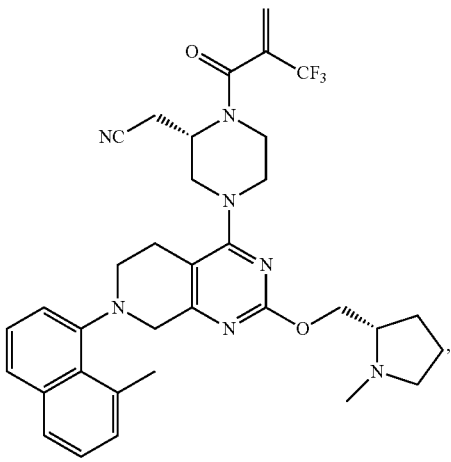

165
-continued
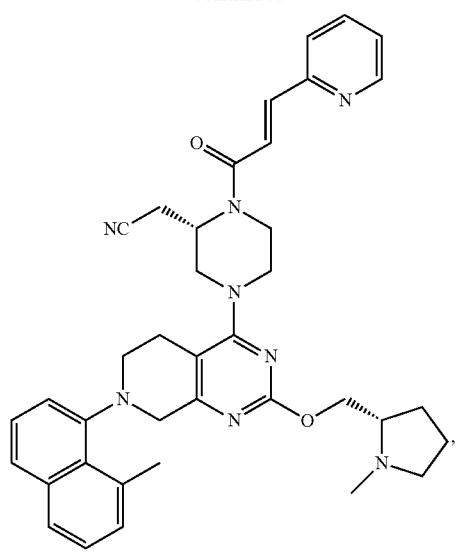
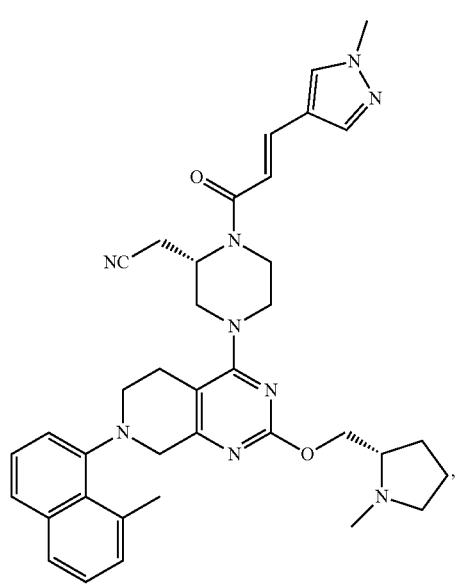
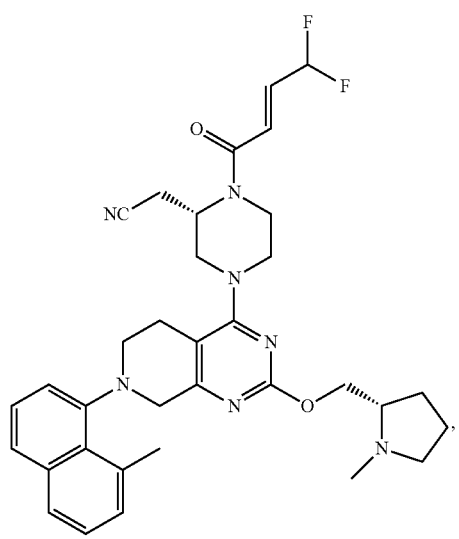
166
-continued
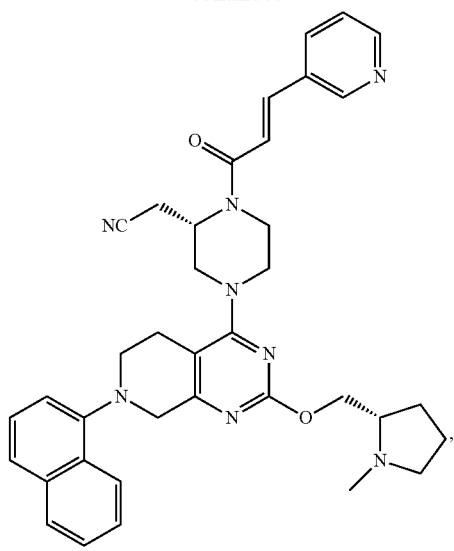
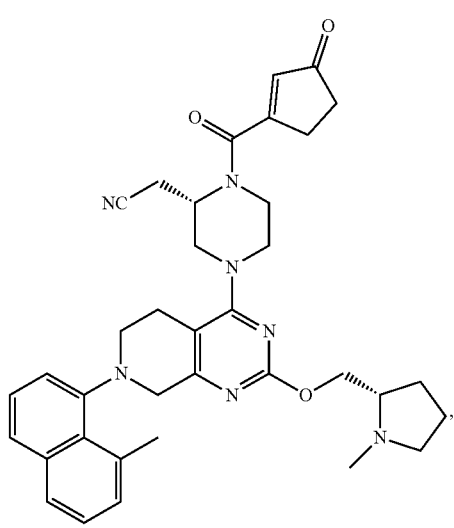
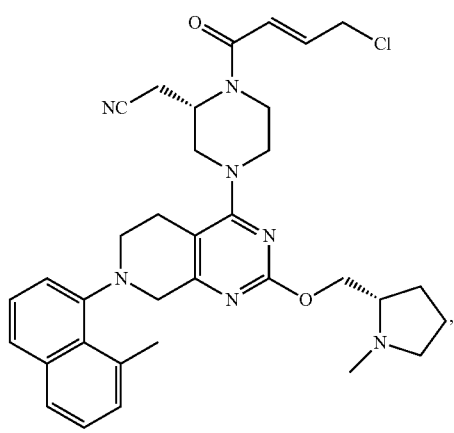

167
-continued
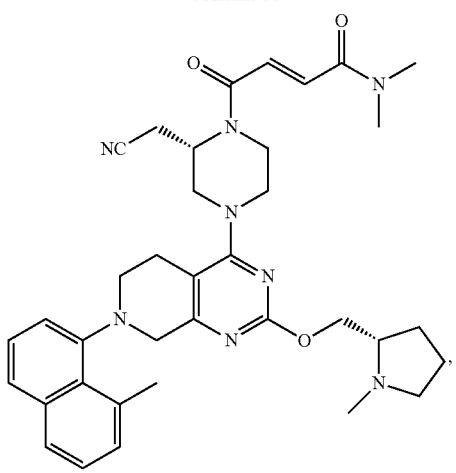
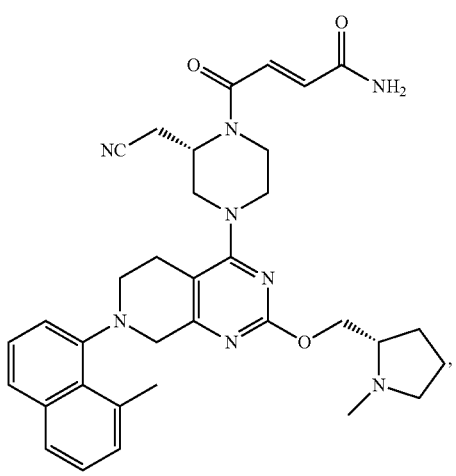
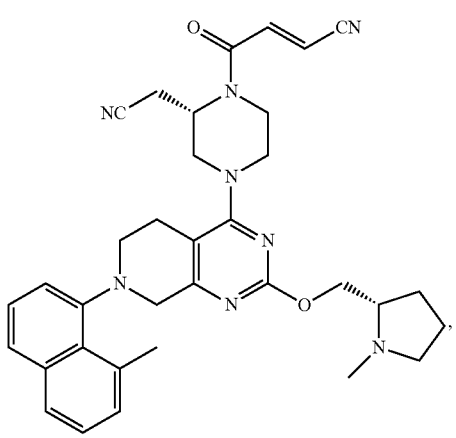
168
-continued
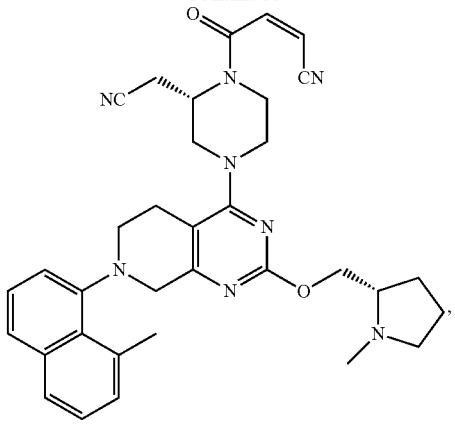
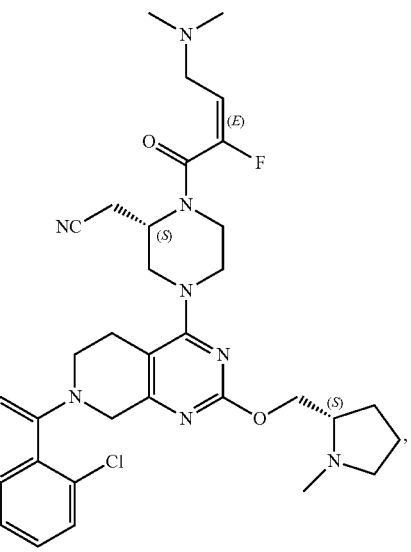

169
-continued
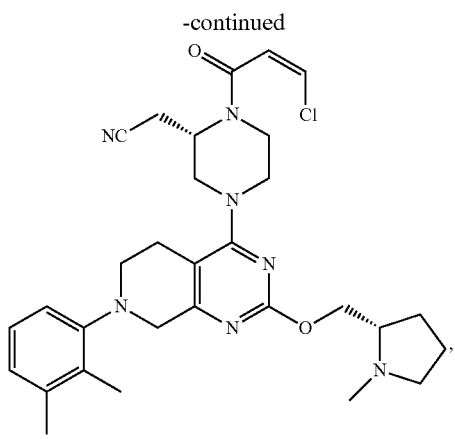
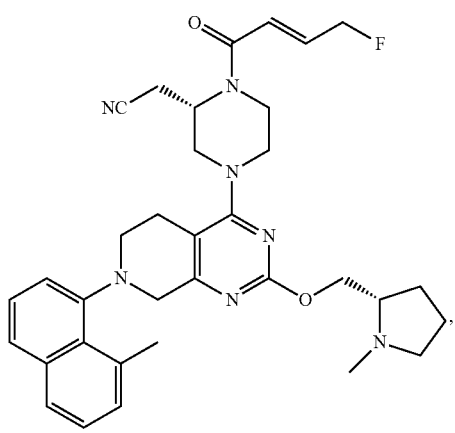
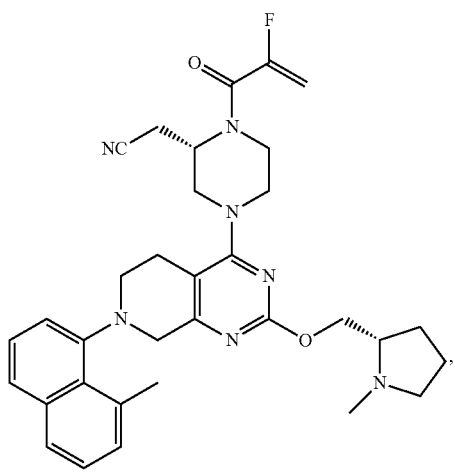
170
-continued
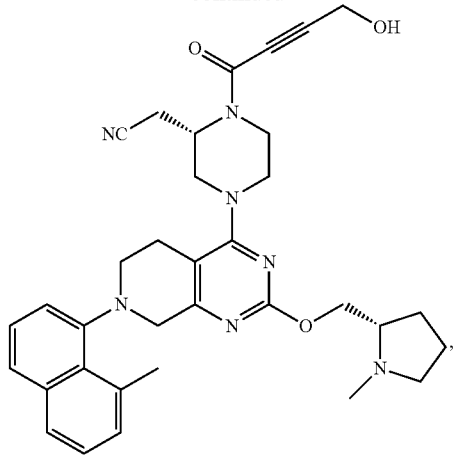
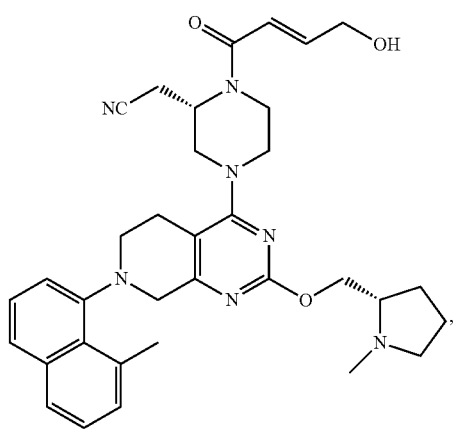

171
-continued
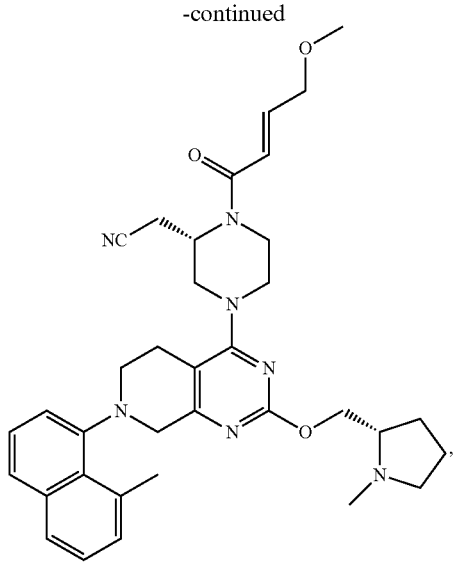
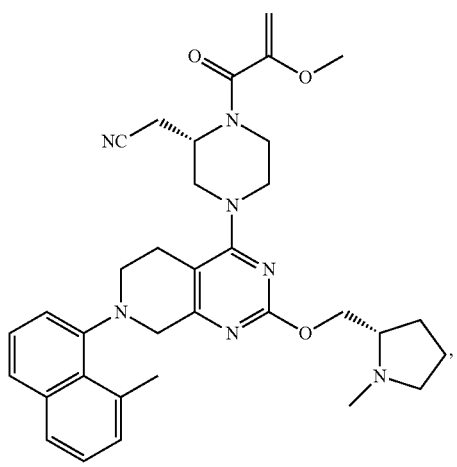
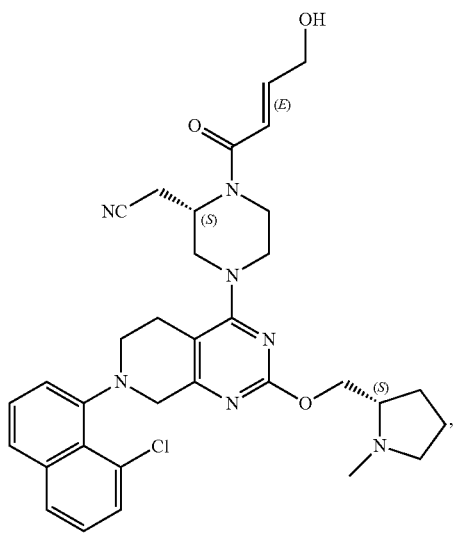
172
-continued
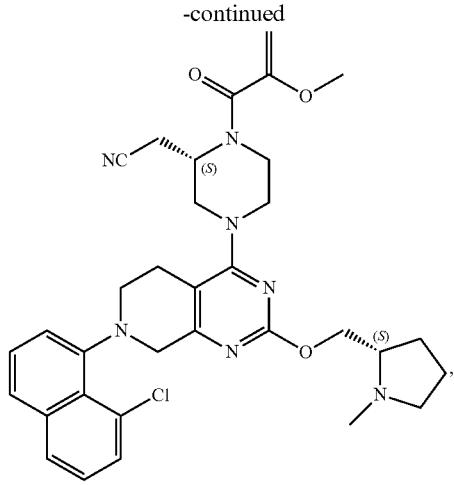
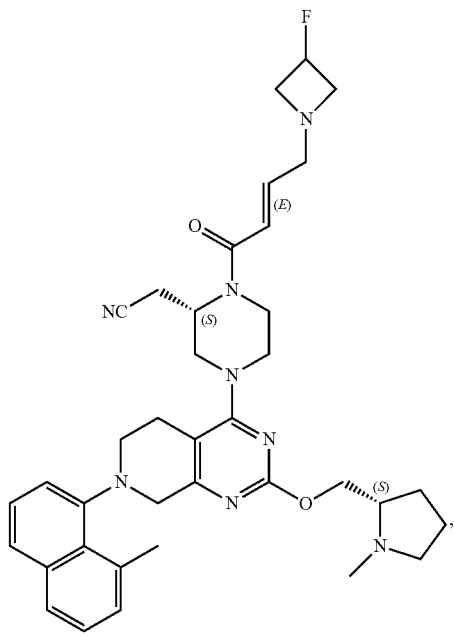
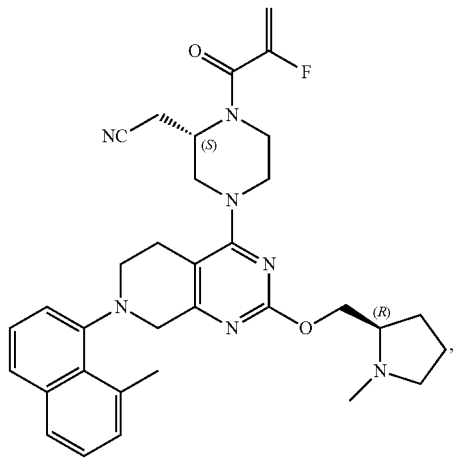

173
-continued
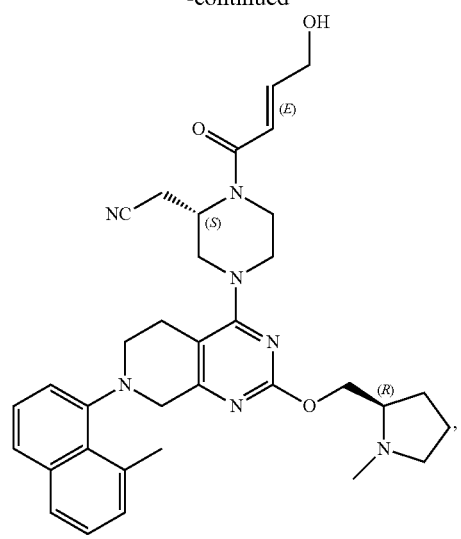
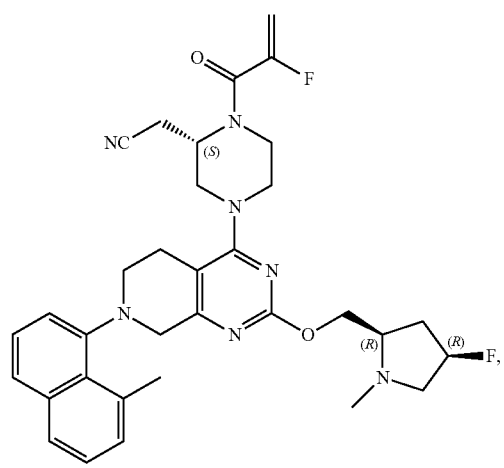
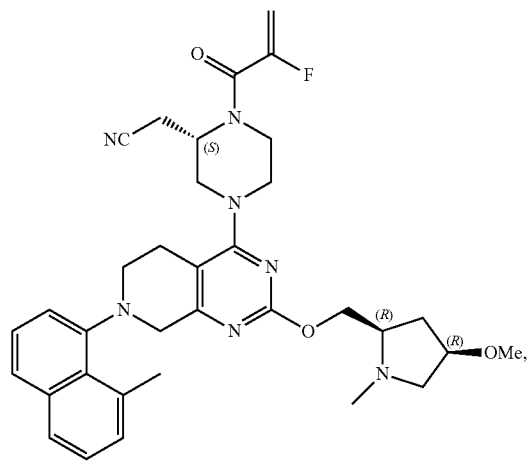
174
-continued
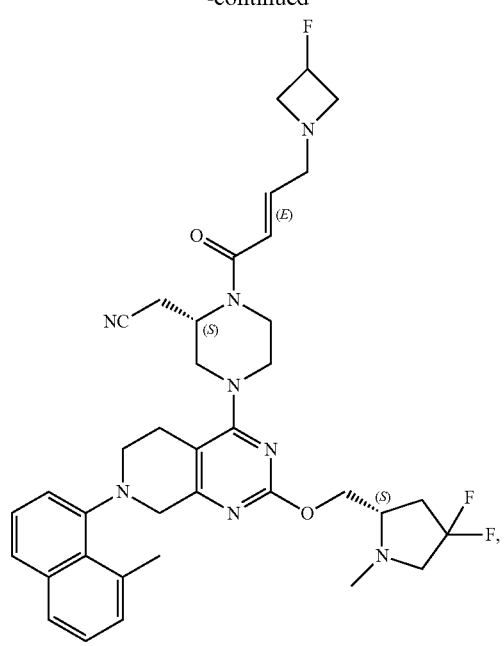
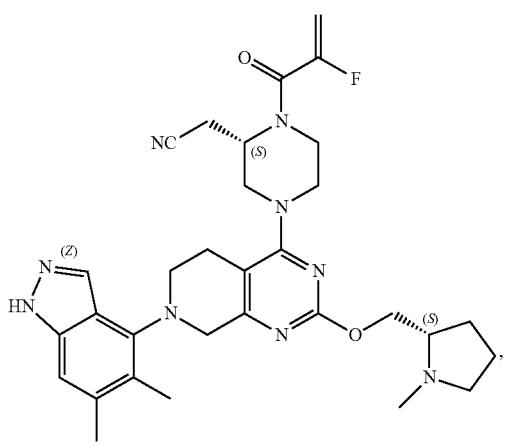
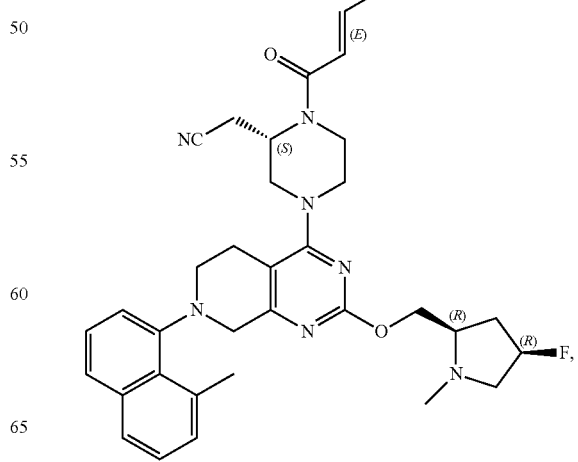

175
-continued
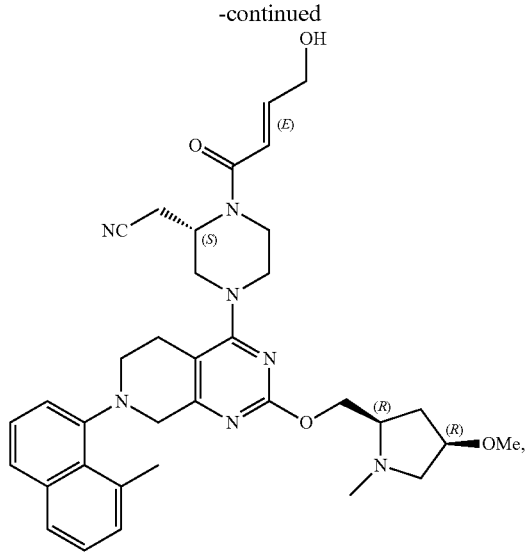
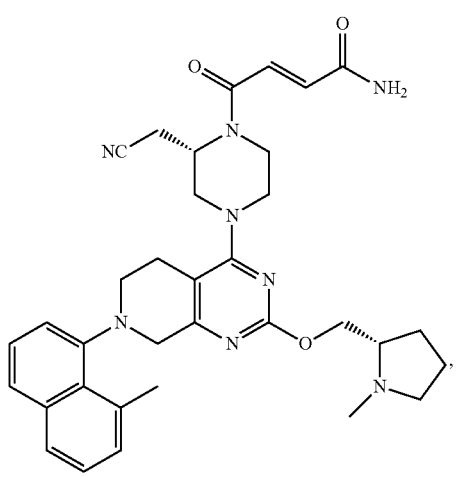
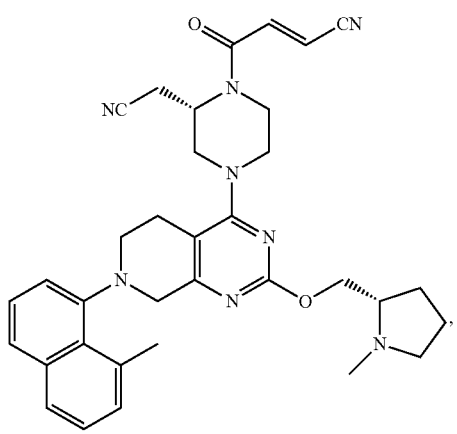
176
-continued
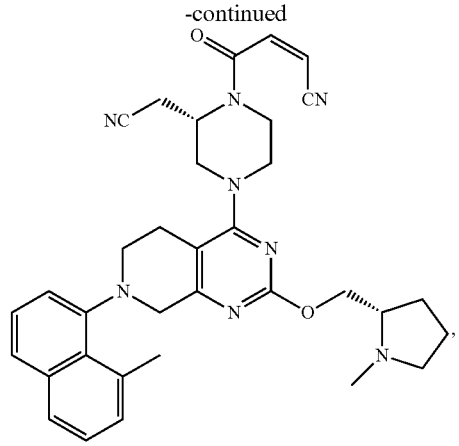
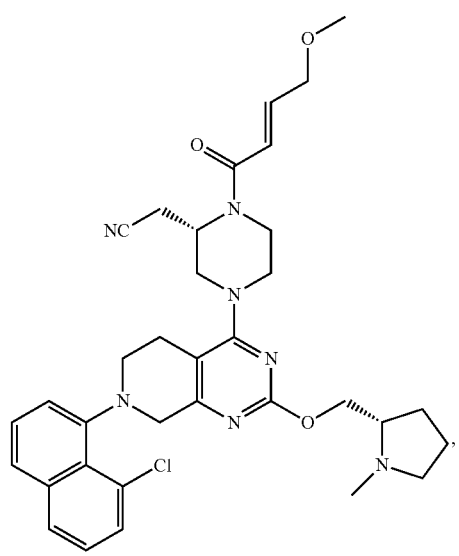
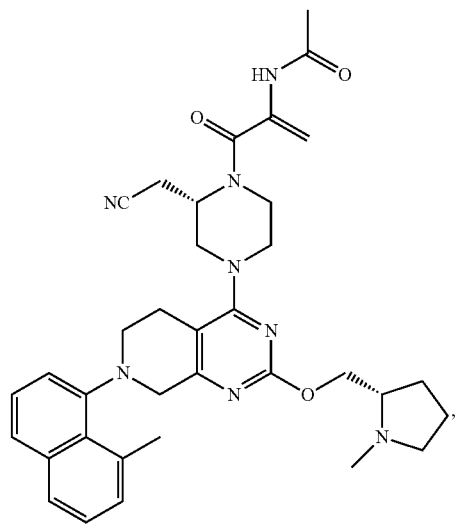

177
-continued
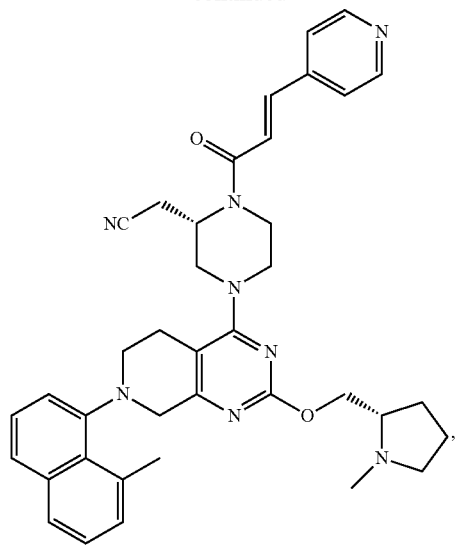
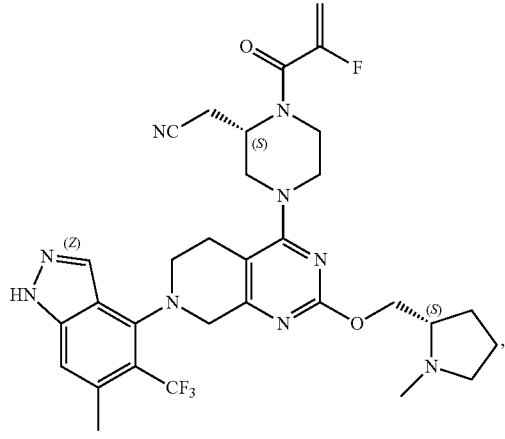
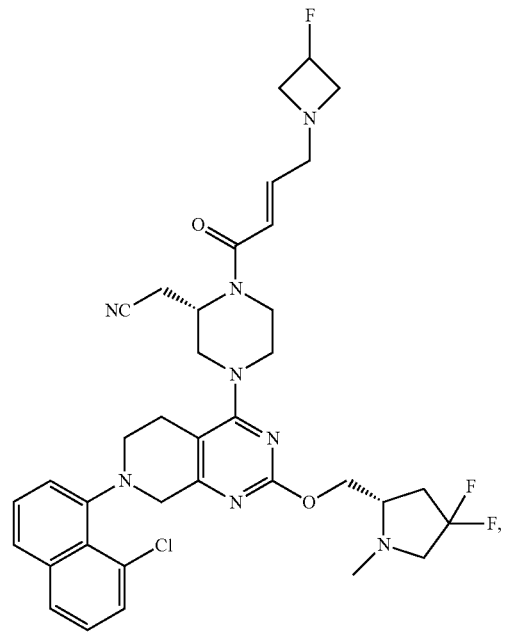
178
-continued
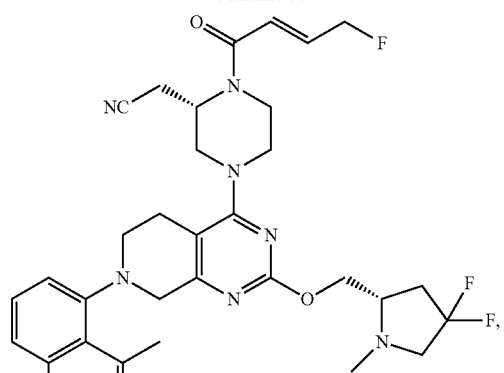
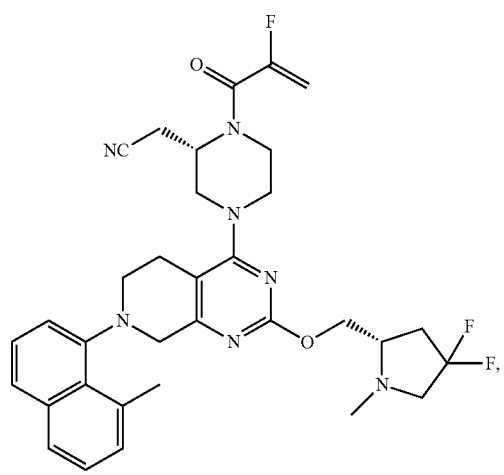

179
-continued
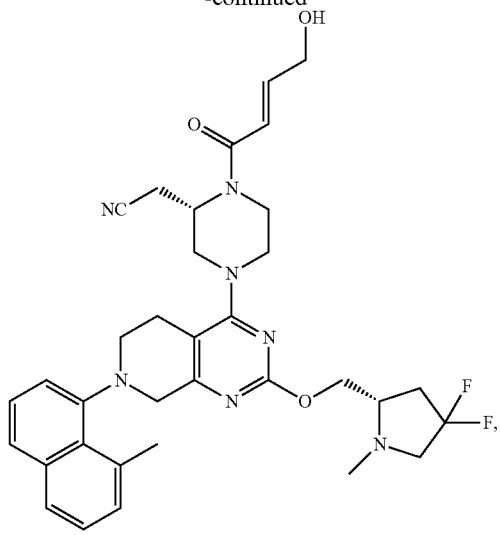
180
-continued
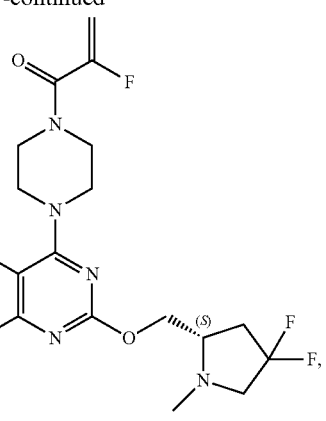
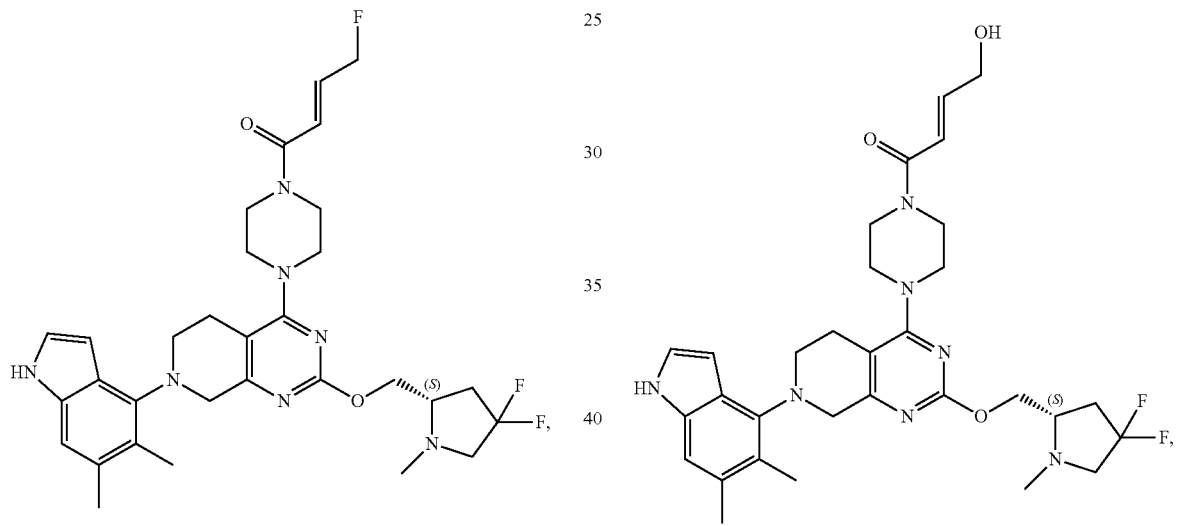
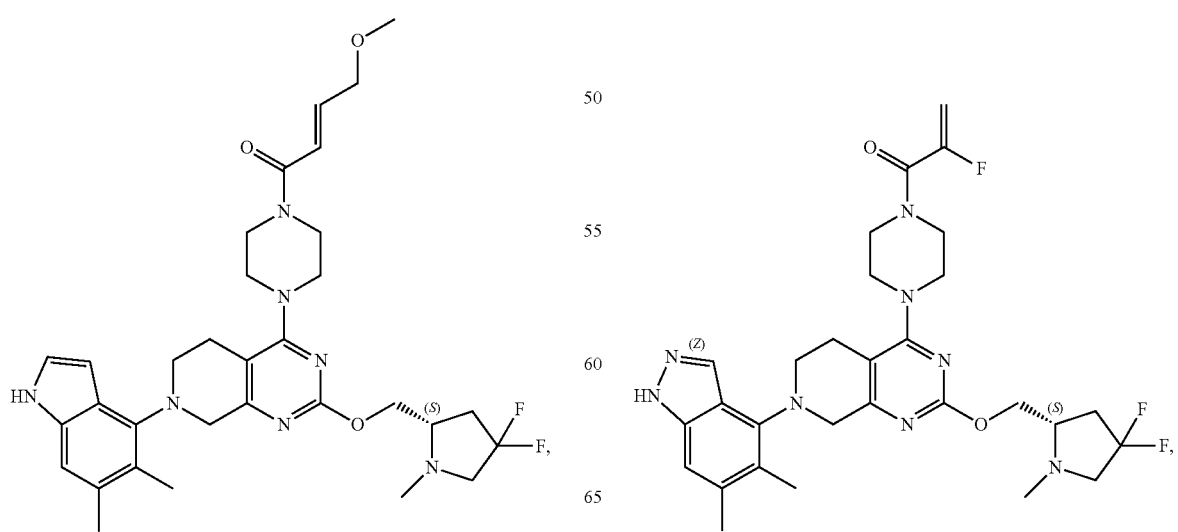

181
-continued
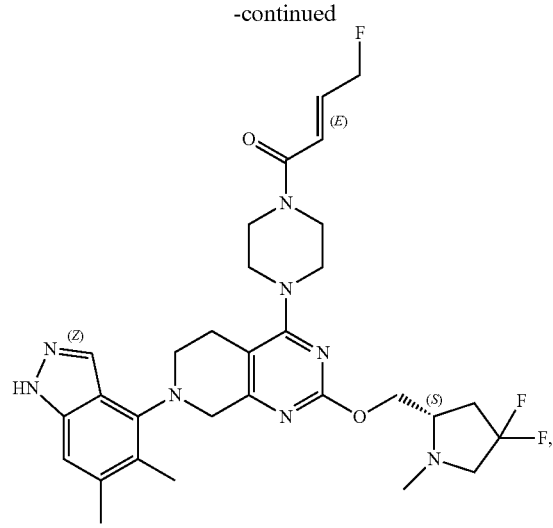
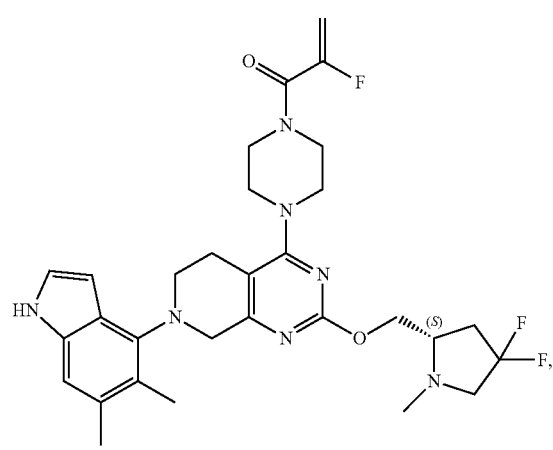
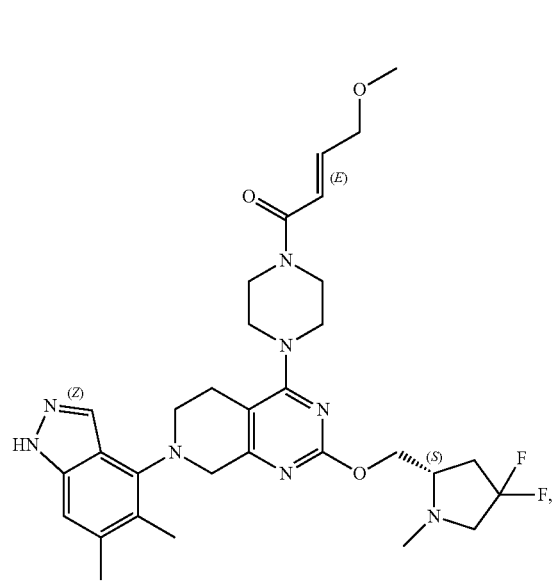
182
-continued
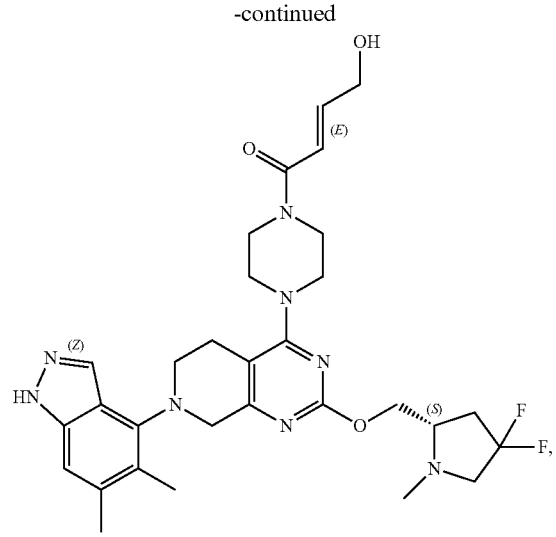
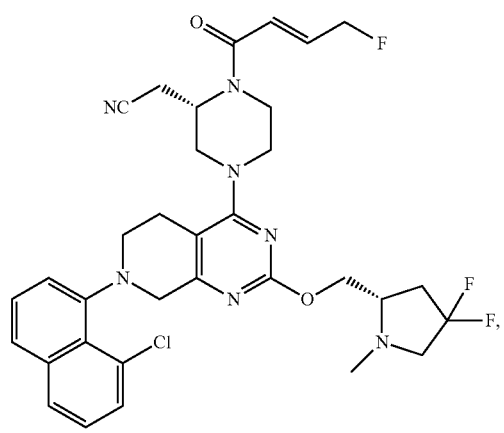
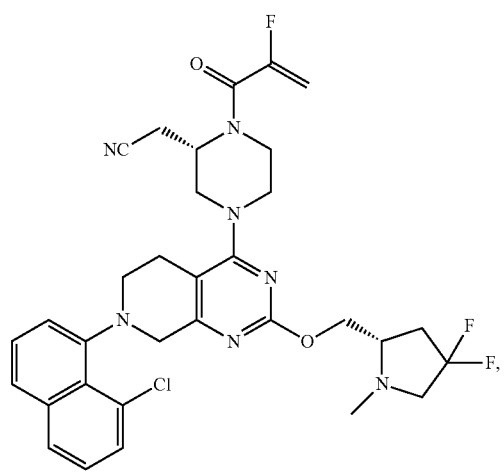

183
-continued
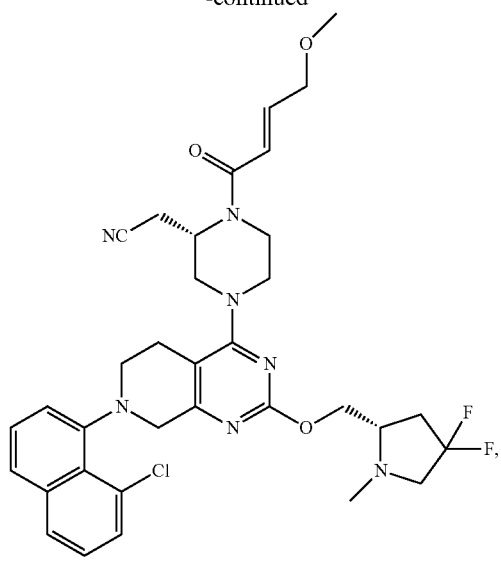
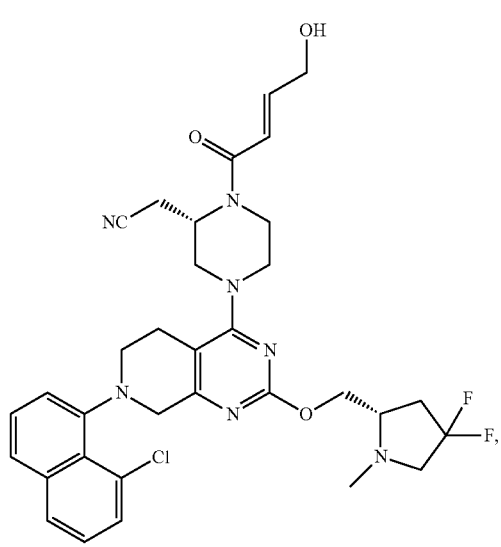
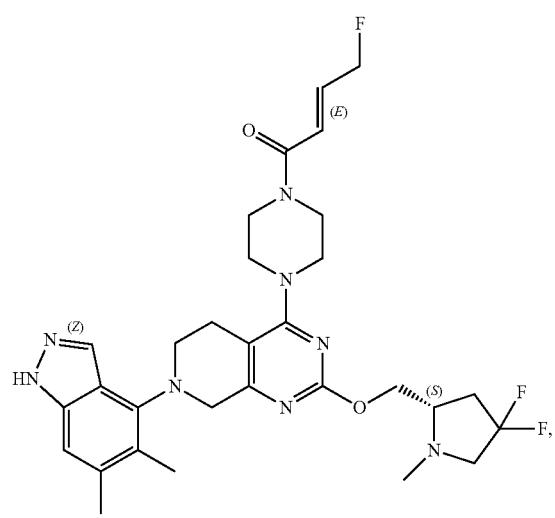
184
-continued
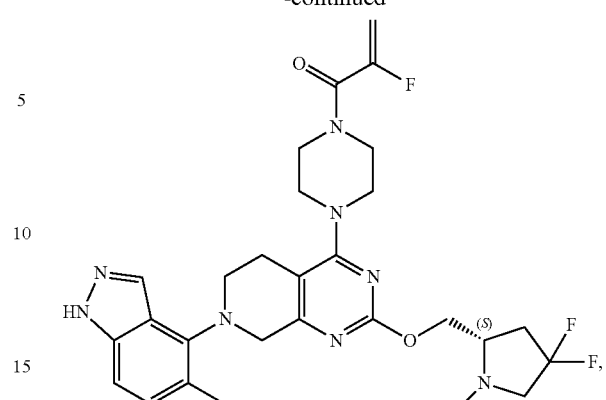
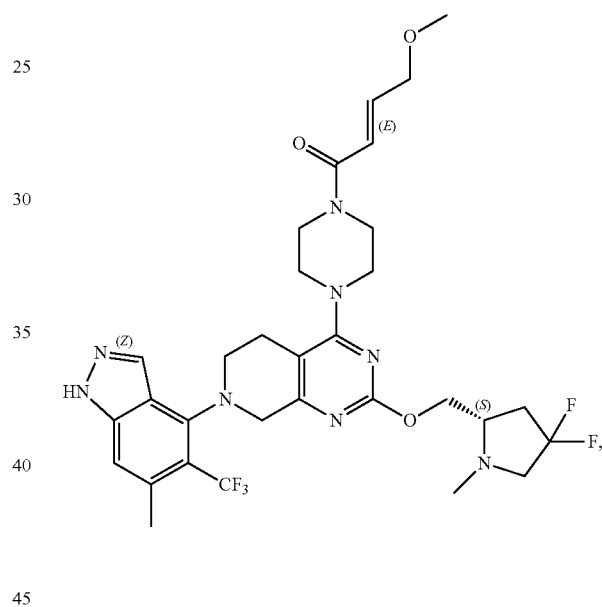
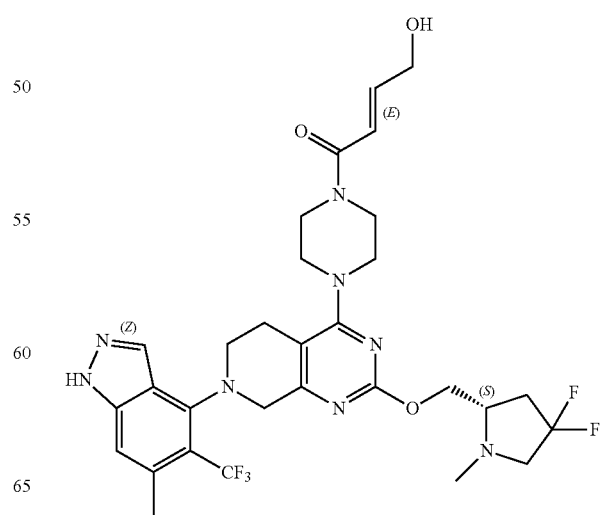

185
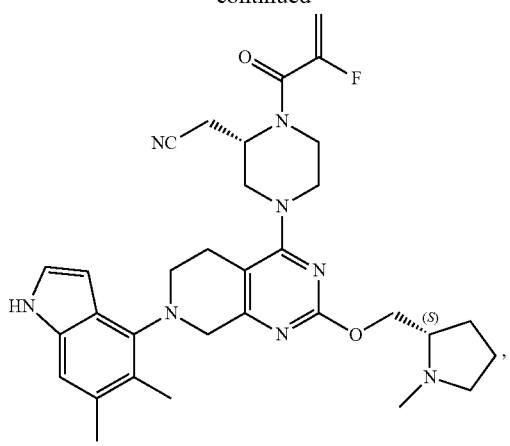
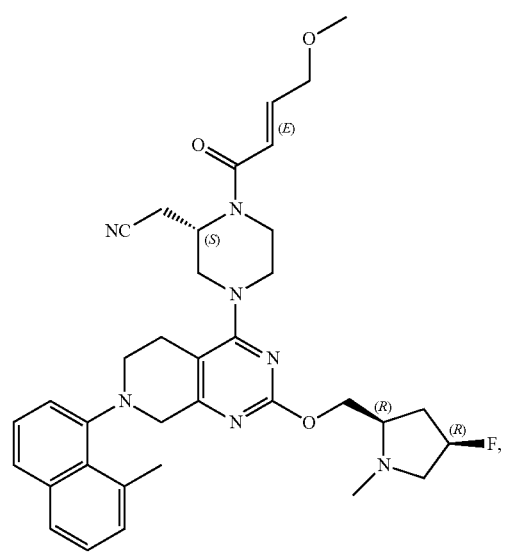
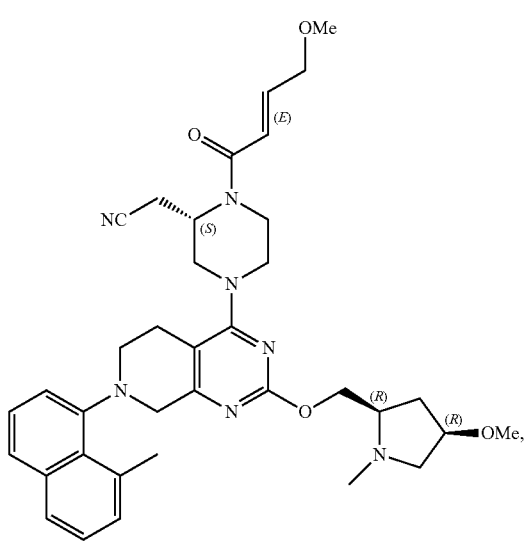
186
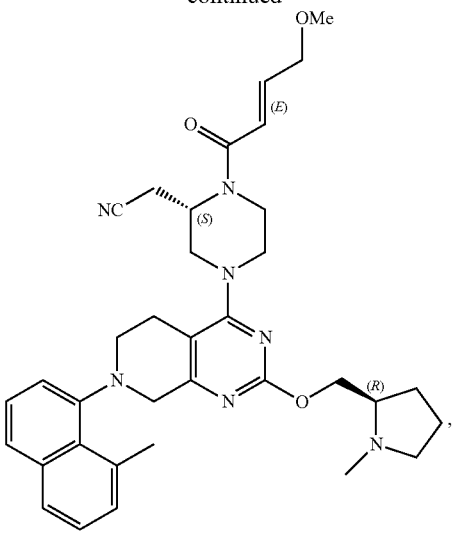
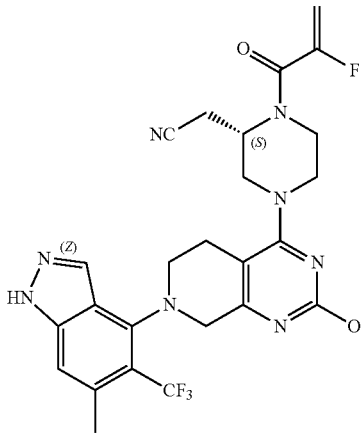
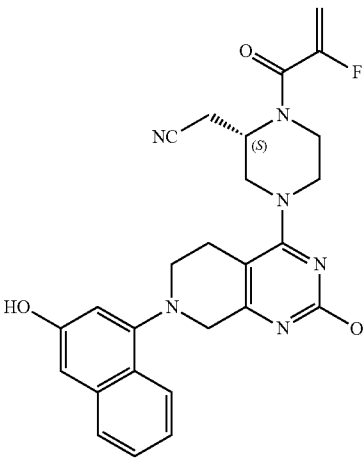

187
-continued
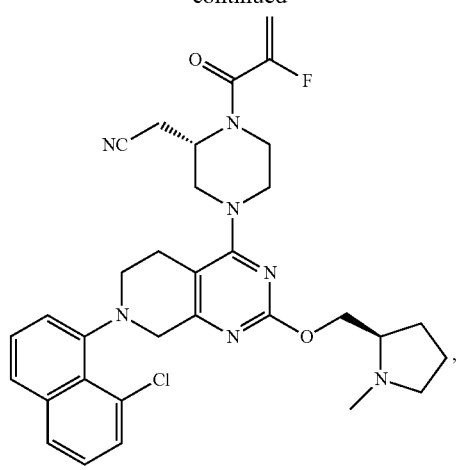
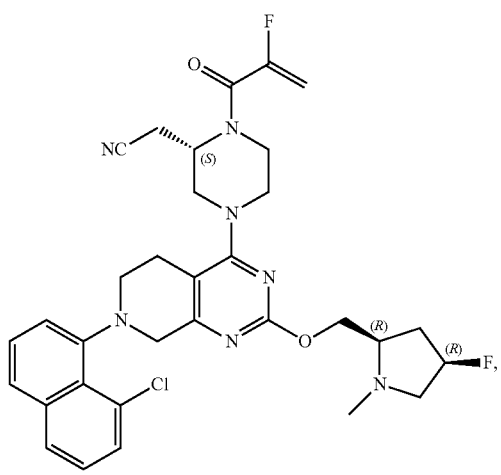
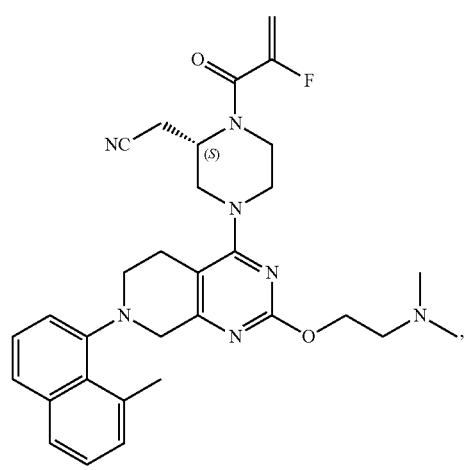
188
-continued
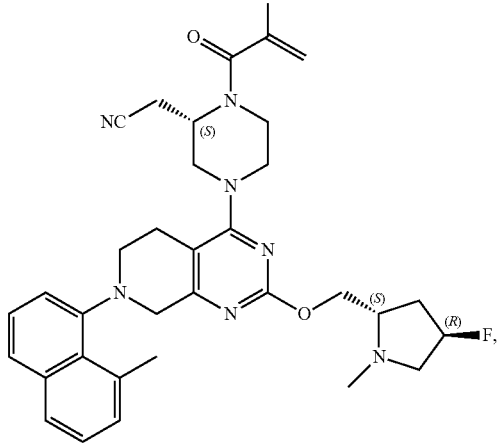
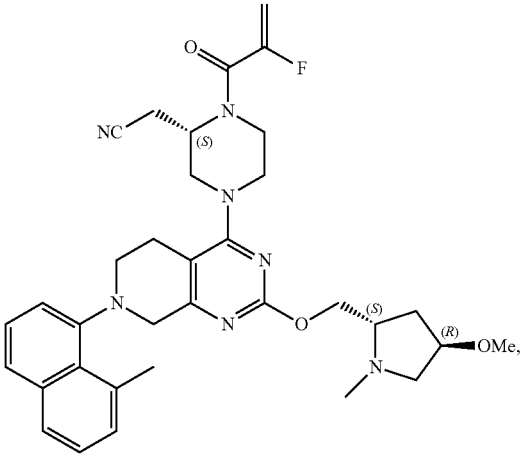
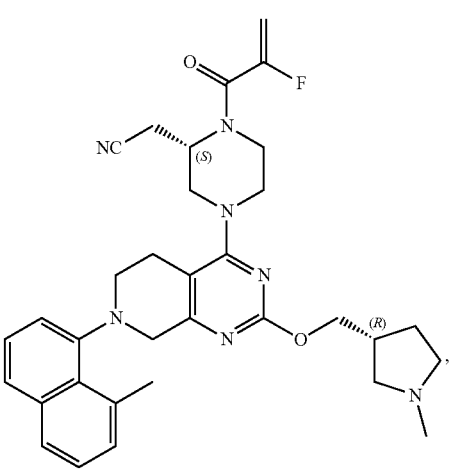

189
-continued
190
-continued
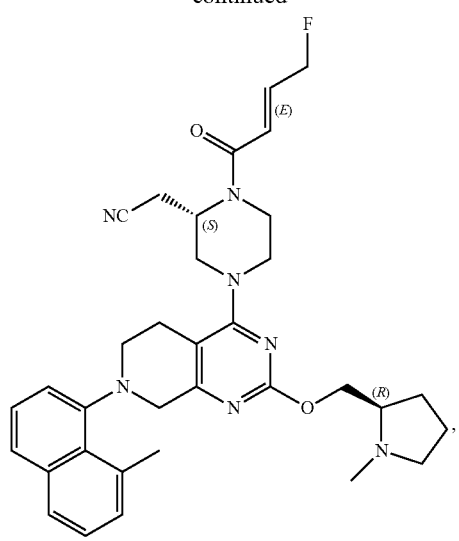
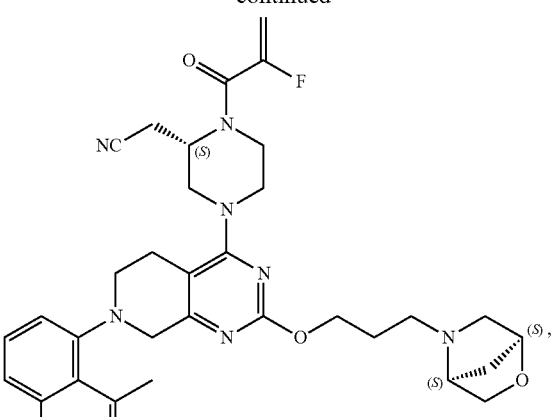
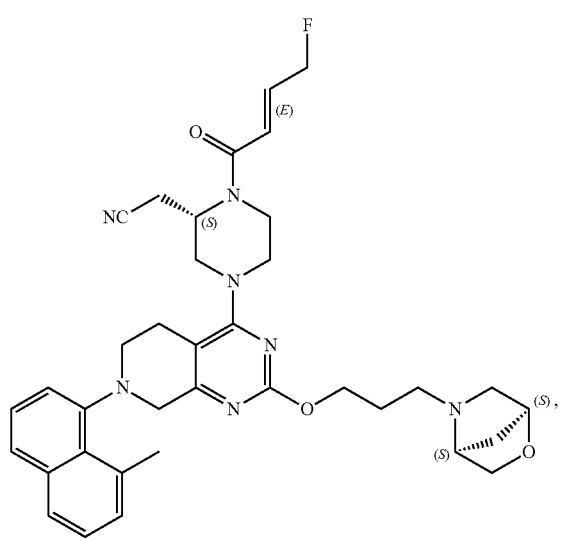
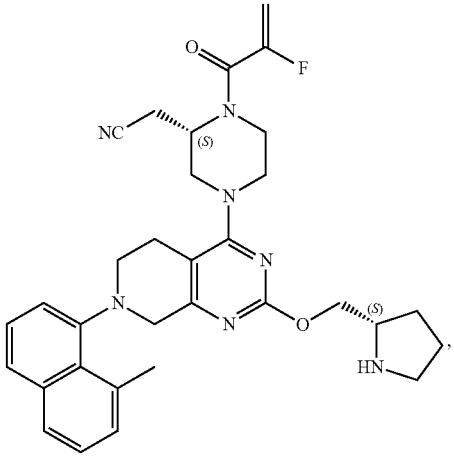

191
-continued
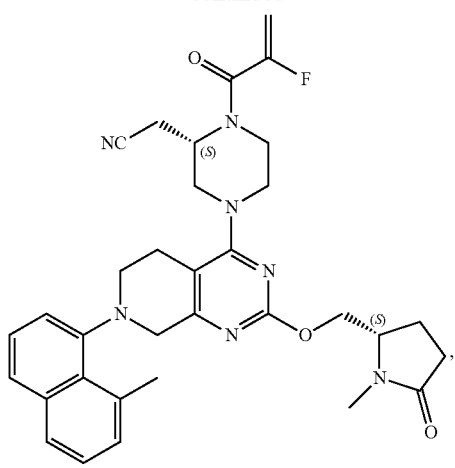
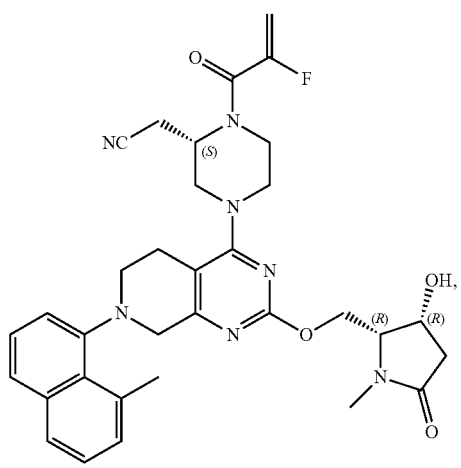
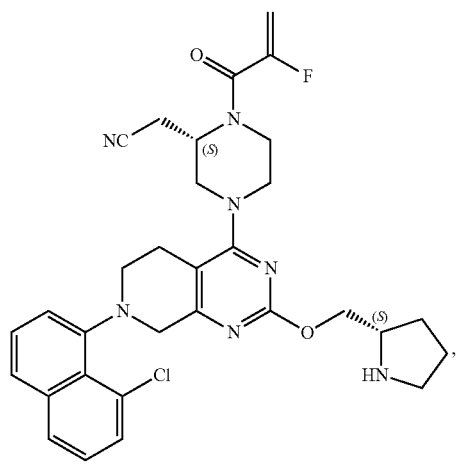
192
-continued
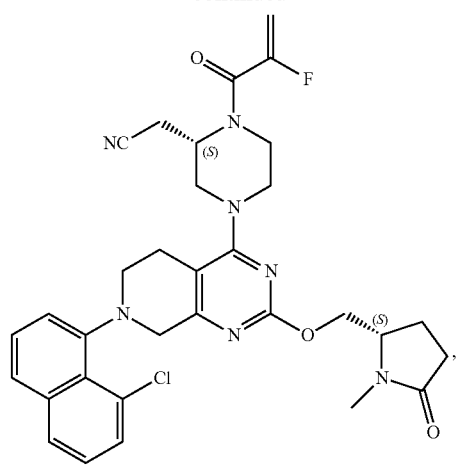
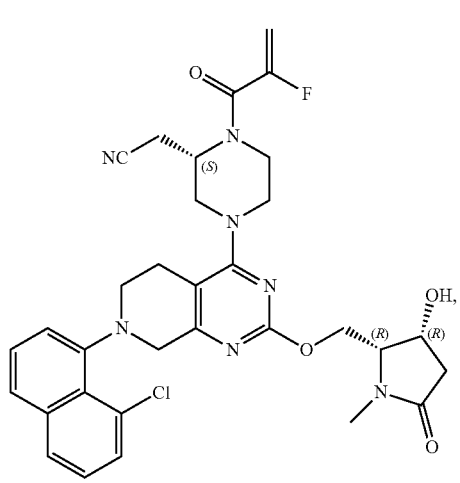
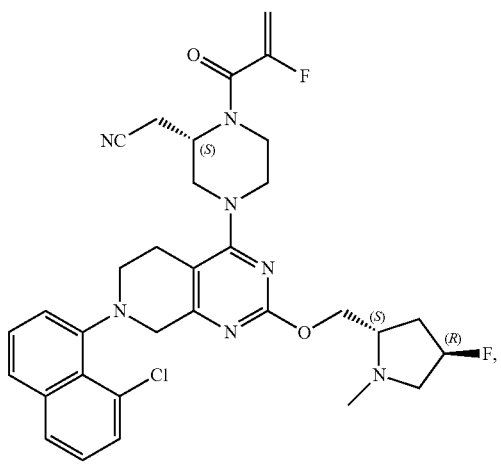

193
-continued
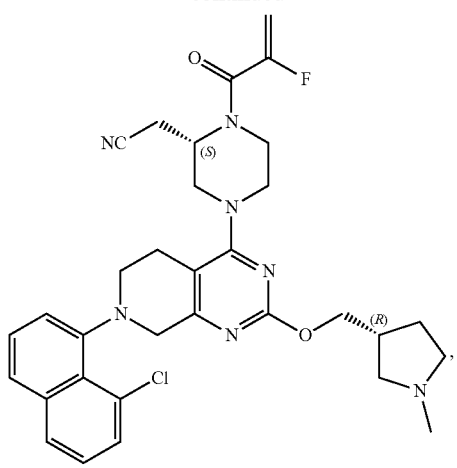
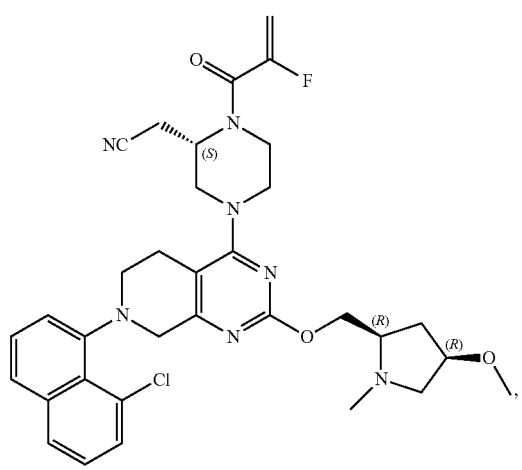
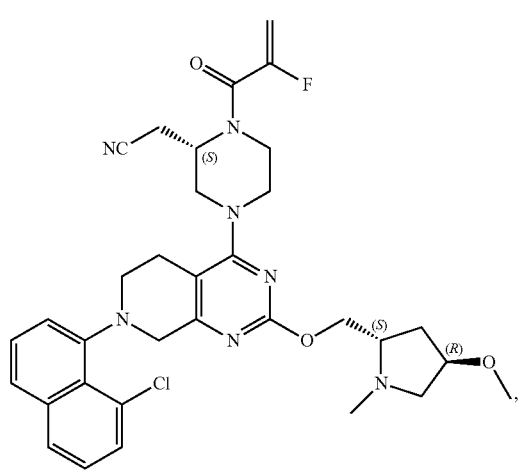
194
-continued
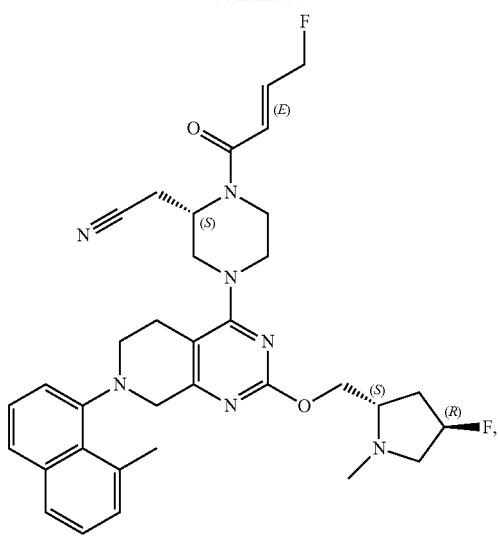
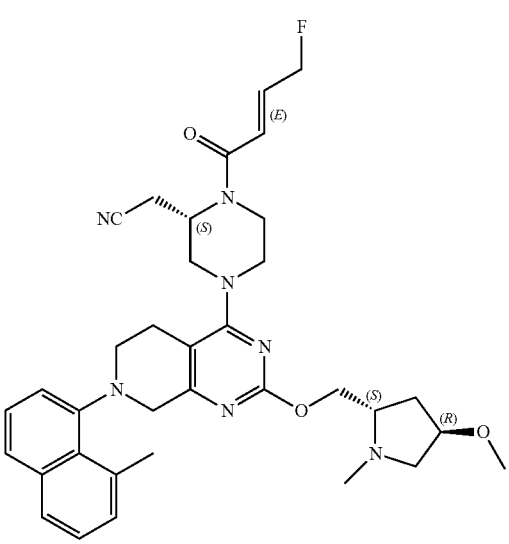

-continued
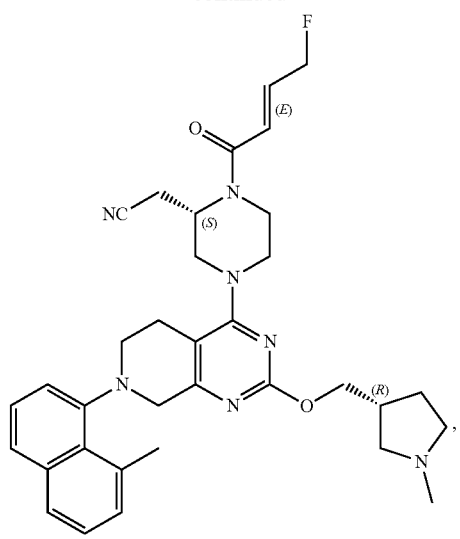
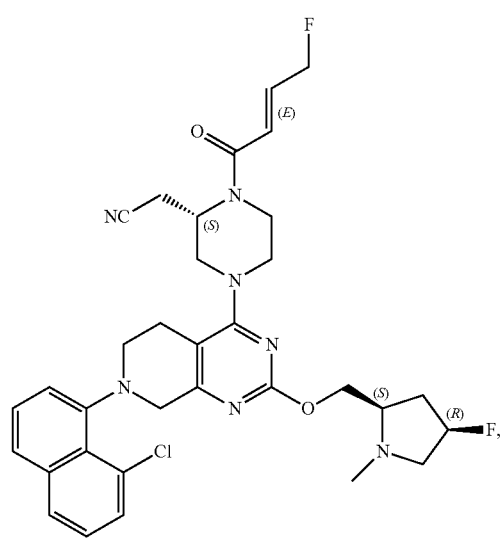
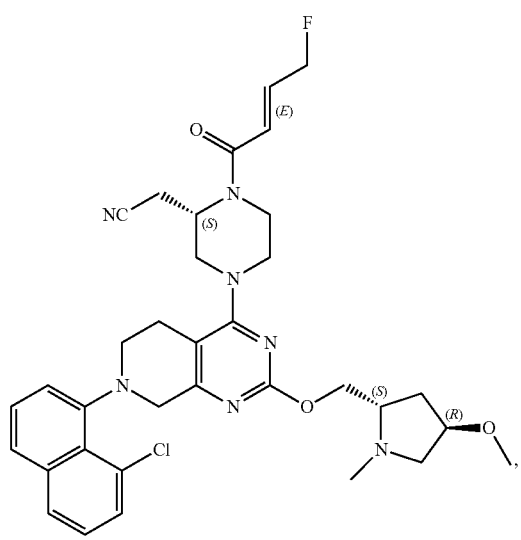
-continued
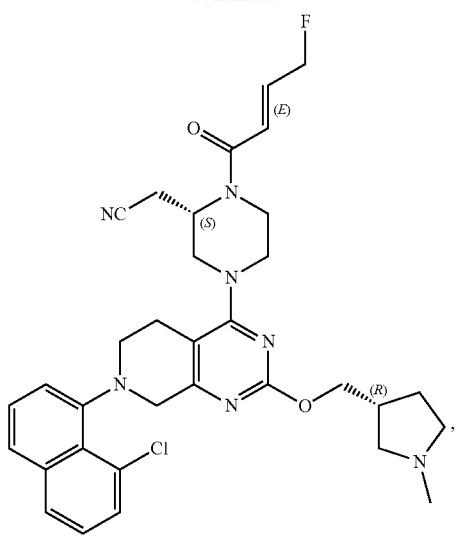
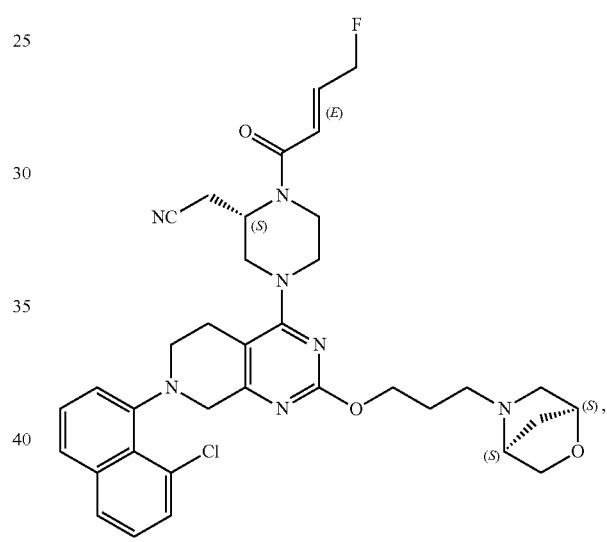
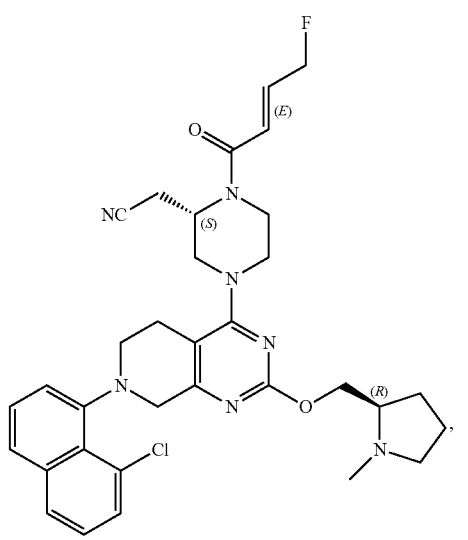

197
-continued
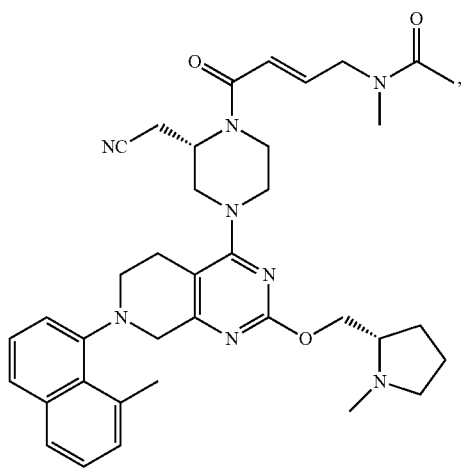
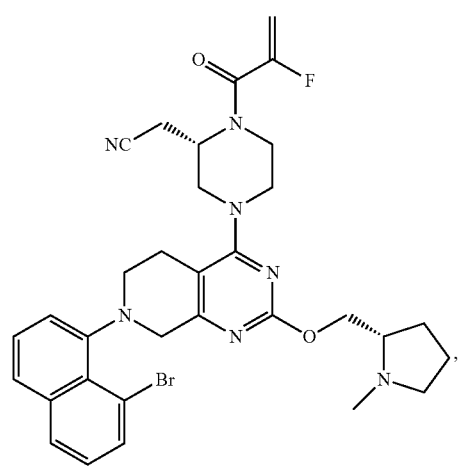
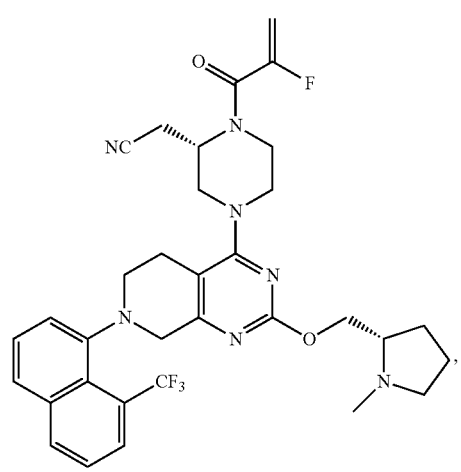
198
-continued
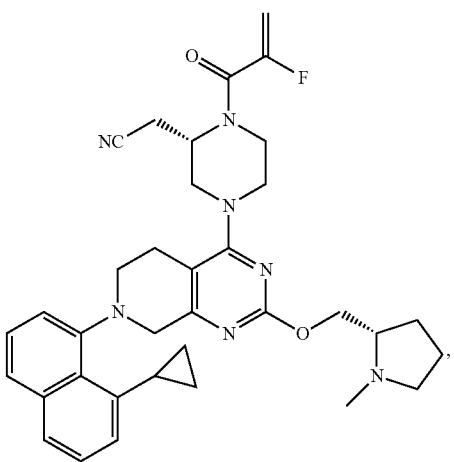
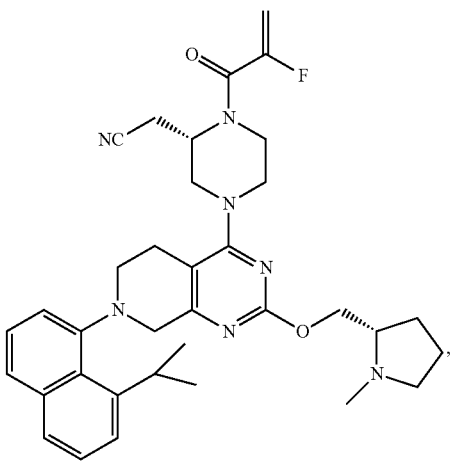
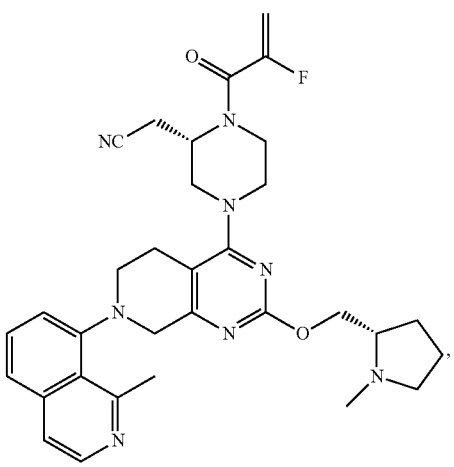

199
-continued
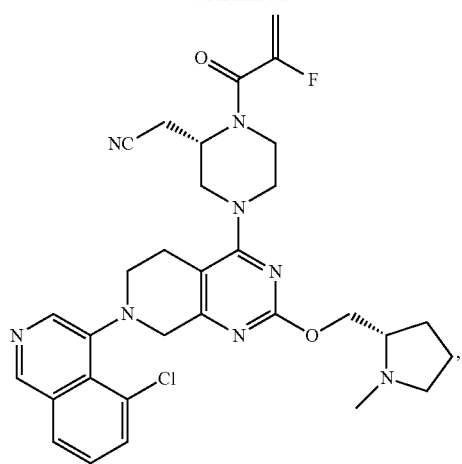
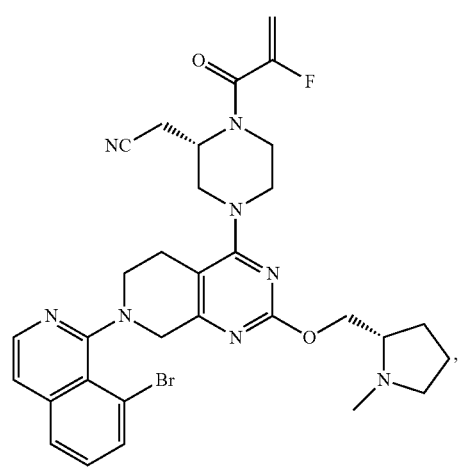
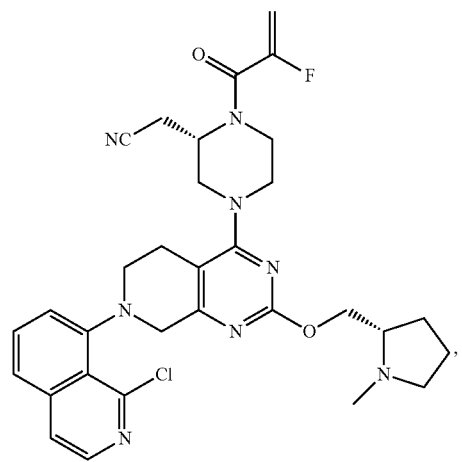
200
-continued
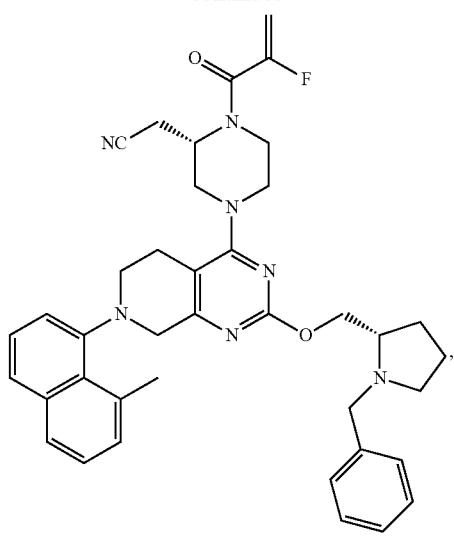
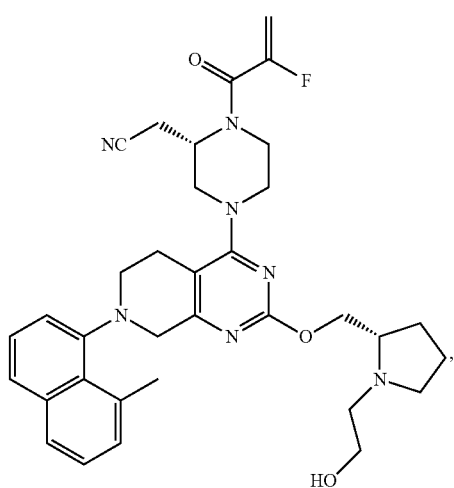
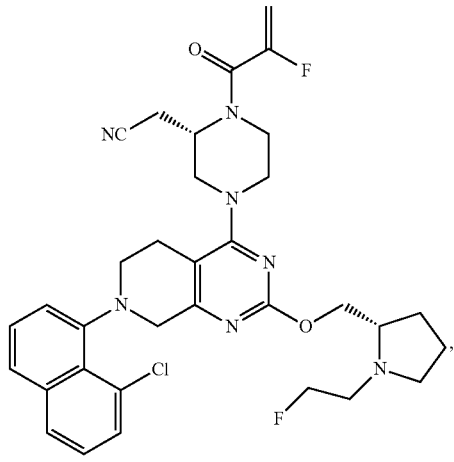

-continued
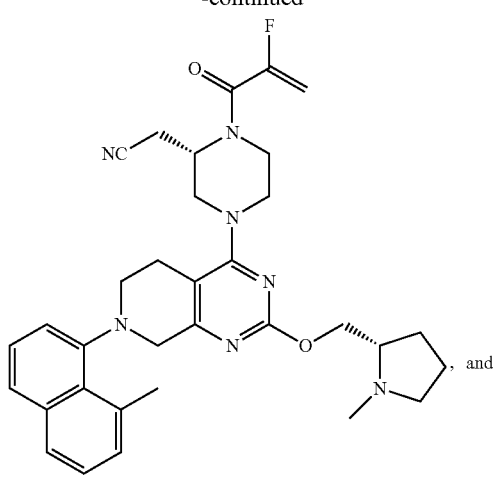
, and
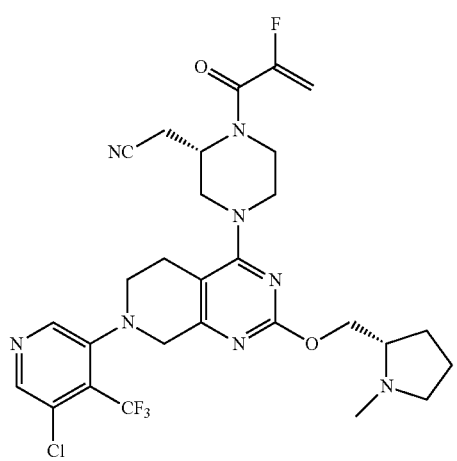
and pharmaceutically acceptable salts thereof.
In one embodiment, the KRas G12C inhibitor is selected from:
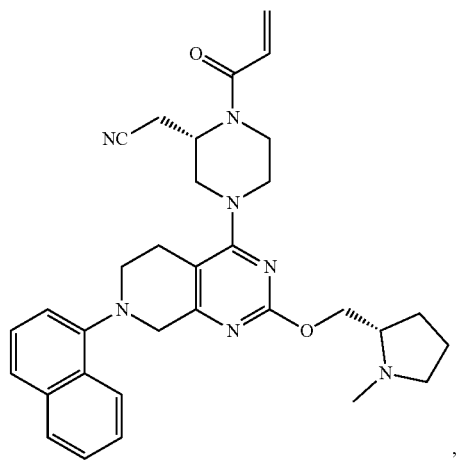
,
-continued
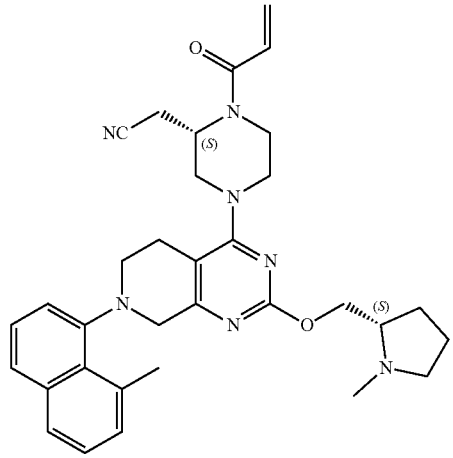
,
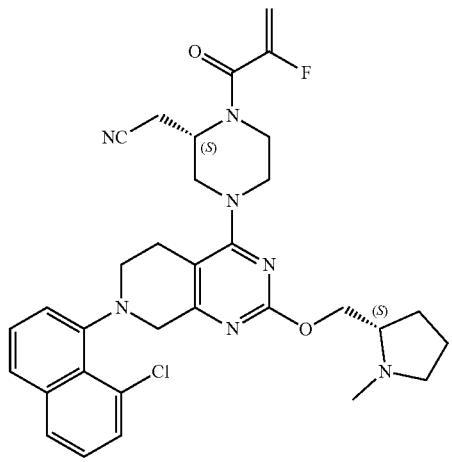
, and
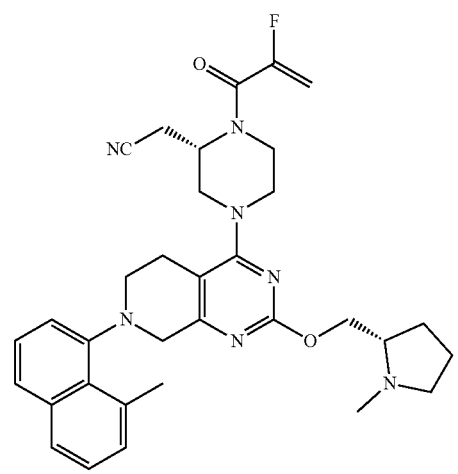 [SMILES: C=C(F)C(=O)N1CCN(c2nc(OC[C@@H]3CCCN3C)nc3c2CCN(c2cccc4cccc(C)c24)C3)C[C@@H]1CC#N]
and pharmaceutically acceptable salts thereof.

In one embodiment, the KRas G12C inhibitor is:

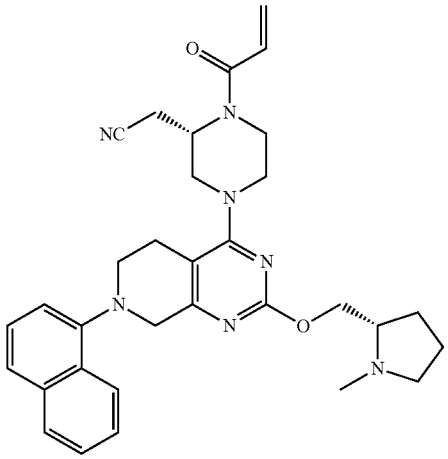 [SMILES: C=CC(=O)N1CCN(c2nc(OC[C@@H]3CCCN3C)nc3c2CCN(c2cccc4ccccc24)C3)C[C@@H]1CC#N]

(also referred to as Example 234) or a pharmaceutically acceptable salt thereof.

In one embodiment, the KRas G12C inhibitor is:

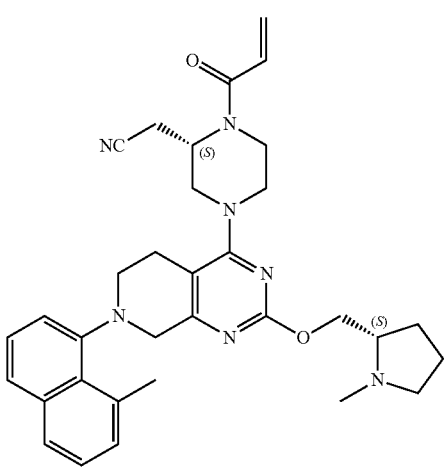

(also referred to as Example 359) or a pharmaceutically acceptable salt thereof.

In one embodiment, the KRas G12C inhibitor is:

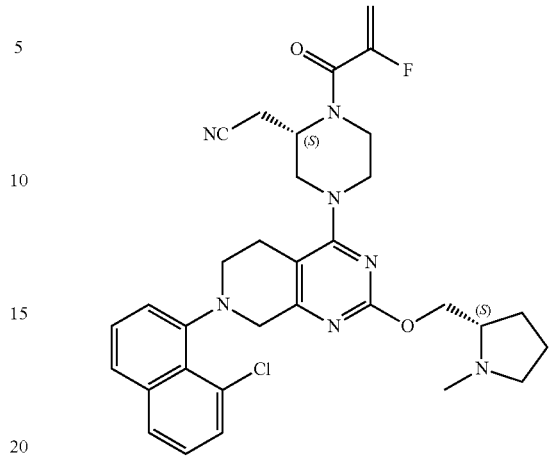

(also referred to as Example 478) or a pharmaceutically acceptable salt thereof.

In one embodiment, the KRas G12C inhibitor is:

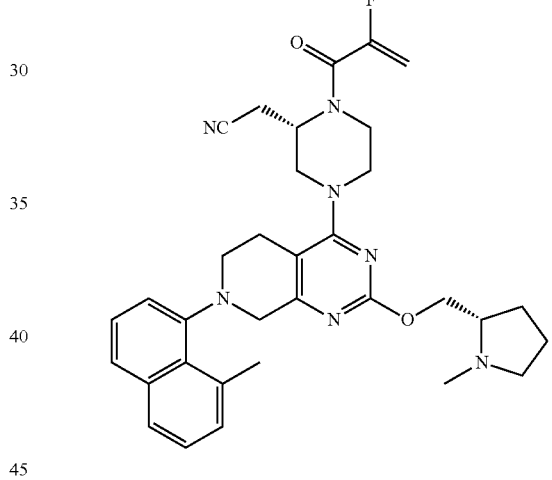

(also referred to as Example 507) or a pharmaceutically acceptable salt thereof.

The KRas G12C inhibitors used in the methods of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

In one embodiment, the KRas G12C inhibitor compounds of Formula I, Formula I-A, or Formula I-B used in the methods include trifluoroacetic acid salts of the above compounds.

Methods for manufacturing the KRas G12C inhibitors disclosed herein are known. For example, commonly owned published international PCT application numbers WO2017201161 and WO2019099524 describe general reaction schemes for preparing compounds of Formula I, Formula I-A, or Formula I-B and pharmaceutically acceptable salts thereof and also provide detailed synthetic routes for the preparation of each KRas G12C inhibitor disclosed herein.

The Pan ErbB inhibitors and the KRas G12C compounds of Formula (I), Formula I-A, or Formula I-B or pharmaceutically acceptable salts thereof may be formulated into pharmaceutical compositions.

Pharmaceutical Compositions

In another aspect, the invention provides pharmaceutical compositions comprising a pan ErbB family inhibitor and KRas G12C inhibitor according to the invention and a pharmaceutically acceptable carrier, excipient, or diluent that may be used in the methods disclosed herein. The pan ErbB family inhibitor and KRas G12C inhibitor may be independently formulated by any method well known in the art and may be prepared for administration by any route, including, without limitation, parenteral, oral, sublingual, transdermal, topical, intranasal, intratracheal, or intrarectal. In certain embodiments, pan ErbB family inhibitor and KRas G12C inhibitor are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising a pan ErbB family inhibitor and a KRas G12C inhibitor may be used in the methods of use described herein.

Co-Adminstration

The pan ErbB family inhibitor and the KRas G12C inhibitor can be formulated into separate or individual dosage forms which can be co-administered one after the other. Another option is that if the route of administration is the same (e.g. oral) two active compounds can be formulated into a single form for co-administration, both methods of co-administration, however, being part of the same therapeutic treatment or regimen.

The pharmaceutical compositions comprising a pan ErbB family inhibitor and/or a KRas G12C inhibitor for use in the methods may be for simultaneous, separate or sequential use. In one embodiment, the pan ErbB family inhibitor is administered prior to administration of the KRas G12C inhibitor compound of Formula (I), Formula I-A or Formula I-B. In another embodiment, the pan ErbB family inhibitor is administered after administration of the KRas G12C inhibitor compound of Formula (I), Formula I-A or Formula I-B. In another embodiment, the pan ErbB family inhibitor is administered at about the same time as administration of the KRas G12C inhibitor compound of Formula (I), Formula I-A or Formula I-B.

Separate administration of each inhibitor, at different times and by different routes, in some cases would be advantageous. Thus, the components in the combination i.e. the KRas G12C inhibitor compound of Formula (I), Formula I-A or Formula I-B, or a pharmaceutically acceptable salt thereof and the pan ErbB family inhibitor or a pharmaceutically acceptable salt thereof, need not be necessarily administered at essentially the same time or in any order.

Oncology drugs are typically administered at the maximum tolerated dose ("MTD"), which is the highest dose of drug that does not cause unacceptable side effects. In one embodiment, the KRas G12C inhibitor or a pharmaceutically acceptable salt or a pharmaceutically composition thereof and the pan ErbB family inhibitor or a pharmaceutically acceptable salt or a pharmaceutically composition thereof are each dosed at their respective MTDs. In one embodiment, the KRas G12C inhibitor or a pharmaceutically acceptable salt or a pharmaceutically composition thereof is dosed at its MTD and the pan ErbB family inhibitor or a pharmaceutically acceptable salt or a pharmaceutically composition thereof is dosed in an amount less than its MTD. In one embodiment, the KRas G12C inhibitor or a pharmaceutically acceptable salt or a pharmaceutically composition thereof is dosed at an amount less than its MTD and the pan ErbB family inhibitor or a pharmaceutically acceptable salt or a pharmaceutically composition thereof is dosed at its MTD. In one embodiment, the KRas G12C inhibitor or a pharmaceutically acceptable salt or a pharmaceutically composition thereof and the pan ErbB family inhibitor or a pharmaceutically acceptable salt or a pharmaceutically composition thereof are each dosed at less than their respective MTDs. The administration can be so timed that the peak pharmacokinetic effect of one compound coincides with the peak pharmacokinetic effect of the other.

In one embodiment, the KRas G12C inhibitor compound of Formula (I), Formula I-A or Formula I-B or a pharmaceutically acceptable salt or a pharmaceutically composition thereof is administered per day (i.e., in about 24 hour intervals) (i.e., QD). In another embodiment, the KRas G12C inhibitor compound of Formula (I), Formula I-A or Formula I-B or a pharmaceutically acceptable salt or a pharmaceutically composition thereof is administered per day (i.e., BID). In another embodiment, the KRas G12C inhibitor compound of Formula (I), Formula I-A or Formula I-B or a pharmaceutically acceptable salt or a pharmaceutically composition thereof is administered per day (i.e., TID).

In one embodiment, the pan ErbB family inhibitor or a pharmaceutically acceptable salt or a pharmaceutically composition thereof is administered QD. In another embodiment, the pan ErbB family inhibitor or a pharmaceutically acceptable salt or a pharmaceutically composition thereof is administered BID. In another embodiment, the pan ErbB family inhibitor or a pharmaceutically acceptable salt or a pharmaceutically composition thereof of the invention are administered TID.

In one embodiment, a single dose of KRas G12C inhibitor compound of Formula (I), Formula I-A or Formula I-B or a pharmaceutically acceptable salt or a pharmaceutically composition thereof and pan ErbB family inhibitor or a pharmaceutically acceptable salt or a pharmaceutically composition thereof are each administered once daily.

In one embodiment, the pan ErbB family inhibitor is an irreversible inhibitor. Exemplary irreversible pan ErbB family inhibitors for use in the methods herein include afatinib ((E)-N-(4-((3-chloro-4-fluorophenyl)amino)-7-((tetrahydrofuran-3-yl)oxy)quinazolin-6-yl)-4-(dimethylamino)but-2-enamide); dacomitinib ((2E)-N-{4-[(3-Chloro-4-fluorophenyl)amino]-7-methoxy-6-quinazolinyl}-4-(1-piperidinyl)-2-butenamide); canertinib (N-(4-((3-chloro-4-fluorophenyl)amino)-7-(3-morpholinopropoxy)quinazolin-6-yl) acrylamide); poziotinib (1-(4-((4-((3,4-dichloro-2-fluorophenyl)amino)-7-methoxyquinazolin-6-yl)oxy) piperidin-1-yl)prop-2-en-1-one); AV 412 (N-[4-[(3-Chloro-4-fluorophenyl)amino]-7-[3-methyl-3-(4-methyl-1-piperazinyl)-1-butyn-1-yl]-6-quinazolinyl]-2-propenamide); PF 6274484 (N-[4-[(3-Chloro-4-fluorophenyl)amino]-7-methoxy-6-quinazolinyl]-2-propenamide) and HKI 357 ((2E)-N-[[4-[[(3-Chloro-4-[(3-fluorophenyl)methoxy]phenyl]amino]-3-cyano-7-ethoxy-6-quinolinyl]-4-(dimethylamino)-2-butenamide), or pharmaceutically acceptable salts or pharmaceutically compositions thereof.

In one embodiment, the pan ErbB family inhibitor is a reversible inhibitor. Exemplary reversible pan EGFR family inhibitors include erlotinib ([6,7-Bis-(2-methoxy-ethoxy)-quinazolin-4-yl]-(3-ethynyl-phenyl)-amine)), gefitinib ((4-(3'-chloro-4'-fluoroanilino)-7-methoxy-6-(3-morpholino-propoxy)quinazoline), sapitinib (2-(4-((4-((3-chloro-2-fluorophenyl)amino)-7-methoxyquinazolin-6-yl)oxy) piperidin-1-yl)-N-methylacetamide); varlitinib ((R)-N4-(3-chloro-4-(thiazol-2-ylmethoxy)phenyl)-N6-(4-methyl-4,5-dihydrooxazol-2-yl)quinazoline-4,6-diamine); TAK-285 (N-(2-(4-((3-chloro-4-(3-(trifluoromethyl)phenoxy)phenyl) amino)-5H-pyrrolo[3,2-d]pyrimidin-5-yl)ethyl)-3-hydroxy-3-methylbutanamide); AEE788 ((S)-6-(4-((4-ethylpiperazin-1-yl)methyl)phenyl)-N-(1-phenylethyl)-7H-pyrrolo[2,3-d]pyrimidin-4-amine); tarloxotinib ([(E)-4-[[4-(3-bromo-4-chloroanilino)pyrido[3,4-d]pyrimidin-6-yl]amino]-4-oxobut-2-enyl]-dimethyl-[(3-methyl-5-nitroimidazol-4-yl) methyl]azanium); BMS 599626 ((3S)-3-Morpholinylmethyl-[4-[[1-[(3-fluorophenyl)methyl]-1H-indazol-5-yl]amino]-5-methylpyrrolo[2,1-f][1,2,4]triazin-6-yl]-carbamate dihydrochloride); and GW 583340 HCl (N-[3-Chloro-4-[(3-fluorophenyl)methoxy]phenyl]-6-[2-[[[2-(methylsulfonyl)ethyl]amino]methyl]-4-thiazolyl]-4-quinazolinamine dihydrochloride), or pharmaceutically acceptable salts or pharmaceutically compositions thereof.

In one embodiment, the pan ErbB family inhibitor is an anti-EGFR antibody, an anti-HER2 antibody or a combination of an anti-EGFR antibody and anti-HER2 antibody, or pharmaceutical compositions thereof. In one embodiment, the anti-EGFR antibody is necitumumab, panitumumab or cetuximab. In one embodiment, the anti-EGFR antibody is cetuximab. In one embodiment, the anti-HER2 antibodies suitable for use in the methods herein is pertuzumab, trastuzumab, or trastuzumab emtansine.

In one embodiment, the pan ErbB family inhibitor is a an EGFR inhibitor and a HER2 inhibitor, wherein the EGFR inhibitor and the HER2 inhibitor are independently selected from two agents selected from the group consisting of: AG 1478 HCl (N-(3-Chlorophenyl)-6,7-dimethoxy-4-quinazolinanine hydrochloride); AG 494 (E)-2-Cyano-3-(3,4-dihydroxyphenyl)-N-phenyl-2-propenamide; AG 555 (E)-2-Cyano-3-(3,4-dihydroxyphenyl)-N-(3-phenylpropyl)-2-propenamide; AG 556 (E)-2-Cyano-3-(3,4-dihydroxyphenyl)-N-(4-phenylbutyl)-2-propenamide; AG 825 (E)-3-[3-[2-Benzothiazolylthio)methyl]-4-hydroxy-5-methoxyphenyl]-2-cyano-2-propenamide; CP 724714 (2-Methoxy-N-[(2E)-3-[4-[[3-methyl-4-[(6-methyl-3-pyridinyl)oxy]phenyl]amino]-6-quinazolinyl]-2-propen-1-yl]acetamide; BIBU 1361 diHCl (N-(3-Chloro-4-fluorophenyl)-6-[4-[(diethylamino)methyl]-1-piperidinyl]-pyrimido [5,4-d]pyrimidin-4-amine dihydrochloride); BIBU 1382 ($N^8$-(3-Chloro-4-fluorophenyl)-$N^2$-(1-methyl-4-piperidinyl)-pyrimido[5,4-d]pyrimidine-2,8-diamine dihydrochloride); JNJ 28871063 HCl (5E-4-Amino-6-(4-benzyloxy-3-chlorophenylamino)pyrimidine-5-carboxaldehyde N-(2-morpholin-4-ylethyl) oxime hydrochloride); PD 153035 (4-[(3-Bromophenyl)amino]-6,7-dimethoxyquinazoline hydrochloride); PD 158780 ($N^4$-(3-Bromophenyl)-N6-methyl-pyrido[3,4-d]pyrimidine-4,6-diamine) or pharmaceutically acceptable salts or pharmaceutically compositions thereof.

Combination Therapies

In one aspect of the invention, provided herein are methods of treating cancer in a subject in need thereof, comprising administering to the subject a therapeutically effective amount of a combination of a pan ErbB family inhibitor, or a pharmaceutically acceptable salt or a pharmaceutically composition thereof and a KRAS G12C inhibitor of Formula (I), Formula I-A or Formula I-B, or a pharmaceutically acceptable salt or a pharmaceutically composition thereof. In one embodiment, the cancer is a KRas G12C-associated cancer. In one embodiment, the KRas G12C-associated cancer is lung cancer.

In yet another aspect, the invention provides for methods for increasing the sensitivity of a cancer cell to a KRas G12C inhibitor, comprising contacting the cancer cell with an effective amount of a combination of a KRas G12C inhibitor compound of Formula (I), Formula I-A, or Formula I-B, or a pharmaceutically acceptable salt or a pharmaceutically composition thereof and a pan ErbB family inhibitor, or a pharmaceutically acceptable salt or a pharmaceutical composition thereof, wherein the pan ErbB family inhibitor synergistically increases the sensitivity of the cancer cell to the KRas G12C inhibitor. In one embodiment, the contacting is in vitro. In one embodiment, the contacting is in vivo.

In one embodiment, the combination therapy comprises a combination of a compound having the formula:

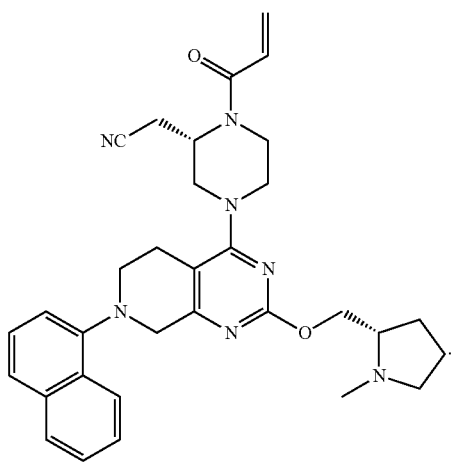 [SMILES: C=CC(=O)N1CCN(c2nc(OC[C@@H]3CCCN3C)nc3c2CCN(c2cccc4ccccc24)C3)C[C@@H]1CC#N]

or a pharmaceutically acceptable salt thereof, and a pan ErbB family inhibitor. In one embodiment, the pan ErbB family inhibitor is afatinib. In one embodiment, the pan ErbB family inhibitor is dacomitinib. In one embodiment, the pan ErbB family inhibitor is poziotinib. In one embodiment, the pan ErbB family inhibitor is erlotinib. In one embodiment, the pan ErbB family inhibitor is Gefitinib. In one embodiment, the pan ErbB family inhibitor is sapitinib. In one embodiment, the pan ErbB family inhibitor is tarloxotinib. In one embodiment, the pan ErbB family inhibitor is an anti-EGFR antibody, wherein the anti-EGFR antibody is cetuximab.

In one embodiment, the combination therapy comprises a combination of a compound having the formula:

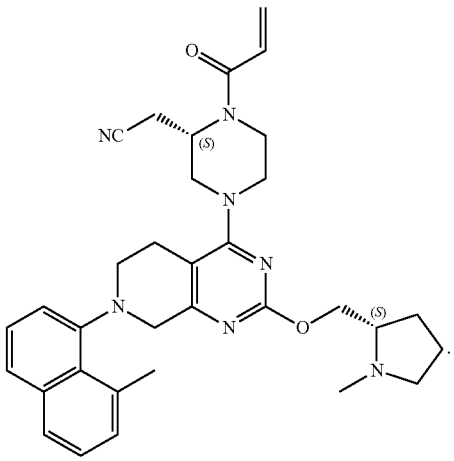

or a pharmaceutically acceptable salt thereof, and a pan ErbB family inhibitor. In one embodiment, the pan ErbB family inhibitor is Afatinib. In one embodiment, the pan ErbB family inhibitor is dacomitinib. In one embodiment, the pan ErbB family inhibitor is poziotinib. In one embodiment, the pan ErbB family inhibitor is erlotinib. In one embodiment, the pan ErbB family inhibitor is gefitinib. In one embodiment, the pan ErbB family inhibitor is sapitinib. In one embodiment, the pan ErbB family inhibitor is tarloxotinib. In one embodiment, the pan ErbB family inhibitor is an anti-EGFR antibody, wherein the anti-EGFR antibody is cetuximab.

In one embodiment, the combination therapy comprises a combination of a compound having the formula:

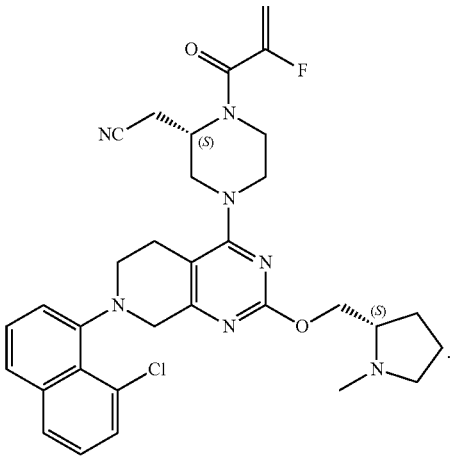

or a pharmaceutically acceptable salt thereof, and a pan ErbB family inhibitor. In one embodiment, the pan ErbB family inhibitor is afatinib. In one embodiment, the pan ErbB family inhibitor is dacomitinib. In one embodiment, the pan ErbB family inhibitor is poziotinib. In one embodiment, the pan ErbB family inhibitor is erlotinib. In one embodiment, the pan ErbB family inhibitor is Gefitinib. In one embodiment, the pan ErbB family inhibitor is sapitinib. In one embodiment, the pan ErbB family inhibitor is tarloxotinib. In one embodiment, the pan ErbB family inhibitor is an anti-EGFR antibody, wherein the anti-EGFR antibody is cetuximab.

In one embodiment, the combination therapy comprises a combination of a compound having the formula:

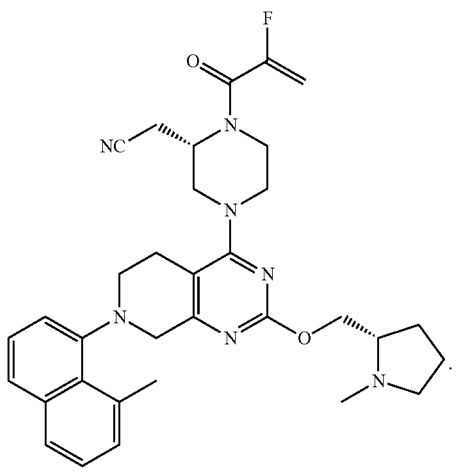 [SMILES: C=C(F)C(=O)N1CCN(c2nc(OC[C@@H]3CCCN3C)nc3c2CCN(c2cccc4cccc(C)c24)C3)C[C@@H]1CC#N]

or a pharmaceutically acceptable salt thereof, and a pan ErbB family inhibitor. In one embodiment, the pan ErbB family inhibitor is afatinib. In one embodiment, the pan ErbB family inhibitor is Dacomitinib. In one embodiment, the pan ErbB family inhibitor is poziotinib. In one embodiment, the pan ErbB family inhibitor is erlotinib. In one embodiment, the pan ErbB family inhibitor is Gefitinib. In one embodiment, the pan ErbB family inhibitor is sapitinib. In one embodiment, the pan ErbB family inhibitor is tarloxotinib. In one embodiment, the pan ErbB family inhibitor is an anti-EGFR antibody, wherein the anti-EGFR antibody is cetuximab.

As used herein, the term "contacting" refers to the bringing together of indicated moieties in an in vitro system or an in vivo system. For example, "contacting" a cancer cell includes the administration of a combination provided herein to an individual or subject, such as a human, having KRas G12C, as well as, for example, introducing a combination provided herein into a sample containing a cellular or purified preparation containing the KRas G12C.

By negatively modulating the activity of KRas G12C, the methods described herein are designed to inhibit undesired cellular proliferation resulting from enhanced KRas G12C activity within the cell. The degree of covalent modification of KRas G12C may be monitored in vitro using well known methods, including those described in published international PCT application numbers WO2017201161 and WO2019099524. In addition, the inhibitory activity of combination in cells may be monitored, for example, by measuring the inhibition of KRas G12C activity of the amount of phosphorylated ERK to assess the effectiveness of treatment and dosages may be adjusted accordingly by the attending medical practitioner.

The compositions and methods provided herein may be used for the treatment of a KRas G12C-associated cancer in a subject in need thereof, comprising administering to said subject a therapeutically effective amount of a combination of a pan ErbB family inhibitor, or a pharmaceutically acceptable salt or a pharmaceutical composition thereof and a KRas G12C inhibitor compound of Formula (I), Formula I-A, or Formula I-B, or a pharmaceutically acceptable salt or a pharmaceutical composition thereof, wherein the pan ErbB family inhibitor synergistically increases the sensitivity of the KRas G12C-associated cancer to the KRas G12C inhibitor. In one embodiment, the KRas G12C-associated cancer is lung cancer.

In one embodiment, the therapeutically effective amount of the combination of a pan ErbB family inhibitor or a pharmaceutically acceptable salt or a pharmaceutically composition thereof and a KRas G12C inhibitor compound of Formula (I), Formula I-A, or Formula I-B, or a pharmaceutically acceptable salt or a pharmaceutical composition thereof, results in an increased duration of overall survival ("OS") in subjects relative to treatment with only the KRas G12C inhibitor. In one embodiment, the therapeutically effective amount of the combination of a pan ErbB family inhibitor or a pharmaceutically acceptable salt or a pharmaceutically composition thereof and a KRas G12C inhibitor compound of Formula (I), Formula I-A, or Formula I-B, or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a pan ErbB family inhibitor or a pharmaceutically acceptable salt or a pharmaceutically composition thereof and a KRas G12C inhibitor compound of Formula (I), Formula I-A, or Formula I-B, or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a pan ErbB family inhibitor or a pharmaceutically acceptable salt or a pharmaceutically composition thereof and a KRas G12C inhibitor compound of Formula (I), Formula I-A, or Formula I-B, or a pharmaceutically acceptable salt or a pharmaceutical composition thereof, results in an improvement in the duration of stable disease in subjects compared to treatment with only the KRas G12C inhibitor. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the pan ErbB family inhibitor is selected from afatinib, dacomitinib, poziotinib, erlotinib, gefitinib, sapitinib, and tarloxotinib. In one embodiment, the therapeutic combination comprises therapeutically effective amounts of Example No. 234 and afatinib. In one embodiment, the therapeutic combination comprises therapeutically effective amounts of Example No. 234 and dacomitinib. In one embodiment, the therapeutic combination comprises therapeutically effective amounts of Example No. 234 and poziotinib. In one embodiment, the therapeutic combination comprises therapeutically effective amounts of Example No. 234 and erlotinib. In one embodiment, the therapeutic combination comprises therapeutically effective amounts of Example No. 234 and gefitinib. In one embodiment, the therapeutic combination comprises therapeutically effective amounts of Example No. 234 and Tarloxotinib. In one embodiment, the therapeutic combination comprises therapeutically effective amounts of Example No. 234 and the anti-EGFR antibody cetuximab. In one embodiment, the therapeutic combination comprises therapeutically effective amounts of Example No. 359 and afatinib. In one embodiment, the therapeutic combination comprises therapeutically effective amounts of Example No. 359 and dacomitinib. In one embodiment, the therapeutic combination comprises therapeutically effective amounts of Example No. 359 and poziotinib. In one embodiment, the therapeutic combination comprises therapeutically effective amounts of Example No. 359 and erlotinib. In one embodiment, the therapeutic combination comprises therapeutically effective amounts of Example No. 359 and gefitinib. In one embodiment, the therapeutic combination comprises therapeutically effective amounts of Example No. 359 and tarloxotinib. In one embodiment, the therapeutic combination comprises therapeutically effective amounts of Example No. 359 and the anti-EGFR antibody cetuximab. In one embodiment, the therapeutic combination comprises therapeutically effective amounts of Example No. 478 and afatinib. In one embodiment, the therapeutic combination comprises therapeutically effective amounts of Example No. 478 and dacomitinib. In one embodiment, the therapeutic combination comprises therapeutically effective amounts of Example No. 478 and poziotinib. In one embodiment, the therapeutic combination comprises therapeutically effective amounts of Example No. 478 and erlotinib. In one embodiment, the therapeutic combination comprises therapeutically effective amounts of Example No. 478 and gefitinib. In one embodiment, the therapeutic combination comprises therapeutically effective amounts of Example No. 478 and tarloxotinib. In one embodiment, the therapeutic combination comprises therapeutically effective amounts of Example No. 478 and the anti-EGFR antibody cetuximab. In one embodiment, the therapeutic combination comprises therapeutically effective amounts of Example No. 507 and afatinib. In one embodiment, the therapeutic combination comprises therapeutically effective amounts of Example No. 507 and dacomitinib. In one embodiment, the therapeutic combination comprises therapeutically effective amounts of Example No. 507 and poziotinib. In one embodiment, the therapeutic combination comprises therapeutically effective amounts of Example No. 507 and erlotinib. In one embodiment, the therapeutic combination comprises therapeutically effective amounts of Example No. 507 and gefitinib. In one embodiment, the therapeutic combination comprises therapeutically effective amounts of Example No. 507 and tarloxotinib. In one embodiment, the therapeutic combination comprises therapeutically effective amounts of Example No. 507 and the anti-EGFR antibody cetuximab. In one embodiment of any of said combination therapies, the combination is useful for treating a KRas G12C-associated cancer. In one embodiment, the KRas G12C-associated cancer is lung cancer.

In another embodiment, the pan ErbB family inhibitor, or a pharmaceutically acceptable salt or a pharmaceutical composition thereof is administered in combination with the KRas G12C inhibitor, or a pharmaceutically acceptable salt or a pharmaceutical composition thereof once disease progression has been observed for KRas G12C monotherapy, in which the combination therapy results in enhanced clinical benefit or time of survival for the patient by increasing OS, PFS, tumor regression, tumor growth inhibition or the duration of stable disease in the patient. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the pan ErbB family inhibitor is selected from afatinib, dacomitinib, poziotinib, erlotinib, gefitinib, sapitinib, and tarloxotinib. In one embodiment, the therapeutic combination comprises therapeutically effective amounts of Example No. 234 and afatinib. In one embodiment, the therapeutic combination comprises therapeutically effective amounts of Example No. 234 and dacomitinib. In one embodiment, the therapeutic combination comprises therapeutically effective amounts of Example No. 234 and poziotinib. In one embodiment, the therapeutic combination comprises therapeutically effective amounts of Example No. 234 and erlotinib. In one embodiment, the therapeutic combination comprises therapeutically effective amounts of Example No. 234 and gefitinib. In one embodiment, the therapeutic combination comprises therapeutically effective amounts of Example No. 234 and tarloxotinib. In one embodiment, the therapeutic combination comprises therapeutically effective amounts of Example No. 234 and the anti-EGFR antibody cetuximab. In one embodiment, the therapeutic combination comprises therapeutically effective amounts of Example No. 359 and afatinib. In one embodiment, the therapeutic combination comprises therapeutically effective amounts of Example No. 359 and dacomitinib. In one embodiment, the therapeutic combination comprises therapeutically effective amounts of Example No. 359 and poziotinib. In one embodiment, the therapeutic combination comprises therapeutically effective amounts of Example No. 359 and Erlotinib. In one embodiment, the therapeutic combination comprises therapeutically effective amounts of Example No. 359 and gefitinib. In one embodiment, the therapeutic combination comprises therapeutically effective amounts of Example No. 359 and tarloxotinib. In one embodiment, the therapeutic combination comprises therapeutically effective amounts of Example No. 359 and the anti-EGFR antibody Cetuximab. In one embodiment, the therapeutic combination comprises therapeutically effective amounts of Example No. 478 and afatinib. In one embodiment, the therapeutic combination comprises therapeutically effective amounts of Example No. 478 and dacomitinib. In one embodiment, the therapeutic combination comprises therapeutically effective amounts of Example No. 478 and poziotinib. In one embodiment, the therapeutic combination comprises therapeutically effective amounts of Example No. 478 and erlotinib. In one embodiment, the therapeutic combination comprises therapeutically effective amounts of Example No. 478 and gefitinib. In one embodiment, the therapeutic combination comprises therapeutically effective amounts of Example No. 478 and tarloxotinib. In one embodiment, the therapeutic combination comprises therapeutically effective amounts of Example No. 478 and the anti-EGFR antibody cetuximab. In one embodiment, the therapeutic combination comprises therapeutically effective amounts of Example No. 507 and afatinib. In one embodiment, the therapeutic combination comprises therapeutically effective amounts of Example No. 507 and dacomitinib. In one embodiment, the therapeutic combination comprises therapeutically effective amounts of Example No. 507 and poziotinib. In one embodiment, the therapeutic combination comprises therapeutically effective amounts of Example No. 507 and erlotinib. In one embodiment, the therapeutic combination comprises therapeutically effective amounts of Example No. 507 and gefitinib. In one embodiment, the therapeutic combination comprises therapeutically effective amounts of Example No. 507 and tarloxotinib. In one embodiment, the therapeutic combination comprises therapeutically effective amounts of Example No. 507 and the anti-EGFR antibody cetuximab. In one embodiment of any of said combination therapies, the combination is useful for treating a KRas G12C-associated cancer. In one embodiment, the KRas G12C-associated cancer is lung cancer.

In one embodiment of any of the methods herein, the pan ErbB family inhibitor and the KRAS G12C inhibitor are administered on the same day.

In one embodiment of any of the methods herein, the pan ErbB family inhibitor and the KRAS G12C inhibitor are administered on different days.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

Also provided herein is a method for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a pan ErbB family inhibitor and a KRas G12C inhibitor compound of Formula I, Formula I-A, Formula I-B, or pharmaceutically acceptable salts or pharmaceutical compositions thereof, wherein the pan ErbB inhibitor synergistically increases the sensitivity of the KRas G12C-associated cancer to the KRas G12C inhibitor. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the pan ErbB family inhibitor is selected from afatinib, dacomitinib, poziotinib, Erlotinib, gefitinib, sapitinib, and tarloxotinib. In one embodiment, the therapeutic combination comprises therapeutically effective amounts of Example No. 234 and afatinib. In one embodiment, the therapeutic combination comprises therapeutically effective amounts of Example No. 234 and dacomitinib. In one embodiment, the therapeutic combination comprises therapeutically effective amounts of Example No. 234 and poziotinib. In one embodiment, the therapeutic combination comprises therapeutically effective amounts of Example No. 234 and erlotinib. In one embodiment, the therapeutic combination comprises therapeutically effective amounts of Example No. 234 and gefitinib. In one embodiment, the therapeutic combination comprises therapeutically effective amounts of Example No. 234 and tarloxotinib. In one embodiment, the therapeutic combination comprises therapeutically effective amounts of Example No. 234 and the anti-EGFR antibody cetuximab. In one embodiment, the therapeutic combination comprises therapeutically effective amounts of Example No. 359 and afatinib. In one embodiment, the therapeutic combination comprises therapeutically effective amounts of Example No. 359 and dacomitinib. In one embodiment, the therapeutic combination comprises therapeutically effective amounts of Example No. 359 and poziotinib. In one embodiment, the therapeutic combination comprises therapeutically effective amounts of Example No. 359 and erlotinib. In one embodiment, the therapeutic combination comprises therapeutically effective amounts of Example No. 359 and gefitinib. In one embodiment, the therapeutic combination comprises therapeutically effective amounts of Example No. 359 and tarloxotinib. In one embodiment, the therapeutic combination comprises therapeutically effective amounts of Example No. 359 and the anti-EGFR antibody cetuximab. In one embodiment, the therapeutic combination comprises therapeutically effective amounts of Example No. 478 and afatinib. In one embodiment, the therapeutic combination comprises therapeutically effective amounts of Example No. 478 and dacomitinib. In one embodiment, the therapeutic combination comprises therapeutically effective amounts of Example No. 478 and poziotinib. In one embodiment, the therapeutic combination comprises therapeutically effective amounts of Example No. 478 and erlotinib. In one embodiment, the therapeutic combination comprises therapeutically effective amounts of Example No. 478 and gefitinib. In one embodiment, the therapeutic combination comprises therapeutically effective amounts of Example No. 478 and tarloxotinib. In one embodiment, the therapeutic combination comprises therapeutically effective amounts of Example No. 478 and the anti-EGFR antibody cetuximab. In one embodiment, the therapeutic combination comprises therapeutically effective amounts of Example No. 507 and afatinib. In one embodiment, the therapeutic combination comprises therapeutically effective amounts of Example No. 507 and dacomitinib. In one embodiment, the therapeutic combination comprises therapeutically effective amounts of Example No. 507 and poziotinib. In one embodiment, the therapeutic combination comprises therapeutically effective amounts of Example No. 507 and erlotinib. In one embodiment, the therapeutic combination comprises therapeutically effective amounts of Example No. 507 and gefitinib. In one embodiment, the therapeutic combination comprises therapeutically effective amounts of Example No. 507 and tarloxotinib. In one embodiment, the therapeutic combination comprises therapeutically effective amounts of Example No. 507 and the anti-EGFR antibody cetuximab. In one embodiment of any of said combination therapies, the combination is useful for treating a KRas G12C-associated cancer. In one embodiment, the KRas G12C-associated cancer is lung cancer.

In another embodiment, the pan ErbB family inhibitor, or a pharmaceutically acceptable salt or a pharmaceutical composition thereof is administered in combination with the KRas G12C inhibitor, or a pharmaceutically acceptable salt or a pharmaceutical composition thereof once disease progression has been observed for KRas G12C monotherapy, in which the combination therapy results in enhanced clinical benefit or time of survival for the patient by increasing OS, PFS, tumor regression, tumor growth inhibition or the duration of stable disease in the patient. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the pan ErbB family inhibitor is selected from Afatinib, dacomitinib, poziotinib, erlotinib, gefitinib, sapitinib, and tarloxotinib. In one embodiment, the therapeutic combination comprises therapeutically effective amounts of Example No. 234 and afatinib. In one embodiment, the therapeutic combination comprises therapeutically effective amounts of Example No. 234 and dacomitinib. In one embodiment, the therapeutic combination comprises therapeutically effective amounts of Example No. 234 and poziotinib. In one embodiment, the therapeutic combination comprises therapeutically effective amounts of Example No. 234 and erlotinib. In one embodiment, the therapeutic combination comprises therapeutically effective amounts of Example No. 234 and gefitinib. In one embodiment, the therapeutic combination comprises therapeutically effective amounts of Example No. 234 and tarloxotinib. In one embodiment, the therapeutic combination comprises therapeutically effective amounts of Example No. 234 and the anti-EGFR antibody cetuximab. In one embodiment, the therapeutic combination comprises therapeutically effective amounts of Example No. 359 and afatinib. In one embodiment, the therapeutic combination comprises therapeutically effective amounts of Example No. 359 and dacomitinib. In one embodiment, the therapeutic combination comprises therapeutically effective amounts of Example No. 359 and poziotinib. In one embodiment, the therapeutic combination comprises therapeutically effective amounts of Example No. 359 and erlotinib. In one embodiment, the therapeutic combination comprises therapeutically effective amounts of Example No. 359 and gefitinib. In one embodiment, the therapeutic combination comprises therapeutically effective amounts of Example No. 359 and tarloxotinib. In one embodiment, the therapeutic combination comprises therapeutically effective amounts of Example No. 359 and the anti-EGFR antibody cetuximab. In one embodiment, the therapeutic combination comprises therapeutically effective amounts of Example No. 478 and afatinib. In one embodiment, the therapeutic combination comprises therapeutically effective amounts of Example No. 478 and dacomitinib. In one embodiment, the therapeutic combination comprises therapeutically effective amounts of Example No. 478 and poziotinib. In one embodiment, the therapeutic combination comprises therapeutically effective amounts of Example No. 478 and erlotinib. In one embodiment, the therapeutic combination comprises therapeutically effective amounts of Example No. 478 and gefitinib. In one embodiment, the therapeutic combination comprises therapeutically effective amounts of Example No. 478 and tarloxotinib. In one embodiment, the therapeutic combination comprises therapeutically effective amounts of Example No. 478 and the anti-EGFR antibody cetuximab. In one embodiment, the therapeutic combination comprises therapeutically effective amounts of Example No. 507 and afatinib. In one embodiment, the therapeutic combination comprises therapeutically effective amounts of Example No. 507 and dacomitinib. In one embodiment, the therapeutic combination comprises therapeutically effective amounts of Example No. 507 and poziotinib. In one embodiment, the therapeutic combination comprises therapeutically effective amounts of Example No. 507 and erlotinib. In one embodiment, the therapeutic combination comprises therapeutically effective amounts of Example No. 507 and gefitinib. In one embodiment, the therapeutic combination comprises therapeutically effective amounts of Example No. 507 and tarloxotinib. In one embodiment, the therapeutic combination comprises therapeutically effective amounts of Example No. 507 and the anti-EGFR antibody cetuximab. In one embodiment of any of said combination therapies, the combination is useful for treating a KRas G12C-associated cancer. In one embodiment, the KRas G12C-associated cancer is lung cancer.

In one embodiment, a compound of Formula I, or a pharmaceutically acceptable salt or pharmaceutical composition thereof, is administered as a capsule during the period of time. In one embodiment, a tablet or capsule formulation of a compound of Formula I comprises about 10 mg to about 100 mg (e.g., about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 100 mg, about 75 mg to about 95 mg, about 75 mg to about 90 mg, about 75 mg to about 85 mg, about 75 mg to about 80 mg, about 80 mg to about 100 mg, about 80 mg to about 95 mg, about 80 mg to about 90 mg, about 85 mg to about 100 mg, about 85 mg to about 95 mg, about 85 mg to about 90 mg, about 90 mg to about 100 mg, about 90 mg to about 95 mg, about 95 mg to about 100 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg) of a compound of Formula I (e.g., a compound selected from compound Nos 1-678 (as numbered in WO2019099524), or pharmaceutically acceptable salts thereof (e.g., Example Nos 234, 359, 478 or 507, or a pharmaceutically acceptable salt thereof). In one embodiment, a compound of Formula I is orally administered once a day (QD) on a daily basis during a period of time. In one embodiment, a compound of Formula I is orally administered twice a day (BID) on a daily basis during a period of time. In one embodiment, a compound of Formula I is orally administered in the amount of about 20 mg to about 500 mg (e.g., about 20 mg to about 480 mg, about 20 mg to about 460 mg, about 20 mg to about 440 mg, about 20 mg to about 420 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 500 mg, about 40 mg to about 480 mg, about 40 mg to about 460 mg, about 40 mg to about 440 mg, about 40 mg to about 420 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 500 mg, about 60 mg to about 480 mg, about 60 mg to about 460 mg, about 60 mg to about 440 mg, about 60 mg to about 420 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 500 mg, about 80 mg to about 480 mg, about 80 mg to about 460 mg, about 80 mg to about 440 mg, about 80 mg to about 420 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 500 mg, about 100 mg to about 480 mg, about 100 mg to about 460 mg, about 100 mg to about 440 mg, about 100 mg to about 420 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 500 mg, about 120 mg to about 480 mg, about 120 mg to about 460 mg, about 120 mg to about 440 mg, about 120 mg to about 420 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 500 mg, about 140 mg to about 480 mg, about 140 mg to about 460 mg, about 140 mg to about 440 mg, about 140 mg to about 420 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 500 mg, about 160 mg to about 480 mg, about 160 mg to about 460 mg, about 160 mg to about 440 mg, about 160 mg to about 420 mg, about 160 mg to about 400 mg, about 160 mg to about 380 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 500 mg, about 180 mg to about 480 mg, about 180 mg to about 460 mg, about 180 mg to about 440 mg, about 180 mg to about 420 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 500 mg, about 200 mg to about 480 mg, about 200 mg to about 460 mg, about 200 mg to about 440 mg, about 200 mg to about 420 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 500 mg, about 220 mg to about 480 mg, about 220 mg to about 460 mg, about 220 mg to about 440 mg, about 220 mg to about 420 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 500 mg, about 240 mg to about 480 mg, about 240 mg to about 460 mg, about 240 mg to about 440 mg, about 240 mg to about 420 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 500 mg, about 260 mg to about 480 mg, about 260 mg to about 460 mg, about 260 mg to about 440 mg, about 260 mg to about 420 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 500 mg, about 280 mg to about 480 mg, about 280 mg to about 460 mg, about 280 mg to about 440 mg, about 280 mg to about 420 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 500 mg, about 300 mg to about 480 mg, about 300 mg to about 460 mg, about 300 mg to about 440 mg, about 300 mg to about 420 mg, about 300 mg to about 400 mg, about 300 mg to about 380 mg, about 300 mg to about 360 mg, about 300 mg to about 340 mg, about 300 mg to about 320 mg, about 320 mg to about 500 mg, about 320 mg to about 480 mg, about 320 mg to about 460 mg, about 320 mg to about 440 mg, about 320 mg to about 420 mg, about 320 mg to about 400 mg, about 320 mg to about 380 mg, about 320 mg to about 360 mg, about 320 mg to about 340 mg, about 340 mg to about 500 mg, about 340 mg to about 480 mg, about 340 mg to about 460 mg, about 340 mg to about 440 mg, about 340 mg to about 420 mg, about 340 mg to about 400 mg, about 340 mg to about 380 mg, about 340 mg to about 360 mg, about 360 mg to about 500 mg, about 360 mg to about 480 mg, about 360 mg to about 460 mg, about 360 mg to about 440 mg, about 360 mg to about 420 mg, about 360 mg to about 400 mg, about 360 mg to about 380 mg, about 380 mg to about 500 mg, about 380 mg to about 480 mg, about 380 mg to about 460 mg, about 380 mg to about 440 mg, about 380 mg to about 420 mg, about 380 mg to about 400 mg, about 400 mg to about 500 mg, about 400 mg to about 480 mg, about 400 mg to about 460 mg, about 400 mg to about 440 mg, about 400 mg to about 420 mg, about 420 mg to about 500 mg, about 420 mg to about 480 mg, about 420 mg to about 460 mg, about 420 mg to about 440 mg, about 440 mg to about 500 mg, about 440 mg to about 480 mg, about 440 mg to about 460 mg, about 460 mg to about 500 mg, about 460 mg to about 480 mg, about 480 mg to about 500 mg, about 25, about 50, about 75, about 100, about 150, about 200, about 250, about 300, about 350, about 400, about 450, or about 500 mg), during a period of time.

In one embodiment, the combination therapy comprises oral administration of a compound of Formula I once or twice a day on a daily basis (during a period of time), e.g., in an amount of about 10 mg to about 400 mg (e.g., about 10 mg to about 380 mg, about 10 mg to about 360 mg, about 10 mg to about 340 mg, about 10 mg to about 320 mg, about 10 mg to about 300 mg, about 10 mg to about 280 mg, about 10 mg to about 260 mg, about 10 mg to about 240 mg, about 10 mg to about 220 mg, about 10 mg to about 200 mg, about 10 mg to about 180 mg, about 10 mg to about 160 mg, about 10 mg to about 140 mg, about 10 mg to about 120 mg, about 10 mg to about 100 mg, about 10 mg to about 80 mg, about 10 mg to about 60 mg, about 10 mg to about 40 mg, about 10 mg to about 20 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 400 mg, about 160 mg to about 380 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 400 mg, about 300 mg to about 380 mg, about 300 mg to about 360 mg, about 300 mg to about 340 mg, about 300 mg to about 320 mg, about 320 mg to about 400 mg, about 320 mg to about 380 mg, about 320 mg to about 360 mg, about 340 mg to about 400 mg, about 340 mg to about 380 mg, about 340 mg to about 360 mg, about 360 mg to about 400 mg, about 360 mg to about 380 mg, about 380 mg to about 400 mg, about 100 mg, about 200 mg, about 300 mg, or about 400 mg), and oral administration of a pan ErbB inhibitor which is administered, for example once a day on a daily basis (during a period of time). In one embodiment, the KRAS G12C inhibitor, or a pharmaceutically acceptable salt or pharmaceutical composition thereof, is orally administered once daily. In one embodiment, the KRAS G12C inhibitor, or a pharmaceutically acceptable salt or pharmaceutical composition thereof, is orally administered twice daily.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Synergy

In one embodiment, the addition of a pan ErbB family inhibitor synergistically increases the activity of KRas G12C inhibitor compound of Formula (I), Formula I-A or Formula I-B against cancer cell lines expressing KRas G12C. Any method for determining whether two compounds exhibit synergy may be used for determining the synergistic effect of the combination.

Several mathematical models have been developed to determine whether two compounds act synergistically, i.e., beyond a mere additive effect. For instance, Loewe Additivity (Loewe (1928) Physiol. 27: 47-187), Bliss Independence (Bliss (1939) Ann. Appl. Biol. 26: 585-615), Highest Single Agent, ZIP (Yadav et al (2015) Comput Struct Biotech J 13: 504-513) and other models (Chou & Talalay (1984) Adv Enzyme Regul 22: 27-55. #6382953; and Greco et al. (1995) Pharmacol Rev 47(2): 331-85. #7568331) are well known models in the pharmaceutical industry and may be used to calculate a "synergy score" that indicates whether synergy was detected and the magnitude of such synergy. Combining these synergy scores produces a composite synergy score which may be used to evaluate and characterize the KRas G12C inhibitor compounds of Formula (I), Formula I-A or Formula I-B in combination with a Pan ErbB inhibitor.

In general, the mathematical models use data obtained from single agent values to determine the predicted additive effect of the combination which is compared to the observed effect for the combination. If the observed effect is greater than the predicted effect, the combination is deemed to be synergistic. For example, the Bliss independence model compares the observed combination response ($Y_O$) with the predicted combination response ($Y_P$), which was obtained based on the assumption that there is no effect from drug-drug interactions. Typically, the combination effect is declared synergistic if $Y_O$ is greater than $Y_P$.

In some embodiments, "synergistic effect" as used herein refers to combination of a KRAS inhibitor or a pharmaceutically acceptable salt thereof, and a pan ErbB family inhibitor or a pharmaceutically acceptable salt thereof producing an effect, for example, any of the beneficial or desired results including clinical results or endpoints as described herein, which is greater than the sum of the effect observed when a compound of Formula I, Formula I-A or Formula I-B or a pharmaceutically acceptable salt thereof (e.g., 1-678 (as numbered in WO2019099524), or a pharmaceutically acceptable salt thereof (e.g., Example No. 234, 359, 478 or 507 or a pharmaceutically acceptable salt thereof) and a pan ErbB family inhibitor or a pharmaceutically acceptable salt thereof are administered alone. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the pan ErbB family inhibitor is selected from afatinib, dacomitinib, gefitinib, sapitinib, tarloxotinib. In one embodiment, the therapeutic combination comprises therapeutically effective amounts of Example No. 234 and afatinib. In one embodiment, the therapeutic combination comprises therapeutically effective amounts of Example No. 234 and dacomitinib. In one embodiment, the therapeutic combination comprises therapeutically effective amounts of Example No. 234 and gefitinib. In one embodiment, the therapeutic combination comprises therapeutically effective amounts of Example No. 234 and tarloxotinib. In one embodiment, the therapeutic combination comprises therapeutically effective amounts of Example No. 234 and the anti-EGFR antibody cetuximab. In one embodiment, the therapeutic combination comprises therapeutically effective amounts of Example No. 359 and afatinib. In one embodiment, the therapeutic combination comprises therapeutically effective amounts of Example No. 359 and dacomitinib. In one embodiment, the therapeutic combination comprises therapeutically effective amounts of Example No. 359 and gefitinib. In one embodiment, the therapeutic combination comprises therapeutically effective amounts of Example No. 359 and tarloxotinib. In one embodiment, the therapeutic combination comprises therapeutically effective amounts of Example No. 359 and the anti-EGFR antibody cetuximab. In one embodiment, the therapeutic combination comprises therapeutically effective amounts of Example No. 478 and afatinib. In one embodiment, the therapeutic combination comprises therapeutically effective amounts of Example No. 478 and dacomitinib. In one embodiment, the therapeutic combination comprises therapeutically effective amounts of Example No. 478 and gefitinib. In one embodiment, the therapeutic combination comprises therapeutically effective amounts of Example No. 478 and tarloxotinib. In one embodiment, the therapeutic combination comprises therapeutically effective amounts of Example No. 478 and the anti-EGFR antibody cetuximab. In one embodiment, the therapeutic combination comprises therapeutically effective amounts of Example No. 507 and afatinib. In one embodiment, the therapeutic combination comprises therapeutically effective amounts of Example No. 507 and dacomitinib. In one embodiment, the therapeutic combination comprises therapeutically effective amounts of Example No. 507 and gefitinib. In one embodiment, the therapeutic combination comprises therapeutically effective amounts of Example No. 507 and tarloxotinib. In one embodiment, the therapeutic combination comprises therapeutically effective amounts of Example No. 507 and the anti-EGFR antibody cetuximab. In one embodiment of any of said combination therapies, the combination is useful for treating a KRas G12C-associated cancer. In one embodiment, the KRas G12C-associated cancer is lung cancer.

In some embodiments, the methods provided herein can result in a 1% to 99% (e.g., 1% to 98%, 1% to 95%, 1% to 90%, 1 to 85%, 1 to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 10% to 5%, 2% to 99%, 2% to 90%, 2% to 85%, 2% to 80%, 2% to 75%, 2% to 70%, 2% to 65%, 2% to 60%, 2% to 55%, 2% to 50%, 2% to 45%, 2% to 40%, 2% to 35%, 2% to 30%, 2% to 25%, 2% to 20%, 2% to 15%, 2% to 10%, 2% to 5%, 4% to 99%, 4% to 95%, 4% to 90%, 4% to 85%, 4% to 80%, 4% to 75%, 4% to 70%, 4% to 65%, 4% to 60%, 4% to 55%, 4% to 50%, 4% to 45%, 4% to 40%, 4% to 35%, 4% to 30%, 4% to 25%, 4% to 20%, 4% to 15%, 4% to 10%, 6% to 99%, 6% to 95%, 6% to 90%, 6% to 85%, 6% to 80%, 6% to 75%, 6% to 70%, 6% to 65%, 6% to 60%, 6% to 55%, 6% to 50%, 6% to 45%, 6% to 40%, 6% to 35%, 6% to 30%, 6% to 25%, 6% to 20%, 6% to 15%, 6% to 10%, 8% to 99%, 8% to 95%, 8% to 90%, 8% to 85%, 8% to 80%, 8% to 75%, 8% to 70%, 8% to 65%, 8% to 60%, 8% to 55%, 8% to 50%, 8% to 45%, 8% to 40%, 8% to 35%, 8% to 30%, 8% to 25%, 8% to 20%, 8% to 15%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 99%, 15% to 95%, 15% to 90%, 15% to 85%, 15% to 80%, 15% to 75%, 15% to 70%, 15% to 65%, 15% to 60%, 15% to 55%, 15% to 50%, 15% to 55%, 15% to 50%, 15% to 45%, 15% to 40%, 15% to 35%, 15% to 30%, 15% to 25%, 15% to 20%, 20% to 99%, 20% to 95%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 99%, 25% to 95%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 99%, 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 99%, 35% to 95%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 99%, 40% to 95%, 40% to 90%, 40% to 85%, 40% to 80%, 40% to 75%, 40% to 70%, 40% to 65%, 40% to 60%, 40% to 55%, 40% to 60%, 40% to 55%, 40% to 50%, 40% to 45%, 45% to 99%, 45% to 95%, 45% to 95%, 45% to 90%, 45% to 85%, 45% to 80%, 45% to 75%, 45% to 70%, 45% to 65%, 45% to 60%, 45% to 55%, 45% to 50%, 50% to 99%, 50% to 95%, 50% to 90%, 50% to 85%, 50% to 80%, 50% to 75%, 50% to 70%, 50% to 65%, 50% to 60%, 50% to 55%, 55% to 99%, 55% to 95%, 55% to 90%, 55% to 85%, 55% to 80%, 55% to 75%, 55% to 70%, 55% to 65%, 55% to 60%, 60% to 99%, 60% to 95%, 60% to 90%, 60% to 85%, 60% to 80%, 60% to 75%, 60% to 70%, 60% to 65%, 65% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 70% to 75%, 75% to 99%, 75% to 95%, 75% to 90%, 75% to 85%, 75% to 80%, 80% to 99%, 80% to 95%, 80% to 90%, 80% to 85%, 85% to 99%, 85% to 95%, 85% to 90%, 90% to 99%, 90% to 95%, or 95% to 100%) reduction in the volume of one or more solid tumors in a patient following treatment with the combination therapy for a period of time between 1 day and 2 years (e.g., between 1 day and 22 months, between 1 day and 20 months, between 1 day and 18 months, between 1 day and 16 months, between 1 day and 14 months, between 1 day and 12 months, between 1 day and 10 months, between 1 day and 9 months, between 1 day and 8 months, between 1 day and 7 months, between 1 day and 6 months, between 1 day and 5 months, between 1 day and 4 months, between 1 day and 3 months, between 1 day and 2 months, between 1 day and 1 month, between one week and 2 years, between 1 week and 22 months, between 1 week and 20 months, between 1 week and 18 months, between 1 week and 16 months, between 1 week and 14 months, between 1 week and 12 months, between 1 week and 10 months, between 1 week and 9 months, between 1 week and 8 months, between 1 week and 7 months, between 1 week and 6 months, between 1 week and 5 months, between 1 week and 4 months, between 1 week and 3 months, between 1 week and 2 months, between 1 week and 1 month, between 2 weeks and 2 years, between 2 weeks and 22 months, between 2 weeks and 20 months, between 2 weeks and 18 months, between 2 weeks and 16 months, between 2 weeks and 14 months, between 2 weeks and 12 months, between 2 weeks and 10 months, between 2 weeks and 9 months, between 2 weeks and 8 months, between 2 weeks and 7 months, between 2 weeks and 6 months, between 2 weeks and 5 months, between 2 weeks and 4 months, between 2 weeks and 3 months, between 2 weeks and 2 months, between 2 weeks and 1 month, between 1 month and 2 years, between 1 month and 22 months, between 1 month and 20 months, between 1 month and 18 months, between 1 month and 16 months, between 1 month and 14 months, between 1 month and 12 months, between 1 month and 10 months, between 1 month and 9 months, between 1 month and 8 months, between 1 month and 7 months, between 1 month and 6 months, between 1 month and 6 months, between 1 month and 5 months, between 1 month and 4 months, between 1 month and 3 months, between 1 month and 2 months, between 2 months and 2 years, between 2 months and 22 months, between 2 months and 20 months, between 2 months and 18 months, between 2 months and 16 months, between 2 months and 14 months, between 2 months and 12 months, between 2 months and 10 months, between 2 months and 9 months, between 2 months and 8 months, between 2 months and 7 months, between 2 months and 6 months, or between 2 months and 5 months, between 2 months and 4 months, between 3 months and 2 years, between 3 months and 22 months, between 3 months and 20 months, between 3 months and 18 months, between 3 months and 16 months, between 3 months and 14 months, between 3 months and 12 months, between 3 months and 10 months, between 3 months and 8 months, between 3 months and 6 months, between 4 months and 2 years, between 4 months and 22 months, between 4 months and 20 months, between 4 months and 18 months, between 4 months and 16 months, between 4 months and 14 months, between 4 months and 12 months, between 4 months and 10 months, between 4 months and 8 months, between 4 months and 6 months, between 6 months and 2 years, between 6 months and 22 months, between 6 months and 20 months, between 6 months and 18 months, between 6 months and 16 months, between 6 months and 14 months, between 6 months and 12 months, between 6 months and 10 months, or between 6 months and 8 months) (e.g., as compared to the size of the one or more solid tumors in the patient prior to treatment).

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

Kits

The present invention also relates to a kit comprising a pan ErbB family inhibitor, or a pharmaceutically acceptable salt thereof and a KRas G12C inhibitor compound of Formula (I), Formula I-A or Formula I-B or a pharmaceutically acceptable salt thereof. Also provided is a kit comprising a pan ErbB family inhibitor or a pharmaceutically acceptable salt thereof and a KRas G12C inhibitor compound of Formula (I), Formula I-A or Formula I-B or a pharmaceutically acceptable salt thereof, for use in treating a KRas G12C-associated cancer.

In a related aspect, the invention provides a kit containing a dose of a pan ErbB family inhibitor and dose of a KRas G12C inhibitor compound of Formula (I), Formula I-A or Formula I-B or a pharmaceutically acceptable salt thereof in an amount effective to inhibit proliferation of cancer cells, particularly KRas G12C-expressing cancer cells, in a subject. The kit in some cases includes an insert with instructions for administration of the pan ErbB family inhibitor and a KRas G12C inhibitor compound of Formula (I), Formula I-A or Formula I-B. The insert may provide a user with one set of instructions for using a pan ErbB family inhibitor in combination with a KRas G12C inhibitor compound of Formula (I), Formula I-A or Formula I-B.

Example A

Pan ErbB Family Inhibitors Synergistically Increase the Activity of KRas G12C Inhibitors Against Cell Lines Expressing KRas G12C This Example illustrates that the combination of exemplary KRas G12C inhibitor compounds of Formula I, Formula I-A and Formula I-B or a pharmaceutically acceptable salt thereof (e.g., a compound selected from compound Example Nos 1-678, or a pharmaceutically acceptable salt thereof, e.g., Example No. 234, 359, 478 or 507, or a pharmaceutically acceptable salt thereof) and a pan ErbB family inhibitor or a pharmaceutically acceptable salt or a pharmaceutical composition thereof synergistically inhibits the growth of tumor cell lines that express KRas G12C.

A panel of 9 lung cancer and 1 colorectal cell lines harboring KRas G12C mutations was assembled to determine whether combining pan ErbB family inhibitors with exemplary KRas G12C inhibitors disclosed herein results in synergistic activity. The collection included NCI-H1373 (ATCC CRL-5866); NCI-H1792 (ATCC CRL-5895); NCI-H2030 (ATCC CRL-5985); NCI-H2122 (ATCC CRL-5985); HCC1171 (KCLB 71171); HCC44 (DSMZ ACC-534); LU99 (RCB1900); SW1573 (ATCC CRL-2170), SW837 (ATCC CCL-235) and KYSE-410 (ECACC 94072023).

Assays for determining the synergy score for the pairwise combinations for each cell line were performed in triplicate. Three 96-well plates plus an additional 4 wells of a separate 96-well control plate for determining baseline luminescence were seeded with 2000 cells/well of a particular cell line in a total volume of 90 µl of a suitable growth medium for that cell line, e.g., RPMI 1640 medium supplemented with 10% FBS and any cell line specific reagents need for growth. The plates were incubated overnight at 37° C. in a 5% $CO_2$ atmosphere.

To each of the designated baseline wells, 30 µl of Cell-Titer Glo reagent (CTG; Promega Corporation) was added to each well and the plates were incubated for 20 min with shaking at room temperature. Baseline luminescence was quantitated using a BMG ClarioStar multimode plate reader according to the manufacturer's instructions.

A series of working stock 1000× drug dilutions in 100% DMSO was prepared that includes an 8 point single agent dilution of the exemplary KRas G12C inhibitor of Formula (I) and a 5-point single agent dilution of the pan ErbB family inhibitor. The dilutions used for the KRas G12C inhibitor and the pan ErbB family inhibitor varied for each individual compound but were in the range of 3- to 6-fold/serial dilution.

Exemplary KRas G12C inhibitors tested in this Example included:

| Example No.* | Structure |
|---|---|
| 234 | |
| 359 | 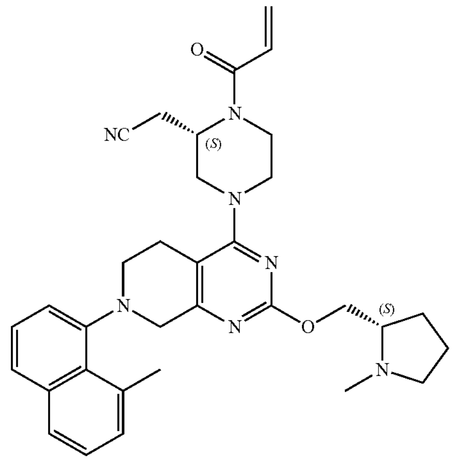 |
| 478 | 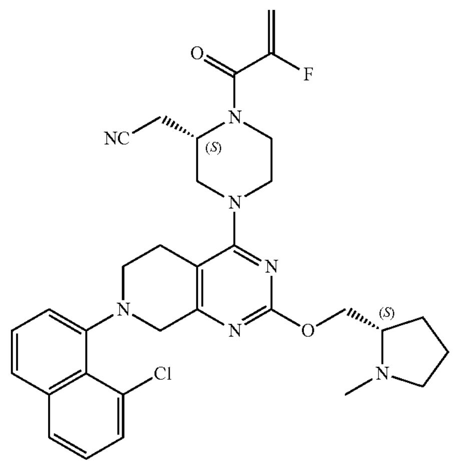 |
| 507 | 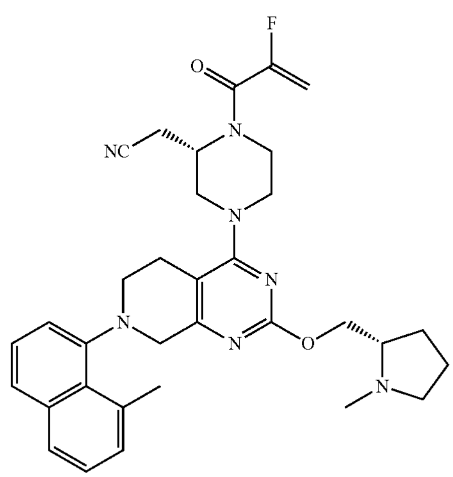 [SMILES: C=C(F)C(=O)N1CCN(c2nc(OC[C@@H]3CCCN3C)nc3c2CCN(c2cccc4cccc(C)c24)C3)C[C@@H]1CC#N] |

*Example Number refers to the example number for each compound as disclosed in published International PCT application WO2019099524.

A 10× intermediate dosing plate was prepared in serum free RPMI medium that contains arrayed single agent dilutions of exemplary KRas G12C inhibitor of Formula (I) or the Pan ErbB inhibitor. In addition, a matrix of 40 dilution combinations of exemplary KRas G12C inhibitor of Formula (I), Formula I-A or Formula I-B and the pan ErbB family inhibitor was prepared as test samples.

To each corresponding well of the three 96-well plates seeded with the appropriate cell line above, 10 µl of each 10× single agent and the 40 combinations of the dose matrix was added and the plates were incubated for 72 hours at 37 C in 5% C02 atmosphere. A 30 µl aliquot of Cell-Titer Glo reagent (CTG) was added to each test well, the plates were incubated for 20 min with shaking at room temperature, and luminescence was quantitated using a BMG ClarioStar multimode plate reader according to the manufacturer's instructions.

The raw data and metadata files were used as input files to calculate percent effect for each treatment condition and analyzed using four independent mathematical reference models designed to determine whether the two test compounds demonstrate synergy: Loewe additivity, Bliss independence, Highest Single Agent and ZIP.

The output of the data from each mathematical model is the assignment of a relative synergy score. The data reported in Table 3 are the aggregate sum of the Loewe additivity, Bliss independence, Highest Single Agent and ZIP scores ("Composite Synergy Score").

complete tumor regression. The third group was administered a single agent dose of the pan ErbB inhibitor at a concentration that yields a maximal biological effect or a less than maximal biological effect, depending on the cell line and the single agent activity, that also does not result in complete tumor regression. The fourth group was administered the single agent dose of the KRas G12C inhibitor in combination with the single agent dose of the pan ErbB family inhibitor. The treatment period varied from cell line to cell line but typically was between 21-35 days. Tumor volumes were measured using a caliper every two-three days and tumor volumes were calculated by the formula: 0.5× (Length×Width)$^2$. A greater degree of tumor regression for the combination in this model demonstrates that the combination therapy is likely to have a clinically meaningful benefit to treated subjects relative to treatment with only a KRas G12C inhibitor.

For example, on Day 1, three sets of 20 nude/nude mice each were inoculated in the right hind limb with 5×10$^6$ H2122 cells, KYSE-410 cells or LU6405 cells (PDX model). When tumor volume reached ~300 mm$^3$ (Day 11),

TABLE 3

Composite Synergy Scores for Exemplary pan ErbB Family Inhibitors Combined with Exemplary KRas G12C Inhibitors of Formula (I) Against KRas G12C Cell Lines

| | Pan ErbB Family Inhibitor | | | | | | | | | | |
|---|---|---|---|---|---|---|---|---|---|---|---|
| | Afatinib | | | | Dacomitinib | Erlotinib | | Gefitinib | | Poziotinib | Sapitinib |
| | KRas G12C Example # | | | | | | | | | | |
| Cell Line | 234 | 507 | 359 | 478 | 234 | 507 | 478 | 234 | 507 | 478 | 507 |
| H1373 | 46.5 | 37.5 | 25.5 | 29.0 | 42.9 | 46.0 | −3.5 | 23.4 | 40.2 | 16.1 | 16.5 |
| H1792 | 42.5 | 19.6 | 24.8 | 27.2 | 34.7 | 13.5 | −15.4 | 12.7 | 2.1 | 41.6 | 15.8 |
| H2030 | 65.6 | 43.9 | 32.2 | 29.4 | 45.7 | 33.9 | 26.9 | 32.1 | 25.2 | 18.6 | 35.5 |
| H2122 | ND | 57.3 | 40.2 | 56.8 | 149.3 | 55.2 | 41.2 | 52.6 | 31.5 | 33.8 | 55.8 |
| HCC1171 | 98.8 | 66.6 | 91.0 | 65.6 | 97.1 | 73.1 | 49.4 | 62.2 | 51.7 | 42.5 | 39.8 |
| HCC44 | 22.0 | 6.7 | 19.6 | 11.5 | 53.3 | −1.5 | −40.3 | −18.0 | −6.0 | 9.6 | 3.0 |
| LU99 | 39.9 | 16.7 | 23.7 | 11.0 | 32.1 | 11.8 | −17.0 | 13.3 | −4.8 | 18.6 | 10.3 |
| SW1573 | 33.3 | 31.8 | 16.1 | 17.0 | −26.6 | 16.5 | −20.9 | −2.6 | −2.2 | 10.7 | 0.9 |
| SW837 | 53.7 | 48.2 | 40.5 | 36.6 | 26.4 | 47.0 | 6.7 | 23.2 | 40.5 | 33.4 | 20.7 |
| KYSE-410 | ND | ND | 28.6 | 21.3 | ND | ND | 7.7 | ND | ND | 35.3 | ND |

A composite score of greater than or equal to 27 was interpreted as a synergistic hit whereas a composite score between 17 and 26 indicates potential synergy. These results demonstrate that a synergistic effect was observed for the combination of a variety of pan ErbB family inhibitors with exemplary KRas G12C inhibitor compounds of Formula (I) in a majority of cell line harboring a KRas G12C mutation listed in Table 1 that are less sensitive to KRas G12C single agent treatment thereby increasing the sensitivity of the KRas G12C cell line to the KRas G12C inhibitor.

Example B

In Vivo Models for Examining KRas G12C inhibitor Plus Pan ErbB Family Inhibitor Combinations Immunocompromised nude/nude mice were inoculated in the right hind flank with cells or patient derived tumor samples harboring a KRas G12C mutation. When tumor volumes reached between 200-400 mm$^3$ in size, the mice were divided into four groups of 5-12 mice each. The first group was administered vehicle only. The second group was administered a single agent dose of the KRas G12C inhibitor at a concentration that yields a maximal biological effect or a less than maximal biological effect, depending on the cell line and the single agent activity, that does not result in 5 mice in each of the four groups were administered p.o. daily for 21 days: vehicle only (10% Captisol), 100 mg/kg of the KRas G12C inhibitor Compound 478 (10% Captisol in 50 mM citrate buffer, pH 5.0), 12.5 mg/kg of the pan ErbB family inhibitor Afatinib (0.5% methylcellulose/0.4% Tween-80), or 100 mg/kg of the KRas G12C inhibitor Compound 478 and 12.5 mg/kg of Afatinib. Tumor volumes were measured at pre-specified days set forth below. Tumor volumes for the five mice per group were averaged and are reported in Table 4a (H2122 cell line), 4b (KYSE-410 cell line) and 4c (LU6405 cells).

TABLE 4a

Average Tumor Volumes (mm$^3$) of H2122 Tumor Bearing Mice Treated with Single Agents and in Combination

| Day Post Implant | Vehicle | Compound 478 | Afatinib | Compound 478 + Afatinib |
|---|---|---|---|---|
| 11 | 324.86 | 325.05 | 324.86 | 329.49 |
| 13 | 519.62 | 339.80 | 429.76 | 257.56 |
| 15 | 688.80 | 337.58 | 573.36 | 186.03 |
| 18 | 954.95 | 381.78 | 694.70 | 170.99 |
| 20 | 1126.81 | 462.40 | 850.85 | 174.29 |
| 22 | 1350.85 | 479.48 | 931.53 | 194.99 |
| 25 | 1504.56 | 492.76 | 1153.42 | 220.34 |

TABLE 4a-continued

Average Tumor Volumes (mm³) of H2122 Tumor
Bearing Mice Treated with Single Agents and in Combination

| Day Post Implant | Vehicle | Compound 478 | Afatinib | Compound 478 + Afatinib |
|---|---|---|---|---|
| 27 | 1574.31 | 541.06 | 1307.50 | 246.90 |
| 29 | 1343.95 | 537.14 | 1137.09 | 246.42 |
| 32 | 1491.71 | 547.06 | 1403.33 | 219.49 |
| 34 | 1559.70 | 546.96 | 1830.13 | 208.05 |

TABLE 4b

Average Tumor Volumes (mm³) of KYSE-410 Tumor
Bearing Mice Treated with Single Agents and in Combination

| Day Post Implant | Vehicle | Compound 478 | Afatinib | Compound 478 + Afatinib |
|---|---|---|---|---|
| 11 | 308.24 | 307.30 | 311.84 | 313.08 |
| 14 | 333.98 | 274.64 | 199.20 | 137.64 |
| 16 | 388.62 | 311.34 | 135.30 | 77.84 |
| 18 | 418.14 | 297.62 | 114.40 | 49.02 |
| 21 | 420.80 | 338.18 | 114.08 | 34.60 |
| 23 | 494.66 | 320.42 | 132.92 | 33.40 |
| 25 | 519.48 | 358.68 | 141.90 | 27.22 |
| 28 | 577.98 | 459.20 | 144.36 | 24.60 |
| 30 | 673.74 | 441.60 | 166.46 | 21.12 |
| 32 | 738.70 | 480.62 | 163.92 | 21.92 |
| 35 | 889.72 | 543.02 | 181.68 | 18.12 |
| 37 | 905.00 | 525.86 | 198.34 | 18.57 |

TABLE 4c

Average Tumor Volumes (mm³) of LU6405 Tumor
Bearing Mice Treated with Single Agents and in Combination

| Day Post Implant | Vehicle | Compound 478 | Afatinib | Compound 478 + Afatinib |
|---|---|---|---|---|
| 11 | 256.45 | 256.06 | 257.48 | 253.48 |
| 14 | 447.44 | 308.98 | 371.98 | 273.28 |
| 18 | 877.95 | 324.46 | 585.54 | 264.33 |
| 21 | 1215.89 | 329.09 | 775.75 | 199.62 |
| 25 | 1727.56 | 310.21 | 1056.23 | 168.34 |
| 28 | 1950.09 | 290.88 | 1197.31 | 144.99 |
| 32 | 2074.33 | 257.34 | 1540.74 | 82.99 |
| 34 | 2074.33 | 249.19 | 1655.49 | 53.55 |

As shown in Table 4a, the administration of Compound 478 or afatinib as a single agent to H2122 tumor bearing mice exhibited 85% and 41% tumor growth inhibition at Day 22 (Treatment Day 10), respectively. The combination of the pan ErbB family inhibitor afatinib and Compound 478 resulted in 41% tumor regression at Day 22.

As shown in Table 4b, the administration of Compound 478 as a single agent to KYSE-410 tumor bearing mice resulted in 64% tumor growth inhibition at Day 37 (Treatment Day 27) whereas the combination of the pan ErbB family inhibitor afatinib and Compound 478 resulted in 93% tumor regression at Day 37 compared to administration of Compound 478 as a single agent.

As shown in Table 4c, the administration of Compound 478 as a single agent to LU6405-implanted mice resulted in 96% tumor growth inhibition at Day 34 (Treatment Day 24) whereas the combination of the pan ErbB family inhibitor afatinib and Compound 478 resulted in 67% tumor regression at Day 37 compared to administration of Compound 478 as a single agent.

In a related experiment, on Day 1, two sets of 20 nude/nude mice each were inoculated in the right hind limb with 5×10⁶ CR6256 cells or CR2528 cells (PDX models). When tumor volume reached ~200-300 mm³ (Day 11), 5 mice in each of the first two groups were administered p.o. daily for 21 days: vehicle only (10% Captisol) or 100 mg/kg of KRas G12C inhibitor Compound 478 (10% Captisol in 50 mM citrate buffer, pH 5.0). The third group of mice were administered every third day 0.25 mg/kg i.p of the pan ErbB family inhibitor antibody Cetuximab (PBS, pH 7.2), or 100 mg/kg of KRas G12C inhibitor Compound 478 p.o and 0.25 mg/kg of Cetuximab i.p every three days. Tumor volumes were measured at pre-specified days set forth below. Tumor volumes for the five mice per group were averaged and are reported in Table 5a (CR6256 cell line) and 5b (CR2528 cell line).

TABLE 5a

Average Tumor Volumes (mm³) of CR6258 Tumor
Bearing Mice Treated with Single Agents and in Combination

| Day Post Implant | Vehicle | Compound 478 | Cetuximab | Compound 478 + Cetuximab |
|---|---|---|---|---|
| 11 | 187.38 | 190.54 | 187.77 | 192.96 |
| 14 | 330.09 | 253.11 | 258.50 | 270.22 |
| 18 | 510.20 | 256.91 | 321.93 | 277.94 |
| 21 | 773.12 | 252.05 | 390.52 | 257.98 |
| 25 | 1135.07 | 201.00 | 503.75 | 90.49 |
| 28 | 1473.99 | 128.77 | 571.30 | 40.33 |
| 32 | 1638.23 | 77.44 | 652.14 | 26.89 |
| 35 | 1775.29 | 56.15 | 678.49 | 0.00 |
| 39 | 1740.94 | 44.24 | 768.49 | 0.00 |
| 42 | 1965.90 | 41.80 | 890.83 | 0.00 |
| 46 | 1995.68 | 29.92 | 975.10 | 0.00 |
| 49 | 2469.47 | 19.79 | 1233.04 | 0 |

TABLE 5b

Average Tumor Volumes (mm³) of CR2528 Tumor
Bearing Mice Treated with Single Agents and in Combination

| Day Post Implant | Vehicle | Compound 478 | Cetuximab | Compound 478 + Cetuximab |
|---|---|---|---|---|
| 11 | 264.96 | 265.11 | 266.03 | 265.85 |
| 14 | 449.44 | 350.48 | 450.64 | 313.82 |
| 17 | 671.85 | 434.64 | 616.52 | 347.80 |
| 20 | 1407.65 | 656.73 | 1208.84 | 352.92 |
| 24 | 1796.07 | 950.91 | 1924.82 | 353.44 |
| 27 | 1776.55 | 1252.80 | 2424.63 | 330.12 |
| 31 | 2215.54 | 1713.13 | 2741.36 | 237.44 |
| 34 | | 2757.63 | | 222.67 |
| 38 | | | | 220.78 |
| 40 | | | | 184.11 |

As shown in Table 5a, the administration of Compound 478 as a single agent to CR6258-implanted mice resulted in 71% tumor regression at Day 37 (Treatment Day 27) whereas the combination of the pan ErbB family inhibitor cetuximab and Compound 478 resulted in a complete response, or 100% tumor regression at Day 37 compared to administration of Compound 478 as a single agent.

As shown in Table 5b, the administration of Compound 478 as a single agent to CR2528-implanted mice resulted in no single-agent anti-tumor activity at Day 34 (Treatment Day 24) whereas the combination of the pan ErbB family inhibitor cetuximab and Compound 478 resulted in 31% tumor regression at Day 37 compared to administration of Compound 478 as a single agent.

In yet another experiment, on Day 1, two sets of 20 nude/nude mice each were inoculated in the right hind limb with 5×10⁶ H2122 cells or KYSE-410 cells. When tumor volume reached ~300 mm³ (Day 11), 5 mice in each of the four groups were administered p.o. daily for 21 days: vehicle only (10% Captisol) or 100 mg/kg of KRas G12C inhibitor Compound 478 (10% Captisol in 50 mM citrate buffer, pH 5.0). The third group of 5 mice were administered every seven days 48 mg/kg i.p. of the pan ErbB family inhibitor tarloxotinib (10 mg/kg Beta-cyclodextrin), or 100 mg/kg of KRas G12C inhibitor Compound 478 p.o and 48 mg/kg of tarloxotinib i.p every seven days. Tumor volumes were measured at pre-specified days set forth below. Tumor volumes for the five mice per group were averaged and are reported in Table 6a (KYSE-410 cell line) and 6b (H2122 cell line).

TABLE 6a

Average Tumor Volumes (mm³) of KYSE-410 Tumor Bearing Mice Treated with Single Agents and in Combination

| Day Post Implant | Vehicle | Compound 478 | Tarloxotinib | Compound 478 + Tarloxotinib |
|---|---|---|---|---|
| 11 | 225.71 | 231.53 | 233.57 | 237.74 |
| 19 | 310.33 | 237.61 | 40.90 | 32.96 |
| 26 | 367.27 | 273.90 | 28.99 | 23.87 |
| 33 | 456.50 | 306.12 | 20.30 | 14.08 |
| 40 | 579.80 | 334.72 | 20.81 | 10.12 |
| 47 | 646.54 | 354.97 | 14.67 | 10.67 |
| 54 | 854.31 | 431.28 | 19.20 | 7.87 |
| 61 | 1129.53 | 488.08 | 15.55 | 7.73 |

TABLE 6b

Average Tumor Volumes (mm³) of H2122 Tumor Bearing Mice Treated with Single Agents and in Combination

| Day Post Implant | Vehicle | Compound 478 | Tarloxotinib | Compound 478 + Tarloxotinib |
|---|---|---|---|---|
| 11 | 313.60 | 314.62 | 305.56 | 296.06 |
| 14 | 395.56 | 281.54 | 287.64 | 163.54 |
| 18 | 494.74 | 233.12 | 380.02 | 101.60 |
| 21 | 650.72 | 277.28 | 374.78 | 91.42 |
| 26 | 749.66 | 252.14 | 443.76 | 72.12 |
| 28 | 887.98 | 277.48 | 450.62 | 50.80 |
| 32 | 1027.62 | 269.90 | 466.00 | 66.14 |
| 35 | 1151.30 | 254.30 | 471.26 | 56.78 |
| 39 | 1202.5 | 276 | 544.78 | 63.38 |
| 43 | 1232.14 | 286.56 | 507.6 | 53.46 |
| 46 | 1243.74 | 304.9 | 640.975 | 62.34 |

As shown in Table 6a, the administration of Compound 478 as a single agent to KYSE-410-implanted mice resulted in 71% tumor growth inhibition at Day 61 (Treatment Day 50) whereas the combination of the pan ErbB family inhibitor Cetuximab and Compound 478 resulted in 97% tumor regression at Day 61 compared to administration of Compound 478 as a single agent.

As shown in Table 6b, the administration of Compound 478 as a single agent to H2122-implanted mice resulted in 3% tumor regression at Day 46 (Treatment Day 35) whereas the combination of the pan ErbB family inhibitor cetuximab and Compound 478 resulted in 79% tumor regression at Day 37 compared to administration of Compound 478 as a single agent.

These results demonstrate that each of the combination therapies resulted in greater amount of tumor growth inhibition compared to either single agent alone demonstrating enhanced in vivo anti-tumor efficacy of the combination.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A method of treating colorectal cancer in a subject in need thereof, comprising administering to the subject a combination therapy, wherein the combination therapy comprises a therapeutically effective amount of cetuximab and a therapeutically effective amount of a KRAS G12C inhibitor of formula:

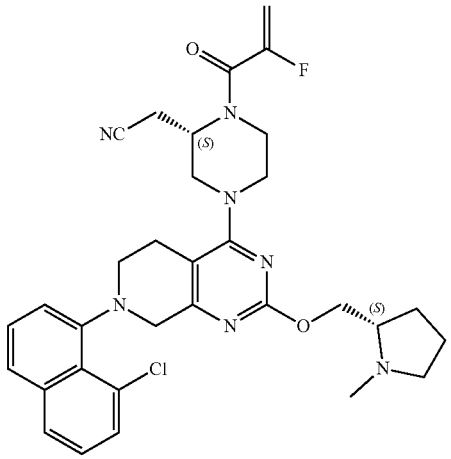

or a pharmaceutically acceptable salt thereof.

2. The method according to claim 1, wherein the therapeutically effective amount of the combination of cetuximab and the KRAS G12C inhibitor or a pharmaceutically acceptable salt thereof results in an increased duration of overall survival, an increased duration of progression free survival, an increase in tumor growth regression, an increase in tumor growth inhibition or an increased duration of stable disease in the subject relative to treatment with only the KRas G12C inhibitor.

3. The method according to claim 1, wherein cetuximab synergistically increases sensitivity of colorectal cancer cells of the colorectal cancer to the KRas G12C inhibitor.

4. The method according to claim 1, wherein the therapeutically effective amount of the KRas G12C inhibitor is between about 0.01 to 100 mg/kg per day.

5. The method of claim 1, wherein cetuximab and the KRAS G12C inhibitor or a pharmaceutically acceptable salt thereof are formulated into separate dosage forms.

6. The method of claim 1, wherein the KRAS G12C inhibitor or a pharmaceutically acceptable salt thereof is administered orally.

7. The method of claim 1, wherein cetuximab is administered parenterally.

8. The method of claim 1, wherein cetuximab is administered intravenously.

9. The method of claim 1, wherein cetuximab is administered prior to the administration of the KRAS G12C inhibitor or a pharmaceutically acceptable salt thereof.

10. The method of claim 1, wherein cetuximab is administered after the administration of the KRAS G12C inhibitor or a pharmaceutically acceptable salt thereof.

11. The method of claim 1, wherein the KRAS G12C inhibitor or a pharmaceutically acceptable salt thereof is administered twice per day.

12. The method of claim 1, wherein cetuximab and the KRAS G12C inhibitor or a pharmaceutically acceptable salt thereof are administered through different administration routes.

13. The method of claim 1, wherein the KRAS G12C inhibitor or a pharmaceutically acceptable salt thereof is administered as a tablet.

14. A method for inhibiting KRas G12C activity in a colorectal cancer cell, comprising contacting the cell in which inhibition of KRas G12C activity is desired with an effective amount of cetuximab and the KRas G12C inhibitor compound or a pharmaceutically acceptable salt thereof according to claim 1, wherein cetuximab synergistically increases sensitivity of the colorectal cancer cell to the KRas G12C inhibitor.

15. A method for increasing the sensitivity of a colorectal cancer cell to a KRas G12C inhibitor compound comprising administering to a subject with colorectal cancer undergoing KRas Gi 2C treatment with a compound of claim 1 or a pharmaceutically acceptable salt thereof, alone or combined with a pharmaceutically acceptable carrier, excipient or diluents, a therapeutically effective amount of cetuximab, wherein cetuximab synergistically increases the sensitivity of the colorectal cancer cell to the KRas G12C inhibitor.

16. A method of treating colorectal cancer in a subject in need thereof, comprising administering to the subject a combination therapy, wherein the combination therapy comprises a therapeutically effective amount of cetuximab and a therapeutically effective amount of a KRAS G12C inhibitor of formula:

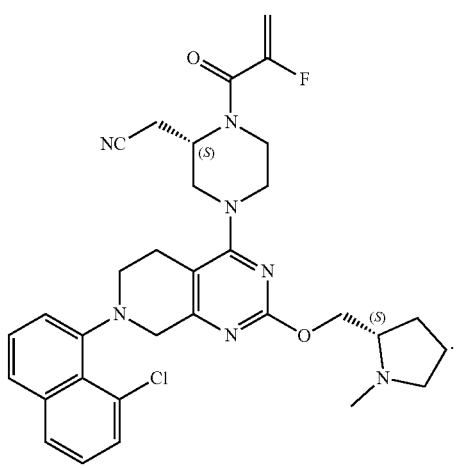

17. The method according to claim 16, wherein the therapeutically effective amount of the combination of cetuximab and the KRAS G12C inhibitor results in an increased duration of overall survival, an increased duration of progression free survival, an increase in tumor growth regression, an increase in tumor growth inhibition or an increased duration of stable disease in the subject relative to treatment with only the KRas G12C inhibitor.

18. The method according to claim 16, wherein cetuximab synergistically increases sensitivity of colorectal cancer cells of the colorectal cancer to the KRas G12C inhibitor.

19. The method according to claim 16, wherein the therapeutically effective amount of the KRas G12C inhibitor is between about 0.01 to 100 mg/kg per day.

20. The method of claim 16, wherein cetuximab and the KRAS G12C inhibitor are formulated into separate dosage forms.

21. The method of claim 16, wherein the KRAS G12C inhibitor or a is administered orally.

22. The method of claim 16, wherein cetuximab is administered parenterally.

23. The method of claim 16, wherein cetuximab is administered intravenously.

24. The method of claim 16, wherein cetuximab is administered prior to the administration of the KRAS G12C inhibitor.

25. The method of claim 16, wherein cetuximab is administered after the administration of the KRAS G12C inhibitor.

26. The method of claim 16, wherein the KRAS G12C inhibitor is administered twice per day.

27. The method of claim 16, wherein cetuximab and the KRAS G12C inhibitor are administered through different administration routes.

28. The method of claim 16, wherein the KRAS G12C inhibitor is administered as a tablet.

29. A method for inhibiting KRas G12C activity in a colorectal cancer cell, comprising contacting the cell in which inhibition of KRas G12C activity is desired with an effective amount of cetuximab and the KRas G12C inhibitor compound according to claim 16, wherein cetuximab synergistically increases sensitivity of the colorectal cancer cell to the KRas G12C inhibitor.

30. A method for increasing sensitivity of a colorectal cancer cell to a KRas G12C inhibitor compound comprising administering to a subject with colorectal cancer undergoing KRas G12C treatment with the KRAS G12C inhibitor of claim 16, alone or combined with a pharmaceutically acceptable carrier, excipient or diluents, a therapeutically effective amount of cetuximab, wherein cetuximab synergistically increases the sensitivity of the colorectal cancer cell to the KRas G12C inhibitor.

31. A pharmaceutical composition, comprising a therapeutically effective amount of a combination of cetuximab and the KRas G12C inhibitor according to claim 1 or a pharmaceutically acceptable salt thereof, and a pharmaceutically acceptable excipient.

32. A pharmaceutical composition, comprising a therapeutically effective amount of a combination of cetuximab and the KRas G12C inhibitor according to claim 16, and a pharmaceutically acceptable excipient.

33. A kit comprising the pharmaceutical composition of claim 31 for treating colorectal cancer in a subject.

34. A kit comprising: a) a pharmaceutical composition comprising cetuximab and b) a pharmaceutical composition comprising a KRas G12C inhibitor of formula:

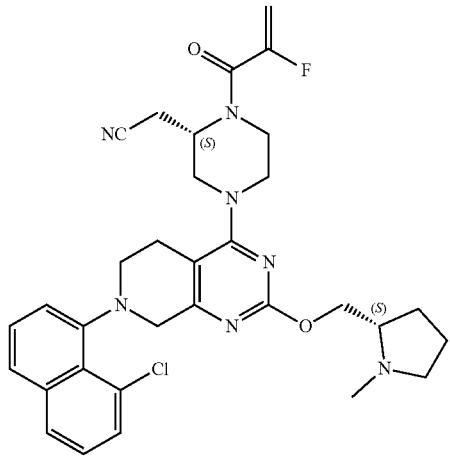

or a pharmaceutically acceptable salt thereof, for treating colorectal cancer in a subject.

35. A kit comprising the pharmaceutical composition of claim 32 for treating colorectal cancer in a subject.

36. A kit comprising: a) a pharmaceutical composition comprising cetuximab and b) a pharmaceutical composition comprising a KRas G12C inhibitor of formula:

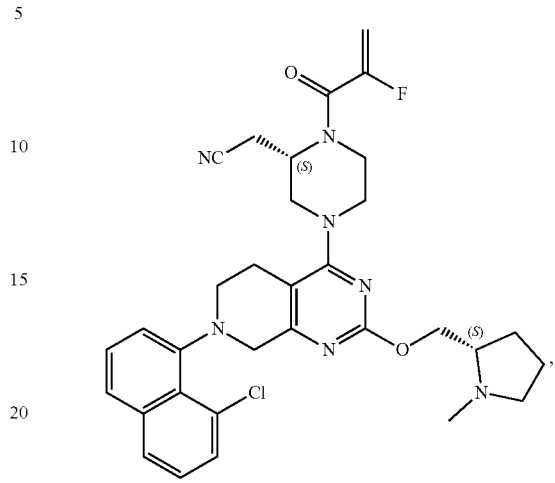

for treating colorectal cancer in a subject.

* * * * *

UNITED STATES PATENT AND TRADEMARK OFFICE
CERTIFICATE OF CORRECTION

| | | |
|---|---|---|
| PATENT NO. | : 12,336,995 B2 | Page 1 of 1 |
| APPLICATION NO. | : 17/275176 | |
| DATED | : June 24, 2025 | |
| INVENTOR(S) | : Lars Engstrom et al. | |

It is certified that error appears in the above-identified patent and that said Letters Patent is hereby corrected as shown below:

In the Claims

Column 237, Claim 15, Line 22 (Approx.), delete "increasing the" and insert -- increasing --.

Column 237, Claim 15, Line 25 (Approx.), delete "Gi 2C treatment with a compound" and insert -- G12C treatment with the KRAS G12C inhibitor --.

Signed and Sealed this
Twenty-first Day of October, 2025

John A. Squires
*Director of the United States Patent and Trademark Office*